(12) United States Patent
Atassi

(10) Patent No.: US 7,670,788 B2
(45) Date of Patent: Mar. 2, 2010

(54) DETERMINING AND REDUCING IMMUNORESISTANCE TO A BOTULINUM TOXIN THERAPY USING BOTULINUM TOXIN B PEPTIDES

(75) Inventor: M. Zouhair Atassi, Houston, TX (US)

(73) Assignees: Allergan, Inc., Irvine, CA (US); Baylor College of Medicine, Houston, TX (US)

( * ) Notice: Subject to any disclaimer, the term of this patent is extended or adjusted under 35 U.S.C. 154(b) by 0 days.

(21) Appl. No.: 12/061,952

(22) Filed: Apr. 3, 2008

(65) Prior Publication Data

US 2008/0213255 A1 Sep. 4, 2008

Related U.S. Application Data

(63) Continuation-in-part of application No. 11/755,161, filed on May 30, 2007.

(60) Provisional application No. 60/810,053, filed on Jun. 1, 2006.

(51) Int. Cl.
*G01N 33/53* (2006.01)
(52) U.S. Cl. ...................................... 435/7.1
(58) Field of Classification Search ................. None
See application file for complete search history.

(56) References Cited

U.S. PATENT DOCUMENTS

| | | | |
|---|---|---|---|
| 4,551,435 | A | 11/1985 | Liberti et al. |
| 4,643,718 | A | 2/1987 | Marten |
| 6,048,529 | A | 4/2000 | Atassi et al. |
| 6,667,158 | B1 | 12/2003 | Bavari et al. |
| 6,676,622 | B2 | 1/2004 | Strahilevitz |
| 2002/0155114 | A1 | 10/2002 | Marks et al. |
| 2002/0197278 | A1 | 12/2002 | Allison |
| 2004/0101534 | A1 | 5/2004 | Diamond |
| 2004/0110284 | A1 | 6/2004 | Bavari et al. |
| 2004/0175385 | A1 | 9/2004 | Marks et al. |
| 2004/0265935 | A1 | 12/2004 | Atassi |
| 2005/0106182 | A1 | 5/2005 | Li et al. |

FOREIGN PATENT DOCUMENTS

| | | |
|---|---|---|
| WO | 94/21684 | 9/1994 |
| WO | 2005/014798 | 2/2005 |
| WO | 2005/030119 | 4/2005 |
| WO | 2006/042149 | 4/2006 |

OTHER PUBLICATIONS

Park et al., J. of Voice, 2003, v 17, p. 255-264.*
Jankovic. ( Neurotoxicity Research, 2006, v.9, pp. 145-148.*
Amersdorfer et al., "Genetic and immunological comparison of anti-botulinum type A antibodies from immune and non-immune human phage libraries," *Vaccine* 20:1640-1648 (2002).
Amersdorfer et al., "Molecular characterization of murine humoral immune response to botulinum neurotoxin type A binding domain as assessed by using phage antibody libraries," *Infect. Immun.* 65:3743-3752 (1997).
Aoki, "Pharmacology and immunology of botulinum toxin serotypes," *J. Neurol.* 248 Suppl. 1:3-10 (2001).
Atassi and Dolimbek, "Mapping of the antibody-binding regions on the HN-domain (residues 449-859) of botulinum neurotoxin A with antitoxin antibodies from four host species. Full profile of the continuous antigenic regions of the H-chain of botulinum neurotoxin A," *Protein J.* 23:39-52 (2004).
Atassi and Oshima, "Structure, activity, and immune (T and B cell) recognition of botulinum neurotoxins," *Crit. Revs. Immunol.* 19:219-260 (1999).
Atassi and Smith, "A proposal for the nomenclature of antigenic sites in peptides and proteins," *Immunochemistry* 15:609-610 (1978).
Kozaki et al., "Development of antitoxin with each of two complementary fragments of *Clostridium botulinum* type B derivative toxin," *Infection and Immunity* 18:761-766 (1977).
Kozaki et al., "Immunological characterization of Papain-induced fragments of *Clostridium botulinum* type A neurotoxin and interaction of the fragments with brain synaptosomes," *Infection and Immunity* 57:2634-2639 (1989).
Kozaki et al., "The use of monoclonal antibodies to analyze the structure of *Clostridium botulinum* type E derivative toxin," *Infection and Immunity* 52:786-791 (1986).
Krieglstein, Kerstin G. et al, Journal of protein Chemistry, vol. 13(1), pp. 49-57, 1994.
Kubota et al., "Epitope regions in the heavy chain of *Clostridium botulinum* type E neurotoxin recognized by monoclonal antibodies," *Applied & Environmental Microbiol.* 63:1214-1218 (1997).
Lacy et al., "Crystal structure of botulinum neurotoxin type A and implications for toxicity," *Nat. Struct. Biol.* 5:898-902 (1998).
Lacy, D. B. et al, "Sequence homology and structural analysis of the Clostridial neurotoxins", Journal of Molecular Biology, vol. 291, 1999, pp. 1091-1104.
LaPenotiere et al., "Expression of a large, nontoxic fragment of botulinum neurotoxin serotype A and its use as an immunogen," *Toxicon* 33:1383-1386 (1995).
Lebeda, Frank J. et al, "Predicting Differential antigen-antibody contact regions based on solvent accessibility", Journal of Protein Chemistry, vol. 16(6), 1997, pp. 607-618.
Atassi et al., "Cross-reaction of mouse antibodies against Tetanus neurotoxin with Botulinum neurotoxins A and B," *International Conference 2002, Basic and Therapeutic Aspects of Botulinum and Tetanus Toxins*, Hannover, Germany, Jun. 8-12, Abstract R12 (2002).

(Continued)

*Primary Examiner*—Michail A Belyavskyi
(74) *Attorney, Agent, or Firm*—Dean G. Stathakis; Joel B. German; Allergan, Inc.

(57) ABSTRACT

The present invention provides BoNT/B peptides, BoNT/B peptide compositions, tolerogizing compositions, immune response inducing compositions, as well as methods of determining immunoresistance to botulinum toxin therapy in an individual, methods of treating immunoresistance to botulinum toxin therapy in an individual, methods of reducing anti-botulinum toxin antibodies in an individual and methods of inducing a BoNT/B immune response an individual.

17 Claims, 6 Drawing Sheets

OTHER PUBLICATIONS

Atassi et al., "Localization and synthesis of the hormone-binding regions of the human thyrotropin receptor," *Proc. Natl. Acad. Sci. USA* 88:3613-3617 (1991).

Atassi et al., "Mapping of the antibody-binding regions on botulinum neurotoxin H-chain domain 855-1296 with anti-toxin antibodies from three host species," *J. Prot. Chem.* 15:691-700 (1996).

Atassi, "Immune recognition and cross-reactivity of botulinum neurotoxins," in *Scientific and Therapeutic Aspects of Botulinum Toxins* (edited by Brin et al.), pp. 385-408, Lippincott Williams and Wilkins, Philadelphia, PA (2002).

Bavari et al., "Identifying the principal protective antigenic determinants of type A botulinum neurotoxin," *Vaccine* 16:1850-1856 (1998).

Beecher, DJ et al, J. Protein Chemistry, vol. 16(7), pp. 701-712, 1997.

Byrne, MP et al, vol. 82, 2000, "Development of vaccines for prevention of botulism", pp. 955-966.

Cenci Di Bello et al., "Antagonism of the intracellular action of botulinum neurotoxin type A with monoclonal antibodies that map to light-chain epitopes," *Eur. J. Biochem.* 219:161-169 (1994).

Chen et al., "Antibody mapping to domains of botulinum neurotoxin serotype A in the complexed and uncomplexed forms," *Infect. Immun.* 65:1626-1630 (1997).

Clayton and Middlebrook, "Vaccination of mice with DNA encoding a large fragment of botulinum neurotoxin serotype A," *Vaccine* 18:1855-1862 (2000).

Clayton et al., "Protective vaccination with a recombinant fragment of *Clostridium botulinum* neurotoxin serotype A expressed from a synthetic gene in *Escherichia coli*," *Infect. Immun.* 63:2738-2742 (1995).

Dertzbaugh and West, "Mapping of protective and cross-reactive domains of the type A neurotoxin of *Clostridium botulinum*," *Vaccine* 14:1538-1544 (1996).

Dineen et al, Swiss Prot sequence Q8KHn9, Oct. 1, 2002.

Dolimbek and Atassi, "Protection against alpha-bungarotoxin poisoning by immunization with synthetic toxin peptides," *Mol. Immunol.* 33:681-689 (1996).

Dolimbek, BZ et al, Molecular Immunology, vol. 44, pp. 1029-1041, 2007.

Dressler et al., "Antibody-induced botulinum toxin therapy failure: Can it be overcome by increased botulinum toxin doses?" *Eur. Neurol.* 47:118-121 (2002).

Gibson et al, Swiss Prot Accession No. Q97TT9, Oct. 1, 2001.

Goschel et al., "Botulinum A toxin therapy: Neutralizing and non-neutralizing antibodies—therapeutic consequences," *Exp. Neurol.* 147:96-102 (1997).

Hambleton et al., "A possible common antigen on clostridial toxins detected by monoclonal anti-botulinum neurotoxin antibodies," 449-450 (1984).

Hanna, Philip A. MD, Neurology, vol. 50(6), pp. 1624-1629, Jun. 1998.

Jankovic, Botulinum Toxin: Clinical Implication sof Antigenicity and Immunoresistancey, in Brin et al. eds., *Scientific and Therapeutic Aspects of Botulinum Toxin*, pp. 409-415, Lippincott Williams & Wilkins, Philadelphia, PA (2002).

Jankovic, Joseph MD et al, Neurology, vol. 45(9), pp. 1743-1746, Sep. 1995.

Kikuyama eta al, Swiss Prot sequence Q9PRU1, May 1, 2000.

Klein, "Complications and adverse reactions with the use of botulinum toxin," *Dis. Mon.* 48:336-356 (2002).

Middlebrook, "Protection strategies against botulinum toxin," in Atassi and Bixler (Eds.), *Immunology of Poreteins and Peptides VIII* p. 93-98 Plunum Press New York (1995).

Mullaney et al., "Epitope mapping of neutralizing botulinum neurotoxin A antibodies by phage display," *Infect. Immun.* 69:6511-6514 (2001).

Naumann et al., "Depletion of neutralizing antibodies resensitises a secondary non-responder to botulinum A neurotoxin," *J. Neurol. Neurosurg. Psychiatry* 65:924-927 (1998).

Oblatt-Montal, M. et al, "Formation of ion channels in lipid bilayers by a peptide with the predicted transmembrane sequence of botulinum neurotoxin A", Protein Science, vol. 4, 1995, pp. 1490-1497.

Oshima et al., "Antibodies and T cells against synthetic peptides of the C-terminal domain ($H_c$) of botulinum neurotoxin type A and their cross-reaction with $H_c$," *Immunol. Letters* 60:7-12 (1998), pp. 1031-1040.

Oshima et al, "Immune recognition of botulinum neurotoxin type A: Regions recognized by T cells and antibodies against the protective $H_c$ fragment (residues 855-1296) of the toxin," *Mol. Immunol.* 34:1031-1040 (1997).

Pittman et al., "Antibody response to a delayed booster dose of anthrax vaccine and botulinum toxoid," *Vaccine* 20:2107-2115 (2002).

Pless et al., "High-affinity, protective antibodies to the binding domain of botulinum neurotoxin type A," *Infect. Immun.* 69:570-574 (2001).

Raju, R. et al, "Epitope repertoire of Human CD4+ lines propagated with Tetanus toxoid or with synthetic tetanus toxin sequences", Journal of autoimmunity, vol. 9, 1996, pp. 79-88.

Rosenberg et al., "Localization of the regions on the C-terminal domain of the heavy chain of botulinum A recognized by T lymphocytes and by antibodies after immunization of mice with pentavalent toxoid," *Immunol. Invest.* 26:491-504 (1997).

Shyu et al., "DNA vaccination using the fragment C of botulinum neurotoxin type A provided protective immunity in mice," *J. Biomed. Sci.* 7:51-57 (2000).

Simeckova-Rosenberg et al., "Protection of mice against lethal viral infection by synthetic peptides corresponding to B- and T-cell recognition sites of influenza A hemagglutinin," *Vaccine* 13:927-932 (1995).

Simpson, "The study of clostridial and related toxins. The search for unique mechanisms and common denominators,"*J. Physiol., Paris* 84:143-151 (1990).

Singh et al, "Immunochemical characterization of Type A botulinum neurotoxin in its purifed and complexed forms.", Toxicon, 1996, vol. 36, No. 2, pp. 267-275.

Spanoyannis et al., "Clostridium botulinum type B neurotoxin demonstrates cross-reactivity with antibodies from patients with cervical dystonia who no longer respond to type A neurotoxin treatment," *Developmental Medicine and Child Neurology* 40:33 Scientific poster SP:8 (1998).

Tsuzuki et al., "Establishment of a monoclonal antibody recognizing an antigenic site common to *Clostridium botulinum* type B, $C_1$, D, and E toxins and tetanus toxin," *Infection and Immunity* 56:898-902 (1988).

Tugnoli, V et al, Expert. Opinion Investig. Drugs, 1997, Oct. vol. 6(10), pp. 1383-1394.

Wu et al., "Characterization of neutralizing antibodies and identification of neutralizing epitope mimics on the *Clostridium botulinum* neurotoxin type A," *Appl. Environ. Microbiol.* 67:3201-3207 (2001).

Office Action Date Mailed Dec. 12, 2007, U.S. Appl. No. 11/693,095, Conf. No. 8710.

Office Action Date Mailed Dec. 28, 2007, U.S. Appl. No. 11/693,104, Conf. No. 8724.

Office Action Date Mailed Dec. 18, 2007, U.S. Appl. No. 11/693,111, Conf. No. 8736.

Office Action Date Mailed Jan. 23, 2008, U.S. Appl. No. 11/576,219, Conf. No. 7939.

Dressler et al, "Botulinum toxin type B de novo therapy of cervical dystonia Frequency of antibody induced therapy failure", J Neurol 252: 904-907, 2005.

Dressler et al, "Mouse Diaphragm Assay for Detection of Antibodies Against Botulinum Toxin Type B", Movement Disorders, vol. 20, No. 12, 1617-1619, 2005.

\* cited by examiner

DETERMINING AND REDUCING IMMUNORESISTANCE TO A BOTULINUM TOXIN THERAPY USING BOTULINUM TOXIN B PEPTIDES

This is a continuation in part that claims priority under 35 U.S.C. §120 to U.S. patent application Ser. No. 11/755,161, filed May 30, 2007, which claims priority pursuant to 35 U.S.C. §119(e) to U.S. Provisional Patent Application Ser. No. 60/810,053 files Jun. 1, 2006, each of which is hereby incorporated by reference in its entirety.

All patents, patent publications and articles cited in this application are hereby incorporated by reference in their entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, COSMETIC AND CLINICAL APPLICATIONS OF BOTULINUM TOXIN (Slack, Inc., 2004). Clostridial toxins commercially available as pharmaceutical compositions include, BoNT/A preparations, such as, e.g., BOTOX® (Allergan, Inc., Irvine, Calif.), Dysport®/Reloxin®, (Beaufour Ipsen, Porton Down, England), Linurase® (Prollenium, Inc., Ontario, Canada), Neuronox® (Medy-Tox, Inc., Ochangmyeon, South Korea) BTX-A (Lanzhou Institute Biological Products, China) and Xeomin® (Merz Pharmaceuticals, GmbH., Frankfurt, Germany); and BoNT/B preparations, such as, e.g., MyoBloc™/NeuroBloc™ (Elan Pharmaceuticals, San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

In addition, Clostridial toxin therapies are proposed for treating neuromuscular disorders, see e.g., Kei Roger Aoki et al., Method for Treating Neuromuscular Disorders and Conditions with Botulinum Toxin Types A and B, U.S. Pat. No. 6,872,397 (Mar. 29, 2005); Rhett M. Schiffman, Methods for Treating Uterine Disorders, U.S. Patent Publication No. 2004/0175399 (Sep. 9, 2004); Richard L. Barron, Methods for Treating Ulcers and Gastroesophageal Reflux Disease, U.S. Patent Publication No. 2004/0086531 (May. 7, 2004); and Kei Roger Aoki, et al., Method for Treating Dystonia with Botulinum Toxin C to G, U.S. Pat. No. 6,319,505 (Nov. 20, 2001); eye disorders, see e.g., Eric R. First, Methods and Compositions for Treating Eye Disorders, U.S. Patent Publication No. 2004/0234532 (Nov. 25, 2004); Kei Roger Aoki et al., Botulinum Toxin Treatment for Blepharospasm, U.S. Patent Publication No. 2004/0151740 (Aug. 5, 2004); and Kei Roger Aoki et al., Botulinum Toxin Treatment for Strabismus, U.S. Patent Publication No. 2004/0126396 (Jul. 1, 2004); pain, see e.g., Kei Roger Aoki et al., Pain Treatment by Peripheral Administration of a Neurotoxin, U.S. Pat. No. 6,869,610 (Mar. 22, 2005); Stephen Donovan, Clostridial Toxin Derivatives and Methods to Treat Pain, U.S. Pat. No. 6,641,820 (Nov. 4, 2003); Kei Roger Aoki, et al., Method for Treating Pain by Peripheral Administration of a Neurotoxin, U.S. Pat. No. 6,464,986 (Oct. 15, 2002); Kei Roger Aoki and Minglei Cui, Methods for Treating Pain, U.S. Pat. No. 6,113,915 (Sep. 5, 2000); Martin A. Voet, Methods for Treating Fibromyalgia, U.S. Pat. No. 6,623,742 (Sep. 23, 2003); Martin A. Voet, Botulinum Toxin Therapy for Fibromyalgia, U.S. Pat. No. Publication No. 2004/0062776 (Apr. 1, 2004); and Kei Roger Aoki et al., Botulinum Toxin Therapy for Lower Back Pain, U.S. Patent Publication No. 2004/0037852 (Feb. 26, 2004); muscle injuries, see e.g., Gregory F. Brooks, Methods for Treating Muscle Injuries, U.S. Pat. No. 6,423,319 (Jul. 23, 2002); headache, see e.g., Martin Voet, Methods for Treating Sinus Headache, U.S. Pat. No. 6,838,434 (Jan. 4, 2005); Kei Roger Aoki et al., Methods for Treating Tension Headache, U.S. Pat. No. 6,776,992 (Aug. 17, 2004); and Kei Roger Aoki et al., Method for Treating Headache, U.S. Pat. No. 6,458,365 (Oct. 1, 2002); William J. Binder, Method for Reduction of Migraine Headache Pain, U.S. Pat. No. 5,714,469 (Feb. 3, 1998); cardiovascular diseases, see e.g., Gregory F. Brooks and Stephen Donovan, Methods for Treating Cardiovascular Diseases with Botulinum Toxin, U.S. Pat. No. 6,767,544 (Jul. 27, 2004); neurological disorders, see e.g., Stephen Donovan, Parkinson's Disease Treatment, U.S. Pat. No. 6,620,415 (Sep. 16, 2003); and Stephen Donovan, Method for Treating Parkinson's Disease with a Botulinum Toxin, U.S. Pat. No. 6,306,403 (Oct. 23, 2001); neuropsychiatric disorders, see e.g., Stephen Donovan, Botulinum Toxin Therapy for Neuropsychiatric Disorders, U.S. Patent Publication No. 2004/0180061 (Sep. 16, 2004); and Steven Donovan, Therapeutic Treatments for Neuropsychiatric Disorders, U.S. Patent Publication No. 2003/0211121 (Nov. 13, 2003); endocrine disorders, see e.g., Stephen Donovan, Method for Treating Endocrine Disorders, U.S. Pat. No. 6,827,931 (Dec. 7, 2004); Stephen Donovan, Method for Treating Thyroid Disorders with a Botulinum Toxin, U.S. Pat. No. 6,740,321 (May. 25, 2004); Kei Roger Aoki et al., Method for Treating a Cholinergic Influenced Sweat Gland, U.S. Pat. No. 6,683,049 (Jan. 27, 2004); Stephen Donovan, Neurotoxin Therapy for Diabetes, U.S. Pat. No. 6,416,765 (Jul. 9, 2002); Stephen Donovan, Methods for Treating Diabetes, U.S. Pat. No. 6,337,075 (Jan. 8, 2002); Stephen Donovan, Method for Treating a Pancreatic Disorder with a Neurotoxin, U.S. Pat. No. 6,261,572 (Jul. 17, 2001); Stephen Donovan, Methods for Treating Pancreatic Disorders, U.S. Pat. No. 6,143,306 (Nov. 7, 2000); cancers, see e.g., Stephen Donovan, Methods for Treating Bone Tumors, U.S. Pat. No. 6,565,870 (May 20, 2003); Stephen Donovan, Method for Treating Cancer with a Neurotoxin to Improve Patient Function, U.S. Pat. No. 6,368,605 (Apr. 9, 2002); Stephen Donovan, Method for Treating Cancer with a Neurotoxin, U.S. Pat. No. 6,139,845 (Oct. 31, 2000); and Mitchell F. Brin and Stephen Donovan, Methods for Treating Diverse Cancers, U.S. Patent Publication No. 2005/0031648 (Feb. 10, 2005); otic disorders, see e.g., Stephen Donovan, Neurotoxin Therapy for Inner Ear Disorders, U.S. Pat. No. 6,358,926 (Mar. 19, 2002); and Stephen Donovan, Method for Treating Otic Disorders, U.S. Pat. No. 6,265,379 (Jul. 24, 2001); autonomic disorders, see, e.g., Pankai J. Pasricha and Anthony N. Kalloo, Method for Treating Gastrointestinal Muscle Disorders and Other Smooth Muscle Dysfunction, U.S. Pat. No. 5,437,291 (Aug. 1, 1995); as well as other disorders, see e.g., William J. Binder, Method for Treatment of Skin Lesions Associated with Cutaneous Cell-proliferative Disorders, U.S. Pat. No. 5,670,484 (Sep. 23, 1997); Eric R. First, Application of Botulinum Toxin to the Management of Neurogenic Inflammatory Disorders, U.S. Pat. No. 6,063,768 (May 16, 2000); Marvin Schwartz and Brian J. Freund, Method to Reduce Hair Loss and Stimulate Hair Growth, U.S. Pat. No. 6,299,893 (Oct. 9, 2001); Jean D. A. Carruthers and Alastair Carruthers, Cosmetic Use of Botulinum Toxin for Treatment of Downturned Mouth, U.S. Pat. No. 6,358,917 (Mar. 19, 2002); Stephen Donovan, Use of a Clostridial Toxin to Reduce Appetite, U.S. Patent Publication No. 2004/40253274 (Dec. 16, 2004); and Howard I. Katz and Andrew M. Blumenfeld, *Botulinum Toxin Dental Therapies and Procedures*, U.S. Patent Publication No. 2004/0115139 (Jun. 17, 2004); Kei Roger Aoki, et al., *Treatment of Neuromuscular Disorders and Conditions with Different Botulinum*, U.S. Patent Publication No. 2002/0010138 (Jan. 24, 2002); and Kei Roger Aoki, et al., *Use of Botulinum Toxins for Treating Various Disorders and Conditions and Associated Pain*, U.S. Patent Publication No. 2004/0013692 (Jan. 22, 2004). In addition, the expected use of Clostridial toxins, such as, e.g., BoNTs and TeNT, in therapeutic and cosmetic treatments of humans and other mammals is anticipated to expand to an ever widening range of diseases and ailments that can benefit from the properties of these toxins.

While a potent and effective treatment, the inhibition of neurotransmitter release and the resulting neuromuscular paralysis elicited by Clostridial toxin therapies is not permanent. The reversible nature of these paralytic effects requires periodic treatments in order to maintain the therapeutic benefits from this toxin. As a consequence of this repeated exposure, an immune response against a Clostridial toxin can occur in some patients which reduce or completely prevent the individual's responsiveness to further treatments, see, e.g., Joseph Jankovic, *Botulinum toxin: Clinical Implications of Antigenicity and Immunoresistance*, (SCIENTIFIC AND THERAPEUTIC ASPECTS OF BOTULINUM TOXIN, 409-415, Mitchell F. Brin et al., eds., Lippincott Williams & Wilkins, 2002); Dirk Dressler, *Clinical Presentation and Management of Antibody-induced Failure of Botulinum Toxin Therapy*, 19(Suppl. 8) MOV. DISORD. S92-S100 (2004); M. Zouhair Atassi, *Basic Immunological Aspects of Botulinum Toxin Therapy*, 19(Suppl. 8) MOV. DISORD. S68-S84, (2004).

Thus, there exists a need for methods of determining immunoresistance in an individual to Clostridial toxin therapy, methods of preventing or reducing immunoresistance in an individual to Clostridial toxin therapy as well as compositions to carry out these methods. The present invention satisfies this need with respect to BoNT/B therapies and provides additional related advantages as well.

BRIEF DESCRIPTION OF THE DRAWINGS

FIG. 1 shows binding of human anti-pentavalent botulinum toxoid antibodies to overlapping synthetic BoNT/B peptides spanning the BoNT/B $H_N$ and $H_C$ domains of BoNT/B. Also shown is the binding to full-length BoNT/B as a positive control.

FIG. 2 shows binding of horse anti-BoNT/B antibodies to overlapping synthetic BoNT/B peptides spanning the BoNT/B $H_N$ and $H_C$ domains of BoNT/B. Also shown is the binding to full-length BoNT/B as a positive control.

FIG. 4 shows a comparison of the BoNT/B peptide-binding profiles of human, horse and mouse antibodies against BoNT/B. The data for horse and mouse antisera are shown here at dilutions of 1:500, (vol/vol), while human antisera are at dilution of 1:1000 (vol/vol) in PBS/0.1% BSA.

Figure 5B:
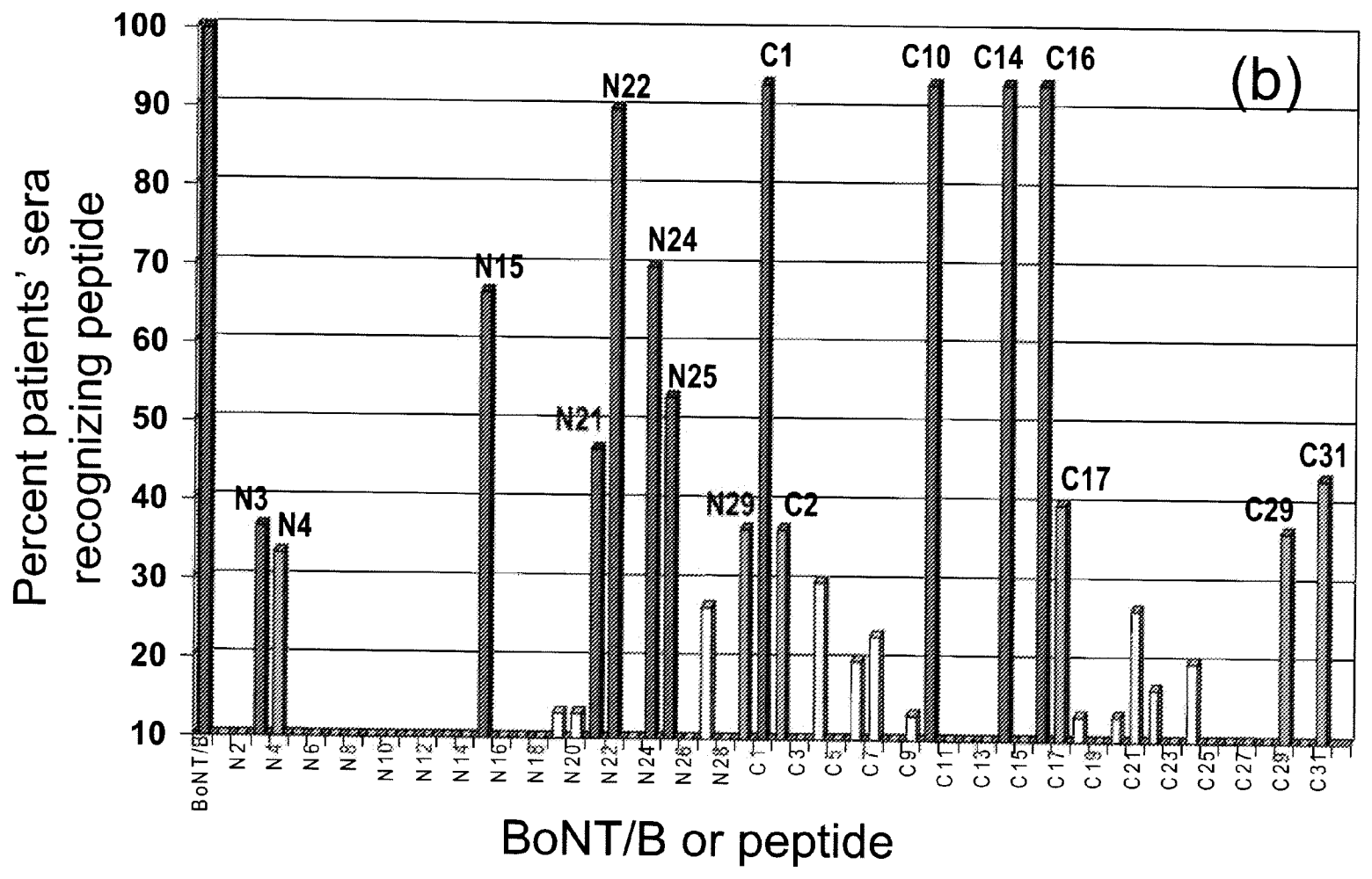

FIG. 5 shows the BoNT/B peptide-binding profiles against sera from MPA-positive CD patients. FIG. 5b shows the recognition frequency of each H-chain peptide in percent of the 30 sera. The darkest bars represent peptides that are recognized by over 15 out of 30 (50%) of the sera. Lighter bars indicate recognition by 12 to 9 sera and white bars by 6 or less sera.

DETAILED DESCRIPTION OF THE INVENTION

Figure 3:
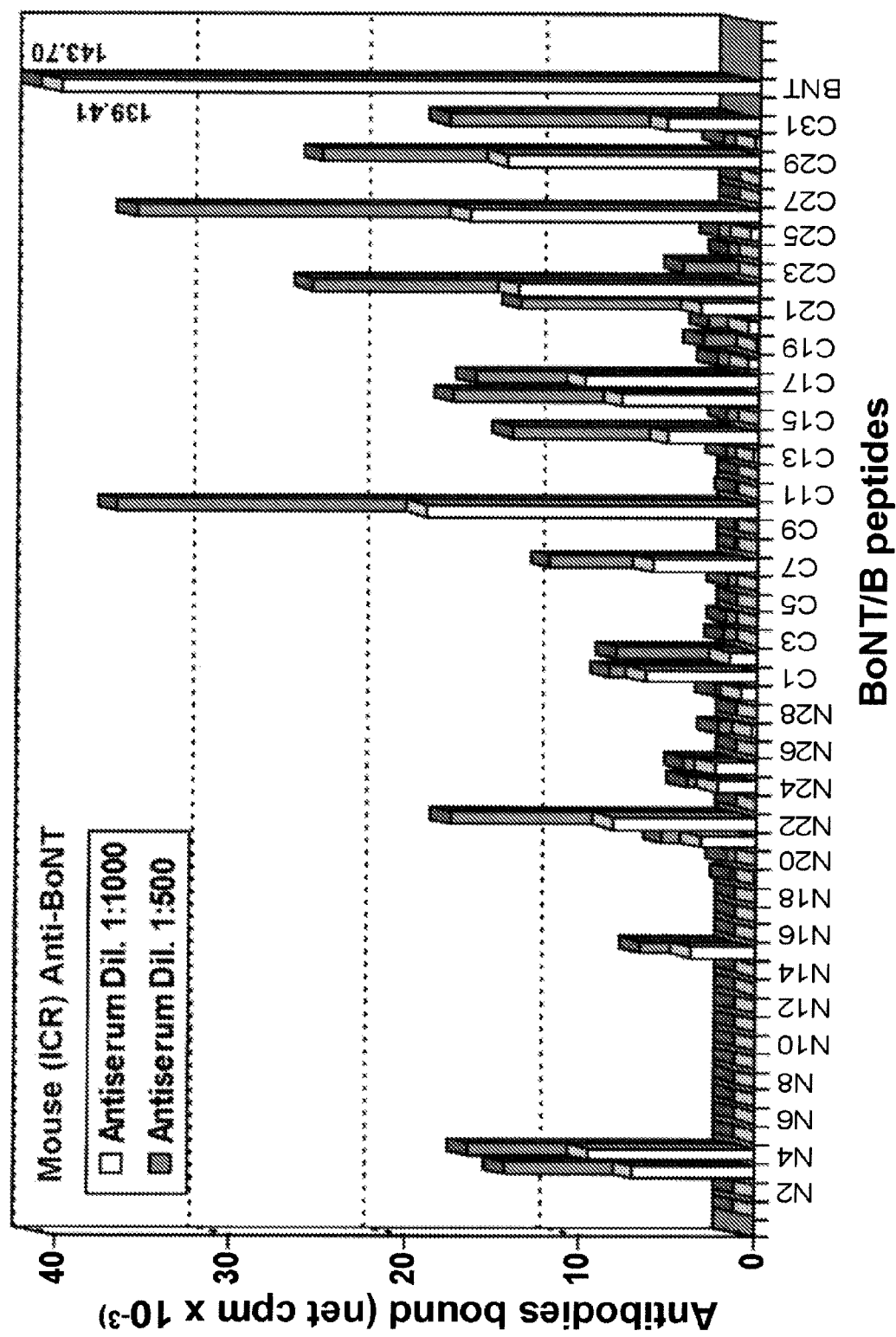
FIG. 3 shows binding of anti-BoNT/B antibodies of ICR outbred mice to overlapping synthetic BoNT/B peptides spanning the BoNT/B $H_N$ and $H_C$ domains of BoNT/B. Also shown is the binding to full-length BoNT/B as a positive controls.
Figure 5A:
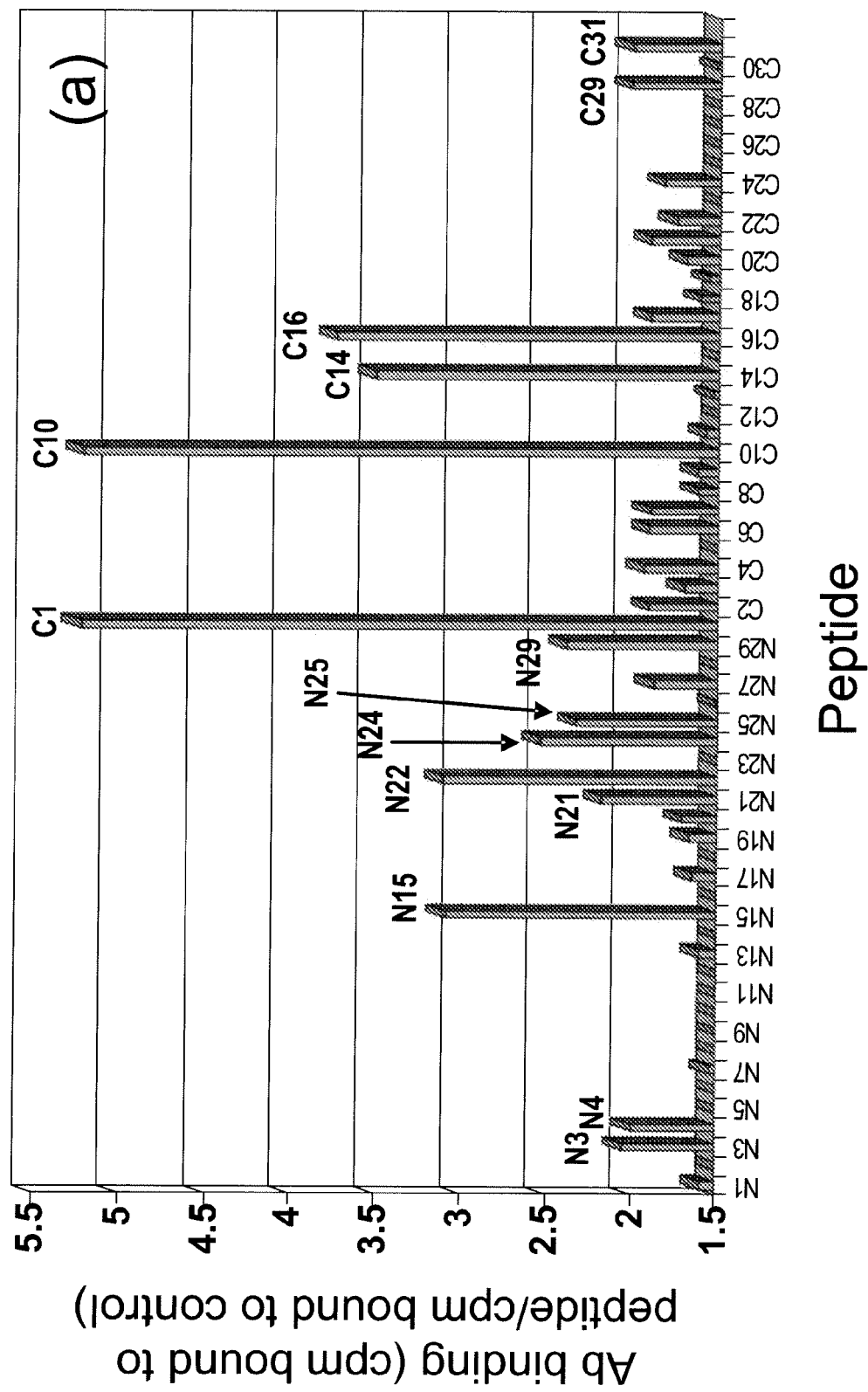
FIG. 5a shows the binding profiles of anti-BoNT/B antiserum to H-chain peptides of BoNT/B. The anti-BoNT/B antiserum was a mixture of equal volumes of antisera from 30 BoNT/B-treated CD patients. The assays were done at antisera dilutions of 1:500 (vol/vol). The results are expressed in ratio of cpm bound to peptide/cpm bound to controls of unrelated protein (BSA) or peptides.

The present invention discloses the discovery of BoNT/B peptides which elicit antibody responses and represent the complete repertoire of epitopes found within the $H_N$ domain and $H_C$ domain of the BoNT/B heavy chain recognized by anti-BoNT/B antibodies present in three animal species, including humans. As shown herein in Examples 1-5, antigenic regions of both domains were mapped using human, horse and mouse sera obtained following immunization with BoNT/B. Mapping was performed using twenty-nine synthetic BoNT/B peptides, each containing nineteen residues, that overlap consecutively by five residues and correspond to the entire length of the $H_N$ domain (Table 2) and thirty-one synthetic BoNT/B peptides, each containing nineteen residues, that overlap consecutively by five residues and correspond to the entire length of the $H_C$ domain, with the exception of C31, which is twenty-two residues in length (Table 3). Results from the mapping studies revealed 1) four segments of BoNT/B that represent the complete repertoire of continuous antigenic regions on the BoNT/B $H_N$ domain; and 2) 1) eleven segments of BoNT/B that represent the complete repertoire of continuous antigenic regions on the BoNT/B $H_C$ domain, see, e.g., Examples 1-5. BoNT/B peptides of the present invention are useful for, e.g., making peptides and peptide compositions and employing methods for determining immunoresistance to a botulinum toxin therapy in an individual, making tolerogizing compositions and employing methods for treating immunoresistance to a botulinum toxin therapy in an individual, making an immune response inducing composition and employing methods of inducing an immune response in an individual and methods of producing an anti-BoNT/B antibody.

Thus, aspects of the present invention provide BoNT/B peptides having a length of at least 5 amino acids and at most 60 amino acids. In other aspects of this embodiment, such a BoNT/B peptide is derived from a naturally occurring BoNT/B, such as, e.g., a BoNT/B isoform or a BoNT/B subtype. In still other aspects of this embodiment, such a BoNT/B peptide is derived from a non-naturally occurring BoNT/B, such as, e.g., a conservative BoNT/B variant, a non-conservative BoNT/B variant, or a chimeric BoNT/B variant. In yet another aspect of this embodiment, such a BoNT/B peptide comprises an immunoreactive fragment of the BoNT/B peptide, the BoNT/B peptide derived from a naturally occurring BoNT/B or a non-naturally occurring BoNT/B.

In other aspects of this embodiment, a BoNT/B peptide comprises a BoNT/B peptide of SEQ ID NO: 1 having a length of at least 5 amino acids and at most 60 amino acids, a BoNT/B peptide of SEQ ID NO: 3 having a length of at least 5 amino acids and at most 60 amino acids, a BoNT/B peptide of SEQ ID NO: 5 having a length of at least 5 amino acids and at most 60 amino acids, a BoNT/B peptide of SEQ ID NO: 7 having a length of at least 5 amino acids and at most 60 amino acids, a BoNT/B peptide of SEQ ID NO: 9 having a length of at least 5 amino acids and at most 60 amino acids, a BoNT/B peptide of SEQ ID NO: 11 having a length of at least 5 amino acids and at most 60 amino acids or a BoNT/B peptide of SEQ ID NO: 11 having a length of at least 5 amino acids and at most 60 amino acids.

In still other aspects of this embodiment, such a BoNT/B peptide comprises an amino acid sequence selected from the group consisting of amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In still other aspects of this embodiment, such a BoNT/B peptide comprises an amino acid sequence selected from the group consisting of amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 932-950 of SEQ ID NO: 1, amino acids 932-950 of SEQ ID NO: 5, amino acids 974-992 of SEQ ID NO: 1, amino acids 974-992 of SEQ ID NO: 3, amino acids 974-992 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In still other aspects of this embodiment, such a BoNT/B peptide comprises an amino acid sequence selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

Other aspects of the present invention provide BoNT/B peptide compositions comprising a BoNT/B peptide having a length of at least 5 amino acids and at most 60 amino acids. It is envisioned that any and all BoNT/B peptides disclosed in the present specification that produce a decreased immunological response can be useful in such a tolerogizing composition, including, without limitation, a BoNT/B derived from a naturally occurring BoNT/B, a BoNT/B derived from a non-naturally occurring BoNT/B and a BoNT/B comprising an immunoreactive fragment of the BoNT/B peptide, the BoNT/B peptide derived from a naturally occurring BoNT/B or a non-naturally occurring BoNT/B.

Other aspects of the present invention provide tolerogizing compositions comprising a tolerogizing agent and a BoNT/B peptide. It is envisioned that any and all tolerogizing agents can be useful in such a tolerogizing composition, including, without limitation, polyethylene glycol (PEG), monomethoxypolyethylene glycol (mPEG) and polyvinyl alcohol (PVA). It is also envisioned that any and all BoNT/B peptides disclosed in the present specification that produce a decreased immunological response can be useful in such a tolerogizing composition, including, without limitation, a BoNT/B derived from a naturally occurring BoNT/B, a BoNT/B derived from a non-naturally occurring BoNT/B and a BoNT/B comprising an immunoreactive fragment of the BoNT/B peptide, the BoNT/B peptide derived from a naturally occurring BoNT/B or a non-naturally occurring BoNT/B.

Other aspects of the present invention provide immune response inducing compositions comprising an adjuvant and a BoNT/B antigen. It is envisioned that any and all adjuvants can be useful in such an immune response inducing composition, including, without limitation, polyethylene glycol (PEG), monomethoxypolyethylene glycol (mPEG) and polyvinyl alcohol (PVA). It is also envisioned that any and all BoNT/B peptides disclosed in the present specification that produce an immunological response can be useful as a BoNT/B antigen, including, without limitation, a BoNT/B derived from a naturally occurring BoNT/B, a BoNT/B derived from a non-naturally occurring BoNT/B and a BoNT/B comprising an immunoreactive fragment of the BoNT/B peptide, the BoNT/B peptide derived from a naturally occurring BoNT/B or a non-naturally occurring BoNT/B.

Still other aspects of the present invention provide methods of determining immunoresistance to BoNT therapy in an individual, the methods comprising the steps of combining a BoNT/B peptide and a test sample under conditions suitable for the selective binding of the BoNT/B peptide to an anti-BoNT antibody and determining the presence of an anti-BoNT antibody-BoNT/B peptide complex, the antibody-peptide complex formed by the selective binding of an anti-BoNT antibody and the BoNT/B peptide, where the presence of the anti-BoNT antibody-BoNT/B peptide complex is indicative of immunoresistance to a BoNT therapy. It is envisioned that any and all BoNT/B peptides disclosed in the present specification can be useful in a method for determining immunoresistance to botulinum toxin therapy in an individual, including, without limitation, a BoNT/B derived from a naturally occurring BoNT/B, a BoNT/B derived from a non-naturally occurring BoNT/B and a BoNT/B comprising an immunoreactive fragment of the BoNT/B peptide, the BoNT/B peptide derived from a naturally occurring BoNT/B or a non-naturally occurring BoNT/B.

Still other aspects of the present invention provide methods of treating immunoresistance to botulinum toxin therapy in an individual, the method comprising the step of administering to the individual a tolerogizing composition, the tolerogizing composition comprising a tolerogizing agent conjugated to a BoNT/B peptide, where the administration of the tolerogizing composition producing a decrease in an immunological response against the botulinum toxin therapy in the individual. It is envisioned that any and all BoNT/B peptides disclosed in the present specification can be useful in a method from preventing or reducing immunoresistance to botulinum toxin therapy in an individual, including, without limitation, a BoNT/B derived from a naturally occurring BoNT/B, a BoNT/B derived from a non-naturally occurring BoNT/B and a BoNT/B comprising an immunoreactive fragment of the BoNT/B peptide, the BoNT/B peptide derived from a naturally occurring BoNT/B or a non-naturally occurring BoNT/B.

Still other aspects of the present invention provide anti-BoNT immunoapheresis methods of treating immunoresistance to a BoNT therapy in an individual, the method comprising the steps of contacting an anti-BoNT antibody containing component from the individual extracorporeally with a BoNT/B peptide immunosorbent under conditions suitable for the selective binding of the BoNT/B peptide to the anti-BoNT antibody, the BoNT/B peptide and returning the anti-BoNT antibody-depleted component back into the individual. It is envisioned that any and all BoNT/B peptides disclosed in the present specification can be useful in an anti-BoNT immunoapheresis methods of treating immunoresistance to a BoNT therapy in an individual, including, without limitation, a BoNT/B derived from a naturally occurring BoNT/B, a BoNT/B derived from a non-naturally occurring BoNT/B and a BoNT/B comprising an immunoreactive fragment of the BoNT/B peptide, the BoNT/B peptide derived from a naturally occurring BoNT/B or a non-naturally occurring BoNT/B.

Still other aspects of the present invention provide methods of inducing a BoNT/B immune response in an individual, the method comprising the step of administering to the individual an immune response inducing composition comprising an adjuvant and a BoNT/B antigen, where administration of the immune response inducing composition produces an immune response in the individual. It is envisioned that any and all BoNT/B peptides disclosed in the present specification can be useful as BoNT/B antigens in methods for inducing an immune response in an individual, including, without limitation, a BoNT/B derived from a naturally occurring BoNT/B, a BoNT/B derived from a non-naturally occurring BoNT/B and a BoNT/B comprising an immunoreactive fragment of the BoNT/B peptide, the BoNT/B peptide derived from a naturally occurring BoNT/B or a non-naturally occurring BoNT/B.

Yet other aspects of the present invention provide methods of producing an anti-BoNT/B antibody in an individual, the method comprising the steps of administering to the individual an immune response inducing composition comprising an adjuvant and a BoNT/B antigen, where administration of the immune response inducing composition produces an immune response in the individual; collecting from the individual a sample containing the anti-BoNT/B antibody or anti-BoNT/B antibody-producing cell; and isolating the anti-BoNT/B antibody from the sample. It is envisioned that antibodies produced according to a method of the invention include polyclonal and monoclonal antibodies. It is also envisioned that any and all BoNT/B peptides disclosed in the present specification can be useful as BoNT/B antigens in methods of producing an anti-BoNT/B antibody in an individual, including, without limitation, a BoNT/B derived from a naturally occurring BoNT/B, a BoNT/B derived from a non-naturally occurring BoNT/B and a BoNT/B comprising an immunoreactive fragment of the BoNT/B peptide, the BoNT/B peptide derived from a naturally occurring BoNT/B or a non-naturally occurring BoNT/B.

Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and /F), animals (BoNT/C1 and /D), or isolated from soil (BoNT/G). While all seven botulinum toxins (BoNT) serotypes have similar structure and pharmacological properties, each also displays heterogeneous bacteriological characteristics. In contrast, tetanus toxin (TeNT) is produced by a uniform group of *C. tetani*. Two other species of *Clostridia, C. baratii* and *C. butyricum*, also produce toxins similar to BoNT/F and BoNT/E, respectively.

Figure 2:
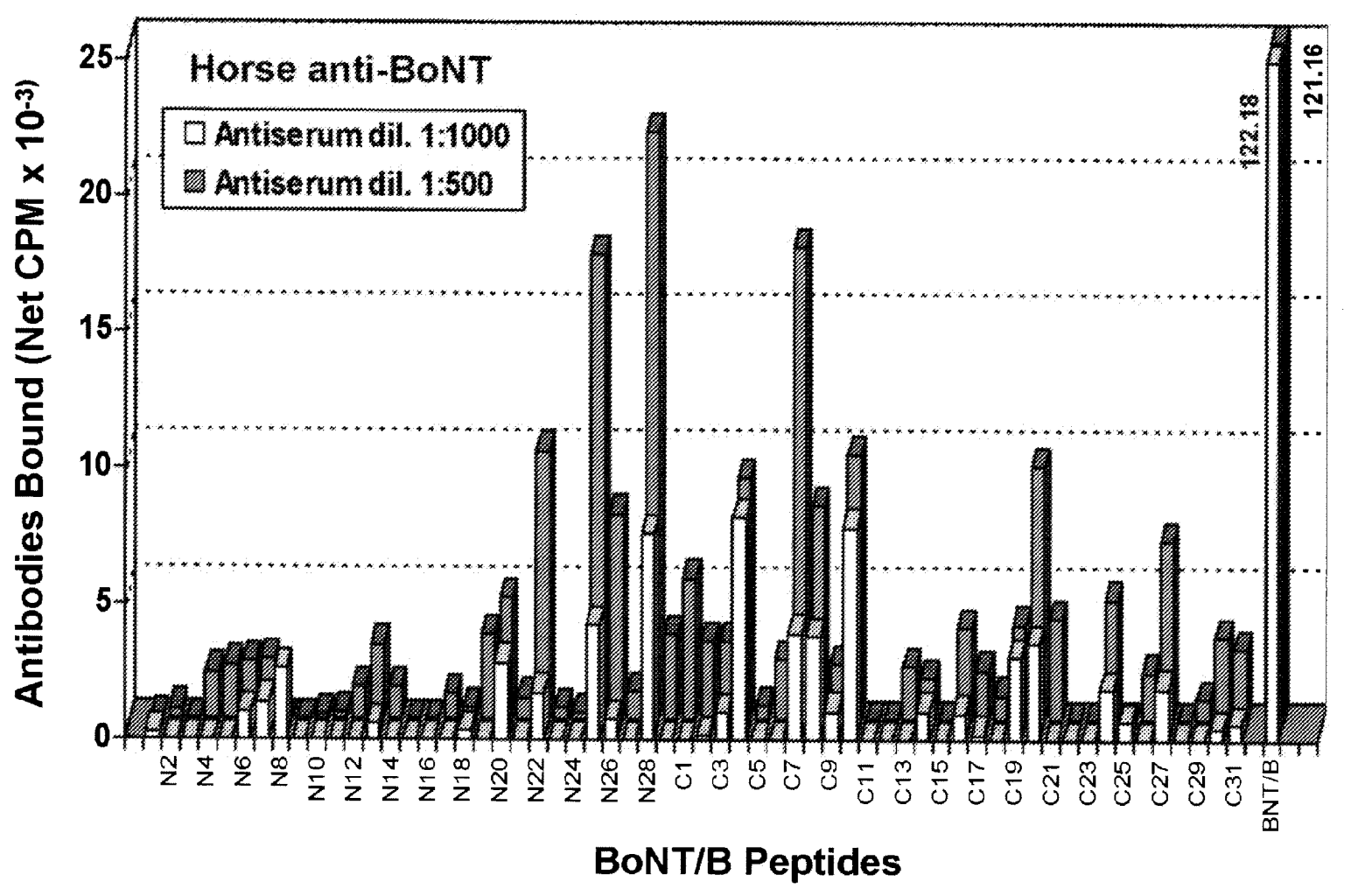

Clostridia toxins possess approximately 35% amino acid identity with each other and share the same functional domain organization and overall structural architecture. Clostridial toxins are each translated as a single chain polypeptide of approximately 150 kDa that is subsequently cleaved by proteolytic scission within a disulfide loop by a naturally-occurring protease, such as, e.g., an endogenous Clostridial toxin protease or a naturally-occurring protease produced in the environment (FIG. 2). This posttranslational processing yields a di-chain molecule comprising an approximately 50 kDa light chain (LC) and an approximately 100 kDa heavy chain (HC) held together by a single disulfide bond and non-covalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus (Table 1); 2) a translocation domain contained within the amino-terminal half of the HC ($H_N$) that facilitates release of the LC from intracellular vesicles into the cytoplasm of the target cell (Table 1); and 3) a binding domain found within the carboxyl-terminal half of the HC ($H_C$) that determines the binding activity and binding specificity of the toxin to the receptor complex located at the surface of the target cell (Table 1).

TABLE 1

Clostridial Toxin Reference Sequences and Regions

| Toxin | SEQ ID NO: | LC | $H_N$ | $H_C$ |
|---|---|---|---|---|
| BoNT/A | 1 | M1-K448 | A449-K871 | N872-L1296 |
| BoNT/B | 2 | M1-K441 | A442-S858 | E859-E1291 |
| BoNT/C1 | 3 | M1-K449 | T450-N866 | N867-E1291 |
| BoNT/D | 4 | M1-R445 | D446-N862 | S863-E1276 |
| BoNT/E | 5 | M1-R422 | K423-K845 | R846-K1252 |
| BoNT/F | 6 | M1-K439 | A440-K864 | K865-E1274 |
| BoNT/G | 7 | M1-K446 | S447-S863 | N864-E1297 |
| TeNT | 8 | M1-A457 | S458-V879 | I880-D1315 |

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification. The process is initiated when the $H_C$ domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation di-chain form of the toxin. Once activated, light chain endopeptidase of the toxin is released from the intracellular vesicle into the cytosol where it appears to specifically target one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release,* 82(5) Biochimie. 427-446 (2000); Kathryn Turton et al., *Botulinum and Tetanus Neurotoxins: Structure, Function and Therapeutic Utility,* 27(11) Trends Biochem. Sci. 552-558. (2002); Giovanna Lalli et al., *The Journey of Tetanus and Botulinum Neurotoxins in Neurons,* 11 (9) Trends Microbiol. 431-437, (2003).

The present invention provides, in part, a BoNT/B peptide. As used herein, the term "BoNT/B peptide," means a peptide having an amino acid sequence length of at least five amino acids and at most 60 amino acids, the amino acid sequence derived from a naturally occurring BoNT/B or a non-naturally occurring BoNT/B. An exemplary BoNT/B is the BoNT/B of SEQ ID NO: 1, encoded by the polynucleotide molecule of SEQ ID NO: 2.

In is envisioned that a BoNT/B peptide disclosed in the present specification can have any of a variety of lengths from at least 5 amino acids to at most 60 amino acids. Therefore, aspects of this embodiment may include a BoNT/B peptide with, e.g., at least five amino acids, at least six amino acids, at least seven amino acids, at least eight amino acids, at least nine amino acids, at least ten amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 25 amino acids, at least 30 amino acids, at least 35 amino acids, at least 40 amino acids, at least 45 amino acids, at least 50 amino acids, or at least 55 amino acids. In other aspects of this embodiment may include a BoNT/B peptide with, e.g., at most six amino acids, at most seven amino acids, at most eight amino acids, at most nine amino acids, at most ten amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 25 amino acids, at most 30 amino acids, at most 35 amino acids, at most 40 amino acids, at most 45 amino acids, at most 50 amino acids, at most 55 amino acids or at most 60 amino acids.

A BoNT/B peptide disclosed in the present specification comprises at least five consecutive amino acids from the BoNT/B from which the BoNT/B peptide is derived. In aspects of this embodiment, a BoNT/B peptide comprises, e.g., at least 5 consecutive amino acids from the BoNT/B from which the BoNT/B peptide is derived, at least 6 consecutive amino acids from the BoNT/B from which the BoNT/B peptide is derived, at least 7 consecutive amino acids from the BoNT/B from which the BoNT/B peptide is derived, at least 8 consecutive amino acids from the BoNT/B from which the BoNT/B peptide is derived, at least 9 consecutive amino acids from the BoNT/B from which the BoNT/B peptide is derived, at least 10 consecutive amino acids from the BoNT/B from which the BoNT/B peptide is derived, at least 12 consecutive amino acids from the BoNT/B from which the BoNT/B peptide is derived, at least 15 consecutive amino acids from the BoNT/B from which the BoNT/B peptide is derived, at least 18 consecutive amino acids from the BoNT/B from which the BoNT/B peptide is derived, at least 20 consecutive amino acids from the BoNT/B from which the BoNT/B peptide is derived, at least 25 consecutive amino acids from the BoNT/B from which the BoNT/B peptide is derived, at least 30 consecutive amino acids from the BoNT/B from which the BoNT/B peptide is derived, at least 40 consecutive amino acids from the BoNT/B from which the BoNT/B peptide is derived or at least 50 consecutive amino acids from the BoNT/B from which the BoNT/B peptide is derived.

In other aspects of this embodiment, a BoNT/B peptide comprises, e.g., at most 5 consecutive amino acids from the BoNT/B from which the BoNT/B peptide is derived, at most 6 consecutive amino acids from the BoNT/B from which the BoNT/B peptide is derived, at most 7 consecutive amino acids from the BoNT/B from which the BoNT/B peptide is derived, at most 8 consecutive amino acids from the BoNT/B from which the BoNT/B peptide is derived, at most 9 consecutive amino acids from the BoNT/B from which the BoNT/B peptide is derived, at most 10 consecutive amino acids from the BoNT/B from which the BoNT/B peptide is derived, at most 12 consecutive amino acids from the BoNT/B from which the BoNT/B peptide is derived, at most 15 consecutive amino acids from the BoNT/B from which the BoNT/B peptide is derived, at most 18 consecutive amino acids from the BoNT/B from which the BoNT/B peptide is derived, at most 20 consecutive amino acids from the BoNT/B from which the BoNT/B peptide is derived, at most 25 consecutive amino acids from the BoNT/B from which the BoNT/B peptide is derived, at most 30 consecutive amino acids from the BoNT/B from which the BoNT/B peptide is derived, at most 40 consecutive amino acids from the BoNT/B from which the BoNT/B peptide is derived or at most 50 consecutive amino acids from the BoNT/B from which the BoNT/B peptide is derived.

In still other aspects of this embodiment, a BoNT/B peptide comprising, e.g., at least five amino acids of SEQ ID NO:1, at least six amino acids of SEQ ID NO:1, at least seven amino acids of SEQ ID NO:1, at least eight amino acids of SEQ ID NO:1, at least nine amino acids of SEQ ID NO:1, at least ten amino acids of SEQ ID NO:1, at least 11 amino acids of SEQ ID NO:1, at least 12 amino acids of SEQ ID NO:1, at least 13 amino acids of SEQ ID NO:1, at least 14 amino acids of SEQ ID NO:1, at least 15 amino acids of SEQ ID NO:1, at least 16 amino acids of SEQ ID NO:1, at least 17 amino acids of SEQ ID NO:1, at least 18 amino acids of SEQ ID NO:1, at least 19 amino acids of SEQ ID NO:1, at least 20 amino acids of SEQ ID NO:1, at least 25 amino acids of SEQ ID NO:1, at least 30 amino acids of SEQ ID NO:1, at least 35 amino acids of SEQ ID NO:1, at least 40 amino acids of SEQ ID NO:1, at least 45 amino acids of SEQ ID NO:1, at least 50 amino acids of SEQ ID NO:1 or at least 55 amino acids.

In still other aspects of this embodiment, a BoNT/B peptide with, e.g., at most six amino acids of SEQ ID NO:1, at most seven amino acids of SEQ ID NO:1, at most eight amino acids of SEQ ID NO:1, at most nine amino acids of SEQ ID NO:1, at most ten amino acids of SEQ ID NO:1, at most 11 amino acids of SEQ ID NO:1, at most 12 amino acids of SEQ ID NO:1, at most 13 amino acids of SEQ ID NO:1, at most 14 amino acids of SEQ ID NO:1, at most 15 amino acids of SEQ ID NO:1, at most 16 amino acids of SEQ ID NO:1, at most 17 amino acids of SEQ ID NO:1, at most 18 amino acids of SEQ ID NO:1, at most 19 amino acids of SEQ ID NO:1, at most 20 amino acids of SEQ ID NO:1, at most 25 amino acids of SEQ ID NO:1, at most 30 amino acids of SEQ ID NO:1, at most 35 amino acids of SEQ ID NO:1, at most 40 amino acids of SEQ ID NO:1, at most 45 amino acids of SEQ ID NO:1, at most 50 amino acids of SEQ ID NO:1, at most 55 amino acids or at most 60 amino acids of SEQ ID NO:1.

In yet other aspects of this embodiment, a BoNT/B peptide comprising, e.g., at least five consecutive amino acids of SEQ ID NO:1, at least six consecutive amino acids of SEQ ID NO:1, at least seven consecutive amino acids of SEQ ID NO:1, at least eight consecutive amino acids of SEQ ID NO:1, at least nine consecutive amino acids of SEQ ID NO:1, at least ten amino consecutive acids of SEQ ID NO:1, at least 11 consecutive amino acids of SEQ ID NO:1, at least 12 consecutive amino acids of SEQ ID NO:1, at least 13 consecutive amino acids of SEQ ID NO:1, at least 14 consecutive amino acids of SEQ ID NO:1, at least 15 consecutive amino acids of SEQ ID NO:1, at least 16 consecutive amino acids of SEQ ID NO:1, at least 17 consecutive amino acids of SEQ ID NO:1, at least 18 consecutive amino acids of SEQ ID NO:1, at least 19 consecutive amino acids of SEQ ID NO:1, at least 20 consecutive amino acids of SEQ ID NO:1, at least 25 consecutive amino acids of SEQ ID NO:1, at least 30 consecutive amino acids of SEQ ID NO:1, at least 35 consecutive amino acids of SEQ ID NO:1, at least 40 consecutive amino acids of SEQ ID NO:1, at least 45 consecutive amino acids of SEQ ID NO:1, at least 50 consecutive amino acids of SEQ ID NO:1 or at least 55 consecutive amino acids.

In yet other aspects of this embodiment, a BoNT/B peptide with, e.g., at most five consecutive amino acids of SEQ ID NO:1, at most six consecutive amino acids of SEQ ID NO:1, at most seven consecutive amino acids of SEQ ID NO:1, at most eight consecutive amino acids of SEQ ID NO:1, at most nine consecutive amino acids of SEQ ID NO:1, at most ten consecutive amino acids of SEQ ID NO:1, at most 11 consecutive amino acids of SEQ ID NO:1, at most 12 consecutive amino acids of SEQ ID NO:1, at most 13 consecutive amino acids of SEQ ID NO:1, at most 14 consecutive amino acids of SEQ ID NO:1, at most 15 consecutive amino acids of SEQ ID NO:1, at most 16 consecutive amino acids of SEQ ID NO:1, at most 17 consecutive amino acids of SEQ ID NO:1, at most 18 consecutive amino acids of SEQ ID NO:1, at most 19 consecutive amino acids of SEQ ID NO:1, at most 20 consecutive amino acids of SEQ ID NO:1, at most 25 consecutive amino acids of SEQ ID NO:1, at most 30 consecutive amino acids of SEQ ID NO:1, at most 35 consecutive amino acids of SEQ ID NO:1, at most 40 consecutive amino acids of SEQ ID NO:1, at most 45 consecutive amino acids of SEQ ID NO:1, at most 50 consecutive amino acids of SEQ ID NO:1, at most 55 consecutive amino acids or at most 60 consecutive amino acids of SEQ ID NO:1.

A BoNT/B peptide includes, without limitation, a BoNT/B peptide comprising an amino acid sequence derived from a naturally occurring BoNT/B variant, such as, e.g., a BoNT/B isoform and a BoNT/B subtype; and a BoNT/B peptide comprising an amino acid sequence derived from a non-naturally occurring BoNT/B variant, such as, e.g., a conservative BoNT/B variant, a non-conservative BoNT/B variant or a chimeric BoNT/B peptide.

As used herein, the term "BoNT/B variant," whether naturally-occurring or non-naturally-occurring, means a BoNT/B that has at least one amino acid change from the corresponding region of the reference BoNT/B of SEQ ID NO: 1 and can be described in percent identity to the corresponding region of that reference sequence. Unless expressly indicated, all BoNT/B variants disclosed in the present specification can function in substantially the same manner as the reference BoNT/B of SEQ ID NO: 1 on which the BoNT/B variant is based, and can be substituted for the reference BoNT/B of SEQ ID NO: 1 in any aspect of the present invention. As a non limiting example, a BoNT/B peptide comprising amino acid sequence 974-992 from a BoNT/B variant will have at least one amino acid difference, such as, e.g., an amino acid substitution, deletion or addition, as compared to the amino acid sequence 974-992 of SEQ ID NO: 1. As another non limiting example, a BoNT/B peptide comprising amino acid sequence 736-754 from a BoNT/B variant will have at least one amino acid difference, such as, e.g., an amino acid substitution, deletion or addition, as compared to the amino acid sequence 736-754 of SEQ ID NO: 1. As still another non limiting example, a BoNT/B peptide comprising amino acid sequence 1058-1076 from a BoNT/B variant will have at least one amino acid difference, such as, e.g., an amino acid substitution, deletion or addition, as compared to the amino acid sequence 1058-1076 of SEQ ID NO: 1. As yet another non limiting example, a BoNT/B peptide comprising amino acid sequence 890-908 from a BoNT/B variant will have at least one amino acid difference, such as, e.g., an amino acid substitution, deletion or addition, as compared to the amino acid sequence 890-908 of SEQ ID NO: 1.

Any of a variety of sequence alignment methods can be used to determine percent identity of a naturally-occurring BoNT/B variant or a non-naturally-occurring BoNT/B variant, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice*, 22(22)

Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments*, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align-M, see, e.g., Ivo Van Walle et al., Align-M—*A New Algorithm for Multiple Alignment of Highly Divergent Sequences*, 20(9) Bioinformatics: 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

It is recognized by those of skill in the art that there are naturally occurring BoNT/B variants that differ somewhat in their amino acid sequence, and also in the nucleic acids encoding these proteins. For example, there are presently four BoNT/B subtypes, BoNT/B1, BoNT/B2, BoNT/B bivalent and BoNT/B non-proteolytic, with specific subtypes showing approximately 95% amino acid identity when compared to another BoNT/B subtype. As used herein, the term "naturally occurring BoNT/B variant" means any BoNT/B produced by a naturally-occurring process, including, without limitation, BoNT/B isoforms produced from alternatively-spliced transcripts, BoNT/B isoforms produced by spontaneous mutation and BoNT/B subtypes. A naturally occurring BoNT/B variant can function in substantially the same manner as the reference BoNT/B of SEQ ID NO: 1 on which the naturally occurring BoNT/B variant is based, and can be substituted for the reference BoNT/B of SEQ ID NO: 1 in any aspect of the present invention. A naturally occurring BoNT/B variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference BoNT/B of SEQ ID NO: 1 on which the naturally occurring BoNT/B variant is based. A naturally occurring BoNT/B variant can also substitute at least 10 contiguous amino acids, at least 15 contiguous amino acids, at least 20 contiguous amino acids, or at least 25 contiguous amino acids from the reference BoNT/B of SEQ ID NO: 1 on which the naturally occurring BoNT/B variant is based, that possess at least 50% amino acid identity, 65% amino acid identity, 75% amino acid identity, 85% amino acid identity or 95% amino acid identity to the reference BoNT/B of SEQ ID NO: 1 on which the naturally occurring BoNT/B variant is based. A non-limiting example of a naturally occurring BoNT/B variant is a BoNT/B isoform.

Another non-limiting example of a naturally occurring BoNT/B variant is a BoNT/B subtype, such as, e.g., BoNT/B1, BoNT/B2, BoNT/B non-proteolytic and BoNT/B bivalents. An exemplary BoNT/B1 is the BoNT/B of SEQ ID NO: 1, encoded by the polynucleotide molecule of SEQ ID NO: 2. An exemplary BoNT/B2 is the BoNT/B of SEQ ID NO: 3, encoded by the polynucleotide molecule of SEQ ID NO: 4. An exemplary BoNT/B non-proteolytic is the BoNT/B of SEQ ID NO: 5, encoded by the polynucleotide molecule of SEQ ID NO: 6. Exemplary BoNT/B bivalents are the BoNT/B of SEQ ID NO: 7, encoded by the polynucleotide molecule of SEQ ID NO: 8; the BoNT/B of SEQ ID NO: 9, encoded by the polynucleotide molecule of SEQ ID NO: 10; the BoNT/B of SEQ ID NO: 11, encoded by the polynucleotide molecule of SEQ ID NO: 12; and the BoNT/B of SEQ ID NO: 13, encoded by the polynucleotide molecule of SEQ ID NO: 14.

Thus in aspects of this embodiment, a BoNT/B peptide is derived from the BoNT/B of SEQ ID NO: 1, the BoNT/B of SEQ ID NO: 3, the BoNT/B of SEQ ID NO: 5, the BoNT/B of SEQ ID NO: 7, the BoNT/B of SEQ ID NO: 9, the BoNT/B of SEQ ID NO: 11 or the BoNT/B of SEQ ID NO: 13. In other aspects of this embodiment, a BoNT/B peptide comprises a BoNT/B peptide of SEQ ID NO: 1 having a length of at least 5 amino acids and at most 60 amino acids, a BoNT/B peptide of SEQ ID NO: 3 having a length of at least 5 amino acids and at most 60 amino acids, a BoNT/B peptide of SEQ ID NO: 5 having a length of at least 5 amino acids and at most 60 amino acids, a BoNT/B peptide of SEQ ID NO: 7 having a length of at least 5 amino acids and at most 60 amino acids, a BoNT/B peptide of SEQ ID NO: 9 having a length of at least 5 amino acids and at most 60 amino acids, a BoNT/B peptide of SEQ ID NO: 11 having a length of at least 5 amino acids and at most 60 amino acids or a BoNT/B peptide of SEQ ID NO: 11 having a length of at least 5 amino acids and at most 60 amino acids.

As used herein, the term "non-naturally occurring BoNT/B variant" means any BoNT/B produced with the aid of human manipulation, including, without limitation, a BoNT/B produced by genetic engineering using random mutagenesis or rational design and a BoNT/B produced by chemical synthesis. Non-limiting examples of non-naturally occurring BoNT/B variants include, e.g., conservative BoNT/B variants, non-conservative BoNT/B variants and chimeric BoNT/B peptides.

As used herein, the term "conservative BoNT/B variant" means a BoNT/B that has at least one amino acid substituted by another amino acid or an amino acid analog that has at least one property similar to that of the original amino acid from the reference BoNT/B of SEQ ID NO: 1. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative BoNT/B variant can function in substantially the same manner as the reference BoNT/B of SEQ ID NO: 1 on which the conservative BoNT/B variant is based, and can be substituted for the reference BoNT/B of SEQ ID NO: 1 in any aspect of the present invention. A conservative BoNT/B variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference BoNT/B of SEQ ID NO: 1 on which the conservative BoNT/B variant is based. A conservative BoNT/B variant can also substitute at least 10 contiguous amino acids, at least 15 contiguous amino acids, at least 20 contiguous amino acids, or at least 25 contiguous amino acids from the reference BoNT/B of SEQ ID NO: 1 on which the conservative BoNT/B variant is based, that possess at least 50% amino acid identity, 65% amino acid identity, 75% amino acid identity, 85% amino acid identity or 95% amino acid identity to the reference BoNT/B of SEQ ID NO: 1 on which the conservative BoNT/B variant is based.

As a non-limiting example, a conservative BoNT/B variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative BoNT/B variant also can be, for example, a sequence in which a first basic amino acid is conservatively substituted with a second basic amino acid such as arginine, lysine, histidine, 5-hydroxylysine, N-methyllysine or an analog thereof. Similarly, a conservative BoNT/B variant can be, for example, a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative BoNT/B variant can be, for example, a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof.

As a non limiting example, a BoNT/B peptide comprising amino acid sequence 974-992 from a conservative BoNT/B variant can have, e.g., leucine 975 substituted with isoleucine, isoleucine 976 substituted with leucine, aspartic acid 977 substituted with glutamic acid, isoleucine 978 substituted with leucine, lysine 981 substituted with arginine, lysine 983 substituted with arginine, phenylalanine 786 substituted with tyrosine, phenylalanine 787 substituted with tyrosine, glutamic acid 988 substituted with aspartic acid, tyrosine 789 substituted with phenylalanine, isoleucine 991 substituted with leucine, arginine 992 substituted with lysine, or any combination thereof.

As another non limiting example, a BoNT/B peptide comprising amino acid sequence 736-754 from a conservative BoNT/B variant can have, e.g., tyrosine 736 substituted with phenylalanine, arginine 737 substituted with lysine, tyrosine 738 substituted with phenylalanine, isoleucine 740 substituted with leucine, tyrosine 741 substituted with phenylalanine, glutamic acid 743 substituted with aspartic acid, lysine 744 substituted with arginine, glutamic acid 745 substituted with aspartic acid, lysine 746 substituted with arginine, isoleucine 749 substituted with leucine, isoleucine 751 substituted with leucine, aspactic acid 752 substituted with glutamic acid, phenylalanine 753 substituted with tyrosine, or any combination thereof.

As still another non limiting example, a BoNT/B peptide comprising amino acid sequence 1058-1076 from a conservative BoNT/B variant can have, e.g., tyrosine 1058 substituted with phenylalanine, phenylalanine 1059 substituted with tyrosine, isoleucine 1061 substituted with leucine, phenylalanine 1062 substituted with tyrosine, glutamic acid 1065 substituted with aspartic acid, leucine 1066 substituted with isoleucine, isoleucine 1071 substituted with leucine, glutamic acid 1072 substituted with aspartic acid, glutamic acid 1073 substituted with aspartic acid, arginine 1074 substituted with lysine, tyrosine 1075 substituted with phenylalanine, lysine 1076 substituted with arginine, or any combination thereof.

As yet another non limiting example, a BoNT/B peptide comprising amino acid sequence 890-908 from a conservative BoNT/B variant can have, e.g., glutamic acid 892 substituted with aspartic acid, leucine 893 substituted with isoleucine, aspartic acid 895 substituted with glutamic acid, lysine 896 substituted with arginine, phenylalanine 899 substituted with tyrosine, lysine 900 substituted with arginine, leucine 901 substituted with isoleucine, lysine 908 substituted with arginine, or any combination thereof.

As used herein, the term "non-conservative BoNT/B variant" means a BoNT/B in which 1) at least one amino acid is deleted from the reference BoNT/B of SEQ ID NO: 1 on which the non-conservative BoNT/B variant is based; 2) at least one amino acid added to the reference BoNT/B of SEQ ID NO:1 on which the non-conservative BoNT/B is based; or 3) at least one amino acid is substituted by another amino acid or an amino acid analog that does not share any property similar to that of the original amino acid from the reference BoNT/B of SEQ ID NO: 1. A non-conservative BoNT/B variant can function in substantially the same manner as the reference BoNT/B of SEQ ID NO: 1 on which the non-conservative BoNT/B variant is based, and can be substituted for the reference BoNT/B of SEQ ID NO: 1 in any aspect of the present invention. A non-conservative BoNT/B variant can delete one or more amino acids, two or more amino acids, three or more amino acids, four or more amino acids, five or more amino acids, and ten or more amino acids from the reference BoNT/B of SEQ ID NO: 1 on which the non-conservative BoNT/B variant is based. A non-conservative BoNT/B variant can add one or more amino acids, two or more amino acids, three or more amino acids, four or more amino acids, five or more amino acids, and ten or more amino acids to the reference BoNT/B of SEQ ID NO: 1 on which the non-conservative BoNT/B variant is based. A non-conservative BoNT/B variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference BoNT/B of SEQ ID NO: 1 on which the non-conservative BoNT/B variant is based. A non-conservative BoNT/B variant can also substitute at least 10 contiguous amino acids, at least 15 contiguous amino acids, at least 20 contiguous amino acids, or at least 25 contiguous amino acids from the reference BoNT/B of SEQ ID NO: 1 on which the non-conservative BoNT/B variant is based, that possess at least 50% amino acid identity, 65% amino acid identity, 75% amino acid identity, 85% amino acid identity or 95% amino acid identity to the reference BoNT/B of SEQ ID NO: 1 on which the non-conservative BoNT/B variant is based.

A BoNT/B peptide disclosed in the present specification, such as, e.g., a BoNT/B peptide derived from a naturally occurring BoNT/B or a BoNT/B peptide derived from a non-naturally occurring BoNT/B can be operably linked with another polypeptide to form a chimeric BoNT/B peptide. As used herein, the term "chimeric BoNT/B peptide" means a molecule comprising at least a portion of a BoNT/B peptide disclosed in the present specification and at least a portion of at least one other polypeptide to form a BoNT/B chimeric peptide. In aspects of this embodiment, a chimeric BoNT/B protein of the invention can have a variety of lengths including, but not limited to, a length of at most 100 residues, at most 200 residues, at most 300 residues, at most 400 residues, at most 500 residues, at most 800 residues or at most 1000 residues. In other aspects of this embodiment, a chimeric BoNT/B protein of the invention can have a variety of lengths including, but not limited to, a length of at least 100 residues, at least 200 residues, at least 300 residues, at least 400 residues, at least 500 residues, at least 800 residues or at least 1000 residues. Non-limiting examples of a chimeric BoNT/B peptide include, e.g., a BoNT/B peptide operably linked with a carrier, such as, e.g., keyhole limpet hemacyanin (KLH), ovalbumin (OVA), thyroglobulin (THY), bovine serum albumin (BSA), soybean trypsin inhibitor (STI) or multiple attachment peptide (MAP) technology; a BoNT/B peptide operably linked with a with an immunogenic polypeptide, such as, e.g., flagellin or cholera enterotoxin; a BoNT/B peptide operably linked with a with an immunomodulatory polypeptide, such as, e.g., IL-2 or B7-1; a BoNT/B peptide operably linked with a with tolerogenic polypeptide, such as, e.g., another BoNT/B peptide or an antibody selectively reactive with interleukin-12; and a BoNT/B peptide operably linked with a synthetic peptide sequence.

As used herein, the term "amino acid" means both naturally occurring and non-naturally occurring amino acids as well as amino acid analogs and mimetics, and includes, but is not limited to, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl. As such, a BoNT/B peptide derived from, e.g., a naturally occurring BoNT/B or a non-naturally occurring BoNT/B, can contain one or more non-amide linkage substitutions between amino acids, one or more naturally occurring amino acid substitutions, one or more non-naturally occurring amino acid substitutions, one or more amino acid analog substitutions, or one or more mimetic substitutions.

As used herein, the term "naturally occurring amino acid substitution" when used in reference to a BoNT/B means a BoNT/B peptide that has been altered from the BoNT/B peptide of SEQ ID NO: 1 in which a first amino acid from the BoNT/B peptide of SEQ ID NO: 1 is substituted by a naturally occurring amino acid that has at least one property similar to that of the first amino acid. Naturally occurring amino acids include the 20 (L)-amino acids utilized during protein biosynthesis as well as others such as, without limitation, 4-hydroxyproline, hydroxylysine, desmosine, isodesmosine, homocysteine, citrulline and ornithine.

As used herein, the term "non-naturally occurring amino acid substitution" when used in reference to a BoNT/B means a BoNT/B peptide that has been altered from the BoNT/B peptide of SEQ ID NO: 1 in which a first amino acid from the BoNT/B peptide of SEQ ID NO: 1 is substituted by a non-naturally occurring amino acid that has at least one property similar to that of the first amino acid. Examples of non-naturally occurring amino acids, include, without limitation, (D)-amino acids, norleucine, norvaline, p-fluorophenylalanine, ethionine and the like.

As used herein, "amino acid analog substitution" when used in reference to a BoNT/B means a BoNT/B peptide that has been altered from the BoNT/B peptide of SEQ ID NO: 1 in which a first amino acid from the BoNT/B peptide of SEQ ID NO: 1 is substituted by a modified natural or non-natural amino acid that has at least one property similar to that of the first amino acid. Examples of modifications to either a naturally occurring amino acid or a non-naturally occurring amino acid, include, without limitation, substitution or replacement of chemical groups or moieties on the amino acid or by derivitization of the amino acid. A BoNT/B amino acid analog can function in substantially the same manner as the BoNT/B peptide of SEQ ID NO: 1 and can be substituted for the BoNT/B peptide of SEQ ID NO: 1 in any aspect of the present invention. A BoNT/B amino acid analog may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids from the BoNT/B peptide of SEQ ID NO: 1, or a portion thereof.

As used herein, the term "mimetic substitution" when used in reference to a BoNT/B means a BoNT/B peptide that has been altered from the BoNT/B peptide of SEQ ID NO: 1 in which a first amino acid from the BoNT/B peptide of SEQ ID NO: 1 is substituted by a non-natural structure that has at least one property similar to that of the first amino acid. Examples of mimetic properties include, without limitation, topography of a peptide primary structural element, functionality of a peptide primary structural element, topology of a peptide secondary structural element, functionality of a peptide secondary structural element, of the like, or any combination thereof. A BoNT/B mimetic can function in substantially the same manner as the BoNT/B peptide of SEQ ID NO: 1 and can be substituted for the BoNT/B peptide of SEQ ID NO: 1 in any aspect of the present invention. A BoNT/B mimetic may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids from the BoNT/B peptide of SEQ ID NO: 1, or a portion thereof. As an example, an organic structure that mimics arginine can have a positive charge moiety located in similar molecular space and having the same degree of mobility as the e-amino group of the side chain of the naturally occurring arginine amino acid.

Non-limiting examples of specific protocols for making and using naturally occurring amino acids, non-naturally occurring amino acids, amino acid analogs and mimetics are described in, e.g., John Jones, AMINO ACID PEPTIDE SYNTHESIS (Oxford University Press, $2^{nd}$ ed., 2002); Roberts and Vellaccio, p. 341 (THE PEPTIDES: ANALYSIS, SYNTHESIS, BIOLOGY Vol. 5, Erhard Gross & Johannes Meinhofer, eds., Academic Press, Inc., 1983); Mark J. Suto et al., Cytokine Restraining Agents, U.S. Pat. No. 5,420,109 (May 30, 1995); Chapter 7 of Bodanzsky, PRINCIPLES OF PEPTIDE SYNTHESIS (Springer-Verlag, $2^{nd}$ ed. 1993); Stewart and Young SOLID PHASE PEPTIDE SYNTHESIS, Pierce Chemical Co., 2 ed. 1984); FMOC SOLID PHASE PEPTIDE SYNTHESIS: A PRACTICAL APPROACH (Weng C. Chan & Peter D. White eds., Oxford University Press, 2000); Amy S. Ripka & Daniel H. Rich, Peptidomimetic design, 2(4) CURR. OPIN. CHEM. BIOL. 441-452 (1998); and M. Angels Estiarte & Daniel H. Rich, Peptidomimetics for Drug Design, 803-861 (BURGER'S MEDICINAL CHEMISTRY AND DRUG DISCOVERY Vol. 1 PRINCIPLE AND PRACTICE, Donald J. Abraham ed., Wiley-Interscience, $6^{th}$ ed 2003). One skilled in the art understands that these and other well known amino acid analogs and mimetics can be useful in the BoNT/B peptides of the invention.

In is envisioned that any and all procedures that can synthesis a BoNT/B peptide disclosed in the present specification can be used. As a non-limiting example, a BoNT/B peptide disclosed in the present specification can be produced by chemical synthesis using an automatic peptide synthesizer employing the chemistry provided by the manufacturer, such as, e.g., a Model 430A automatic peptide synthesizer or a 431A automatic peptide synthesizer (Applied Biosystems, Inc., Foster City, Calif.). Methods for synthesizing peptides are well known in the art, see, e.g., Bodanzsky, *Principles of Peptide Synthesis* (1st ed. & 2d rev. ed.), Springer-Verlag, New York, N.Y. (1984 & 1993), and Chapter 7; Stewart and Young, *Solid Phase Peptide Synthesis*, (2d ed.), Pierce Chemical Co., Rockford, Ill. (1984).

Thus, in an embodiment, a BoNT/B peptide has a length of at least 5 amino acids and at most 60 amino acids. In an aspect of this embodiment, a BoNT/B peptide of SEQ ID NO: 1 has a length of at least 5 amino acids and at most 60 amino acids. In other aspects of this embodiment, a BoNT/B peptide comprises an amino acid sequence selected from the group consisting of amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, a BoNT/B peptide comprises an amino acid sequence selected from the group consisting of amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 932-950 of SEQ ID NO: 1, amino acids 932-950 of SEQ ID NO: 5, amino acids 974-992 of SEQ ID NO: 1, amino acids 974-992 of SEQ ID NO: 3, amino acids 974-992 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In still other aspects of this embodiment, a BoNT/B peptide comprises an amino acid sequence selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In another embodiment, a BoNT/B peptide has a length of at least 5 amino acids and at most 60 amino acids and is derived from a naturally occurring BoNT/B. In aspects of this embodiment, the naturally occurring BoNT/B is a BoNT/B isoform or a BoNT/B subtype.

In another embodiment, a BoNT/B peptide has a length of at least 5 amino acids and at most 60 amino acids and is derived from a non-naturally occurring BoNT/B. In aspects of this embodiment, the naturally occurring BoNT/B is a conservative BoNT/B variant or a non-conservative BoNT/B variant.

In aspects of this embodiment, a BoNT/B peptide comprises, e.g., 1-4 conservative amino acid substitutions to amino acids 610-628 of SEQ ID NO: 1, 1-4 conservative amino acid substitutions to amino acids 736-754 of SEQ ID NO: 1, 1-4 conservative amino acid substitutions to amino acids 736-754 of SEQ ID NO: 5, 1-4 conservative amino acid substitutions to amino acids 778-796 of SEQ ID NO: 1, 1-4 conservative amino acid substitutions to amino acids 778-796 of SEQ ID NO: 5, 1-4 conservative amino acid substitutions to amino acids 820-838 of SEQ ID NO: 1, 1-4 conservative amino acid substitutions to amino acids 820-838 of SEQ ID NO: 3, 1-4 conservative amino acid substitutions to amino acids 820-838 of SEQ ID NO: 5, 1-4 conservative amino acid substitutions to amino acids 820-838 of SEQ ID NO: 7, 1-4 conservative amino acid substitutions to amino acids 862-880 of SEQ ID NO: 1, 1-4 conservative amino acid substitutions to amino acids 862-880 of SEQ ID NO: 7, 1-4 conservative amino acid substitutions to amino acids 890-908 of SEQ ID NO: 1, 1-4 conservative amino acid substitutions to amino acids 890-908 of SEQ ID NO: 3, 1-4 conservative amino acid substitutions to amino acids 890-908 of SEQ ID NO: 5, 1-4 conservative amino acid substitutions to amino acids 890-908 of SEQ ID NO: 7, 1-4 conservative amino acid substitutions to amino acids 918-936 of SEQ ID NO: 1, 1-4 conservative amino acid substitutions to amino acids 918-936 of SEQ ID NO: 3, 1-4 conservative amino acid substitutions to amino acids 932-950 of SEQ ID NO: 1, 1-4 conservative amino acid substitutions to amino acids 932-950 of SEQ ID NO: 5, 1-4 conservative amino acid substitutions to amino acids 960-978 of SEQ ID NO: 1, 1-4 conservative amino acid substitutions to amino acids 960-978 of SEQ ID NO: 3, 1-4 conservative amino acid substitutions to amino acids 960-978 of SEQ ID NO: 7, 1-4 conservative amino acid substitutions to amino acids 974-992 of SEQ ID NO: 1, 1-4 conservative amino acid substitutions to amino acids 974-992 of SEQ ID NO: 3, 1-4 conservative amino acid substitutions to amino acids 974-992 of SEQ ID NO: 7, 1-4 conservative amino acid substitutions to amino acids 1030-1048 of SEQ ID NO: 1, 1-4 conservative amino acid substitutions to amino acids 1030-1048 of SEQ ID NO: 3, 1-4 conservative amino acid substitutions to amino acids 1030-1048 of SEQ ID NO: 5, 1-4 conservative amino acid substitutions to amino acids 1030-1048 of SEQ ID NO: 7, 1-4 conservative amino acid substitutions to amino acids 1058-1076 of SEQ ID NO: 1, 1-4 conservative amino acid substitutions to amino acids 1058-1076 of SEQ ID NO: 3, 1-4 conservative amino acid substitutions to amino acids 1058-1076 of SEQ ID NO: 5, 1-4 conservative amino acid substitutions to amino acids 1058-1076 of SEQ ID NO: 7, 1-4 conservative amino acid substitutions to amino acids 1072-1090 of SEQ ID NO: 1, 1-4 conservative amino acid substitutions to amino acids 1072-1090 of SEQ ID NO: 3, 1-4 conservative amino acid substitutions to amino acids 1072-1090 of SEQ ID NO: 7, 1-4 conservative amino acid substitutions to amino acids 1254-1272 of SEQ ID NO: 1, 1-4 conservative amino acid substitutions to amino acids 1254-1272 of SEQ ID NO: 3, 1-4 conservative amino acid substitutions to amino acids 1268-1291 of SEQ ID NO: 1, 1-4 conservative amino acid substitutions to amino acids 1268-1291 of SEQ ID NO: 3, 1-4 conservative amino acid substitutions to amino acids 1268-1291 of SEQ ID NO: 5 or 1-4 conservative amino acid substitutions to amino acids 1268-1291 of SEQ ID NO: 7.

In other aspects of this embodiment, a BoNT/B peptide comprises, e.g., 1-4 conservative amino acid substitutions to amino acids 736-754 of SEQ ID NO: 1, 1-4 conservative amino acid substitutions to amino acids 736-754 of SEQ ID NO: 5, 1-4 conservative amino acid substitutions to amino acids 778-796 of SEQ ID NO: 1, 1-4 conservative amino acid substitutions to amino acids 778-796 of SEQ ID NO: 5, 1-4 conservative amino acid substitutions to amino acids 890-908 of SEQ ID NO: 1, 1-4 conservative amino acid substitutions to amino acids 890-908 of SEQ ID NO: 3, 1-4 conservative amino acid substitutions to amino acids 890-908 of SEQ ID NO: 5, 1-4 conservative amino acid substitutions to amino acids 890-908 of SEQ ID NO: 7, 1-4 conservative amino acid substitutions to amino acids 932-950 of SEQ ID NO: 1, 1-4 conservative amino acid substitutions to amino acids 932-950 of SEQ ID NO: 5, 1-4 conservative amino acid substitutions to amino acids 974-992 of SEQ ID NO: 1, 1-4 conservative amino acid substitutions to amino acids 974-992 of SEQ ID NO: 3, 1-4 conservative amino acid substitutions to amino acids 974-992 of SEQ ID NO: 7, 1-4 conservative amino acid substitutions to amino acids 1058-1076 of SEQ ID NO: 1, 1-4 conservative amino acid substitutions to amino acids 1058-1076 of SEQ ID NO: 3, 1-4 conservative amino acid substitutions to amino acids 1058-1076 of SEQ ID NO: 5, 1-4 conservative amino acid substitutions to amino acids 1058-1076 of SEQ ID NO: 7, 1-4 conservative amino acid substitutions to amino acids 1268-1291 of SEQ ID NO: 1, 1-4 conservative amino acid substitutions to amino acids 1268-1291 of SEQ ID NO: 3, 1-4 conservative amino acid substitutions to amino acids 1268-1291 of SEQ ID NO: 5 or 1-4 conservative amino acid substitutions to amino acids 1268-1291 of SEQ ID NO: 7.

In other aspects of this embodiment, a BoNT/B peptide comprises, e.g., 1-4 conservative amino acid substitutions to amino acids 616-626 of SEQ ID NO: 1, 1-4 conservative amino acid substitutions to amino acids 735-745 of SEQ ID NO: 1, 1-4 conservative amino acid substitutions to amino acids 735-745 of SEQ ID NO: 5, 1-4 conservative amino acid substitutions to amino acids 778-789 of SEQ ID NO: 1, 1-4 conservative amino acid substitutions to amino acids 867-877 of SEQ ID NO: 1, 1-4 conservative amino acid substitutions to amino acids 867-877 of SEQ ID NO: 7, 1-4 conservative amino acid substitutions to amino acids 895-905 of SEQ ID NO: 1, 1-4 conservative amino acid substitutions to amino acids 895-905 of SEQ ID NO: 3, 1-4 conservative amino acid substitutions to amino acids 929-939 of SEQ ID NO: 1, 1-4 conservative amino acid substitutions to amino acids 974-984 of SEQ ID NO: 1, 1-4 conservative amino acid substitutions to amino acids 974-984 of SEQ ID NO: 3, 1-4 conservative amino acid substitutions to amino acids 974-984 of SEQ ID NO: 7, 1-4 conservative amino acid substitutions to amino acids 1039-1049 of SEQ ID NO: 1, 1-4 conservative amino acid substitutions to amino acids 1039-1049 of SEQ ID NO: 5, 1-4 conservative amino acid substitutions to amino acids 1039-1049 of SEQ ID NO: 7, 1-4 conservative amino acid substitutions to amino acids 1065-1075 of SEQ ID NO: 1, 1-4 conservative amino acid substitutions to amino acids 1065-1075 of SEQ ID NO: 3, 1-4 conservative amino acid substitutions to amino acids 1065-1075 of SEQ ID NO: 5, 1-4 conservative amino acid substitutions to amino acids 1065-1075 of SEQ ID NO: 7, 1-4 conservative amino acid substitutions to amino acids 1269-1281 of SEQ ID NO: 1, 1-4 conservative amino acid substitutions to amino acids 1269-1281 of SEQ ID NO: 3, 1-4 conservative amino acid substitutions to amino acids 1269-1281 of SEQ ID NO: 5 or 1-4 conservative amino acid substitutions to amino acids 1269-1281 of SEQ ID NO: 7.

In still aspects of this embodiment, a BoNT/B peptide comprises, e.g., 1-4 non-conservative amino acid substitutions to amino acids 610-628 of SEQ ID NO: 1, 1-4 non-conservative amino acid substitutions to amino acids 736-754 of SEQ ID NO: 1, 1-4 non-conservative amino acid substitutions to amino acids 736-754 of SEQ ID NO: 5, 1-4 non-conservative amino acid substitutions to amino acids 778-796 of SEQ ID NO: 1, 1-4 non-conservative amino acid substitutions to amino acids 778-796 of SEQ ID NO: 5, 1-4 non-conservative amino acid substitutions to amino acids 820-838 of SEQ ID NO: 1, 1-4 non-conservative amino acid substitutions to amino acids 820-838 of SEQ ID NO: 3, 1-4 non-conservative amino acid substitutions to amino acids 820-838 of SEQ ID NO: 5, 1-4 non-conservative amino acid substitutions to amino acids 820-838 of SEQ ID NO: 7, 1-4 non-conservative amino acid substitutions to amino acids 862-880 of SEQ ID NO: 1, 1-4 non-conservative amino acid substitutions to amino acids 862-880 of SEQ ID NO: 7, 1-4 non-conservative amino acid substitutions to amino acids 890-908 of SEQ ID NO: 1, 1-4 non-conservative amino acid substitutions to amino acids 890-908 of SEQ ID NO: 3, 1-4 non-conservative amino acid substitutions to amino acids 890-908 of SEQ ID NO: 5, 1-4 non-conservative amino acid substitutions to amino acids 890-908 of SEQ ID NO: 7, 1-4 non-conservative amino acid substitutions to amino acids 918-936 of SEQ ID NO: 1, 1-4 non-conservative amino acid substitutions to amino acids 918-936 of SEQ ID NO: 3, 1-4 non-conservative amino acid substitutions to amino acids 932-950 of SEQ ID NO: 1, 1-4 non-conservative amino acid substitutions to amino acids 932-950 of SEQ ID NO: 5, 1-4 non-conservative amino acid substitutions to amino acids 960-978 of SEQ ID NO: 1, 1-4 non-conservative amino acid substitutions to amino acids 960-978 of SEQ ID NO: 3, 1-4 non-conservative amino acid substitutions to amino acids 960-978 of SEQ ID NO: 7, 1-4 non-conservative amino acid substitutions to amino acids 974-992 of SEQ ID NO: 1, 1-4 non-conservative amino acid substitutions to amino acids 974-992 of SEQ ID NO: 3, 1-4 non-conservative amino acid substitutions to amino acids 974-992 of SEQ ID NO: 7, 1-4 non-conservative amino acid substitutions to amino acids 1030-1048 of SEQ ID NO: 1, 1-4 non-conservative amino acid substitutions to amino acids 1030-1048 of SEQ ID NO: 3, 1-4 non-conservative amino acid substitutions to amino acids 1030-1048 of SEQ ID NO: 5, 1-4 non-conservative amino acid substitutions to amino acids 1030-1048 of SEQ ID NO: 7, 1-4 non-conservative amino acid substitutions to amino acids 1058-1076 of SEQ ID NO: 1, 1-4 non-conservative amino acid substitutions to amino acids 1058-1076 of SEQ ID NO: 3, 1-4 non-conservative amino acid substitutions to amino acids 1058-1076 of SEQ ID NO: 5, 1-4 non-conservative amino acid substitutions to amino acids 1058-1076 of SEQ ID NO: 7, 1-4 non-conservative amino acid substitutions to amino acids 1072-1090 of SEQ ID NO: 1, 1-4 non-conservative amino acid substitutions to amino acids 1072-1090 of SEQ ID NO: 3, 1-4 non-conservative amino acid substitutions to amino acids 1072-1090 of SEQ ID NO: 7, 1-4 non-conservative amino acid substitutions to amino acids 1254-1272 of SEQ ID NO: 1, 1-4 non-conservative amino acid substitutions to amino acids 1254-1272 of SEQ ID NO: 3, 1-4 non-conservative amino acid substitutions to amino acids 1268-1291 of SEQ ID NO: 1, 1-4 non-conservative amino acid substitutions to amino acids 1268-1291 of SEQ ID NO: 3, 1-4 non-conservative amino acid substitutions to amino acids 1268-1291 of SEQ ID NO: 5 or 1-4 non-conservative amino acid substitutions to amino acids 1268-1291 of SEQ ID NO: 7.

In still other aspects of this embodiment, a BoNT/B peptide comprises, e.g., 1-4 non-conservative amino acid substitutions to amino acids 736-754 of SEQ ID NO: 1, 1-4 non-conservative amino acid substitutions to amino acids 736-754 of SEQ ID NO: 5, 1-4 non-conservative amino acid substitutions to amino acids 778-796 of SEQ ID NO: 1, 1-4 non-conservative amino acid substitutions to amino acids 778-796 of SEQ ID NO: 5, 1-4 non-conservative amino acid substitutions to amino acids 890-908 of SEQ ID NO: 1, 1-4 non-conservative amino acid substitutions to amino acids 890-908 of SEQ ID NO: 3, 1-4 non-conservative amino acid substitutions to amino acids 890-908 of SEQ ID NO: 5, 1-4 non-conservative amino acid substitutions to amino acids 890-908 of SEQ ID NO: 7, 1-4 non-conservative amino acid substitutions to amino acids 932-950 of SEQ ID NO: 1, 1-4 non-conservative amino acid substitutions to amino acids 932-950 of SEQ ID NO: 5, 1-4 non-conservative amino acid substitutions to amino acids 974-992 of SEQ ID NO: 1, 1-4 non-conservative amino acid substitutions to amino acids 974-992 of SEQ ID NO: 3, 1-4 non-conservative amino acid substitutions to amino acids 974-992 of SEQ ID NO: 7, 1-4 non-conservative amino acid substitutions to amino acids 1058-1076 of SEQ ID NO: 1, 1-4 non-conservative amino acid substitutions to amino acids 1058-1076 of SEQ ID NO: 3, 1-4 non-conservative amino acid substitutions to amino acids 1058-1076 of SEQ ID NO: 5, 1-4 non-conservative amino acid substitutions to amino acids 1058-1076 of SEQ ID NO: 7, 1-4 non-conservative amino acid substitutions to amino acids 1268-1291 of SEQ ID NO: 1, 1-4 non-conservative amino acid substitutions to amino acids 1268-1291 of SEQ ID NO: 3, 1-4 non-conservative amino acid substitutions to amino acids 1268-1291 of SEQ ID NO: 5 or 1-4 non-conservative amino acid substitutions to amino acids 1268-1291 of SEQ ID NO: 7.

In still other aspects of this embodiment, a BoNT/B peptide comprises, e.g., 1-4 non-conservative amino acid substitutions to amino acids 616-626 of SEQ ID NO: 1, 1-4 non-conservative amino acid substitutions to amino acids 735-745 of SEQ ID NO: 1, 1-4 non-conservative amino acid substitutions to amino acids 735-745 of SEQ ID NO: 5, 1-4 non-conservative amino acid substitutions to amino acids 778-789 of SEQ ID NO: 1, 1-4 non-conservative amino acid substitutions to amino acids 867-877 of SEQ ID NO: 1, 1-4 non-conservative amino acid substitutions to amino acids 867-877 of SEQ ID NO: 7, 1-4 non-conservative amino acid substitutions to amino acids 895-905 of SEQ ID NO: 1, 1-4 non-conservative amino acid substitutions to amino acids 895-905 of SEQ ID NO: 3, 1-4 non-conservative amino acid substitutions to amino acids 929-939 of SEQ ID NO: 1, 1-4 non-conservative amino acid substitutions to amino acids 974-984 of SEQ ID NO: 1, 1-4 non-conservative amino acid substitutions to amino acids 974-984 of SEQ ID NO: 3, 1-4 non-conservative amino acid substitutions to amino acids 974-984 of SEQ ID NO: 7, 1-4 non-conservative amino acid substitutions to amino acids 1039-1049 of SEQ ID NO: 1, 1-4 non-conservative amino acid substitutions to amino acids 1039-1049 of SEQ ID NO: 5, 1-4 non-conservative amino acid substitutions to amino acids 1039-1049 of SEQ ID NO: 7, 1-4 non-conservative amino acid substitutions to amino acids 1065-1075 of SEQ ID NO: 1, 1-4 non-conservative amino acid substitutions to amino acids 1065-1075 of SEQ ID NO: 3, 1-4 non-conservative amino acid substitutions to amino acids 1065-1075 of SEQ ID NO: 5, 1-4 non-conservative amino acid substitutions to amino acids 1065-1075 of SEQ ID NO: 7, 1-4 non-conservative amino acid substitutions to amino acids 1269-1281 of SEQ ID NO: 1, 1-4 non-conservative amino acid substitutions to amino acids 1269-1281 of SEQ ID NO: 3, 1-4 non-conservative amino acid substitutions to amino acids 1269-1281 of SEQ ID NO: 5 or 1-4 non-conservative amino acid substitutions to amino acids 1269-1281 of SEQ ID NO: 7.

A BoNT/B peptide disclosed in the present specification has a length of at least five amino acids and at most 60 amino acids. Such a BoNT/B peptide can comprise an immunoreactive BoNT/B fragment. As used herein, the term "immunoreactive BoNT/B fragment" when used in reference to a BoNT/B means a portion of a BoNT/B peptide capable of selectively binding to an anti-BoNT/B antibody. As used herein, the term "selectively" means having a unique effect or influence or reacting in only one way or with only one thing. An immunoreactive BoNT/B fragment can function in substantially the same manner as the BoNT/B peptide of SEQ ID NO: 1 and can be substituted for the BoNT/B peptide of SEQ ID NO: 1 in any aspect of the present invention. An immunoreactive BoNT/B fragment can function in substantially the same manner as the reference BoNT/B peptide on which the immunoreactive BoNT/B fragment is based, and can be substituted for the reference BoNT/B peptide in any aspect of the present invention. An immunoreactive BoNT/B fragment is capable of selective binding to anti-BoNT/B antibodies from one or more species. An immunoreactive BoNT/B fragment of a BoNT/B peptide generally has from at least six amino acids to at most 60 amino acids. An immunoreactive BoNT/B fragment of a BoNT/B peptide can have a length of, e.g., at least 6 amino acids, at least 7 amino acids, at least 8 amino acids, at least 9 amino acids, at least 10 amino acids, at least 12 amino acids, at least 15 amino acids, at least 18 amino acids, at least 20 amino acids, at least 25 amino acids at least 30 amino acids or at least 35 amino acids. An immunoreactive fragment of a BoNT/B peptide also can have a length of, e.g., at most 6 amino acids, at most 7 amino acids, at most 8 amino acids, at most 9 amino acids, at most 10 amino acids, at most 12 amino acids, at most 15 amino acids, at most 18 amino acids, at most 20 amino acids, at most 25 amino acids, at most 30 amino acids or at most 35 amino acids. An immunoreactive BoNT/B fragment disclosed in the present specification can comprise at least six consecutive amino acids or can comprise at least six non-consecutive amino acids and can have any number of conservative, non-conservative, analog or mimetic amino acid substitutions, and the like, as disclosed in the present specification.

An immunoreactive fragment can be identified using any of a variety of routine assays for detecting peptide antigen-antibody complexes, the presence of which is an indicator of selective binding. Such assays include, without limitation, enzyme-linked immunosorbent assays, radioimmunoassays, western blotting, enzyme immunoassays, fluorescence immunoassays, luminescent immunoassays and the like and generally are equivalent to the radioimmunoassay disclosed herein in Example 2. Methods for detecting a complex between a peptide and an antibody, and thereby determining if the peptide is an immunoreactive fragment are well known to those skilled in the art and are described, e.g., in ANTIBODIES: A LABORATORY MANUAL (Edward Harlow & David Lane, eds., Cold Spring Harbor Laboratory Press, $2^{nd}$ ed. 1998a); and USING ANTIBODIES: A LABORATORY MANUAL: PORTABLE PROTOCOL No. I (Edward Harlow & David Lane, Cold Spring Harbor Laboratory Press, 1998b).

Thus, in an embodiment, an immunoreactive fragment of a BoNT/B peptide has a length of at least five amino acids and at most 60 amino acids. In aspects of this embodiment, an immunoreactive fragment of a BoNT/B peptide comprises, e.g., at least 6 consecutive amino acids, at least 7 consecutive amino acids, at least 8 consecutive amino acids, at least 9 consecutive amino acids, at least 10 consecutive amino acids, at least 12 consecutive amino acids, at least 15 consecutive amino acids, at least 18 consecutive amino acids or at least 20 consecutive amino acids. In other aspects of this embodiment, an immunoreactive fragment of a BoNT/B peptide comprises, e.g., at most 6 consecutive amino acids, at most 7 consecutive amino acids, at most 8 consecutive amino acids, at most 9 consecutive amino acids, at most 10 consecutive amino acids, at most 12 consecutive amino acids, at most 15 consecutive amino acids, at most 18 consecutive amino acids or at most 20 consecutive amino acids.

In still other aspects of this embodiment, an immunoreactive fragment of a BoNT/B peptide comprises, e.g., at least 6 non-consecutive amino acids, at least 7 non-consecutive amino acids, at least 8 non-consecutive amino acids, at least 9 non-consecutive amino acids, at least 10 non-consecutive amino acids, at least 12 non-consecutive amino acids, at least 15 non-consecutive amino acids, at least 18 non-consecutive amino acids or at least 20 non-consecutive amino acids. In still other aspects of this embodiment, an immunoreactive fragment of a BoNT/B peptide comprises, e.g., at most 6 non-consecutive amino acids, at most 7 non-consecutive amino acids, at most 8 non-consecutive amino acids, at most 9 non-consecutive amino acids, at most 10 non-consecutive amino acids, at most 12 non-consecutive amino acids, at most 15 non-consecutive amino acids, at most 18 non-consecutive amino acids or at most 20 non-consecutive amino acids.

In still other aspects of this embodiment, an immunoreactive fragment of a BoNT/B peptide can comprise, e.g., from five to sixty amino acids, from five to fifty amino acids, from eight to fifty amino acids, from ten to fifty amino acids, from five to twenty amino acids, from eight to twenty amino acids, from ten to twenty amino acids, from twelve to twenty amino acids or from fifteen to twenty amino acids.

In another embodiment, a BoNT/B peptide comprises an immunogenic BoNT/B fragment. In an aspect of this embodiment, an immunogenic BoNT/B fragment comprises at least six consecutive amino acids of a BoNT/B peptide. In other aspects of this embodiment, an immunogenic BoNT/B fragment comprises at least six consecutive amino acids from, e.g., amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, an immunogenic BoNT/B fragment comprises at least six consecutive amino acids from, e.g., amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In still another aspect of this embodiment, an immunogenic BoNT/B fragment comprises at least six non-consecutive amino acids of a BoNT/B peptide. In still other aspects of this embodiment, an immunogenic BoNT/B fragment comprises at least six non-consecutive amino acids from, e.g., amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In still other aspects of this embodiment, an immunogenic BoNT/B fragment comprises at least six non-consecutive amino acids from, e.g., amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

The present invention provides, in part, a BoNT/B peptide composition. It is envisioned that a BoNT/B peptide composition can comprise any of the BoNT/B peptides disclosed in the present specification, including, without limitation, a BoNT/B peptide derived from a naturally occurring BoNT/B, such as, e.g., the BoNT/B of SEQ ID NO: 1, SEQ ID NO: 3, SEQ ID NO: 5, SEQ ID NO: 7, SEQ ID NO: 9, SEQ ID NO: 11 or SEQ ID NO: 13, a BoNT/B isoform or a BoNT/B subtype; and a BoNT/B peptide derived from a non-naturally occurring BoNT/B, such as, e.g., a conservative BoNT/B variant, a non-conservative BoNT/B variant and a chimeric BoNT/B peptide. BoNT/B peptides disclosed in the present specification can be selected, for example, depending on immunological factors, such as potency of the peptide in inducing an immune response, and technical factors, such as chemical synthesis yields. It is also understood that the two or more different BoNT/B peptides can be provided separately or as part of a compound molecule such as a chimeric peptide or heterologous protein. Examples of BoNT/B peptide compositions, include, without limitation, tolerogizing compositions comprising a tolerogizing agent and a BoNT/B peptide and immune response inducing compositions comprising an adjuvant and a BoNT/B peptide.

In an embodiment, a BoNT/B peptide composition can comprise one BoNT/B peptide disclosed in the present specification. In another embodiment, a BoNT/B peptide composition can comprise a plurality of different BoNT/B peptides disclosed in the present specification. Thus, in aspects of this embodiment, a BoNT/B peptide composition comprises one or more different BoNT/B peptides, two or more different BoNT/B peptides, three or more different BoNT/B peptides, four or more different BoNT/B peptides, five or more different BoNT/B peptides, six or more different BoNT/B peptides, seven or more different BoNT/B peptides, eight or more different BoNT/B peptides, nine or more different BoNT/B peptides, ten or more different BoNT/B peptides, 15 or more different BoNT/B peptides or 20 or more different BoNT/B peptides.

In other aspects of this embodiment, a BoNT/B peptide composition comprises one or more different BoNT/B peptides derived from the BoNT/B of SEQ ID NO: 1, the BoNT/B of SEQ ID NO: 3, the BoNT/B of SEQ ID NO: 5, the BoNT/B of SEQ ID NO: 7, the BoNT/B of SEQ ID NO: 9, the BoNT/B of SEQ ID NO: 11 or the BoNT/B of SEQ ID NO: 13.

In still other aspects of this embodiment, a BoNT/B peptide composition comprises one or more different BoNT/B peptides comprising an amino acid sequence selected from the group consisting of amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In still other aspects of this embodiment, a BoNT/B peptide composition comprises one or more different BoNT/B peptides, each comprising an amino acid sequence selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In another aspect of this embodiment, a BoNT/B peptide composition comprises a BoNT/B peptide comprising amino acid sequence is 974-992 of SEQ ID NO: 1. In another aspect of this embodiment, a BoNT/B peptide composition comprises a BoNT/B peptide comprising amino acid sequence is 736-754 of SEQ ID NO: 1. In another aspect of this embodiment, a BoNT/B peptide composition comprises a BoNT/B peptide comprising amino acid sequence is 1058-1076 of SEQ ID NO: 1. In another aspect of this embodiment, a BoNT/B peptide composition comprises a BoNT/B peptide comprising amino acid sequence is 890-908 of SEQ ID NO: 1. In another aspect of this embodiment, a BoNT/B peptide composition comprises a BoNT/B peptide comprising amino acid sequence is 778-796 of SEQ ID NO: 1. In another aspect of this embodiment, a BoNT/B peptide composition comprises a BoNT/B peptide comprising amino acid sequence is 932-950 of SEQ ID NO: 1. In another aspect of this embodiment, a BoNT/B peptide composition comprises a BoNT/B peptide comprising amino acid sequence is 1268-1291 of SEQ ID NO: 1.

In another aspect of this embodiment, a BoNT/B peptide composition comprises a BoNT/B peptide comprising amino acid sequence is 616-626 of SEQ ID NO: 1. In another aspect of this embodiment, a BoNT/B peptide composition comprises a BoNT/B peptide comprising amino acid sequence is 735-745 of SEQ ID NO: 1. In another aspect of this embodiment, a BoNT/B peptide composition comprises a BoNT/B peptide comprising amino acid sequence is 778-789 of SEQ ID NO: 1.

In another aspect of this embodiment, a BoNT/B peptide composition comprises a BoNT/B peptide comprising amino acid sequence is 867-877 of SEQ ID NO: 1. In another aspect of this embodiment, a BoNT/B peptide composition comprises a BoNT/B peptide comprising amino acid sequence is 895-905 of SEQ ID NO: 1. In another aspect of this embodiment, a BoNT/B peptide composition comprises a BoNT/B peptide comprising amino acid sequence is 929-939 of SEQ ID NO: 1. In another aspect of this embodiment, a BoNT/B peptide composition comprises a BoNT/B peptide comprising amino acid sequence is 974-984 of SEQ ID NO: 1. In another aspect of this embodiment, a BoNT/B peptide composition comprises a BoNT/B peptide comprising amino acid sequence is 1039-1049 of SEQ ID NO: 1. In another aspect of this embodiment, a BoNT/B peptide composition comprises a BoNT/B peptide comprising amino acid sequence is 1065-1075 of SEQ ID NO: 1. In another aspect of this embodiment, a BoNT/B peptide composition comprises a BoNT/B peptide comprising amino acid sequence is 1269-1281 of SEQ ID NO: 1.

In yet another aspect of this embodiment, a BoNT/B peptide composition comprises a BoNT/B peptide comprising amino acid sequence is 974-992 of SEQ ID NO:1 and a BoNT/B peptide comprising amino acid sequence is 736-754 of SEQ ID NO: 1. In yet another aspect of this embodiment, a BoNT/B peptide composition comprises a BoNT/B peptide comprising amino acid sequence is 974-992 of SEQ ID NO:1 and a BoNT/B peptide comprising amino acid sequence is 1058-1076 of SEQ ID NO: 1. In yet another aspect of this embodiment, a BoNT/B peptide composition comprises a BoNT/B peptide comprising amino acid sequence is 974-992 of SEQ ID NO:1 and a BoNT/B peptide comprising amino acid sequence is 890-908 of SEQ ID NO: 1.

In yet another aspect of this embodiment, a BoNT/B peptide composition comprises a BoNT/B peptide comprising amino acid sequence is 974-984 of SEQ ID NO:1 and a BoNT/B peptide comprising amino acid sequence is 735-745 of SEQ ID NO: 1. In yet another aspect of this embodiment, a BoNT/B peptide composition comprises a BoNT/B peptide comprising amino acid sequence is 974-984 of SEQ ID NO:1 and a BoNT/B peptide comprising amino acid sequence is 1065-1075 of SEQ ID NO: 1. In yet another aspect of this embodiment, a BoNT/B peptide composition comprises a BoNT/B peptide comprising amino acid sequence is 974-984 of SEQ ID NO:1 and a BoNT/B peptide comprising amino acid sequence is 895-905 of SEQ ID NO: 1.

In still another aspect of this embodiment, a BoNT/B peptide composition comprises a BoNT/B peptide comprising amino acid sequence is 974-992 of SEQ ID NO:1, a BoNT/B peptide comprising amino acid sequence is 736-754 of SEQ ID NO: 1 and a BoNT/B peptide comprising amino acid sequence is 1058-1076 of SEQ ID NO: 1. In still another aspect of this embodiment, a BoNT/B peptide composition comprises a BoNT/B peptide comprising amino acid sequence is 974-992 of SEQ ID NO:1, a BoNT/B peptide comprising amino acid sequence is 736-754 of SEQ ID NO: 1 and a BoNT/B peptide comprising amino acid sequence is 890-908 of SEQ ID NO: 1.

In still another aspect of this embodiment, a BoNT/B peptide composition comprises a BoNT/B peptide comprising amino acid sequence is 974-984 of SEQ ID NO:1, a BoNT/B peptide comprising amino acid sequence is 735-745 of SEQ ID NO: 1 and a BoNT/B peptide comprising amino acid sequence is 1065-1075 of SEQ ID NO: 1. In still another aspect of this embodiment, a BoNT/B peptide composition comprises a BoNT/B peptide comprising amino acid sequence is 974-984 of SEQ ID NO:1, a BoNT/B peptide comprising amino acid sequence is 735-745 of SEQ ID NO: 1 and a BoNT/B peptide comprising amino acid sequence is 895-905 of SEQ ID NO: 1.

In another embodiment, a BoNT/B peptide composition comprises one or more different BoNT/B peptides derived from a non-naturally occurring BoNT/B. In aspects of this embodiment, the non-naturally occurring BoNT/B is a conservative BoNT/B variant or a non-conservative BoNT/B variant.

In aspects of this embodiment, a BoNT/B peptide composition comprises one or more different BoNT/B peptides derived from a conservative BoNT/B variant, two or more different BoNT/B peptides derived from a conservative BoNT/B variant, three or more different BoNT/B peptides derived from a conservative BoNT/B variant, four or more different BoNT/B peptides derived from a conservative BoNT/B variant, five or more different BoNT/B peptides derived from a conservative BoNT/B variant, six or more different BoNT/B peptides derived from a conservative BoNT/B variant, seven or more different BoNT/B peptides derived from a conservative BoNT/B variant, eight or more different BoNT/B peptides derived from a conservative BoNT/B variant, nine or more different BoNT/B peptides derived from a conservative BoNT/B variant, ten or more different BoNT/B peptides derived from a conservative BoNT/B variant, 15 or more different BoNT/B peptides derived from a conservative BoNT/B variant or 20 or more different BoNT/B peptides derived from a conservative BoNT/B variant.

In aspects of this embodiment, a BoNT/B peptide composition comprises one or more BoNT/B peptides selected from the group consisting of a BoNT/B peptide comprising 1-4 conservative amino acid substitutions to amino acids 610-628 of SEQ ID NO: 1, a BoNT/B peptide comprising 1-4 conservative amino acid substitutions to amino acids 736-754 of SEQ ID NO: 1, a BoNT/B peptide comprising 1-4 conservative amino acid substitutions to amino acids 778-796 of SEQ ID NO: 1, a BoNT/B peptide comprising 1-4 conservative amino acid substitutions to amino acids 820-838 of SEQ ID NO: 1, a BoNT/B peptide comprising 1-4 conservative amino acid substitutions to amino acids 862-880 of SEQ ID NO: 1, a BoNT/B peptide comprising 1-4 conservative amino acid substitutions to amino acids 890-908 of SEQ ID NO: 1, a BoNT/B peptide comprising 1-4 conservative amino acid substitutions to amino acids 918-936 of SEQ ID NO: 1, a BoNT/B peptide comprising 1-4 conservative amino acid substitutions to amino acids 932-950 of SEQ ID NO: 1, a BoNT/B peptide comprising 1-4 conservative amino acid substitutions to amino acids 960-978 of SEQ ID NO: 1, a BoNT/B peptide comprising 1-4 conservative amino acid substitutions to amino acids 974-992 of SEQ ID NO: 1, a BoNT/B peptide comprising 1-4 conservative amino acid substitutions to amino acids 1030-1048 of SEQ ID NO: 1, a BoNT/B peptide comprising 1-4 conservative amino acid substitutions to amino acids 1058-1076 of SEQ ID NO: 1, a BoNT/B peptide comprising 1-4 conservative amino acid substitutions to amino acids 1072-1090 of SEQ ID NO: 1, a BoNT/B peptide comprising 1-4 conservative amino acid substitutions to amino acids 1254-1272 of SEQ ID NO: 1, and a BoNT/B peptide comprising 1-4 conservative amino acid substitutions to amino acids 1268-1291 of SEQ ID NO: 1.

In aspects of this embodiment, a BoNT/B peptide composition comprises one or more BoNT/B peptides selected from the group consisting of a BoNT/B peptide comprising 1-4 conservative amino acid substitutions to amino acids 736-754 of SEQ ID NO: 1, a BoNT/B peptide comprising 1-4 conservative amino acid substitutions to amino acids 778-796 of SEQ ID NO: 1, a BoNT/B peptide comprising 1-4 conservative amino acid substitutions to amino acids 890-908 of SEQ ID NO: 1, a BoNT/B peptide comprising 1-4 conservative amino acid substitutions to amino acids 932-950 of SEQ ID NO: 1, a BoNT/B peptide comprising 1-4 conservative amino acid substitutions to amino acids 974-992 of SEQ ID NO: 1, a BoNT/B peptide comprising 1-4 conservative amino acid substitutions to amino acids 1058-1076 of SEQ ID NO: 1, and a BoNT/B peptide comprising 1-4 conservative amino acid substitutions to amino acids 1268-1291 of SEQ ID NO: 1.

In further aspects of this embodiment, a BoNT/B peptide composition comprises one or more BoNT/B peptides selected from the group consisting of a BoNT/B peptide comprising 1-4 conservative amino acid substitutions to amino acids 616-626 of SEQ ID NO: 1, a BoNT/B peptide comprising 1-4 conservative amino acid substitutions to amino acids 735-745 of SEQ ID NO: 1, a BoNT/B peptide comprising 1-4 conservative amino acid substitutions to amino acids 778-789 of SEQ ID NO: 1, a BoNT/B peptide comprising 1-4 conservative amino acid substitutions to amino acids 867-877 of SEQ ID NO: 1, a BoNT/B peptide comprising 1-4 conservative amino acid substitutions to amino acids 895-905 of SEQ ID NO: 1, a BoNT/B peptide comprising 1-4 conservative amino acid substitutions to amino acids 929-939 of SEQ ID NO: 1, a BoNT/B peptide comprising 1-4 conservative amino acid substitutions to amino acids 974-984 of SEQ ID NO: 1, a BoNT/B peptide comprising 1-4 conservative amino acid substitutions to amino acids 1039-1049 of SEQ ID NO: 1, a BoNT/B peptide comprising 1-4 conservative amino acid substitutions to amino acids 1065-1075 of SEQ ID NO: 1 or a BoNT/B peptide comprising 1-4 conservative amino acid substitutions to amino acids 1269-1281 of SEQ ID NO: 1.

In further aspects of this embodiment, a BoNT/B peptide composition comprises one or more different BoNT/B peptides derived from a non-conservative BoNT/B variant, two or more different BoNT/B peptides derived from a non-conservative BoNT/B variant, three or more different BoNT/B peptides derived from a non-conservative BoNT/B variant, four or more different BoNT/B peptides derived from a non-conservative BoNT/B variant, five or more different BoNT/B peptides derived from a non-conservative BoNT/B variant, six or more different BoNT/B peptides derived from a non-conservative BoNT/B variant, seven or more different BoNT/B peptides derived from a non-conservative BoNT/B variant, eight or more different BoNT/B peptides derived from a non-conservative BoNT/B variant, nine or more different BoNT/B peptides derived from a non-conservative BoNT/B variant, ten or more different BoNT/B peptides derived from a non-conservative BoNT/B variant, 15 or more different BoNT/B peptides derived from a non-conservative BoNT/B variant or 20 or more different BoNT/B peptides derived from a non-conservative BoNT/B variant.

In further aspects of this embodiment, a BoNT/B peptide composition comprises one or more BoNT/B peptides selected from the group consisting of a BoNT/B peptide comprising 1-4 non-conservative amino acid substitutions to amino acids 610-628 of SEQ ID NO: 1, a BoNT/B peptide comprising 1-4 non-conservative amino acid substitutions to amino acids 736-754 of SEQ ID NO: 1, a BoNT/B peptide comprising 1-4 non-conservative amino acid substitutions to amino acids 778-796 of SEQ ID NO: 1, a BoNT/B peptide comprising 1-4 non-conservative amino acid substitutions to amino acids 820-838 of SEQ ID NO: 1, a BoNT/B peptide comprising 1-4 non-conservative amino acid substitutions to amino acids 862-880 of SEQ ID NO: 1, a BoNT/B peptide comprising 1-4 non-conservative amino acid substitutions to amino acids 890-908 of SEQ ID NO: 1, a BoNT/B peptide comprising 1-4 non-conservative amino acid substitutions to amino acids 918-936 of SEQ ID NO: 1, a BoNT/B peptide comprising 1-4 non-conservative amino acid substitutions to amino acids 932-950 of SEQ ID NO: 1, a BoNT/B peptide comprising 1-4 non-conservative amino acid substitutions to amino acids 960-978 of SEQ ID NO: 1, a BoNT/B peptide comprising 1-4 non-conservative amino acid substitutions to amino acids 974-992 of SEQ ID NO: 1, a BoNT/B peptide comprising 1-4 non-conservative amino acid substitutions to amino acids 1030-1048 of SEQ ID NO: 1, a BoNT/B peptide comprising 1-4 non-conservative amino acid substitutions to amino acids 1058-1076 of SEQ ID NO: 1, a BoNT/B peptide comprising 1-4 non-conservative amino acid substitutions to amino acids 1072-1090 of SEQ ID NO: 1, a BoNT/B peptide comprising 1-4 non-conservative amino acid substitutions to amino acids 1254-1272 of SEQ ID NO: 1, and a BoNT/B peptide comprising 1-4 non-conservative amino acid substitutions to amino acids 1268-1291 of SEQ ID NO: 1.

In further aspects of this embodiment, a BoNT/B peptide composition comprises one or more BoNT/B peptides selected from the group consisting of a BoNT/B peptide comprising 1-4 non-conservative amino acid substitutions to amino acids 736-754 of SEQ ID NO: 1, a BoNT/B peptide comprising 1-4 non-conservative amino acid substitutions to amino acids 778-796 of SEQ ID NO: 1, a BoNT/B peptide comprising 1-4 non-conservative amino acid substitutions to amino acids 890-908 of SEQ ID NO: 1, a BoNT/B peptide comprising 1-4 non-conservative amino acid substitutions to amino acids 932-950 of SEQ ID NO: 1, a BoNT/B peptide comprising 1-4 non-conservative amino acid substitutions to amino acids 974-992 of SEQ ID NO: 1, a BoNT/B peptide comprising 1-4 non-conservative amino acid substitutions to amino acids 1058-1076 of SEQ ID NO: 1, and a BoNT/B peptide comprising 1-4 non-conservative amino acid substitutions to amino acids 1268-1291 of SEQ ID NO: 1.

In further other aspects of this embodiment, a BoNT/B peptide composition comprises one or more BoNT/B peptides selected from the group consisting of a BoNT/B peptide comprising 1-4 non-conservative amino acid substitutions to amino acids 616-626 of SEQ ID NO: 1, a BoNT/B peptide comprising 1-4 non-conservative amino acid substitutions to amino acids 735-745 of SEQ ID NO: 1, a BoNT/B peptide comprising 1-4 non-conservative amino acid substitutions to amino acids 778-789 of SEQ ID NO: 1, a BoNT/B peptide comprising 1-4 non-conservative amino acid substitutions to amino acids 867-877 of SEQ ID NO: 1, a BoNT/B peptide comprising 1-4 non-conservative amino acid substitutions to amino acids 895-905 of SEQ ID NO: 1, a BoNT/B peptide comprising 1-4 non-conservative amino acid substitutions to amino acids 929-939 of SEQ ID NO: 1, a BoNT/B peptide comprising 1-4 non-conservative amino acid substitutions to amino acids 974-984 of SEQ ID NO: 1, a BoNT/B peptide comprising 1-4 non-conservative amino acid substitutions to amino acids 1039-1049 of SEQ ID NO: 1, a BoNT/B peptide comprising 1-4 non-conservative amino acid substitutions to amino acids 1065-1075 of SEQ ID NO: 1 or a BoNT/B peptide comprising 1-4 non-conservative amino acid substitutions to amino acids 1269-1281 of SEQ ID NO: 1.

In still other aspects of this embodiment, a BoNT/B peptide composition comprises one or more different BoNT/B peptides each peptide comprising a different BoNT/B immunoreactive fragment, two or more different BoNT/B peptides each peptide comprising a different BoNT/B immunoreactive fragment, three or more different BoNT/B peptides each peptide comprising a different BoNT/B immunoreactive fragment, four or more different BoNT/B peptides each peptide comprising a different BoNT/B immunoreactive fragment, five or more different BoNT/B peptides each peptide comprising a different BoNT/B immunoreactive fragment, six or more different BoNT/B peptides each peptide comprising a different BoNT/B immunoreactive fragment, seven or more different BoNT/B peptides each peptide comprising a different BoNT/B immunoreactive fragment, eight or more different BoNT/B peptides each peptide comprising a different BoNT/B immunoreactive fragment, nine or more different BoNT/B peptides each peptide comprising a different BoNT/B immunoreactive fragment, ten or more different BoNT/B peptides each peptide comprising a different BoNT/B immunoreactive fragment, 15 or more different BoNT/B peptides each peptide comprising a different BoNT/B immunoreactive fragment, 20 or more different BoNT/B peptides each peptide comprising a different BoNT/B immunoreactive fragment, 25 or more different BoNT/B peptides each peptide comprising a different BoNT/B immunoreactive fragment or 30 or more different BoNT/B peptides each peptide comprising a different BoNT/B immunoreactive fragment.

In other aspects of this embodiment, a BoNT/B peptide composition comprises one or more BoNT/B peptides, each peptide comprising a different BoNT/B immunoreactive fragment selected from the group consisting of at least six consecutive amino acids of 610-628 of SEQ ID NO: 1, at least six consecutive amino acids of 736-754 of SEQ ID NO: 1, at least six consecutive amino acids of 778-796 of SEQ ID NO: 1, at least six consecutive amino acids of 820-838 of SEQ ID NO: 1, at least six consecutive amino acids of 862-880 of SEQ ID NO: 1, at least six consecutive amino acids of 890-908 of SEQ ID NO: 1, at least six consecutive amino acids of 918-936 of SEQ ID NO: 1, at least six consecutive amino acids of 932-950 of SEQ ID NO: 1, at least six consecutive amino acids of 960-978 of SEQ ID NO: 1, at least six consecutive amino acids of 974-992 of SEQ ID NO: 1, at least six consecutive amino acids of 1030-1048 of SEQ ID NO: 1, at least six consecutive amino acids of 1058-1076 of SEQ ID NO: 1, at least six consecutive amino acids of 1072-1090 of SEQ ID NO: 1, at least six consecutive amino acids of 1254-1272 of SEQ ID NO: 1, or at least six consecutive amino acids of 1268-1291 of SEQ ID NO: 1. In other aspects of this embodiment, a BoNT/B peptide composition comprises two or more BoNT/B peptides, each peptide comprising a different BoNT/B immunoreactive fragment selected from the group consisting of at least six consecutive amino acids of 616-626 of SEQ ID NO: 1, at least six consecutive amino acids of 735-745 of SEQ ID NO: 1, at least six consecutive amino acids of 778-789 of SEQ ID NO: 1, at least six consecutive amino acids of 867-877 of SEQ ID NO: 1, at least six consecutive amino acids of 895-905 of SEQ ID NO: 1, at least six consecutive amino acids of 929-939 of SEQ ID NO: 1, at least six consecutive amino acids of 974-984 of SEQ ID NO: 1, at least six consecutive amino acids of 1039-1049 of SEQ ID NO: 1, at least six consecutive amino acids of 1065-1075 of SEQ ID NO: 1 or at least six consecutive amino acids of 1269-1281 of SEQ ID NO: 1.

In another embodiment, a BoNT/B peptide composition comprises one or more BoNT/B peptides, each peptide comprising a different BoNT/B immunoreactive fragment selected from the group consisting of at least six non-consecutive amino acids of 610-628 of SEQ ID NO: 1, at least six non-consecutive amino acids of 736-754 of SEQ ID NO: 1, at least six non-consecutive amino acids of 778-796 of SEQ ID NO: 1, at least six non-consecutive amino acids of 820-838 of SEQ ID NO: 1, at least six non-consecutive amino acids of 862-880 of SEQ ID NO: 1, at least six non-consecutive amino acids of 890-908 of SEQ ID NO: 1, at least six non-consecutive amino acids of 918-936 of SEQ ID NO: 1, at least six non-consecutive amino acids of 932-950 of SEQ ID NO: 1, at least six non-consecutive amino acids of 960-978 of SEQ ID NO: 1, at least six non-consecutive amino acids of 974-992 of SEQ ID NO: 1, at least six non-consecutive amino acids of 1030-1048 of SEQ ID NO: 1, at least six non-consecutive amino acids of 1058-1076 of SEQ ID NO: 1, at least six non-consecutive amino acids of 1072-1090 of SEQ ID NO: 1, at least six non-consecutive amino acids of 1254-1272 of SEQ ID NO: 1, or at least six non-consecutive amino acids of 1268-1291 of SEQ ID NO: 1. In other aspects of this embodiment, a BoNT/B peptide composition comprises two or more BoNT/B peptides, each peptide comprising a different BoNT/B immunoreactive fragment selected from the group consisting of at least six non-consecutive amino acids of 616-626 of SEQ ID NO: 1, at least six non-consecutive amino acids of 735-745 of SEQ ID NO: 1, at least six non-consecutive amino acids of 778-789 of SEQ ID NO: 1, at least six non-consecutive amino acids of 867-877 of SEQ ID NO: 1, at least six non-consecutive amino acids of 895-905 of SEQ ID NO: 1, at least six non-consecutive amino acids of 929-939 of SEQ ID NO: 1, at least six non-consecutive amino acids of 974-984 of SEQ ID NO: 1, at least six non-consecutive amino acids of 1039-1049 of SEQ ID NO: 1, at least six non-consecutive amino acids of 1065-1075 of SEQ ID NO: 1 or at least six non-consecutive amino acids of 1269-1281 of SEQ ID NO: 1.

It is also envisioned that any and all combinations of BoNT/B peptides disclosed in the specification can be useful in a BoNT/B peptide composition, including, without limitation, a BoNT/B peptide derived from a naturally occurring BoNT/B, such as, e.g., the BoNT/B of SEQ ID NO: 1, SEQ ID NO: 3, SEQ ID NO: 5, SEQ ID NO: 7, SEQ ID NO: 9, SEQ ID NO: 11 or SEQ ID NO: 13, a BoNT/B isoform or a BoNT/B subtype; and a BoNT/B peptide derived from a non-naturally occurring BoNT/B, such as, e.g., a conservative BoNT/B variant, a non-conservative BoNT/B variant and a chimeric BoNT/B peptide. Thus, aspects of this embodiment, a BoNT/B peptide composition comprises, e.g., one or more BoNT/B peptides derived from a naturally occurring BoNT/B and one or more BoNT/B peptides derived from a non-naturally occurring BoNT/B. In other aspects of this embodiment, a BoNT/B peptide composition comprises, e.g., one or more BoNT/B peptides comprising one or more BoNT/B peptides derived from SEQ ID NO: 1 and one or more BoNT/B peptides derived from a conservative BoNT/B variant; one or more BoNT/B peptides of SEQ ID NO: 1 and one or more BoNT/B peptides derived from a non-conservative variant; one or more BoNT/B peptides derived from a conservative BoNT/B variant and one or more BoNT/B peptides derived from a non-conservative BoNT/B variant; and one or more BoNT/B peptides derived from SEQ ID NO: 1, one or more BoNT/B peptides derived from a conservative BoNT/B variant and one or more BoNT/B peptides derived from a non-conservative BoNT/B variant.

Tolerance is an active antigen-dependent process that occurs in an individual in response to the antigen that results from a previous exposure to the same antigen. Generally speaking, the production of antibodies by an immune response occurs by a two-step process. Initially, B lymphocytes migrating through the lymphoid tissue are exposed to an antigen whereby these cells become partially activated. Subsequently, if a partially activated B cell encounters a T cell that has also been activated by the same antigen, antibodies against that antigen are produced. If the B cell does not receive the appropriate signal from the corresponding T cell, it will become inactive or die. Immune tolerance is a natural mechanism that eliminates development of B cells that target "self," rather than foreign antigens. Therapeutic methods using tolerogizing compositions can exploit this immune tolerance system. For example, binding of a tolerogizing composition to a specific B cell is thought to stop production of pathogenic antibodies by causing the inactivatation or death of these pathogenic B cells. In general, a tolerogizing composition that can be used to tolerize B cells in an antigen-specific manner lacks the ability to activate T cells, but retains the ability to bind immune B cells. Therefore, an individual suffering from an immune response to a particular antigen can be treated with a tolerogizing composition and become "tolerized" to that particular antigen.

The present invention provides, in part, a tolerogizing composition comprising a BoNT/B peptide operably linked to a tolerogizing agent. Such tolerogizing compositions are useful for inducing specific immunological non-reactivity (tolerance) to a botulinum toxin antigen. It is envisioned that any of the BoNT/B peptides disclosed in the present specification can be useful in a tolerogizing composition, with the proviso that the BoNT/B peptide induces a specific immunological non-reactivity (tolerance) to a botulinum toxin antigen. Non-limiting examples include a BoNT/B peptide derived from a naturally occurring BoNT/B, such as, e.g., the BoNT/B of SEQ ID NO: 1, SEQ ID NO: 3, SEQ ID NO: 5, SEQ ID NO: 7, SEQ ID NO: 9, SEQ ID NO: 11 or SEQ ID NO: 13, a BoNT/B isoform or a BoNT/B subtype; and a BoNT/B peptide derived from a non-naturally occurring BoNT/B, such as, e.g., a conservative BoNT/B variant, a non-conservative BoNT/B variant and a chimeric BoNT/B peptide. BoNT/B peptides disclosed in the present specification can be selected, e.g., depending on immunological factors, such as potency of the peptide in inducing a tolerogizing response, and technical factors, such as chemical synthesis yields. It is also understood that the two or more different BoNT/B peptides can be provided separately or as part of a compound molecule such as a chimeric BoNT/B peptide.

It is envisioned that a wide variety of tolerogizing agents can be useful in a tolerogizing composition disclosed in the present specification. As used herein, the term "tolerogizing agent" means a molecule, compound or polymer that causes, promotes or enhances tolerogenic activity when combined with a BoNT/B peptide disclosed in the present specification. As non-limiting examples, a tolerogizing agent can be a liquid, solid, or emulsion, depending, for example, on the route of administration and physical properties of the tolerogizing agent. A tolerogizing agent is operably linked to a BoNT/B peptide disclosed in the present specification. As used herein, the term "operably linked" when used in reference to a tolerogizing composition means to covalently attach a tolerogizing agent to a BoNT/B peptide in a manner that renders the peptide tolerogenic. Such tolerogizing agents can be operably linked to a BoNT/B peptide, for example, as described in M. Zouhair Atassi & Tetsuo Ashizawa, PVA or PEG Conjugates of Peptides for Epitope-Specific Immunosuppression, U.S. Pat. No. 6,048,529 (Apr. 11, 2000); Emilio Barbera-Guillem & M. Bud Nelson, Compositions and Methods for Tolerization in Immune Complex-Mediated Disease Progression, U.S. Pat. No. 6,245,752 (Jun. 12, 2001); and Edward Jess Victoria et al., APL Immunoreactive Peptides, Conjugates Thereof and Methods of Treatment for APL Antibody-Mediated Pathologies, U.S. Pat. No. 6,410,775 (Jun. 25, 2002). A variety of tolerogizing agents are useful in the invention including, without limitation, polyethylene glycol (PEG), monomethoxypolyethylene glycol (mPEG), and polyvinyl alcohol (PVA). Additional molecules are also known in the art to cause, promote or enhance tolerance, see, e.g., Paul A. Barstad, & Gilbert M. Iverson, Composition For Inducing Humoral Anergy to an Immunogen Comprising a T Cell Epitope-Deficient Analog of the Immunogen Conjugated to a Nonimmunogenic Carrier, U.S. Pat. No. 5,268,454 (Dec. 7, 1993); M. Zouhair Atassi & Tetsuo Ashizawa, PVA or PEG Conjugates of Peptides for Epitope-Specific Immunosuppression, U.S. Pat. No. 6,048,529 (Apr. 11, 2000); and Stephen M. Coutts et al., Composition for Inducing Humoral Anergy to an Immunogen Comprising a T Cell Epitope-Deficient Analog of the Immunogen Conjugated to a Nonimmunogenic Valency Platform Molecule, U.S. Pat. No. 6,060,056 (May 9, 2000).

As used herein, the term "tolerogizing response" when used in reference to a tolerogizing composition comprising a BoNT/B peptide means a BoNT/B disclosed in the present specification that has tolerogenic activity as defined by the ability either alone, or in combination with one or more other molecules, to produce a decreased immunological response to an anti-BoNT antibody. A BoNT/B peptide exhibiting a tolerogizing response can be identified using any of a variety of assays, including in vitro assays such as T-cell proliferation or cytokine secretion assays and in vivo assays such as the induction of tolerance in animal models of botulinum toxicity. T-cell proliferation assays, for example, are well recognized in the art as predictive of tolerogenic activity, see, e.g., H. Miyahara et al., *Identification and Characterization Of A Major Tolerogenic T-Cell Epitope of Type II Collagen That Suppresses Arthritis in B10.RIII Mice*, 86(1) IMMUNOLOGY 110-115 (1995); and Knut E. A. Lundin et al, *Gliadin-Specific, HLA-DQ(Alpha 1*0501,Beta 1*0201) Restricted T Cells Isolated From the Small Intestinal Mucosa of Celiac Disease Patients*, 178(1) J. EXP. MED. 187-196 (1993). A T-cell proliferation assay can be performed, for example, by culturing T-cells with irradiated antigen-presenting cells, such as normal spleen cells, in microtiter wells for 3 days with varying concentrations of the BoNT/B peptide to be assayed; adding $^3$H-thymidine; and measuring incorporation of $^3$H-thymidine into DNA.

A BoNT/B peptide exhibiting a tolerogizing response can also be identified using a T-cell cytokine secretion assay known in the art. In such an assay, T cells can be cultured, for example, with irradiated antigen-presenting cells in microtiter wells with varying concentrations of the fragment of interest and, after three days, the culture supernatants can be assayed for IL-2, IL-4 or IFN-γ as described in C. Czerkinsky et al., *Detection of Human Cytokine-Secreting Cells in Distinct Anatomical Compartments*, 119 IMMUNOL. REV. 5-22 (1991).

A BoNT/B peptide exhibiting a tolerogizing response can additionally be identified by its ability to induce tolerance in vivo, as indicated by a decreased immunological response, which can be a decreased T-cell response, such as a decreased proliferative response or cytokine secretion response as described above, or a decreased antibody titer to the antigen. A neonatal or adult mouse can be tolerized with a fragment of a BoNT/B peptide, and a T-cell response or anti-BoNT/B antibody titer can be assayed after challenging by immunization. As an example, a neonatal mouse can be tolerized within 48 hours of birth by intraperitoneal administration of about 100 μg of a fragment of a BoNT/B peptide emulsified with incomplete Freund's adjuvant and subsequently immunized with BoNT/B at about 8 weeks of age, see, for example, Miyahara et al., supra, 1995. An adult mouse can be tolerized intravenously with about 0.33 mg of a fragment of a BoNT/B peptide, administered daily for three days (total dose 1 mg), and immunized one week later with BoNT/B. A decreased T-cell response, such as decreased proliferation or cytokine secretion, which indicates tolerogenic activity, can be measured using T-cells harvested 10 days after immunization. In addition, a decreased anti-BoNT/B antibody titer, which also indicates tolerogenic activity, can be assayed using blood harvested 4-8 weeks after immunization. Methods for assaying a T-cell response or anti-BoNT/B antibody titer are described above and are well known in the art.

Several well-accepted models of botulinum toxicity can be useful in identifying a BoNT/B peptide exhibiting a tolerogizing response. Such models include, without limitation, rodent, rabbit and monkey models of foodborne botulism, rodent and chicken models of infant botulism and rodent models of wound botulism, which are described, for example, in Simpson (Ed.) *Botulinum Neurotoxin and Tetanus Toxin* Academic Press, Inc., San Diego, Calif. (1989). The skilled person understands that these and a variety of other well known in vitro and in vivo assays can be useful for identifying a tolerogenic fragment of a BoNT/B peptide.

In is envisioned that a tolerogizing composition can also optionally comprises one or more adjuvants. As used herein, the term "adjuvant" when used in reference to a tolerogizing composition means any substance or mixture of substances that promotes or enhances tolerogenic activity. A tolerogizing adjuvant can, for example, serve to increase the solubility of a tolerogizing composition. The use of tolerogizing adjuvants in a tolerogizing composition is well known. These tolerogizing adjuvants are diverse in nature. They may, e.g., consist of liposomes, oily phases, including, without limitation, the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); and lipopolysaccharide (LPS). Such adjuvants are generally used in the form of an emulsion with an aqueous phase, or, more commonly, may consist of water-insoluble inorganic salts. These inorganic salts may consist, for example, of aluminum hydroxide, zinc sulfate, colloidal iron hydroxide, calcium phosphate or calcium chloride. Aluminum hydroxide $(Al(OH)_3)$ is a commonly used adjuvant. Currently, the only FDA-approved adjuvant for use in humans is aluminum salts (Alum) which are used to "depot" antigens by precipitation of the antigens. Adjuvants provided above are merely exemplary. In fact, any tolerogizing adjuvant may be used in a tolerogizing composition disclosed in the present specification as long as the adjuvant satisfies the requisite characteristics that are necessary for practicing the present invention.

Thus, in an embodiment, a tolerogizing composition comprises a BoNT/B peptide disclosed in the present specification operably linked to a tolerogizing agent. In another embodiment, a tolerogizing composition can comprise a plurality of different BoNT/B peptides disclosed in the present specification each BoNT/B peptide operably linked to a tolerogizing agent. Thus, in aspects of this embodiment, a tolerogizing composition comprises one or more different BoNT/B peptides each BoNT/B peptide operably linked to a tolerogizing agent, two or more different BoNT/B peptides each BoNT/B peptide operably linked to a tolerogizing agent, three or more different BoNT/B peptides each BoNT/B peptide operably linked to a tolerogizing agent, four or more different BoNT/B peptides each BoNT/B peptide operably linked to a tolerogizing agent, five or more different BoNT/B peptides each BoNT/B peptide operably linked to a tolerogizing agent, six or more different BoNT/B peptides each BoNT/B peptide operably linked to a tolerogizing agent, seven or more different BoNT/B peptides each BoNT/B peptide operably linked to a tolerogizing agent, eight or more different BoNT/B peptides each BoNT/B peptide operably linked to a tolerogizing agent, nine or more different BoNT/B peptides each BoNT/B peptide operably linked to a tolerogizing agent, ten or more different BoNT/B peptides each BoNT/B peptide operably linked to a tolerogizing agent, 15 or more different BoNT/B peptides each BoNT/B peptide operably linked to a tolerogizing agent or 20 or more different BoNT/B peptides each BoNT/B peptide operably linked to a tolerogizing agent.

In aspects of this embodiment, a tolerogizing composition comprises one or more different BoNT/B peptides comprising an amino acid sequence selected from the group consisting of amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, a tolerogizing composition comprises two or more amino acid sequences selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In another aspect of this embodiment, a tolerogizing composition comprises a BoNT/B peptide operably linked to a tolerogizing agent, the BoNT/B peptide comprising an amino acid sequence selected from the group consisting of amino acids amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In another aspect of this embodiment, a tolerogizing composition comprises a BoNT/B peptide operably linked to a tolerogizing agent, the BoNT/B peptide comprising an amino acid sequence selected from the group consisting of amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 932-950 of SEQ ID NO: 1, amino acids 932-950 of SEQ ID NO: 5, amino acids 974-992 of SEQ ID NO: 1, amino acids 974-992 of SEQ ID NO: 3, amino acids 974-992 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In another aspect of this embodiment, a tolerogizing composition comprises a BoNT/B peptide operably linked to a tolerogizing agent, the BoNT/B peptide comprising an amino acid sequence selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In yet another aspect of this embodiment, a tolerogizing composition comprises a BoNT/B peptide comprising amino acid sequence is 974-992 of SEQ ID NO: 1 operably linked to a tolerogizing agent and a BoNT/B peptide comprising amino acid sequence is 736-754 of SEQ ID NO: 1 operably linked to a tolerogizing agent. In yet another aspect of this embodiment, a tolerogizing composition comprises a BoNT/B peptide comprising amino acid sequence is 974-992 of SEQ ID NO: 1 operably linked to a tolerogizing agent and a BoNT/B peptide comprising amino acid sequence is 1058-1076 of SEQ ID NO: 1 operably linked to a tolerogizing agent. In yet another aspect of this embodiment, a tolerogizing composition comprises a BoNT/B peptide comprising amino acid sequence is 974-992 of SEQ ID NO: 1 operably linked to a tolerogizing agent and a BoNT/B peptide comprising amino acid sequence is 890-908 of SEQ ID NO: 1 operably linked to a tolerogizing agent.

In yet another aspect of this embodiment, a tolerogizing composition comprises a BoNT/B peptide comprising amino acid sequence is 974-984 of SEQ ID NO: 1 operably linked to a tolerogizing agent and a BoNT/B peptide comprising amino acid sequence is 735-745 of SEQ ID NO: 1 operably linked to a tolerogizing agent. In yet another aspect of this embodiment, a tolerogizing composition comprises a BoNT/B peptide comprising amino acid sequence is 974-984 of SEQ ID NO: 1 operably linked to a tolerogizing agent and a BoNT/B peptide comprising amino acid sequence is 1065-1075 of SEQ ID NO: 1 operably linked to a tolerogizing agent. In yet another aspect of this embodiment, a tolerogizing composition comprises a BoNT/B peptide comprising amino acid sequence is 974-984 of SEQ ID NO: 1 operably linked to a tolerogizing agent and a BoNT/B peptide comprising amino acid sequence is 895-905 of SEQ ID NO: 1 operably linked to a tolerogizing agent.

In still another aspect of this embodiment, a tolerogizing composition comprises a BoNT/B peptide comprising amino acid sequence is 974-992 of SEQ ID NO: 1 operably linked to a tolerogizing agent, a BoNT/B peptide comprising amino acid sequence is 736-754 of SEQ ID NO: 1 operably linked to a tolerogizing agent and a BoNT/B peptide comprising amino acid sequence is 1058-1076 of SEQ ID NO: 1 operably linked to a tolerogizing agent. In still another aspect of this embodiment, a tolerogizing composition comprises a BoNT/B peptide comprising amino acid sequence is 974-992 of SEQ ID NO: 1 operably linked to a tolerogizing agent, a BoNT/B peptide comprising amino acid sequence is 736-754 of SEQ ID NO: 1 operably linked to a tolerogizing agent and a BoNT/B peptide comprising amino acid sequence is 890-908 of SEQ ID NO: 1 operably linked to a tolerogizing agent.

In still another aspect of this embodiment, a tolerogizing composition comprises a BoNT/B peptide comprising amino acid sequence is 974-984 of SEQ ID NO: 1 operably linked to a tolerogizing agent, a BoNT/B peptide comprising amino acid sequence is 735-745 of SEQ ID NO: 1 operably linked to a tolerogizing agent and a BoNT/B peptide comprising amino acid sequence is 1065-1075 of SEQ ID NO: 1 operably linked to a tolerogizing agent. In still another aspect of this embodiment, a tolerogizing composition comprises a BoNT/B peptide comprising amino acid sequence is 974-984 of SEQ ID NO: 1 operably linked to a tolerogizing agent, a BoNT/B peptide comprising amino acid sequence is 735-745 of SEQ ID NO: 1 operably linked to a tolerogizing agent and a BoNT/B peptide comprising amino acid sequence is 895-905 of SEQ ID NO: 1 operably linked to a tolerogizing agent.

In another embodiment, a tolerogizing composition comprises one or more different BoNT/B peptides derived from a non-naturally occurring BoNT/B, each BoNT/B peptide operably linked to a tolerogizing agent. In aspects of this embodiment, the non-naturally occurring BoNT/B is a conservative BoNT/B variant or a non-conservative BoNT/B variant.

In aspects of this embodiment, a tolerogizing composition comprises one or more different BoNT/B peptides derived from a conservative BoNT/B variant, two or more different BoNT/B peptides derived from a conservative BoNT/B variant, three or more different BoNT/B peptides derived from a conservative BoNT/B variant, four or more different BoNT/B peptides derived from a conservative BoNT/B variant, five or more different BoNT/B peptides derived from a conservative BoNT/B variant, six or more different BoNT/B peptides derived from a conservative BoNT/B variant, seven or more different BoNT/B peptides derived from a conservative BoNT/B variant, eight or more different BoNT/B peptides derived from a conservative BoNT/B variant, nine or more different BoNT/B peptides derived from a conservative BoNT/B variant, ten or more different BoNT/B peptides derived from a conservative BoNT/B variant, 15 or more different BoNT/B peptides derived from a conservative BoNT/B variant or 20 or more different BoNT/B peptides derived from a conservative BoNT/B variant.

In aspects of this embodiment, a tolerogizing composition comprises one or more BoNT/B peptides selected from the group consisting of a BoNT/B peptide comprising 1-4 conservative amino acid substitutions to amino acids 610-628 of SEQ ID NO: 1 operably linked to a tolerogizing agent, a BoNT/B peptide comprising 1-4 conservative amino acid substitutions to amino acids 736-754 of SEQ ID NO: 1 operably linked to a tolerogizing agent, a BoNT/B peptide comprising 1-4 conservative amino acid substitutions to amino acids 778-796 of SEQ ID NO: 1 operably linked to a tolerogizing agent, a BoNT/B peptide comprising 1-4 conservative amino acid substitutions to amino acids 820-838 of SEQ ID NO: 1 operably linked to a tolerogizing agent, a BoNT/B peptide comprising 1-4 conservative amino acid substitutions to amino acids 862-880 of SEQ ID NO: 1 operably linked to a tolerogizing agent, a BoNT/B peptide comprising 1-4 conservative amino acid substitutions to amino acids 890-908 of SEQ ID NO: 1 operably linked to a tolerogizing agent, a BoNT/B peptide comprising 1-4 conservative amino acid substitutions to amino acids 918-936 of SEQ ID NO: 1 operably linked to a tolerogizing agent, a BoNT/B peptide comprising 1-4 conservative amino acid substitutions to amino acids 932-950 of SEQ ID NO: 1 operably linked to a tolerogizing agent, a BoNT/B peptide comprising 1-4 conservative amino acid substitutions to amino acids 960-978 of SEQ ID NO: 1 operably linked to a tolerogizing agent, a BoNT/B peptide comprising 1-4 conservative amino acid substitutions to amino acids 974-992 of SEQ ID NO: 1 operably linked to a tolerogizing agent, a BoNT/B peptide comprising 1-4 conservative amino acid substitutions to amino acids 1030-1048 of SEQ ID NO: 1 operably linked to a tolerogizing agent, a BoNT/B peptide comprising 1-4 conservative amino acid substitutions to amino acids 1058-1076 of SEQ ID NO: 1 operably linked to a tolerogizing agent, a BoNT/B peptide comprising 1-4 conservative amino acid substitutions to amino acids 1072-1090 of SEQ ID NO: 1 operably linked to a tolerogizing agent, a BoNT/B peptide comprising 1-4 conservative amino acid substitutions to amino acids 1254-1272 of SEQ ID NO: 1 operably linked to a tolerogizing agent, and a BoNT/B peptide comprising 1-4 conservative amino acid substitutions to amino acids 1268-1291 of SEQ ID NO: 1 operably linked to a tolerogizing agent.

In another aspect of this embodiment, a tolerogizing composition comprises one or more BoNT/B peptides derived from a conservative BoNT/B and operably linked to a tolerogizing agent. In aspects of this embodiment, a tolerogizing composition comprises one or more BoNT/B peptides selected from the group consisting of a BoNT/B peptide comprising 1-4 conservative amino acid substitutions to amino acids 736-754 of SEQ ID NO: 1 operably linked to a tolerogizing agent, a BoNT/B peptide comprising 1-4 conservative amino acid substitutions to amino acids 778-796 of SEQ ID NO: 1 operably linked to a tolerogizing agent, a BoNT/B peptide comprising 1-4 conservative amino acid substitutions to amino acids 890-908 of SEQ ID NO: 1 operably linked to a tolerogizing agent, a BoNT/B peptide comprising 1-4 conservative amino acid substitutions to amino acids 932-950 of SEQ ID NO: 1 operably linked to a tolerogizing agent, a BoNT/B peptide comprising 1-4 conservative amino acid substitutions to amino acids 974-992 of SEQ ID NO: 1 operably linked to a tolerogizing agent, a BoNT/B peptide comprising 1-4 conservative amino acid substitutions to amino acids 1058-1076 of SEQ ID NO: 1 operably linked to a tolerogizing agent, and a BoNT/B peptide comprising 1-4 conservative amino acid substitutions to amino acids 1268-1291 of SEQ ID NO: 1 operably linked to a tolerogizing agent.

In further aspects of this embodiment, a tolerogizing composition comprises one or more BoNT/B peptides selected from the group consisting of a BoNT/B peptide comprising 1-4 conservative amino acid substitutions to amino acids 616-626 of SEQ ID NO: 1 operably linked to a tolerogizing agent, a BoNT/B peptide comprising 1-4 conservative amino acid substitutions to amino acids 735-745 of SEQ ID NO: 1 operably linked to a tolerogizing agent, a BoNT/B peptide comprising 1-4 conservative amino acid substitutions to amino acids 778-789 of SEQ ID NO: 1 operably linked to a tolerogizing agent, a BoNT/B peptide comprising 1-4 conservative amino acid substitutions to amino acids 867-877 of SEQ ID NO: 1 operably linked to a tolerogizing agent, a BoNT/B peptide comprising 1-4 conservative amino acid substitutions to amino acids 895-905 of SEQ ID NO: 1 operably linked to a tolerogizing agent, a BoNT/B peptide comprising 1-4 conservative amino acid substitutions to amino acids 929-939 of SEQ ID NO: 1 operably linked to a tolerogizing agent, a BoNT/B peptide comprising 1-4 conservative amino acid substitutions to amino acids 974-984 of SEQ ID NO: 1 operably linked to a tolerogizing agent, a BoNT/B peptide comprising 1-4 conservative amino acid substitutions to amino acids 1039-1049 of SEQ ID NO: 1 operably linked to a tolerogizing agent, a BoNT/B peptide comprising 1-4 conservative amino acid substitutions to amino acids 1065-1075 of SEQ ID NO: 1 operably linked to a tolerogizing agent or a BoNT/B peptide comprising 1-4 conservative amino acid substitutions to amino acids 1269-1281 of SEQ ID NO: 1 operably linked to a tolerogizing agent.

In further aspects of this embodiment, a tolerogizing composition comprises one or more different BoNT/B peptides derived from a non-conservative BoNT/B variant, two or more different BoNT/B peptides derived from a non-conservative BoNT/B variant, three or more different BoNT/B peptides derived from a non-conservative BoNT/B variant, four or more different BoNT/B peptides derived from a non-conservative BoNT/B variant, five or more different BoNT/B peptides derived from a non-conservative BoNT/B variant, six or more different BoNT/B peptides derived from a non-conservative BoNT/B variant, seven or more different BoNT/B peptides derived from a non-conservative BoNT/B variant, eight or more different BoNT/B peptides derived from a non-conservative BoNT/B variant, nine or more different BoNT/B peptides derived from a non-conservative BoNT/B variant, ten or more different BoNT/B peptides derived from a non-conservative BoNT/B variant, 15 or more different BoNT/B peptides derived from a non-conservative BoNT/B variant or 20 or more different BoNT/B peptides derived from a non-conservative BoNT/B variant.

In another aspect of this embodiment, a tolerogizing composition comprises one or more BoNT/B peptides derived from a non-conservative BoNT/B and operably linked to a tolerogizing agent. In further aspects of this embodiment, a tolerogizing composition comprises one or more BoNT/B peptides selected from the group consisting of a BoNT/B peptide comprising 1-4 non-conservative amino acid substitutions to amino acids 610-628 of SEQ ID NO: 1 operably linked to a tolerogizing agent, a BoNT/B peptide comprising 1-4 non-conservative amino acid substitutions to amino acids 736-754 of SEQ ID NO: 1 operably linked to a tolerogizing agent, a BoNT/B peptide comprising 1-4 non-conservative amino acid substitutions to amino acids 778-796 of SEQ ID NO: 1 operably linked to a tolerogizing agent, a BoNT/B peptide comprising 1-4 non-conservative amino acid substitutions to amino acids 820-838 of SEQ ID NO: 1 operably linked to a tolerogizing agent, a BoNT/B peptide comprising 1-4 non-conservative amino acid substitutions to amino acids 862-880 of SEQ ID NO: 1 operably linked to a tolerogizing agent, a BoNT/B peptide comprising 1-4 non-conservative amino acid substitutions to amino acids 890-908 of SEQ ID NO: 1 operably linked to a tolerogizing agent, a BoNT/B peptide comprising 1-4 non-conservative amino acid substitutions to amino acids 918-936 of SEQ ID NO: 1 operably linked to a tolerogizing agent, a BoNT/B peptide comprising 1-4 non-conservative amino acid substitutions to amino acids 932-950 of SEQ ID NO: 1 operably linked to a tolerogizing agent, a BoNT/B peptide comprising 1-4 non-conservative amino acid substitutions to amino acids 960-978 of SEQ ID NO: 1 operably linked to a tolerogizing agent, a BoNT/B peptide comprising 1-4 non-conservative amino acid substitutions to amino acids 974-992 of SEQ ID NO: 1 operably linked to a tolerogizing agent, a BoNT/B peptide comprising 1-4 non-conservative amino acid substitutions to amino acids 1030-1048 of SEQ ID NO: 1 operably linked to a tolerogizing agent, a BoNT/B peptide comprising 1-4 non-conservative amino acid substitutions to amino acids 1058-1076 of SEQ ID NO: 1 operably linked to a tolerogizing agent, a BoNT/B peptide comprising 1-4 non-conservative amino acid substitutions to amino acids 1072-1090 of SEQ ID NO: 1 operably linked to a tolerogizing agent, a BoNT/B peptide comprising 1-4 non-conservative amino acid substitutions to amino acids 1254-1272 of SEQ ID NO: 1 operably linked to a tolerogizing agent, and a BoNT/B peptide comprising 1-4 non-conservative amino acid substitutions to amino acids 1268-1291 of SEQ ID NO: 1 operably linked to a tolerogizing agent.

In further aspects of this embodiment, a tolerogizing composition comprises one or more BoNT/B peptides selected from the group consisting of a BoNT/B peptide comprising 1-4 non-conservative amino acid substitutions to amino acids 736-754 of SEQ ID NO: 1 operably linked to a tolerogizing agent, a BoNT/B peptide comprising 1-4 non-conservative amino acid substitutions to amino acids 778-796 of SEQ ID NO: 1 operably linked to a tolerogizing agent, a BoNT/B peptide comprising 1-4 non-conservative amino acid substitutions to amino acids 890-908 of SEQ ID NO: 1 operably linked to a tolerogizing agent, a BoNT/B peptide comprising 1-4 non-conservative amino acid substitutions to amino acids 932-950 of SEQ ID NO: 1 operably linked to a tolerogizing agent, a BoNT/B peptide comprising 1-4 non-conservative amino acid substitutions to amino acids 974-992 of SEQ ID NO: 1 operably linked to a tolerogizing agent, a BoNT/B peptide comprising 1-4 non-conservative amino acid substitutions to amino acids 1058-1076 of SEQ ID NO: 1 operably linked to a tolerogizing agent, and a BoNT/B peptide comprising 1-4 non-conservative amino acid substitutions to amino acids 1268-1291 of SEQ ID NO: 1 operably linked to a tolerogizing agent.

In further other aspects of this embodiment, a tolerogizing composition comprises one or more BoNT/B peptides selected from the group consisting of a BoNT/B peptide comprising 1-4 non-conservative amino acid substitutions to amino acids 616-626 of SEQ ID NO: 1 operably linked to a tolerogizing agent, a BoNT/B peptide comprising 1-4 non-conservative amino acid substitutions to amino acids 735-745 of SEQ ID NO: 1 operably linked to a tolerogizing agent, a BoNT/B peptide comprising 1-4 non-conservative amino acid substitutions to amino acids 778-789 of SEQ ID NO: 1 operably linked to a tolerogizing agent, a BoNT/B peptide comprising 1-4 non-conservative amino acid substitutions to amino acids 867-877 of SEQ ID NO: 1 operably linked to a tolerogizing agent, a BoNT/B peptide comprising 1-4 non-conservative amino acid substitutions to amino acids 895-905 of SEQ ID NO: 1 operably linked to a tolerogizing agent, a BoNT/B peptide comprising 1-4 non-conservative amino acid substitutions to amino acids 929-939 of SEQ ID NO: 1 operably linked to a tolerogizing agent, a BoNT/B peptide comprising 1-4 non-conservative amino acid substitutions to amino acids 974-984 of SEQ ID NO: 1 operably linked to a tolerogizing agent, a BoNT/B peptide comprising 1-4 non-conservative amino acid substitutions to amino acids 1039-1049 of SEQ ID NO: 1 operably linked to a tolerogizing agent, a BoNT/B peptide comprising 1-4 non-conservative amino acid substitutions to amino acids 1065-1075 of SEQ ID NO: 1 operably linked to a tolerogizing agent or a BoNT/B peptide comprising 1-4 non-conservative amino acid substitutions to amino acids 1269-1281 of SEQ ID NO: 1 operably linked to a tolerogizing agent.

In still other aspects of this embodiment, a tolerogizing composition comprises one or more different BoNT/B peptides each peptide comprising a different BoNT/B immunoreactive fragment, two or more different BoNT/B peptides each peptide comprising a different BoNT/B immunoreactive fragment, three or more different BoNT/B peptides each peptide comprising a different BoNT/B immunoreactive fragment, four or more different BoNT/B peptides each peptide comprising a different BoNT/B immunoreactive fragment, five or more different BoNT/B peptides each peptide comprising a different BoNT/B immunoreactive fragment, six or more different BoNT/B peptides each peptide comprising a different BoNT/B immunoreactive fragment, seven or more different BoNT/B peptides each peptide comprising a different BoNT/B immunoreactive fragment, eight or more different BoNT/B peptides each peptide comprising a different BoNT/B immunoreactive fragment, nine or more different BoNT/B peptides each peptide comprising a different BoNT/B immunoreactive fragment, ten or more different BoNT/B peptides each peptide comprising a different BoNT/B immunoreactive fragment, 15 or more different BoNT/B peptides each peptide comprising a different BoNT/B immunoreactive fragment, 20 or more different BoNT/B peptides each peptide comprising a different BoNT/B immunoreactive fragment, 25 or more different BoNT/B peptides each peptide comprising a different BoNT/B immunoreactive fragment or 30 or more different BoNT/B peptides each peptide comprising a different BoNT/B immunoreactive fragment.

In an aspect of this embodiment, a tolerogizing composition comprises one or more BoNT/B peptides, each BoNT/B peptide operably linked to a tolerogizing agent and each peptide comprising a different BoNT/B immunoreactive fragment capable of reducing an immunogenic response. In other aspects of this embodiment, a tolerogizing composition comprises one or more BoNT/B peptides, each peptide comprising a different BoNT/B immunoreactive fragment, each BoNT/B immunoreactive fragment comprising at least six consecutive amino acids selected from the group consisting of amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, a tolerogizing composition comprises one or more BoNT/B peptides, each peptide comprising a different BoNT/B immunoreactive fragment, each BoNT/B immunoreactive fragment comprising at least six consecutive amino acids selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In still other aspects of this embodiment, a tolerogizing composition comprises one or more BoNT/B peptides, each peptide comprising a different BoNT/B immunoreactive fragment, each BoNT/B immunoreactive fragment comprising at least six non-consecutive amino acids selected from the group consisting of amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In still other aspects of this embodiment, a tolerogizing composition comprises one or more BoNT/B peptides, each peptide comprising a different BoNT/B immunoreactive fragment, each BoNT/B immunoreactive fragment comprising at least six non-consecutive amino acids selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

It is also envisioned that any and all combinations of BoNT/B peptides disclosed in the specification can be used in a tolerogizing composition, including, without limitation, a BoNT/B peptide derived from a naturally occurring BoNT/B, such as, e.g., the BoNT/B of SEQ ID NO: 1, SEQ ID NO: 3, SEQ ID NO: 5, SEQ ID NO: 7, SEQ ID NO: 9, SEQ ID NO: 11 or SEQ ID NO: 13, a BoNT/B isoform or a BoNT/B subtype; and a BoNT/B peptide derived from a non-naturally occurring BoNT/B, such as, e.g., a conservative BoNT/B variant, a non-conservative BoNT/B variant and a chimeric BoNT/B peptide. Thus, aspects of this embodiment, a tolerogizing composition comprises, e.g., one or more BoNT/B peptides derived from a naturally occurring BoNT/B and one or more BoNT/B peptides derived from a non-naturally occurring BoNT/B. In other aspects of this embodiment, a tolerogizing composition comprises, e.g., one or more BoNT/B peptides comprising one or more BoNT/B peptides derived from SEQ ID NO: 1 and one or more BoNT/B peptides derived from a conservative BoNT/B variant; one or more BoNT/B peptides of SEQ ID NO: 1 and one or more BoNT/B peptides derived from a non-conservative variant; one or more BoNT/B peptides derived from a conservative BoNT/B variant and one or more BoNT/B peptides derived from a non-conservative BoNT/B variant; and one or more BoNT/B peptides derived from SEQ ID NO: 1, one or more BoNT/B peptides derived from a conservative BoNT/B variant and one or more BoNT/B peptides derived from a non-conservative BoNT/B variant.

In another embodiment, a tolerogizing composition comprises a tolerogizing agent. In an aspect of this embodiment, a BoNT/B peptide is operably linked to polyethylene glycol (PEG). In another aspect of this embodiment, a BoNT/B peptide is operably linked to monomethoxypolyethylene glycol (mPEG). In another aspect of this embodiment, a BoNT/B peptide is operably linked to polyvinyl alcohol (PVA).

The present invention provides, in part, an immune response inducing composition comprising an adjuvant and a BoNT/B antigen. Such immune response inducing compositions are useful for inducing specific immunity against one or more botulinum toxins such as, e.g., BoNT/B. Such specific immunity can protect an individual from intoxication produced by exposure to botulinum toxin. As used herein, the term "immune response inducing composition" means a composition which, when administered to an individual, stimulates an immune response against an antigen. The term "immune response" refers to any response by the immune system of an individual to an immune response inducing composition or other immunogenic compound. Exemplary immune responses include, but not limited to cellular as well as local and systemic humoral immunity, such as CTL responses, including antigen-specific induction of CD8+ CTLs, helper T-cell responses, including T-cell proliferative responses and cytokine release, and B-cell responses including, e.g., an antibody producing response. The term "inducing an immune response" refers to administration of an immune response inducing composition or other immunogenic compound or a nucleic acid encoding the immune response inducing composition or other immunogenic compound, wherein an immune response is affected, i.e., stimulated, initiated or induced. An immune response inducing composition can be useful, for example, for preventing or ameliorating intoxication produced by unwanted exposure to botulinum toxin. Administration of an immune response inducing composition has been shown to effectively block the effect of protein toxins, see, e.g., Behzod Z. Dolimbek & M. Zouhair Atassi, 13(5) J. PROT. CHEM. 490-493 (1994); M. Zouhair Atassi et al., *Antibody and T-Cell Recognition of Alpha-Bungarotoxin and its Synthetic Loop-Peptides*, 32(12) MOL. IMMUNOL. 919-929 (1995); and Behzod Z. Dolimbek et al., *Protection Against Alpha-Bungarotoxin Poisoning by Immunization with Synthetic Toxin Peptides*, 33(7-8) MOL. IMMUNOL. 681-689 (1996).

Aspects of the present invention provide, in part, a BoNT/B antigen. An antigen is a molecule that elicits an immune response and includes, without limitation, peptides, polysaccharides and conjugates of lipids, such as, e.g., lipoproteins and glycolipids. It is envisioned that any of the BoNT/B peptides disclosed in the present specification can be useful as a BoNT/B antigen, with the proviso that the BoNT/B peptide elicits an immunogenic response necessary to produce an anti-BoNT antibody that provides specific immunity against one or more botulinum toxins, such as, e.g., BoNT/B. Non-limiting examples include a BoNT/B peptide derived from a naturally occurring BoNT/B, such as, e.g., the BoNT/B of SEQ ID NO: 1, SEQ ID NO: 3, SEQ ID NO: 5, SEQ ID NO: 7, SEQ ID NO: 9, SEQ ID NO: 11 or SEQ ID NO: 13, a BoNT/B isoform or a BoNT/B subtype; and a BoNT/B peptide derived from a non-naturally occurring BoNT/B, such as, e.g., a conservative BoNT/B variant, a non-conservative BoNT/B variant and a chimeric BoNT/B peptide. BoNT/B peptides disclosed in the present specification can be selected, e.g., depending on immunological factors, such as potency of the peptide in inducing a tolerogizing response, and technical factors, such as chemical synthesis yields. It is also understood that the two or more different BoNT/B peptides can be provided separately or as part of a compound molecule such as a chimeric BoNT/B peptide. An BoNT/B antigen disclosed in the present specification can be, e.g., prepared from natural sources, produced recombinantly, or synthesized chemically.

Thus, in an embodiment, a BoNT/B antigen has a length of at least 5 amino acids and at most 60 amino acids. In an aspect of this embodiment, a BoNT/B antigen of SEQ ID NO: 1 has a length of at least 5 amino acids and at most 60 amino acids. In other aspects of this embodiment, a BoNT/B antigen comprises an amino acid sequence selected from the group consisting of amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, a BoNT/B antigen comprises an amino acid sequence selected from the group consisting of amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 932-950 of SEQ ID NO: 1, amino acids 932-950 of SEQ ID NO: 5, amino acids 974-992 of SEQ ID NO: 1, amino acids 974-992 of SEQ ID NO: 3, amino acids 974-992 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In still other aspects of this embodiment, a BoNT/B antigen comprises an amino acid sequence selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In another embodiment, a BoNT/B antigen has a length of at least 5 amino acids and at most 60 amino acids and is derived from a naturally occurring BoNT/B. In aspects of this embodiment, the naturally occurring BoNT/B is a BoNT/B isoform or a BoNT/B subtype. In other aspects of this embodiment, a BoNT/B peptide is derived from the BoNT/B of SEQ ID NO: 1, the BoNT/B of SEQ ID NO: 3, the BoNT/B of SEQ ID NO: 5, the BoNT/B of SEQ ID NO: 7, the BoNT/B of SEQ ID NO: 9, the BoNT/B of SEQ ID NO: 11 or the BoNT/B of SEQ ID NO: 13.

In another embodiment, a BoNT/B antigen has a length of at least 5 amino acids and at most 60 amino acids and is derived from a non-naturally occurring BoNT/B. In aspects of this embodiment, the naturally occurring BoNT/B is a conservative BoNT/B variant or a non-conservative BoNT/B variant.

In aspects of this embodiment, a BoNT/B antigen comprises, e.g., 1-4 conservative amino acid substitutions to amino acids 610-628 of SEQ ID NO: 1, 1-4 conservative amino acid substitutions to amino acids 736-754 of SEQ ID NO: 1, 1-4 conservative amino acid substitutions to amino acids 736-754 of SEQ ID NO: 5, 1-4 conservative amino acid substitutions to amino acids 778-796 of SEQ ID NO: 1, 1-4 conservative amino acid substitutions to amino acids 778-796 of SEQ ID NO: 5, 1-4 conservative amino acid substitutions to amino acids 820-838 of SEQ ID NO: 1, 1-4 conservative amino acid substitutions to amino acids 820-838 of SEQ ID NO: 3, 1-4 conservative amino acid substitutions to amino acids 820-838 of SEQ ID NO: 5, 1-4 conservative amino acid substitutions to amino acids 820-838 of SEQ ID NO: 7, 1-4 conservative amino acid substitutions to amino acids 862-880 of SEQ ID NO: 1, 1-4 conservative amino acid substitutions to amino acids 862-880 of SEQ ID NO: 7, 1-4 conservative amino acid substitutions to amino acids 890-908 of SEQ ID NO: 1, 1-4 conservative amino acid substitutions to amino acids 890-908 of SEQ ID NO: 3, 1-4 conservative amino acid substitutions to amino acids 890-908 of SEQ ID NO: 5, 1-4 conservative amino acid substitutions to amino acids 890-908 of SEQ ID NO: 7, 1-4 conservative amino acid substitutions to amino acids 918-936 of SEQ ID NO: 1, 1-4 conservative amino acid substitutions to amino acids 918-936 of SEQ ID NO: 3, 1-4 conservative amino acid substitutions to amino acids 932-950 of SEQ ID NO: 1, 1-4 conservative amino acid substitutions to amino acids 932-950 of SEQ ID NO: 5, 1-4 conservative amino acid substitutions to amino acids 960-978 of SEQ ID NO: 1, 1-4 conservative amino acid substitutions to amino acids 960-978 of SEQ ID NO: 3, 1-4 conservative amino acid substitutions to amino acids 960-978 of SEQ ID NO: 7, 1-4 conservative amino acid substitutions to amino acids 974-992 of SEQ ID NO: 1, 1-4 conservative amino acid substitutions to amino acids 974-992 of SEQ ID NO: 3, 1-4 conservative amino acid substitutions to amino acids 974-992 of SEQ ID NO: 7, 1-4 conservative amino acid substitutions to amino acids 1030-1048 of SEQ ID NO: 1, 1-4 conservative amino acid substitutions to amino acids 1030-1048 of SEQ ID NO: 3, 1-4 conservative amino acid substitutions to amino acids 1030-1048 of SEQ ID NO: 5, 1-4 conservative amino acid substitutions to amino acids 1030-1048 of SEQ ID NO: 7, 1-4 conservative amino acid substitutions to amino acids 1058-1076 of SEQ ID NO: 1, 1-4 conservative amino acid substitutions to amino acids 1058-1076 of SEQ ID NO: 3, 1-4 conservative amino acid substitutions to amino acids 1058-1076 of SEQ ID NO: 5, 1-4 conservative amino acid substitutions to amino acids 1058-1076 of SEQ ID NO: 7, 1-4 conservative amino acid substitutions to amino acids 1072-1090 of SEQ ID NO: 1, 1-4 conservative amino acid substitutions to amino acids 1072-1090 of SEQ ID NO: 3, 1-4 conservative amino acid substitutions to amino acids 1072-1090 of SEQ ID NO: 7, 1-4 conservative amino acid substitutions to amino acids 1254-1272 of SEQ ID NO: 1, 1-4 conservative amino acid substitutions to amino acids 1254-1272 of SEQ ID NO: 3, 1-4 conservative amino acid substitutions to amino acids 1268-1291 of SEQ ID NO: 1, 1-4 conservative amino acid substitutions to amino acids 1268-1291 of SEQ ID NO: 3, 1-4 conservative amino acid substitutions to amino acids 1268-1291 of SEQ ID NO: 5 or 1-4 conservative amino acid substitutions to amino acids 1268-1291 of SEQ ID NO: 7.

In other aspects of this embodiment, a BoNT/B antigen comprises, e.g., 1-4 conservative amino acid substitutions to amino acids 736-754 of SEQ ID NO: 1, 1-4 conservative amino acid substitutions to amino acids 736-754 of SEQ ID NO: 5, 1-4 conservative amino acid substitutions to amino acids 778-796 of SEQ ID NO: 1, 1-4 conservative amino acid substitutions to amino acids 778-796 of SEQ ID NO: 5, 1-4 conservative amino acid substitutions to amino acids 890-908 of SEQ ID NO: 1, 1-4 conservative amino acid substitutions to amino acids 890-908 of SEQ ID NO: 3, 1-4 conservative amino acid substitutions to amino acids 890-908 of SEQ ID NO: 5, 1-4 conservative amino acid substitutions to amino acids 890-908 of SEQ ID NO: 7, 1-4 conservative amino acid substitutions to amino acids 932-950 of SEQ ID NO: 1, 1-4 conservative amino acid substitutions to amino acids 932-950 of SEQ ID NO: 5, 1-4 conservative amino acid substitutions to amino acids 974-992 of SEQ ID NO: 1, 1-4 conservative amino acid substitutions to amino acids 974-992 of SEQ ID NO: 3, 1-4 conservative amino acid substitutions to amino acids 974-992 of SEQ ID NO: 7, 1-4 conservative amino acid substitutions to amino acids 1058-1076 of SEQ ID NO: 1, 1-4 conservative amino acid substitutions to amino acids 1058-1076 of SEQ ID NO: 3, 1-4 conservative amino acid substitutions to amino acids 1058-1076 of SEQ ID NO: 5, 1-4 conservative amino acid substitutions to amino acids 1058-1076 of SEQ ID NO: 7, 1-4 conservative amino acid substitutions to amino acids 1268-1291 of SEQ ID NO: 1, 1-4 conservative amino acid substitutions to amino acids 1268-1291 of SEQ ID NO: 3, 1-4 conservative amino acid substitutions to amino acids 1268-1291 of SEQ ID NO: 5 or 1-4 conservative amino acid substitutions to amino acids 1268-1291 of SEQ ID NO: 7.

In still other aspects of this embodiment, a BoNT/B antigen comprises, e.g., 1-4 conservative amino acid substitutions to amino acids 616-626 of SEQ ID NO: 1, 1-4 conservative amino acid substitutions to amino acids 735-745 of SEQ ID NO: 1, 1-4 conservative amino acid substitutions to amino acids 735-745 of SEQ ID NO: 5, 1-4 conservative amino acid substitutions to amino acids 778-789 of SEQ ID NO: 1, 1-4 conservative amino acid substitutions to amino acids 867-877 of SEQ ID NO: 1, 1-4 conservative amino acid substitutions to amino acids 867-877 of SEQ ID NO: 7, 1-4 conservative amino acid substitutions to amino acids 895-905 of SEQ ID NO: 1, 1-4 conservative amino acid substitutions to amino acids 895-905 of SEQ ID NO: 3, 1-4 conservative amino acid substitutions to amino acids 929-939 of SEQ ID NO: 1, 1-4 conservative amino acid substitutions to amino acids 974-984 of SEQ ID NO: 1, 1-4 conservative amino acid substitutions to amino acids 974-984 of SEQ ID NO: 3, 1-4 conservative amino acid substitutions to amino acids 974-984 of SEQ ID NO: 7, 1-4 conservative amino acid substitutions to amino acids 1039-1049 of SEQ ID NO: 1, 1-4 conservative amino acid substitutions to amino acids 1039-1049 of SEQ ID NO: 5, 1-4 conservative amino acid substitutions to amino acids 1039-1049 of SEQ ID NO: 7, 1-4 conservative amino acid substitutions to amino acids 1065-1075 of SEQ ID NO: 1, 1-4 conservative amino acid substitutions to amino acids 1065-1075 of SEQ ID NO: 3, 1-4 conservative amino acid substitutions to amino acids 1065-1075 of SEQ ID NO: 5, 1-4 conservative amino acid substitutions to amino acids 1065-1075 of SEQ ID NO: 7, 1-4 conservative amino acid substitutions to amino acids 1269-1281 of SEQ ID NO: 1, 1-4 conservative amino acid substitutions to amino acids 1269-1281 of SEQ ID NO: 3, 1-4 conservative amino acid substitutions to amino acids 1269-1281 of SEQ ID NO: 5 or 1-4 conservative amino acid substitutions to amino acids 1269-1281 of SEQ ID NO: 7.

In aspects of this embodiment, a BoNT/B antigen comprises, e.g., 1-4 non-conservative amino acid substitutions to amino acids 610-628 of SEQ ID NO: 1, 1-4 non-conservative amino acid substitutions to amino acids 736-754 of SEQ ID NO: 1, 1-4 non-conservative amino acid substitutions to amino acids 736-754 of SEQ ID NO: 5, 1-4 non-conservative amino acid substitutions to amino acids 778-796 of SEQ ID NO: 1, 1-4 non-conservative amino acid substitutions to amino acids 778-796 of SEQ ID NO: 5, 1-4 non-conservative amino acid substitutions to amino acids 820-838 of SEQ ID NO: 1, 1-4 non-conservative amino acid substitutions to amino acids 820-838 of SEQ ID NO: 3, 1-4 non-conservative amino acid substitutions to amino acids 820-838 of SEQ ID NO: 5, 1-4 non-conservative amino acid substitutions to amino acids 820-838 of SEQ ID NO: 7, 1-4 non-conservative amino acid substitutions to amino acids 862-880 of SEQ ID NO: 1, 1-4 non-conservative amino acid substitutions to amino acids 862-880 of SEQ ID NO: 7, 1-4 non-conservative amino acid substitutions to amino acids 890-908 of SEQ ID NO: 1, 1-4 non-conservative amino acid substitutions to amino acids 890-908 of SEQ ID NO: 3, 1-4 non-conservative amino acid substitutions to amino acids 890-908 of SEQ ID NO: 5, 1-4 non-conservative amino acid substitutions to amino acids 890-908 of SEQ ID NO: 7, 1-4 non-conservative amino acid substitutions to amino acids 918-936 of SEQ ID NO: 1, 1-4 non-conservative amino acid substitutions to amino acids 918-936 of SEQ ID NO: 3, 1-4 non-conservative amino acid substitutions to amino acids 932-950 of SEQ ID NO: 1, 1-4 non-conservative amino acid substitutions to amino acids 932-950 of SEQ ID NO: 5, 1-4 non-conservative amino acid substitutions to amino acids 960-978 of SEQ ID NO: 1, 1-4 non-conservative amino acid substitutions to amino acids 960-978 of SEQ ID NO: 3, 1-4 non-conservative amino acid substitutions to amino acids 960-978 of SEQ ID NO: 7, 1-4 non-conservative amino acid substitutions to amino acids 974-992 of SEQ ID NO: 1, 1-4 non-conservative amino acid substitutions to amino acids 974-992 of SEQ ID NO: 3, 1-4 non-conservative amino acid substitutions to amino acids 974-992 of SEQ ID NO: 7, 1-4 non-conservative amino acid substitutions to amino acids 1030-1048 of SEQ ID NO: 1, 1-4 non-conservative amino acid substitutions to amino acids 1030-1048 of SEQ ID NO: 3, 1-4 non-conservative amino acid substitutions to amino acids 1030-1048 of SEQ ID NO: 5, 1-4 non-conservative amino acid substitutions to amino acids 1030-1048 of SEQ ID NO: 7, 1-4 non-conservative amino acid substitutions to amino acids 1058-1076 of SEQ ID NO: 1, 1-4 non-conservative amino acid substitutions to amino acids 1058-1076 of SEQ ID NO: 3, 1-4 non-conservative amino acid substitutions to amino acids 1058-1076 of SEQ ID NO: 5, 1-4 non-conservative amino acid substitutions to amino acids 1058-1076 of SEQ ID NO: 7, 1-4 non-conservative amino acid substitutions to amino acids 1072-1090 of SEQ ID NO: 1, 1-4 non-conservative amino acid substitutions to amino acids 1072-1090 of SEQ ID NO: 3, 1-4 non-conservative amino acid substitutions to amino acids 1072-1090 of SEQ ID NO: 7, 1-4 non-conservative amino acid substitutions to amino acids 1254-1272 of SEQ ID NO: 1, 1-4 non-conservative amino acid substitutions to amino acids 1254-1272 of SEQ ID NO: 3, 1-4 non-conservative amino acid substitutions to amino acids 1268-1291 of SEQ ID NO: 1, 1-4 non-conservative amino acid substitutions to amino acids 1268-1291 of SEQ ID NO: 3, 1-4 non-conservative amino acid substitutions to amino acids 1268-1291 of SEQ ID NO: 5 or 1-4 non-conservative amino acid substitutions to amino acids 1268-1291 of SEQ ID NO: 7.

In other aspects of this embodiment, a BoNT/B antigen comprises, e.g., 1-4 non-conservative amino acid substitutions to amino acids 736-754 of SEQ ID NO: 1, 1-4 non-conservative amino acid substitutions to amino acids 736-754 of SEQ ID NO: 5, 1-4 non-conservative amino acid substitutions to amino acids 778-796 of SEQ ID NO: 1, 1-4 non-conservative amino acid substitutions to amino acids 778-796 of SEQ ID NO: 5, 1-4 non-conservative amino acid substitutions to amino acids 890-908 of SEQ ID NO: 1, 1-4 non-conservative amino acid substitutions to amino acids 890-908 of SEQ ID NO: 3, 1-4 non-conservative amino acid substitutions to amino acids 890-908 of SEQ ID NO: 5, 1-4 non-conservative amino acid substitutions to amino acids 890-908 of SEQ ID NO: 7, 1-4 non-conservative amino acid substitutions to amino acids 932-950 of SEQ ID NO: 1, 1-4 non-conservative amino acid substitutions to amino acids 932-950 of SEQ ID NO: 5, 1-4 non-conservative amino acid substitutions to amino acids 974-992 of SEQ ID NO: 1, 1-4 non-conservative amino acid substitutions to amino acids 974-992 of SEQ ID NO: 3, 1-4 non-conservative amino acid substitutions to amino acids 974-992 of SEQ ID NO: 7, 1-4 non-conservative amino acid substitutions to amino acids 1058-1076 of SEQ ID NO: 1, 1-4 non-conservative amino acid substitutions to amino acids 1058-1076 of SEQ ID NO: 3, 1-4 non-conservative amino acid substitutions to amino acids 1058-1076 of SEQ ID NO: 5, 1-4 non-conservative amino acid substitutions to amino acids 1058-1076 of SEQ ID NO: 7, 1-4 non-conservative amino acid substitutions to amino acids 1268-1291 of SEQ ID NO: 1, 1-4 non-conservative amino acid substitutions to amino acids 1268-1291 of SEQ ID NO: 3, 1-4 non-conservative amino acid substitutions to amino acids 1268-1291 of SEQ ID NO: 5 or 1-4 non-conservative amino acid substitutions to amino acids 1268-1291 of SEQ ID NO: 7.

In still other aspects of this embodiment, a BoNT/B antigen comprises, e.g., 1-4 non-conservative amino acid substitutions to amino acids 616-626 of SEQ ID NO: 1, 1-4 non-conservative amino acid substitutions to amino acids 735-745 of SEQ ID NO: 1, 1-4 non-conservative amino acid substitutions to amino acids 735-745 of SEQ ID NO: 5, 1-4 non-conservative amino acid substitutions to amino acids 778-789 of SEQ ID NO: 1, 1-4 non-conservative amino acid substitutions to amino acids 867-877 of SEQ ID NO: 1, 1-4 non-conservative amino acid substitutions to amino acids 867-877 of SEQ ID NO: 7, 1-4 non-conservative amino acid substitutions to amino acids 895-905 of SEQ ID NO: 1, 1-4 non-conservative amino acid substitutions to amino acids 895-905 of SEQ ID NO: 3, 1-4 non-conservative amino acid substitutions to amino acids 929-939 of SEQ ID NO: 1, 1-4 non-conservative amino acid substitutions to amino acids 974-984 of SEQ ID NO: 1, 1-4 non-conservative amino acid substitutions to amino acids 974-984 of SEQ ID NO: 3, 1-4 non-conservative amino acid substitutions to amino acids 974-984 of SEQ ID NO: 7, 1-4 non-conservative amino acid substitutions to amino acids 1039-1049 of SEQ ID NO: 1, 1-4 non-conservative amino acid substitutions to amino acids 1039-1049 of SEQ ID NO: 5, 1-4 non-conservative amino acid substitutions to amino acids 1039-1049 of SEQ ID NO: 7, 1-4 non-conservative amino acid substitutions to amino acids 1065-1075 of SEQ ID NO: 1, 1-4 non-conservative amino acid substitutions to amino acids 1065-1075 of SEQ ID NO: 3, 1-4 non-conservative amino acid substitutions to amino acids 1065-1075 of SEQ ID NO: 5, 1-4 non-conservative amino acid substitutions to amino acids 1065-1075 of SEQ ID NO: 7, 1-4 non-conservative amino acid substitutions to amino acids 1269-1281 of SEQ ID NO: 1, 1-4 non-conservative amino acid substitutions to amino acids 1269-1281 of SEQ ID NO: 3, 1-4 non-conservative amino acid substitutions to amino acids 1269-1281 of SEQ ID NO: 5 or 1-4 non-conservative amino acid substitutions to amino acids 1269-1281 of SEQ ID NO: 7.

In another embodiment, an immunoreactive fragment of a BoNT/B antigen has a length of at least five amino acids and at most 60 amino acids. In aspects of this embodiment, an immunoreactive fragment of a BoNT/B antigen comprises, e.g., at least 6 consecutive amino acids, at least 7 consecutive amino acids, at least 8 consecutive amino acids, at least 9 consecutive amino acids, at least 10 consecutive amino acids, at least 12 consecutive amino acids, at least 15 consecutive amino acids, at least 18 consecutive amino acids or at least 20 consecutive amino acids. In other aspects of this embodiment, an immunoreactive fragment of a BoNT/B antigen comprises, e.g., at most 6 consecutive amino acids, at most 7 consecutive amino acids, at most 8 consecutive amino acids, at most 9 consecutive amino acids, at most 10 consecutive amino acids, at most 12 consecutive amino acids, at most 15 consecutive amino acids, at most 18 consecutive amino acids or at most 20 consecutive amino acids.

In still other aspects of this embodiment, an immunoreactive fragment of a BoNT/B antigen comprises, e.g., at least 6 non-consecutive amino acids, at least 7 non-consecutive amino acids, at least 8 non-consecutive amino acids, at least 9 non-consecutive amino acids, at least 10 non-consecutive amino acids, at least 12 non-consecutive amino acids, at least 15 non-consecutive amino acids, at least 18 non-consecutive amino acids or at least 20 non-consecutive amino acids. In still other aspects of this embodiment, an immunoreactive fragment of a BoNT/B antigen comprises, e.g., at most 6 non-consecutive amino acids, at most 7 non-consecutive amino acids, at most 8 non-consecutive amino acids, at most 9 non-consecutive amino acids, at most 10 non-consecutive amino acids, at most 12 non-consecutive amino acids, at most 15 non-consecutive amino acids, at most 18 non-consecutive amino acids or at most 20 non-consecutive amino acids.

In still other aspects of this embodiment, an immunoreactive fragment of a BoNT/B antigen has from five to sixty amino acids, from five to fifty amino acids, from eight to fifty amino acids, from ten to fifty amino acids, from five to twenty amino acids, from eight to twenty amino acids, from ten to twenty amino acids, from twelve to twenty amino acids or from fifteen to twenty amino acids.

In another embodiment, a BoNT/B antigen comprises an immunogenic BoNT/B fragment. In an aspect of this embodiment, an immunogenic BoNT/B fragment comprises at least six consecutive amino acids of a BoNT/B antigen. In other aspects of this embodiment, an immunogenic BoNT/B fragment comprises at least six consecutive amino acids from, e.g., amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, an immunogenic BoNT/B fragment comprises at least six consecutive amino acids from, e.g., amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In another aspect of this embodiment, an immunogenic BoNT/B fragment comprises at least six non-consecutive amino acids of a BoNT/B antigen. In other aspects of this embodiment, an immunogenic BoNT/B fragment comprises at least six non-consecutive amino acids from, e.g., amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, an immunogenic BoNT/B fragment comprises at least six non-consecutive amino acids from, e.g., amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In is envisioned that an immune response inducing composition can optionally comprises one or more carriers to enhance the immunogenicity of an antigen, a hapten, or any other antigenic compound that is immunogenic, non-immunogenic, or weakly immunogenic when not associated with the carrier. As is well known in the art, a non-antigenic or weakly antigenic antigen can be made antigenic by coupling the antigen to a carrier, such as, e.g., keyhole limpet hemacyanin (KLH), ovalbumin (OVA), thyroglobulin (THY), bovine serum albumin (BSA), soybean trypsin inhibitor (STI) or multiple attachment peptide (MAP) technology. Various other carrier and methods for coupling an antigen to a carrier are well known in the art, see, e.g., Harlow and Lane, supra, 1998a; Harlow and Lane, supra, 1998b; and David W. Waggoner, Jr. et al., Immunogenicity-enhancing carriers and compositions thereof and methods of using the same, U.S. Patent Publication No. 20040057958 (Mar. 25, 2004). An epitope can also be generated by expressing the epitope as a fusion protein, for example, fused to glutathione S transferase, poly-His or the like. Methods for expressing polypeptide fusions are well known to those skilled in the art as described, for example, in Ausubel et al., Current Protocols in Molecular Biology (Supplement 47), John Wiley & Sons, New York (1999).

In is envisioned that an immune response inducing composition also optionally comprises one or more adjuvants. As used herein, the term "adjuvant" when used in reference to an immune response inducing composition means any substance or mixture of substances that increases or diversifies the immune response to an antigenic compound. An immune response inducing adjuvant can, for example, serve to reduce the number of immunizations or the amount of antigen required for protective immunization. The use of immune response inducing adjuvants in an immune response inducing composition is well known. The main objective of these adjuvants is to allow an increase in the immune response. These adjuvants are diverse in nature. They may, e.g., consist of liposomes, oily phases, including, without limitation, the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); and lipopolysaccharide (LPS). Such adjuvants are generally used in the form of an emulsion with an aqueous phase, or, more commonly, may consist of water-insoluble inorganic salts. These inorganic salts may consist, for example, of aluminum hydroxide, zinc sulfate, colloidal iron hydroxide, calcium phosphate or calcium chloride. Aluminum hydroxide ($Al(OH)_3$) is a commonly used adjuvant. Currently, the only FDA-approved adjuvant for use in humans is aluminum salts (Alum) which are used to "depot" antigens by precipitation of the antigens. Adjuvants provided above are merely exemplary. In fact, any immune response inducing adjuvant may be used in an immune response inducing composition disclosed in the present specification as long as the adjuvant satisfies the requisite characteristics that are necessary for practicing the present invention.

As indicated above, the carrier of the compositions of the present invention itself may act as an adjuvant. Specific adjuvants and methods of making and using are described in, e.g., Gupta et al. Vaccine, 11: 993-306, 1993; Arnon, R. (Ed.) Synthetic Vaccines 1:83-92, CRC Press, Inc., Boca Raton, Fla., 1987; and David W. Waggoner, Jr. et al., Immunogenicity-Enhancing Carriers and Compositions Thereof and Methods of Using the Same, U.S. Patent Publication No. 20040057958 (Mar. 25, 2004). Additional adjuvants include any compound described in Chapter 7 (pp 141-227) of "Vaccine Design, The Subunit and Adjuvant Approach" (eds. Powell, M. F. and Newman, M. J.) Pharmaceutical Biotechnology, Volume 6, Plenum Press (New York). Examples from this compendium include Muramyl Dipeptide (MDP) and Montanide 720. Molecules such as Poly Inosine:Cytosine (Poly I:C) or plasmid DNA containing CpG motifs can also be administered as adjuvants in combination with antigens encapsulated in microparticles. In another example, the adjuvant is an agent that facilitates entry of the antigenic compound into the cytoplasm of a cell such as listeriolysin, streptolysin or a mixture thereof.

In an embodiment, an immune response inducing composition comprises a BoNT/B antigen disclosed in the present specification operably linked to a carrier. In another embodiment, an immune response inducing composition can comprise a plurality of different BoNT/B antigens disclosed in the present specification each BoNT/B antigen operably linked to a carrier. Thus, in aspects of this embodiment, an immune response inducing composition comprises one or more different BoNT/B antigens each BoNT/B antigen operably linked to a carrier, two or more different BoNT/B antigens each BoNT/B peptide operably linked to a carrier, three or more different BoNT/B antigens each BoNT/B antigen operably linked to a carrier, four or more different BoNT/B antigens each BoNT/B antigen operably linked to a carrier, five or more different BoNT/B antigens, each BoNT/B antigen operably linked to a carrier, six or more different BoNT/B antigens each BoNT/B antigen operably linked to a carrier, seven or more different BoNT/B antigens each BoNT/B antigen operably linked to a carrier, eight or more different BoNT/B antigens each BoNT/B antigen operably linked to a carrier, nine or more different BoNT/B antigens each BoNT/B antigen operably linked to a carrier, ten or more different BoNT/B antigens each BoNT/B antigen operably linked to a carrier, 15 or more different BoNT/B antigens each BoNT/B antigen operably linked to a carrier or 20 or more different BoNT/B antigens each BoNT/B antigen operably linked to a carrier.

In another embodiment, an immune response inducing composition comprises one or more different BoNT/B antigens derived from the BoNT/B of SEQ ID NO: 1, the BoNT/B of SEQ ID NO: 3, the BoNT/B of SEQ ID NO: 5, the BoNT/B of SEQ ID NO: 7, the BoNT/B of SEQ ID NO: 9, the BoNT/B of SEQ ID NO: 11 or the BoNT/B of SEQ ID NO: 13.

In aspects of this embodiment, an immune response inducing composition comprises one or more different BoNT/B antigens comprising an amino acid sequence selected from the group consisting of amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, an immune response inducing composition comprises one or more amino acid sequences selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In another aspect of this embodiment, an immune response inducing composition comprises a BoNT/B antigen operably linked to a carrier. In other aspects of this embodiment, an immune response inducing composition comprises a BoNT/B antigen operably linked to a carrier, the BoNT/B antigen comprising amino acid sequence selected from the group consisting of amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In another aspect of this embodiment, an immune response inducing composition comprises a BoNT/B antigen operably linked to a carrier, the BoNT/B antigen comprising amino acid sequence selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In yet another aspect of this embodiment, an immune response inducing composition comprises a BoNT/B antigen comprising amino acid sequence is 974-992 of SEQ ID NO: 1 operably linked to a carrier and a BoNT/B antigen comprising amino acid sequence is 736-754 of SEQ ID NO: 1 operably linked to a carrier. In yet another aspect of this embodiment, an immune response inducing composition comprises a BoNT/B antigen comprising amino acid sequence is 974-992 of SEQ ID NO: 1 operably linked to a carrier and a BoNT/B antigen comprising amino acid sequence is 1058-1076 of SEQ ID NO: 1 operably linked to a carrier. In yet another aspect of this embodiment, an immune response inducing composition comprises a BoNT/B antigen comprising amino acid sequence is 974-992 of SEQ ID NO: 1 operably linked to a carrier and a BoNT/B antigen comprising amino acid sequence is 890-908 of SEQ ID NO: 1 operably linked to a carrier.

In yet another aspect of this embodiment, an immune response inducing composition comprises a BoNT/B antigen comprising amino acid sequence is 974-984 of SEQ ID NO: 1 operably linked to a carrier and a BoNT/B antigen comprising amino acid sequence is 735-745 of SEQ ID NO: 1 operably linked to a carrier. In yet another aspect of this embodiment, an immune response inducing composition comprises a BoNT/B antigen comprising amino acid sequence is 974-984 of SEQ ID NO: 1 operably linked to a carrier and a BoNT/B antigen comprising amino acid sequence is 1065-1075 of SEQ ID NO: 1 operably linked to a carrier. In yet another aspect of this embodiment, an immune response inducing composition comprises a BoNT/B antigen comprising amino acid sequence is 974-984 of SEQ ID NO: 1 operably linked to a carrier and a BoNT/B antigen comprising amino acid sequence is 895-905 of SEQ ID NO: 1 operably linked to a carrier.

In still another aspect of this embodiment, an immune response inducing composition comprises a BoNT/B antigen comprising amino acid sequence is 974-992 of SEQ ID NO: 1 operably linked to a carrier, a BoNT/B antigen comprising amino acid sequence is 736-754 of SEQ ID NO: 1 operably linked to a carrier and a BoNT/B antigen comprising amino acid sequence is 1058-1076 of SEQ ID NO: 1 operably linked to a carrier. In still another aspect of this embodiment, an immune response inducing composition comprises a BoNT/B antigen comprising amino acid sequence is 974-992 of SEQ ID NO: 1 operably linked to a carrier, a BoNT/B antigen comprising amino acid sequence is 736-754 of SEQ ID NO: 1 operably linked to a carrier and a BoNT/B antigen comprising amino acid sequence is 890-908 of SEQ ID NO: 1 operably linked to a carrier.

In still another aspect of this embodiment, an immune response inducing composition comprises a BoNT/B antigen comprising amino acid sequence is 974-984 of SEQ ID NO: 1 operably linked to a carrier, a BoNT/B antigen comprising amino acid sequence is 735-745 of SEQ ID NO: 1 operably linked to a carrier and a BoNT/B antigen comprising amino acid sequence is 1065-1075 of SEQ ID NO: 1 operably linked to a carrier. In still another aspect of this embodiment, an immune response inducing composition comprises a BoNT/B antigen comprising amino acid sequence is 974-984 of SEQ ID NO: 1 operably linked to a carrier, a BoNT/B antigen comprising amino acid sequence is 735-745 of SEQ ID NO: 1 operably linked to a carrier and a BoNT/B antigen comprising amino acid sequence is 895-905 of SEQ ID NO: 1 operably linked to a carrier.

In another embodiment, an immune response inducing composition comprises one or more different BoNT/B antigens derived from a non-naturally occurring BoNT/B, each BoNT/B peptide operably linked to a carrier. In aspects of this embodiment, the non-naturally occurring BoNT/B is a conservative BoNT/B variant or a non-conservative BoNT/B variant.

In aspects of this embodiment, an immune response inducing composition comprises one or more different BoNT/B antigens derived from a conservative BoNT/B variant, two or more different BoNT/B antigens derived from a conservative BoNT/B variant, three or more different BoNT/B antigens derived from a conservative BoNT/B variant, four or more different BoNT/B antigens derived from a conservative BoNT/B variant, five or more different BoNT/B antigens derived from a conservative BoNT/B variant, six or more different BoNT/B antigens derived from a conservative BoNT/B variant, seven or more different BoNT/B antigens derived from a conservative BoNT/B variant, eight or more different BoNT/B antigens derived from a conservative BoNT/B variant, nine or more different BoNT/B antigens derived from a conservative BoNT/B variant, ten or more different BoNT/B antigens derived from a conservative BoNT/B variant, 15 or more different BoNT/B antigens derived from a conservative BoNT/B variant or 20 or more different BoNT/B antigens derived from a conservative BoNT/B variant.

In aspects of this embodiment, an immune response inducing composition comprises one or more BoNT/B antigens selected from the group consisting of a BoNT/B antigen comprising 1-4 conservative amino acid substitutions to amino acids 610-628 of SEQ ID NO: 1 operably linked to a carrier, a BoNT/B antigen comprising 1-4 conservative amino acid substitutions to amino acids 736-754 of SEQ ID NO: 1 operably linked to a carrier, a BoNT/B antigen comprising 1-4 conservative amino acid substitutions to amino acids 778-796 of SEQ ID NO: 1 operably linked to a carrier, a BoNT/B antigen comprising 1-4 conservative amino acid substitutions to amino acids 820-838 of SEQ ID NO: 1 operably linked to a carrier, a BoNT/B antigen comprising 1-4 conservative amino acid substitutions to amino acids 862-880 of SEQ ID NO: 1 operably linked to a carrier, a BoNT/B antigen comprising 1-4 conservative amino acid substitutions to amino acids 890-908 of SEQ ID NO: 1 operably linked to a carrier, a BoNT/B antigen comprising 1-4 conservative amino acid substitutions to amino acids 918-936 of SEQ ID NO: 1 operably linked to a carrier, a BoNT/B antigen comprising 1-4 conservative amino acid substitutions to amino acids 932-950 of SEQ ID NO: 1 operably linked to a carrier, a BoNT/B antigen comprising 1-4 conservative amino acid substitutions to amino acids 960-978 of SEQ ID NO: 1 operably linked to a carrier, a BoNT/B antigen comprising 1-4 conservative amino acid substitutions to amino acids 974-992 of SEQ ID NO: 1 operably linked to a carrier, a BoNT/B antigen comprising 1-4 conservative amino acid substitutions to amino acids 1030-1048 of SEQ ID NO: 1 operably linked to a carrier, a BoNT/B antigen comprising 1-4 conservative amino acid substitutions to amino acids 1058-1076 of SEQ ID NO: 1 operably linked to a carrier, a BoNT/B antigen comprising 1-4 conservative amino acid substitutions to amino acids 1072-1090 of SEQ ID NO: 1 operably linked to a carrier, a BoNT/B antigen comprising 1-4 conservative amino acid substitutions to amino acids 1254-1272 of SEQ ID NO: 1 operably linked to a carrier, and a BoNT/B antigen comprising 1-4 conservative amino acid substitutions to amino acids 1268-1291 of SEQ ID NO: 1 operably linked to a carrier.

In aspects of this embodiment, an immune response inducing composition comprises one or more BoNT/B antigens selected from the group consisting of a BoNT/B antigen comprising 1-4 conservative amino acid substitutions to amino acids 736-754 of SEQ ID NO: 1 operably linked to a carrier, a BoNT/B antigen comprising 1-4 conservative amino acid substitutions to amino acids 778-796 of SEQ ID NO: 1 operably linked to a carrier, a BoNT/B antigen comprising 1-4 conservative amino acid substitutions to amino acids 890-908 of SEQ ID NO: 1 operably linked to a carrier, a BoNT/B antigen comprising 1-4 conservative amino acid substitutions to amino acids 932-950 of SEQ ID NO: 1 operably linked to a carrier, a BoNT/B antigen comprising 1-4 conservative amino acid substitutions to amino acids 974-992 of SEQ ID NO: 1 operably linked to a carrier, a BoNT/B antigen comprising 1-4 conservative amino acid substitutions to amino acids 1058-1076 of SEQ ID NO: 1 operably linked to a carrier, and a BoNT/B antigen comprising 1-4 conservative amino acid substitutions to amino acids 1268-1291 of SEQ ID NO: 1 operably linked to a carrier.

In further aspects of this embodiment, an immune response inducing composition comprises one or more BoNT/B antigens selected from the group consisting of a BoNT/B antigen comprising 1-4 conservative amino acid substitutions to amino acids 616-626 of SEQ ID NO: 1 operably linked to a carrier, a BoNT/B antigen comprising 1-4 conservative amino acid substitutions to amino acids 735-745 of SEQ ID NO: 1 operably linked to a carrier, a BoNT/B antigen comprising 1-4 conservative amino acid substitutions to amino acids 778-789 of SEQ ID NO: 1 operably linked to a carrier, a BoNT/B antigen comprising 1-4 conservative amino acid substitutions to amino acids 867-877 of SEQ ID NO: 1 operably linked to a carrier, a BoNT/B antigen comprising 1-4 conservative amino acid substitutions to amino acids 895-905 of SEQ ID NO: 1 operably linked to a carrier, a BoNT/B antigen comprising 1-4 conservative amino acid substitutions to amino acids 929-939 of SEQ ID NO: 1 operably linked to a carrier, a BoNT/B antigen comprising 1-4 conservative amino acid substitutions to amino acids 974-984 of SEQ ID NO: 1 operably linked to a carrier, a BoNT/B antigen comprising 1-4 conservative amino acid substitutions to amino acids 1039-1049 of SEQ ID NO: 1 operably linked to a carrier, a BoNT/B antigen comprising 1-4 conservative amino acid substitutions to amino acids 1065-1075 of SEQ ID NO: 1 operably linked to a carrier or a BoNT/B antigen comprising 1-4 conservative amino acid substitutions to amino acids 1269-1281 of SEQ ID NO: 1 operably linked to a carrier.

In further aspects of this embodiment, an immune response inducing composition comprises one or more different BoNT/B antigens derived from a non-conservative BoNT/B variant, two or more different BoNT/B antigens derived from a non-conservative BoNT/B variant, three or more different BoNT/B antigens derived from a non-conservative BoNT/B variant, four or more different BoNT/B antigens derived from a non-conservative BoNT/B variant, five or more different BoNT/B antigens derived from a non-conservative BoNT/B variant, six or more different BoNT/B antigens derived from a non-conservative BoNT/B variant, seven or more different BoNT/B antigens derived from a non-conservative BoNT/B variant, eight or more different BoNT/B antigens derived from a non-conservative BoNT/B variant, nine or more different BoNT/B antigens derived from a non-conservative BoNT/B variant, ten or more different BoNT/B antigens derived from a non-conservative BoNT/B variant, 15 or more different BoNT/B antigens derived from a non-conservative BoNT/B variant or 20 or more different BoNT/B antigens derived from a non-conservative BoNT/B variant.

In further aspects of this embodiment, an immune response inducing composition comprises one or more BoNT/B antigens selected from the group consisting of a BoNT/B antigen comprising 1-4 non-conservative amino acid substitutions to amino acids 610-628 of SEQ ID NO: 1 operably linked to a carrier, a BoNT/B antigen comprising 1-4 non-conservative amino acid substitutions to amino acids 736-754 of SEQ ID NO: 1 operably linked to a carrier, a BoNT/B antigen comprising 1-4 non-conservative amino acid substitutions to amino acids 778-796 of SEQ ID NO: 1 operably linked to a carrier, a BoNT/B antigen comprising 1-4 non-conservative amino acid substitutions to amino acids 820-838 of SEQ ID NO: 1 operably linked to a carrier, a BoNT/B antigen comprising 1-4 non-conservative amino acid substitutions to amino acids 862-880 of SEQ ID NO: 1 operably linked to a carrier, a BoNT/B antigen comprising 1-4 non-conservative amino acid substitutions to amino acids 890-908 of SEQ ID NO: 1 operably linked to a carrier, a BoNT/B antigen comprising 1-4 non-conservative amino acid substitutions to amino acids 918-936 of SEQ ID NO: 1 operably linked to a carrier, a BoNT/B antigen comprising 1-4 non-conservative amino acid substitutions to amino acids 932-950 of SEQ ID NO: 1 operably linked to a carrier, a BoNT/B antigen comprising 1-4 non-conservative amino acid substitutions to amino acids 960-978 of SEQ ID NO: 1 operably linked to a carrier, a BoNT/B antigen comprising 1-4 non-conservative amino acid substitutions to amino acids 974-992 of SEQ ID NO: 1 operably linked to a carrier, a BoNT/B antigen comprising 1-4 non-conservative amino acid substitutions to amino acids 1030-1048 of SEQ ID NO: 1 operably linked to a carrier, a BoNT/B antigen comprising 1-4 non-conservative amino acid substitutions to amino acids 1058-1076 of SEQ ID NO: 1 operably linked to a carrier, a BoNT/B antigen comprising 1-4 non-conservative amino acid substitutions to amino acids 1072-1090 of SEQ ID NO: 1 operably linked to a carrier, a BoNT/B antigen comprising 1-4 non-conservative amino acid substitutions to amino acids 1254-1272 of SEQ ID NO: 1 operably linked to a carrier, and a BoNT/B antigen comprising 1-4 non-conservative amino acid substitutions to amino acids 1268-1291 of SEQ ID NO: 1 operably linked to a carrier.

In further aspects of this embodiment, an immune response inducing composition comprises one or more BoNT/B antigens selected from the group consisting of a BoNT/B antigen comprising 1-4 non-conservative amino acid substitutions to amino acids 736-754 of SEQ ID NO: 1 operably linked to a carrier, a BoNT/B antigen comprising 1-4 non-conservative amino acid substitutions to amino acids 778-796 of SEQ ID NO: 1 operably linked to a carrier, a BoNT/B antigen comprising 1-4 non-conservative amino acid substitutions to amino acids 890-908 of SEQ ID NO: 1 operably linked to a carrier, a BoNT/B antigen comprising 1-4 non-conservative amino acid substitutions to amino acids 932-950 of SEQ ID NO: 1 operably linked to a carrier, a BoNT/B antigen comprising 1-4 non-conservative amino acid substitutions to amino acids 974-992 of SEQ ID NO: 1 operably linked to a carrier, a BoNT/B antigen comprising 1-4 non-conservative amino acid substitutions to amino acids 1058-1076 of SEQ ID NO: 1 operably linked to a carrier, and a BoNT/B antigen comprising 1-4 non-conservative amino acid substitutions to amino acids 1268-1291 of SEQ ID NO: 1 operably linked to a carrier.

In further other aspects of this embodiment, an immune response inducing composition comprises one or more BoNT/B antigens selected from the group consisting of a BoNT/B antigen comprising 1-4 non-conservative amino acid substitutions to amino acids 616-626 of SEQ ID NO: 1 operably linked to a carrier, a BoNT/B antigen comprising 1-4 non-conservative amino acid substitutions to amino acids 735-745 of SEQ ID NO: 1 operably linked to a carrier, a BoNT/B antigen comprising 1-4 non-conservative amino acid substitutions to amino acids 778-789 of SEQ ID NO: 1 operably linked to a carrier, a BoNT/B antigen comprising 1-4 non-conservative amino acid substitutions to amino acids 867-877 of SEQ ID NO: 1 operably linked to a carrier, a BoNT/B antigen comprising 1-4 non-conservative amino acid substitutions to amino acids 895-905 of SEQ ID NO: 1 operably linked to a carrier, a BoNT/B antigen comprising 1-4 non-conservative amino acid substitutions to amino acids 929-939 of SEQ ID NO: 1 operably linked to a carrier, a BoNT/B antigen comprising 1-4 non-conservative amino acid substitutions to amino acids 974-984 of SEQ ID NO: 1 operably linked to a carrier, a BoNT/B antigen comprising 1-4 non-conservative amino acid substitutions to amino acids 1039-1049 of SEQ ID NO: 1 operably linked to a carrier, a BoNT/B antigen comprising 1-4 non-conservative amino acid substitutions to amino acids 1065-1075 of SEQ ID NO: 1 operably linked to a carrier or a BoNT/B antigen comprising 1-4 non-conservative amino acid substitutions to amino acids 1269-1281 of SEQ ID NO: 1 operably linked to a carrier.

In still other aspects of this embodiment, an immune response inducing composition comprises one or more different BoNT/B antigens each peptide comprising a different BoNT/B immunoreactive fragment, two or more different BoNT/B antigens each antigen comprising a different BoNT/B immunoreactive fragment, three or more different BoNT/B antigens each antigen comprising a different BoNT/B immunoreactive fragment, four or more different BoNT/B antigens each antigen comprising a different BoNT/B immunoreactive fragment, five or more different BoNT/B antigens each antigen comprising a different BoNT/B immunoreactive fragment, six or more different BoNT/B antigens each antigen comprising a different BoNT/B immunoreactive fragment, seven or more different BoNT/B antigens each antigen comprising a different BoNT/B immunoreactive fragment, eight or more different BoNT/B antigens each antigen comprising a different BoNT/B immunoreactive fragment, nine or more different BoNT/B antigens each antigen comprising a different BoNT/B immunoreactive fragment, ten or more different BoNT/B antigens each antigen comprising a different BoNT/B immunoreactive fragment, 15 or more different BoNT/B antigens each antigen comprising a different BoNT/B immunoreactive fragment, 20 or more different BoNT/B antigens each antigen comprising a different BoNT/B immunoreactive fragment, 25 or more different BoNT/B antigens each antigen comprising a different BoNT/B immunoreactive fragment or 30 or more different BoNT/B antigens each antigen comprising a different BoNT/B immunoreactive fragment.

In an aspect of this embodiment, an immunogenic BoNT/B fragment comprises at least six consecutive amino acids of a BoNT/B antigen. In other aspects of this embodiment, an immunogenic BoNT/B fragment comprises at least six consecutive amino acids from, e.g., amino acids 610-628 of SEQ ID NO: 1

In an aspect of this embodiment, an immune response inducing composition comprises one or more BoNT/B antigens, each antigen comprising a different BoNT/B immunoreactive fragment. In another aspect of this embodiment, an immune response inducing composition comprises one or more BoNT/B antigens, each BoNT/B antigen comprising a different BoNT/B immunoreactive fragment, each BoNT/B immunoreactive fragment comprising at least six consecutive amino acids of a BoNT/B antigen. In aspects of this embodiment, an immune response inducing composition comprises one or more BoNT/B antigens, each BoNT/B antigen comprising a different BoNT/B immunoreactive fragment, each BoNT/B immunoreactive fragment comprises at least six consecutive amino acids from, e.g., amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, an immune response inducing composition comprises one or more BoNT/B antigens, each BoNT/B antigen comprising a different BoNT/B immunoreactive fragment, each BoNT/B immunoreactive fragment comprises at least six consecutive amino acids from, e.g., amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 932-950 of SEQ ID NO: 1, amino acids 932-950 of SEQ ID NO: 5, amino acids 974-992 of SEQ ID NO: 1, amino acids 974-992 of SEQ ID NO: 3, amino acids 974-992 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In another aspect of this embodiment, an immune response inducing composition comprises one or more BoNT/B antigens, each BoNT/B antigen comprising a different BoNT/B immunoreactive fragment, each BoNT/B immunoreactive fragment comprising at least six non-consecutive amino acids of a BoNT/B peptide. In aspects of this embodiment, an immune response inducing composition comprises one or more BoNT/B peptides, each BoNT/B peptide comprising a different BoNT/B immunoreactive fragment, each BoNT/B immunoreactive fragment comprises at least six non-consecutive amino acids from, e.g., amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, an immune response inducing composition comprises one or more BoNT/B antigens, each BoNT/B antigen comprising a different BoNT/B immunoreactive fragment, each BoNT/B immunoreactive fragment comprises at least six non-consecutive amino acids from, e.g., amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 932-950 of SEQ ID NO: 1, amino acids 932-950 of SEQ ID NO: 5, amino acids 974-992 of SEQ ID NO: 1, amino acids 974-992 of SEQ ID NO: 3, amino acids 974-992 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

It is also envisioned that any and all combinations of BoNT/B antigens disclosed in the specification, including, without limitation, a BoNT/B antigen derived from a naturally occurring BoNT/B, such as, e.g., the BoNT/B of SEQ ID NO: 1, SEQ ID NO: 3, SEQ ID NO: 5, SEQ ID NO: 7, SEQ ID NO: 9, SEQ ID NO: 11 or SEQ ID NO: 13, a BoNT/B isoform or a BoNT/B subtype; and a BoNT/B peptide derived from a non-naturally occurring BoNT/B, such as, e.g., a conservative BoNT/B variant, a non-conservative BoNT/B variant and a chimeric BoNT/B peptide. Thus, aspects of this embodiment, an immune response inducing composition comprises, e.g., one or more BoNT/B antigens derived from a naturally occurring BoNT/B and one or more BoNT/B antigens derived from a non-naturally occurring BoNT/B. In other aspects of this embodiment, an immune response inducing composition comprises, e.g., one or more BoNT/B antigens comprising one or more BoNT/B antigens derived from SEQ ID NO: 1 and one or more BoNT/B antigens derived from a conservative BoNT/B variant; one or more BoNT/B peptides of SEQ ID NO: 1 and one or more BoNT/B antigens derived from a non-conservative variant; one or more BoNT/B antigens derived from a conservative BoNT/B variant and one or more BoNT/B antigens derived from a non-conservative BoNT/B variant; and one or more BoNT/B antigens derived from SEQ ID NO: 1, one or more BoNT/B antigens derived from a conservative BoNT/B variant and one or more BoNT/B antigens derived from a non-conservative BoNT/B variant.

In another embodiment, an immune response inducing composition comprises a carrier. In an aspect of this embodiment, a BoNT/B antigen is operably linked to cholera enterotoxin A2. In another aspect of this embodiment, a BoNT/B antigen is operably linked to a peptide adjuvant.

In an embodiment, an immune response inducing composition comprising a BoNT/B antigen disclosed in the present specification operably linked to a carrier further comprises an adjuvant. In an aspect of this embodiment, an adjuvant comprises a water-insoluble inorganic salt. In another aspect of this embodiment, an adjuvant comprises an aluminum salt. In other aspects of this embodiment, an adjuvant comprises a water-insoluble inorganic salt selected from the group consisting of aluminum hydroxide, zinc sulfate, colloidal iron hydroxide, calcium phosphate and calcium chloride. In yet another aspect of this embodiment, an adjuvant comprises listeriolysin, streptolysin or an admixture thereof.

Patients treated with a BoNT therapy can develop immunoresistance to the treatment, thereby reducing or eliminating the beneficial effect of the BoNT therapy. Therefore, methods that determine whether a patient is mounting an immune response against a BoNT therapy are of major importance. These assays would allow the immunoresponsive state of the patient to be evaluated periodically during the course of a BoNT therapy. By knowing the predisposition of an individual 1) the potential value of a specific BoNT treatment can be determined prior to its administration to a patient; and 2) the possible benefit from continued BoNT therapy can be assessed and any possible adjustments to a treatment determined. Therefore, these assays present a major benefit in terms of providing better patient care and reducing health care costs. The BoNT/B peptides disclosed in the present specification are useful in methods of determining immunoresistance to BoNT therapy in an individual. For example, these peptides each contain one or more epitopes recognized by anti-BoNT/B antibodies contained in antisera from animals immunized with BoNT/B, and thus can serve as binding substrates for anti-BoNT antibodies.

Thus, the present invention provides, in part, a method of determining immunoresistance to botulinum toxin therapy in an individual by determining the presence or absence in the individual of anti-BoNT antibodies immunoreactive with a BoNT/B peptide disclosed in the present specification, where the presence of anti-BoNT antibodies immunoreactive with the a BoNT/B peptide indicates immunoresistance to BoNT/B therapy.

The present invention also provides, in part, a method of determining immunoresistance to BoNT therapy in an individual, the method comprising the steps of combining a BoNT/B peptide and test sample and detecting the amount of complexes formed by the BoNT/B peptide and an anti-BoNT antibody, where the presence of the antibody-peptide complex indicates immunoresistance to a BoNT therapy.

The present invention also provides, in part, a method of determining immunoresistance to BoNT therapy in an individual, the method comprising the steps of combining a BoNT/B peptide and a test sample, detecting the amount of complexes formed by the BoNT/B peptide and anti-BoNT antibody and correlating the amount of the antibody-peptide complexes formed from the test sample relative to the amount of complexes formed by the BoNT/B peptide and the anti-BoNT antibody from a control sample.

It is further is understood that a methods of determining immunoresistance to BoNT therapy in an individual can be used to predict the likelihood of the individual developing immunoresistance or to confirm that the presence of anti-BoNT antibodies are a cause underlying immunoresistance to botulinum toxin therapy.

Aspects of the present invention provide, in part, determining immunoresistance to BoNT therapy in an individual. As used herein, the term "immunoresistance," when used in reference to botulinum toxin therapy, means an individual that does not fully respond to a botulinum toxin therapy, or shows a reduced beneficial effect of botulinum toxin therapy resulting from the presence in the individual of anti-BoNT antibodies that bind to a botulinum toxin. Non-limiting examples of a botulinum toxin immunoresistance include, e.g., a BoNT/A immunoresistance, a BoNT/B immunoresistance, a BoNT/C1 immunoresistance, a BoNT/D immunoresistance, a BoNT/E immunoresistance, a BoNT/F immunoresistance and a BoNT/G immunoresistance. A non-limiting example of reduced efficacy would be the presence in an individual of at least one neutralizing anti-BoNT/A antibody that binds to a BoNT/B toxin in a manner that reduces or prevents the specificity or activity of the toxin. Another non-limiting example of reduced efficacy would be the presence in an individual of at least one neutralizing anti-BoNT/B antibody that binds to a BoNT/B toxin in a manner that reduces or prevents the specificity or activity of the toxin. As used herein, the term "botulinum toxin therapy" is synonymous with "BoNT therapy" and means a treatment, remedy, cure, healing, rehabilitation or any other means of counteracting something undesirable in a mammal requiring neuromodulation using a botulinum toxin or administering to a mammal one or more controlled doses of a medication, preparation or mixture of a botulinum toxin that has medicinal, therapeutic, curative, cosmetic, remedial or any other beneficial effect. Non-limiting examples of a botulinum toxin therapy include, e.g., a BoNT/A therapy, a BoNT/B therapy, a BoNT/C1 therapy, a BoNT/D therapy, a BoNT/E therapy, a BoNT/F therapy and a BoNT/G therapy. The term botulinum toxin therapy encompasses, without limitation, the use of any naturally occurring or modified or engineered form of a botulinum toxin or a domain or fragment thereof, in any formulation, combined with any carrier or active ingredient and administered by any route of administration. Well-known botulinum toxin therapies include, without limitation, a BoNT/A therapy, such as, e.g., a BOTOX® therapy, a Dysport®/Reloxin® therapy, a Linurase® therapy, a Neuronox® therapy, a BTX-A therapy, and a Xeomin® therapy; and a BoNT/B therapy, such as, e.g., a MyoBloc™/NeuroBloc™ therapy. Appropriate therapeutic and cosmetic uses of a botulinum toxin therapy are known in the art. As used herein, the term "individual," when used in reference to botulinum toxin therapy, means any organism capable of raising anti-BoNT antibodies against a BoNT toxin, including, but not limited to, birds and mammals, including mice, rats, goats, sheep, horses, donkeys, cows, primates and humans.

Aspects of the present invention provide, in part, a BoNT/B peptide. It is envisioned that any of the BoNT/B peptides disclosed in the present specification can be useful in a method of determining immunoresistance to botulinum toxin therapy in an individual, with the proviso that the BoNT/B peptide can selectively bind to a anti-BoNT antibody. Non-limiting examples include a BoNT/B peptide derived from a naturally occurring BoNT/B, such as, e.g., the BoNT/B of SEQ ID NO: 1, SEQ ID NO: 3, SEQ ID NO: 5, SEQ ID NO: 7, SEQ ID NO: 9, SEQ ID NO: 11 or SEQ ID NO: 13, a BoNT/B isoform or a BoNT/B subtype; and a BoNT/B peptide derived from a non-naturally occurring BoNT/B, such as, e.g., a conservative BoNT/B variant, a non-conservative BoNT/B variant and a chimeric BoNT/B peptide. BoNT/B peptides disclosed in the present specification can be selected, e.g., depending on immunological factors, such as the selectivity of the BoNT/B peptide for an anti-BoNT antibody, and technical factors, such as chemical synthesis yields. It is also understood that the two or more different BoNT/B peptides can be provided separately or as part of a compound molecule such as a chimeric BoNT/B peptide.

Aspects of the present invention provide, in part, a sample. As used herein, the term "sample" means any biological matter that contains or potentially contains at least one anti-BoNT antibody. An anti-BoNT antibody can be a neutralizing anti-BoNT antibody or a non-neutralizing anti-BoNT antibody. As used herein, the term "neutralizing anti-BoNT antibodies" means any anti-BoNT antibody that will, under physiological conditions, bind to a region of a BoNT toxin in such a manner as to reduce or prevent the toxin from exerting its effect in a BoNT therapy. Non-limiting examples of a neutralizing anti-BoNT antibody include, e.g., a neutralizing anti-BoNT/A antibody, a neutralizing anti-BoNT/B antibody, a neutralizing anti-BoNT/C1 antibody, a neutralizing anti-BoNT/D antibody, a neutralizing anti-BoNT/E antibody, a neutralizing anti-BoNT/F antibody and a neutralizing anti-BoNT/G antibody. As used herein, the term "non-neutralizing anti-BoNT antibodies" means any anti-BoNT antibody that will, under physiological conditions, bind to a region of a BoNT toxin, but not prevent the toxin from exerting its effect in a BoNT therapy. Non-limiting examples of a non-neutralizing anti-BoNT antibody include, e.g., a non-neutralizing anti-BoNT/A antibody, a non-neutralizing anti-BoNT/B antibody, a non-neutralizing anti-BoNT/C1 antibody, a non-neutralizing anti-BoNT/D antibody, a non-neutralizing anti-BoNT/E antibody, a non-neutralizing anti-BoNT/F antibody and a non-neutralizing anti-BoNT/G antibody. It is envisioned that any and all samples that can contain anti-BoNT antibodies can be used in this method, including, without limitation, blood, plasma, serum and lymph fluid. As used herein, the term "blood" means a bodily fluid including a cellular component and plasma and encompasses both whole blood and a blood component thereof. In addition, any and all individuals capable of raising anti-BoNT antibodies against a BoNT toxin can serve as a source for a sample including, but not limited to, birds and mammals, including mice, rats, goats, sheep, horses, donkeys, cows, primates and humans. Non-limiting examples of specific protocols for blood collection and serum preparation are described in, e.g., Marjorie Schaub Di Lorenzo & Susan King Strasinger, BLOOD COLLECTION IN HEALTHCARE (F. A. Davis Company, 2001); and Diana Garza & Kathleen Becan-McBride, PHLEBOTOMY HANDBOOK: BLOOD COLLECTION ESSENTIALS (Prentice Hall, $6^{th}$ ed., 2002). These protocols are routine procedures well within the scope of one skilled in the art and from the teaching herein.

A sample can be a test sample, or a sample can be a control sample. As used herein, the term "test sample" means any sample in which the presence or absence of an anti-BoNT antibody is sought to be determined. A test sample can be obtained from an individual prior to exposure to a BoNT toxin, after a single BoNT treatment, after multiple BoNT toxin treatments, before onset of resistance to a BoNT therapy, or after onset of resistance to a BoNT therapy. As used herein, the term "control sample" means any sample in which the presence or absence of an anti-BoNT antibody is known, and includes both negative and positive control samples. A negative control sample can be obtained from an individual who was never exposed to BoNT toxin and may include, without limitation, a sample from the same individual supplying the test sample, but taken before undergoing a BoNT therapy; a sample taken from a different individual; a pooled sample taken from a plurality of different individuals. A positive control sample can be obtained from an individual manifesting BoNT immunoresistance and includes, without limitation, samples testing positive in a patient-based testing assays; samples testing positive in an in vivo bioassay; and samples showing hyperimmunity against an anti-BoNT antiserum.

Any of the above methods of the invention can be practiced, if desired, by selectively determining the presence or absence in the individual of IgG antibodies immunoreactive with each BoNT/B peptide. Thus, it is foreseen that anti-BoNT antibodies can be purified from a sample. Anti-BoNT antibodies can be purified from a sample, using a variety of procedures including, without limitation, Protein A/G chromatography and affinity chromatography. Non-limiting examples of specific protocols for purifying antibodies from a sample are described in, e.g., ANTIBODIES: A LABORATORY MANUAL (Edward Harlow & David Lane, eds., Cold Spring Harbor Laboratory Press, $2^{nd}$ ed. 1998); USING ANTIBODIES: A LABORATORY MANUAL: PORTABLE PROTOCOL No. I (Edward Harlow & David Lane, Cold Spring Harbor Laboratory Press, 1998); and MOLECULAR CLONING, A LABORATORY MANUAL, supra, (2001). In addition, non-limiting examples of antibody purification methods as well as well-characterized reagents, conditions and protocols are readily available from commercial vendors that include, without limitation, Pierce Biotechnology, Inc., Rockford, Ill.; and Zymed Laboratories, Inc., South San Francisco, Calif. These protocols are routine procedures well within the scope of one skilled in the art.

Techniques for determining a level of IgG antibodies immunoreactive with a BoNT/B peptide are well known in the art. For example, a solid-phase radioimmunoassay for IgG anti-BoNT antibodies can be performed using an anti-mouse IgG secondary antibody. A variety of additional anti-IgG antibodies, including anti-human IgG antibodies, are well known in the art and are commercially available, including, but not limited to, rabbit anti-human IgG from Bethyl Laboratories, Inc. (Montgomery, Tex.) and goat anti-human IgG from Zymed Laboratories, Inc (San Francisco, Calif.). Thus, the methods of the invention can be practiced using any of the immunoassays described hereinabove or well known in the art which are specific for detection of IgG antibodies, for example, through use of an anti-IgG secondary antibody.

The present invention additionally provides a method of determining immunoresistance to botulinum toxin therapy in an individual by determining the level of IgG antibodies immunoreactive with the botulinum toxin in the individual; and comparing the level of IgG antibodies to a control level of IgG antibodies, where an increase in the level of IgG antibodies in the individual as compared to the control level indicates immunoresistance to the botulinum toxin therapy. Such an increase can be, for example, at least a 5-fold increase or at least a 10-fold increase. In one embodiment, the control level of IgG antibodies is determined in a individual that has not been treated with botulinum toxin therapy. In another embodiment, the control level of IgG antibodies is determined in an individual that is responsive to the botulinum toxin therapy. The methods of the invention can be used to determine immunoresistance to any of several botulinum toxin therapies including, without limitation, a BoNT/A therapy, a BoNT/B therapy, a BoNT/C1 therapy, a BoNT/D therapy, a BoNT/E therapy, a BoNT/F therapy and a BoNT/G therapy.

Thus, an embodiment, the sample comprises blood. In aspect of this embodiment, the sample comprises mouse blood, rat blood, goat blood, sheep blood, horse blood, donkey blood, cow blood, primate blood and human blood. In another embodiment, the sample comprises plasma. In aspect of this embodiment, the sample comprises mouse plasma, rat plasma, goat plasma, sheep plasma, horse plasma, donkey plasma, cow plasma, primate plasma and human plasma. In another embodiment, the sample comprises serum. In aspect of this embodiment, the sample comprises mouse serum, rat serum, goat serum, sheep serum, horse serum, donkey serum, cow serum, primate serum and human serum. In another embodiment, the sample comprises lymph fluid. In aspect of this embodiment, the sample comprises mouse lymph fluid, rat lymph fluid, goat lymph fluid, sheep lymph fluid, horse lymph fluid, donkey lymph fluid, cow lymph fluid, primate lymph fluid and human lymph fluid. In yet another embodiment, the sample is a test sample. In yet another embodiment, the sample is a control sample.

Aspects of the present invention provide, in part, determining the presence or absence of anti-BoNT antibodies immunoreactive with a BoNT/B peptide. In is envisioned that any and all assay formats suitable for indicating the presence or absence of anti-BoNT antibody-BoNT/B peptide complexes and, therefore, to determine immunoresistance to botulinum toxin therapy according to a method of the present invention. Such assay formats generally involve detecting an antigen-antibody interaction. Non-limiting examples include radioimmunoassays, enzyme-linked immunosorbent assays, enzyme immunoassays, fluorescence immunoassays, luminescent immunoassays and other nonradioisotopic assay formats, see e.g., MOLECULAR CLONING, A LABORATORY MANUAL, supra, 2001; and CURRENT PROTOCOLS IN MOLECULAR BIOLOGY, supra, 2004. Non-competitive assays can be performed, for example, by attaching one or more selected BoNT/B peptides to a solid support; adding a test specimen; adding a secondary antibody, which is an antibody selective for the test antibody; and detecting the secondary antibody, typically by a physical property or enzymatic activity of the secondary antibody. In such an assay, the amount of signal that is detected can be proportional to the amount of antibodies which are immunoreactive with the one or more BoNT/B peptides and are present in the test specimen.

It is further foreseen that an assay format can either qualitatively or quantitatively determine the presence of an anti-BoNT antibody-BoNT/B peptide complex. Qualitative measurements can be determined by a wide variety of methods, such as, e.g., audioradiography, immunoblotting techniques, and the like. Quantitative measurements can be determined by a wide variety of methods, such as, e.g., scintillation counters, spectrophotometers, densitometers, fluorometers, spectroluminometers, luminometers, high pressure liquid chromatography, and the like. In addition, control samples can also be assayed with a test sample using this method in order to provide baseline values useful for comparisons with a test sample. Thus, a negative control comprises a sample known not to contain any anti-BoNT antibodies. A negative control can establish a parameter for background noise levels and provide a means to distinguish false positive results from an actual BoNT immune resistance response. A sample known to contain high levels of neutralizing anti-BoNT antibodies from an individual diagnosed with BoNT immunoresistance could serve as a positive control. A positive control can provide a parameter from which a test sample can be evaluated to determine the relative severity of immunoresistance occurring in a test patient. One skilled in the art understands that, if desired, a quantitative method can be used for qualitative measurements. In addition, one skilled in the art understands that the selection of a method of measurement is determined by the detection means employed.

In one aspect of the present invention, all steps of a method for determining the presence or absence of an anti-BoNT antibody are performed in solution. In other aspects of the method disclosed in the present specification, it is also envisioned that a method can optionally attach an assay component to a solid or insoluble material. Such a solid support can be, without limitation, e.g., a tube; plate; pins or "dipsticks", column; particle, bead or other spherical or fibrous chromatographic media, such as, e.g., agarose beads, sepharose beads, silica beads and plastic beads; sheets or membranes, such as, e.g., nitrocellulose and polyvinylidene fluoride (PVDF). The solid support selected can have a physical property that renders it readily separable from soluble or unbound material and generally allows unbound materials, such as, e.g., unbound antibodies, excess reagents, reaction by-products, or solvents, to be separated or otherwise removed (by, e.g., washing, filtration, centrifugation, etc.) from solid support-bound assay components. Non-limiting examples of how to make and use a solid support-bound assay component are described in, e.g., MOLECULAR CLONING, A LABORATORY MANUAL, supra, 2001; and CURRENT PROTOCOLS IN MOLECULAR BIOLOGY, supra, 2004.

As a general procedure, because the exact amount of a BoNT/B peptide can be readily determined by one skilled in the art, the assay amounts of a sample and an anti-BoNT antibody can be determined based on a fixed assay amount of a BoNT/B peptide.

In an embodiment, it is envisioned that detecting the presence of any and all binding levels of a BoNT/B peptide to an anti-BoNT antibody capable of being detected by an assay format disclosed in the present specification are useful in aspects of the present invention. Thus, aspects of this embodiment may include detecting the presence of, e.g., at least 10% complex formation of a BoNT/B peptide with an anti-BoNT antibody, at least 20% complex formation of a BoNT/B peptide with an anti-BoNT antibody, at least 30% complex formation of a BoNT/B peptide with an anti-BoNT antibody, at least 40% complex formation of a BoNT/B peptide with an anti-BoNT antibody, at least 50% complex formation of a BoNT/B peptide with an anti-BoNT antibody, at least 60% complex formation of a BoNT/B peptide with an anti-BoNT antibody, at least 70% complex formation of a BoNT/B peptide with an anti-BoNT antibody, at least 80% complex formation of a BoNT/B peptide with an anti-BoNT antibody, or at least 90% complex formation of a BoNT/B peptide with an anti-BoNT antibody. In other aspects of this embodiment may include detecting the presence of, e.g., at most 10% complex formation of a BoNT/B peptide with an anti-BoNT antibody, at most 20% complex formation of a BoNT/B peptide with an anti-BoNT antibody, at most 30% complex formation of a BoNT/B peptide with an anti-BoNT antibody, at most 40% complex formation of a BoNT/B peptide with an anti-BoNT antibody, at most 50% complex formation of a BoNT/B peptide with an anti-BoNT antibody, at most 60% complex formation of a BoNT/B peptide with an anti-BoNT antibody, at most 70% complex formation of a BoNT/B peptide with an anti-BoNT antibody, at most 80% complex formation of a BoNT/B peptide with an anti-BoNT antibody, or at most 90% complex formation of a BoNT/B peptide with an anti-BoNT antibody. To ascertain an appropriate assay amount of a BoNT/B peptide in this embodiment, the binding capacity of a BoNT/B peptide preparation towards an anti-BoNT antibody is determined using a fixed amount of an anti-BoNT antibody and a range of BoNT/B peptide amounts in order to generate an saturation curve for anti-BoNT antibody-BoNT/B peptide complex formation. This protocol is routine procedure well within the scope of one skilled in the art and from the teaching herein.

In yet another embodiment, a wide range of BoNT/B peptide amounts can be used in methods disclosed in the present specification. The assay amount of a BoNT/B peptide can be varied as appropriate by one skilled in the art and generally depends, in part, on the amount of anti-BoNT antibodies used, the volume of sample used and the assay format employed. Therefore, aspects of this embodiment may include a BoNT/B peptide amount of, e.g., at least 1 ng, at least 10 ng, at least 100 ng, at least 1 µg, at least 2.5 µg, at least 5.0 µg or at least 10 µg. In other aspects of this embodiment may include a BoNT/B peptide amount of, e.g., at most 1 ng, at most 10 ng, at most 100 ng, at most 1 µg, at most 2.5 µg, at most 5.0 µg or at most 10 µg. In an aspect of this embodiment, the assay amount of a BoNT/B peptide is 100 ng. In another aspect of this embodiment, the assay amount of a BoNT/B peptide is 1 µg. In another aspect of this embodiment, the assay amount of a BoNT/BA peptide is 2.5 µg.

In yet another embodiment of the present invention, a wide range of sample volumes can be used in methods disclosed in the present specification. The assay amount of a sample can be varied as appropriate by one skilled in the art and generally depends, in part, on the amount of sample available, the BoNT/B peptide amount being used, the anti-BoNT antibody amount present in a sample and the assay format employed. Thus, aspects of this embodiment a sample volume can include, e.g., at least 1 µL, at least 2.5 µL, at least 5 µL, at least 10 µL, at least 20 µL, at least 30 µL, at least 40 µL, at least 50 µL, or at least 100 µL. In other aspects of this embodiment a sample volume can include, e.g., at most 1 µL, at most 2.5 µL, at most 5 µL, at most 10 µL, at most 20 µL, at most 30 µL, at most 40 µL, at most 50 µL, or at most 100 µL. In an aspect of this embodiment, the assay amount of a sample is 50 µL.

In still another embodiment, it is envisioned that a wide range of assay volumes can be used in methods disclosed in the present specification. Thus aspects of this embodiment an assay volume can include, e.g. at least, 1 µL, at least 2 µL, at least 3 µL, at least 4 µL, at least 5 µL, at least 10 µL, at least 20 µL, at least 30 µL, at least 40 µL, at least 50 µL, at least 100 µL, at least 200 µL, at least 300 µL, at least 400 µL, at least 500 µL, or at least 1000 µL. In other aspects of this embodiment assay volume can include, e.g. at most 1 µL, at most 2 µL, at most 3 µL, at most 4 µL, at most 5 µL, at most 10 µL, at most 20 µL, at most 30 µL, at most 40 µL, at most 50 µL, at most 100 µL, at most 200 µL, at most 300 µL, at most 400 µL, at most 500 µL, or at most 1000 µL.

In still another embodiment, it is envisioned that any and all temperatures that allow the formation of an anti-BoNT antibody-BoNT/B peptide complex can be used in methods disclosed in the present specification. Assay temperatures can be varied as appropriate by one skilled in the art and generally depend, in part, on the BoNT/B peptide amount, the anti-BoNT antibody amount present in a sample, the sample volume used, the assay volume used, the assay format employed and assay time. Thus, an assay temperature should not be as low as to cause the solution to freeze and should not be as high as to denature the BoNT/B peptides, anti-BoNT antibodies or other proteins disclosed in the present specification. In an aspect of this embodiment, the assay is performed within a temperature range above 0° C., but below 40° C. In another aspect of this embodiment, the assay is performed within a temperature range of about 4° C. to about 37° C. In yet another aspect of this embodiment, the assay is performed within a temperature range of about 2° C. to 10° C. In yet another aspect of this embodiment, the assay is performed at about 4° C. In still another aspect of this embodiment, the assay is performed within a temperature range of about 10° C. to about 18° C. In still another aspect of this embodiment, the assay is performed at about 16° C. In yet another aspect of this embodiment, the assay is performed within a temperature range of about 18° C. to about 32° C. In yet another aspect of this embodiment, the assay is performed at about 20° C. In another aspect of this embodiment, the assay is performed within a temperature range of about 32° C. to about 40° C. In another aspect of this embodiment, the assay is performed at about 37° C.

In still another embodiment, it is foreseen that any and all times sufficient for the formation of an anti-BoNT antibody-BoNT/B peptide complex can be used in methods disclosed in the present specification. Assay times can be varied as appropriate by one skilled in the art and generally depend, in part, on the BoNT/B peptide amount, the anti-BoNT antibody amount present in a sample, the sample volume used, the assay volume used, the assay format employed and the incubation temperature. Therefore, aspects of this embodiment include assay times of, e.g., at least 1 minute, at least 2 minutes, at least 3 minutes, at least 4 minutes, at least 5 minutes, at least 10 minutes, at least 15 minutes, at least 20 minutes, at least 25 minutes, at least 30 minutes, at least 45 minutes, at least 60 minutes, or at least 120 minutes. It is understood by one skilled in the art that an assay temperature can affect the formation of an anti-BoNT antibody-BoNT/B peptide complex disclosed in the present invention, and thereby can influence the length of time required to achieve sufficient complex formation. Thus, in an aspect of this embodiment, assay times of at least 45 minutes are used in an assay temperature range of about 2° C. to about 10° C. In another aspect of this embodiment, assay times of at least 30 minutes are used in an assay temperature range of about 10° C. to about 18° C. In yet another aspect of this embodiment, assay times of at least 15 minutes are used in an assay temperature range of about 18° C. to about 32° C. In another aspect of this embodiment, assay times of at least 5 minutes are used in an assay temperature range of about 32° C. to about 40° C. In another aspect of this embodiment, an assay time of 15 minutes is used at an assay temperature of about 37° C.

In a further embodiment, it is also envisioned that any and all buffers that allow the formation of an anti-BoNT antibody-BoNT/B peptide complex can optionally be used in methods disclosed in the present specification. Assay buffers can be varied as appropriate by one skilled in the art and generally depend, in part, on the pH value desired for the assay format employed, the BoNT/B peptide, the anti-BoNT antibody and the assay format employed. Therefore, aspects of this embodiment may optionally include, e.g., 2-amino-2-hydroxymethyl-1,3-propanediol (Tris) buffers; Phosphate buffers, such as, e.g., potassium phosphate buffers and sodium phosphate buffers; Good buffers, such as, e.g., 2-(N-morpholino) ethanesulfonic acid (MES), piperazine-N,N'-bis(2-ethanesulfonic acid) (PIPES), N,N'-bis(2-hydroxyethyl)-2-aminoethanesulfonic acid (BES), 3-(N-morpholino) propanesulfonic acid (MOPS), N-(2-hydroxyethyl) piperazine-N'-(2-ethanesulfonic acid) (HEPES), piperazine-N,N'-bis(2-hydroxypropanesulfonic acid) (POPSO), N-tris(hydroxymethyl) methylglycine (Tricine), N-tris (hydroxymethyl)methyl-3-aminopropanesulfonic acid (TAPS), 3-[(1,1-dimethyl-2-hydroxyethyl)amino]-2-hydroxypropanesulfonic acid (AMPSO), 3-(cyclohexylamino)-2-hydroxy-1-propanesulfonic acid (CAPSO), and 3-(cyclohexylamino)-1-propanesulfonic acid (CAPS); saline buffers, such as, e.g., Phosphate-buffered saline (PBS), HEPES-buffered saline, and Tris-buffered saline (TBS); Acetate buffers, such as, e.g., magnesium acetate, potassium acetate, and Tris acetate; and the like, or any combination thereof. In addition, the buffer concentration in a method disclosed in the present specification can be varied as appropriate by one skilled in the art and generally depend, in part, on the buffering capacity of a particular buffer being used and the detection means employed. Thus, aspects of this embodiment may include a buffer concentration of, e.g., at least 1 mM, at least 5 mM, at least 10 mM, at least 20 mM, at least 30 mM, at least 40 mM, at least 50 mM, at least 60 mM, at least 70 mM, at least 80 mM, at least 90 mM, or at least 100 mM. Non-limiting examples of how to make and use specific buffers are described in, e.g., MOLECULAR CLONING, A LABORATORY MANUAL, supra, (2001); and CURRENT PROTOCOLS IN MOLECULAR BIOLOGY, supra, (2004).

In a further embodiment, it is also envisioned that any and all salts that allow the formation of an anti-BoNT antibody-BoNT/B peptide complex can optionally be used in methods disclosed in the present specification. Assay salts can be varied as appropriate by one skilled in the art and generally depend, in part, on the physiological conditions desired for the assay format employed, the BoNT/B peptide, the anti-BoNT antibody and the assay format employed. Therefore, aspects of this embodiment may optionally include, e.g., sodium chloride, potassium chloride, calcium chloride, magnesium chloride, manganese chloride, zinc chloride, magnesium sulfate, zinc sulfate, and the like, or any combination thereof. In addition, the salt concentration in a method disclosed in the present specification can be varied as appropriate by one skilled in the art and generally depend, in part, on the buffering capacity of a particular buffer being used and the detection means employed. Thus, aspects of this embodiment may include a salt concentration of, e.g., at least 1 mM, at least 5 mM, at least 10 mM, at least 20 mM, at least 30 mM, at least 40 mM, at least 50 mM, at least 60 mM, at least 70 mM, at least 80 mM, at least 90 mM, or at least 100 mM. Non-limiting examples of how to make and use specific salts are described in, e.g., MOLECULAR CLONING, A LABORATORY MANUAL, supra, (2001); and CURRENT PROTOCOLS IN MOLECULAR BIOLOGY, supra, (2004).

In a further embodiment, it is also envisioned that any and all enhancing agents that allow the formation of an anti-BoNT antibody-BoNT/B peptide complex can optionally be used in methods disclosed in the present specification. Assay enhancing agents can be varied as appropriate by one skilled in the art and generally depend, in part, on the assay conditions desired for the assay format employed, the BoNT/B peptide, the anti-BoNT antibody and the assay format employed. Therefore, aspects of this embodiment may optionally include, e.g., stabilizing agents including proteins, such as, e.g., bovine serum albumin and milk proteins, such as, e.g., casein, thyroglobulin, fetuin, asialofetuin, cytochrome c and bovine submaxillary mucin and polyamines, such as, e.g., spermidine and spermine; chelating agents including, e.g., ethylenediamine tetraacetic acid (EDTA) and ethylene glycol bis(β-aminoethyl ether) N,N,N',N'-tetraacetic acid (EGTA); reducing agents, including, e.g., -mercaptoethanol and dithiothreitol (DTT); dimethylsulfoxide (DMSO); and the like, or any combination thereof. In addition, the enhancing agent concentration in a method disclosed in the present specification can be varied as appropriate by one skilled in the art and generally depend, in part, on the assay conditions desired for the assay and the detection means employed. In an aspect of this embodiment, concentrations for a stabilizing agent may include, e.g., at least 10 µg/mL, at least 50 µg/mL, at least 100 µg/mL, at least 200 µg/mL or at least 500 µg/mL. In another aspect of this embodiment, concentrations for a chelating agent may include, e.g., at least 10 nM, at least 50 nM, at least 100 nM, at least 500 nM, at least 1 mM or at least 10 mM. In yet another aspect of this embodiment, concentrations for a reducing agent may include, e.g., at least 10 nM, at least 50 nM, at least 100 nM, at least 500 nM, at least 1 mM, at least 10 mM or at least 100 mM. Non-limiting examples of how to make and use specific enhancing agents are described in, e.g., MOLECULAR CLONING, A LABORATORY MANUAL, supra, (2001); and CURRENT PROTOCOLS IN MOLECULAR BIOLOGY, supra, (2004).

In an additional embodiment of the invention, it is also foreseen that a wide variety of processing formats can be used in conjunction with the methods of the present invention, including, without limitation, manual processing, partial automated-processing, semi-automated-processing, full automated-processing, high throughput processing, high content processing, and the like or any combination thereof.

It is understood by one skilled in the art that a wide variety of factors can influence assay conditions, including, without limitation, solution variations, buffer variations, reagent variations, equipment variations and facility variations. Thus, any particular assay condition selected by one skilled in the art will require routine experimentation in order to optimize the method to account for such factors. These optimization protocols are routine procedures well within the scope of one skilled in the art and the teaching herein.

As a non-limiting example, a competitive assay can be performed by attaching one or more selected BoNT/B peptides to a solid support; adding simultaneously a test specimen and an enzyme-labeled secondary antibody; and adding a substrate that produces a detectable compound when acted upon by the enzyme. In this type of assay format, the amount of signal that is detected is inversely proportional to the amount of anti-BoNT antibody present in the test specimen.

In one embodiment, the presence or absence of anti-BoNT antibodies immunoreactive with a BoNT/B peptide is determined using an enzyme-linked immunosorbent assay (ELISA). In another embodiment, the presence or absence of anti-BoNT antibodies immunoreactive with a BoNT/B peptide is determined using a radioimmunoassay.

Various detection methods can be employed in any of the assay formats disclosed in the present specification, including without limitation, a radiation detection method, a fluorescence detection method, a fluorescence resonance energy transfer (FRET) detection method, a phosphorescence detection method, a chemiluminescence detection method, a bioluminescence detection method, an electrochemiluminescence detection method, a chromagenic detection method and an enzyme-activity detection method. In addition, any of a variety of marker compounds suitable for the detection system selected, can be operably-linked to a BoNT/B peptide as a labeled molecule including, without limitation, a radioisotope, fluorescent compound, a phosphorescent compound, a chemiluminescent compound, a bioluminescent compound, and the like. Thus, in one aspect of the present invention, a marker compound suitable for the selected detection system is operably-linked to a BoNT/B peptide as the labeled molecule suitable for any method. As used herein, the term "operably linked" when used in reference to a labeled molecule, means any of a variety of chemical reactions that can join a marker compound disclosed in the present specification to a BoNT/B peptide disclosed in the present specification such that a single peptide, comprising a peptide and marker compound, suitable to perform a method disclosed in the present specification is produced.

Non-limiting examples of radioisotopes that may be operably-linked to a BoNT/B peptide disclosed in the specification include, e.g., $^{3}$Hydrogen, $^{14}$Carbon, $^{22}$Sodium, $^{32}$Phosphorus, $^{33}$Phosphorus, $^{35}$Sulfer, $^{36}$Chlorine, $^{45}$Calcium, 51 Chromium, $^{57}$Cobalt, $^{58}$Cobalt, $^{59}$Iron, $^{63}$Nickel, $^{65}$Zinc, $^{75}$Selenium, $^{86}$Rubidum, $^{103}$Ruthenium, $^{109}$Cadmium, $^{125}$Iodine, $^{13}$Iodine, and the like. Non-limiting examples of fluorescent compounds that may be operably-linked to a BoNT/B peptide disclosed in the specification include, e.g., fluorescein, fluorescamine, isocyanate, isothiocyanate, rhodamine, phycoerythrin, phycocyanin, allophycocyanin, o-phthaldehyde, Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Cy-2, Cy-3, Cy-5, Cy-7 and the like. Non-limiting examples of chemiluminescent compounds that may be operably-linked to a BoNT/B peptide disclosed in the specification include, e.g., imidazoles, such as, e.g., lophine; acylhydrazines, such as, e.g., luminal and isoluminol; acridinium salts and esters, such as, e.g., lucigenin; oxalate salts and esters, such as, e.g., bis(2,4,6-trichloropheryl) oxalate (TCPO) and bis(2,4,-dinitrophenyl) oxalate (DNPO); Tris (2,2N-bipyridine) ruthenium compounds, such as, e.g., ruthenium(bipyridine)$_3$, and the like. Non-limiting examples of bioluminescent compounds that may be operably-linked to a BoNT/B peptide disclosed in the specification include, e.g., bacterial luciferins, dinoflagellate luciferins, vargulins, porichthys luciferins, coelenterazines, beetle luciferins, 4-methylumbelliferone esters, and the like.

Likewise, any of a variety of peptides suitable for the detection method selected, can be operably-linked to a BoNT/B peptide as a fusion protein including, without limitation, a peptide necessary for producing florescence, a peptide necessary for producing phosphorescence, a peptide necessary for producing chemiluminescence, a peptide necessary for producing bioluminescence, and the like. As used herein, the term "operably linked" when used in reference to a fusion protein, means any of a variety of cloning methods that can join a first nucleic acid sequence composition encoding a first peptide disclosed in the present specification in-frame with a second nucleic acid sequence composition encoding a second peptide disclosed in the present specification such that a single peptide, comprising both the first and second peptides, suitable to perform a method disclosed in the present specification is produced when expressed. In one embodiment, a peptide suitable for the detection method selected, is operably-linked to a BoNT/B peptide.

Non-limiting examples of a peptide necessary for producing florescence that may be operably-linked to a BoNT/B peptide disclosed in the specification include, e.g., photoproteins, such as, e.g., aequorin; obelin; Aequorea fluorescent proteins, such, e.g., green fluorescent protein (GFP), cyan fluorescent protein (CFP), blue fluorescent protein (BFP), red fluorescent protein (RFP), yellow fluorescent protein (YFP), ultraviolet fluorescent protein (GFPuv), their fluorescence-enhancement variants, including EGFP, ECFP, EBFP and EYFP, their peptide destabilization variants, and the like; and Red coral reef fluorescent proteins (RCFPs), such, e.g., Discosoma red fluorescent protein (DsRed), Anemonia red fluorescent protein (AsRed), Heteractis far-red fluorescent protein (HcRed), Anemonia cyan fluorescent protein (AmCyan), Zoanthus green fluorescent protein (ZsGreen), Zoanthus yellow fluorescent protein (ZsYellow), their fluorescence-enhancement variants, including DsRed2, AsRed2, their peptide destabilization variants, and the like. Non-limiting examples of a peptide necessary for producing chemiluminescence that may be operably-linked to a BoNT/B peptide disclosed in the specification include, e.g., alkaline phosphatases, horseradish peroxidases, xanthine oxidases, glucose oxidases and β-galatosidases. Non-limiting examples of a peptide necessary for producing bioluminescence that may be operably-linked to a BoNT/B peptide disclosed in the specification include, e.g., bacterial luciferases, dinoflagellate luciferases, vargula luciferases, coelenterate luciferases, beetle luciferases, and the like. Non-limiting examples of a peptide necessary for producing chromogenic compound that may be operably-linked to a BoNT/B peptide disclosed in the specification include, e.g., alkaline phosphatases, horseradish peroxidases, ureases, β-glucourinidases, glucose oxidases and β-galatosidases.

Non-limiting examples of specific protocols for selecting, making and using detection systems, making and using peptides labeled with a marker compound and making and using fusion proteins are described in, e.g., MOLECULAR CLONING A LABORATORY MANUAL, supra, (2001); METHODS IN ENZYMOLOGY, VOL. 305, BIOLUMINESCENCE AND CHEMILUMINESCENCE, PART C (Miriam M. Ziegler & Thomas O. Baldwin eds., Academic Press, 2000); Y. Fuster Mestre et al., *Flow-chemiluminescence: A Growing Modality of Pharmaceutocal Analysis*, 16 LUMINESCENCE 213-235, (2001); Lee F. Greer III & Aladar A. Szalay, *Imaging of Light Emission From the Expression of Luciferases in Living Cells and Organisms: A Review*, 17 LUMINESCENCE 43-74, (2002); Richard W. Horobin & John A. Kiernan, CONN'S BIOLOGICAL STAINS: A HANDBOOK OF DYES, STAINS AND FLUOROCHROMES FOR USE IN BIOLOGY AND MEDICINE (BIOS Scientific Publishers, $10^{th}$ ed. 2002); HANDBOOK OF FLUORESCENT PROBES AND RESEARCH CHEMICALS, http://www.probes.com/ handbook (Molecular Probes, Inc., $9^{th}$ ed, 2004), and CURRENT PROTOCOLS IN MOLECULAR BIOLOGY, supra, (2004). In addition, non-limiting examples of how to make and use detection systems, labeled peptides and fusion protein disclosed in the present specification, as well as well-characterized reagents, conditions and protocols are readily available from commercial vendors that include, without limitation, Amersham Biosciences, Piscataway, N.J.; BD Biosciences-Clontech, Palo Alto, Calif.; Bio-Rad Laboratories, Hercules, Calif.; Cayman Chemical Co., Ann Arbor, Mich.; Molecular Probes, Inc., Eugene, Oreg.; PerkinElmer Life and Analytical Sciences, Inc., Boston, Mass.; Pierce Biotechnology, Inc., Rockford, Ill.; Princeton Separations, Adelphia, N.J.; and Vector Laboratories, Burlingame, Calif. These protocols are routine procedures within the scope of one skilled in the art and from the teaching herein.

Thus, in an embodiment, a BoNT/B peptide is operably-linked to a radioisotope. In an aspect of this embodiment, a BoNT/B peptide is operably-linked to $^{3}$Hydrogen, $^{14}$Carbon, $^{22}$Sodium, $^{32}$Phosphorus, $^{33}$Phosphorus, $^{35}$Sulfer, $^{36}$Chlorine, $^{45}$Calcium, $^{51}$Chromium, $^{57}$Cobalt, $^{58}$Cobalt, $^{59}$Iron, $^{63}$Nickel, $^{65}$Zinc, $^{75}$Selenium, $^{86}$Rubidum, $^{103}$Ruthenium, $^{109}$Cadmium, $^{125}$Iodine or $^{131}$Iodine. In another aspect of this embodiment, the presence of anti-BoNT antibody-BoNT/B peptide complexes is quantitatively determined using a scintillation counter. In another aspect of this embodiment, the absence of anti-BoNT antibody-BoNT/B peptide complexes is quantitatively determined using a scintillation counter.

In yet another embodiment, a BoNT/B peptide is operably-linked to a fluorescent compound. In an aspect of this embodiment, a BoNT/B peptide is operably-linked to a fluorescein, a fluorescamine, an isocyanate, an isothiocyanate, a rhodamine, a phycoerythrin, a phycocyanin, an allophycocyanin, an o-phthaldehyde, an Alexa Fluor® 350, an Alexa Fluor® 430, an Alexa Fluor® 488, an Alexa Fluor® 532, an Alexa Fluor® 546, an Alexa Fluor® 555, an Alexa Fluor® 568, an Alexa Fluor® 594, an Alexa Fluor® 633, an Alexa Fluor® 647, an Alexa Fluor® 660, an Alexa Fluor® 680, an Alexa Fluor® 700, an Alexa Fluor® 750, a Cy-2, a Cy-3, a Cy-5 or a Cy-7. In another aspect of this embodiment, the presence of anti-BoNT antibody-BoNT/B peptide complexes is quantitatively determined using a spectrofluorometer (see, e.g., Example 7). In another aspect of this embodiment, the absence of anti-BoNT antibody-BoNT/B peptide complexes is quantitatively determined using a spectrofluorometer.

In another embodiment, a BoNT/B peptide is operably-linked to a photoprotein. In an aspect of this embodiment, a BoNT/B peptide is operably linked to an aequorin, an obelin, a GFP, an EGFP, a CFP, an ECFP, a BFP, an EBFP, a YFP, an EYFP, a GFPuv, a DsRed, a DsRed2, a AsRed, a AsRed2, a HcRed, an AmCyan, a ZsGreen or a ZsYellow. In another aspect of this embodiment, the presence of anti-BoNT antibody-BoNT/B peptide complexes is quantitatively determined using a spectrofluorometer.

In another aspect of this embodiment, the absence of anti-BoNT antibody-BoNT/B peptide complexes is quantitatively determined using a spectrofluorometer.

In yet another embodiment, a BoNT/B peptide is operably-linked to a chemiluminescent compound. In an aspect of this embodiment, a BoNT/B peptide is operably linked to an imidazole, an acridinium salt, an acridinium ester, an oxalate salt, an oxalate ester, or a Tris (2,2N-bipyridine) ruthenium compound. In another aspect of this embodiment, the presence of anti-BoNT antibody-BoNT/B peptide complexes is quantitatively determined using a luminometer. In another aspect of this embodiment, the absence of anti-BoNT antibody-BoNT/B peptide complexes is quantitatively determined using a luminometer.

In yet another embodiment, a BoNT/B peptide is operably-linked to a peptide necessary for producing chemiluminescence. In an aspect of this embodiment, a BoNT/B peptide is operably linked to an alkaline phosphatase, a horseradish peroxidase, a xanthine oxidase, a glucose oxidase or a β-galactosidase. In another aspect of this embodiment, the presence of anti-BoNT antibody-BoNT/B peptide complexes is quantitatively determined using a luminometer. In another aspect of this embodiment, the absence of anti-BoNT antibody-BoNT/B peptide complexes is quantitatively determined using a luminometer.

In yet another embodiment, a BoNT/B peptide is operably-linked to a peptide necessary for producing bioluminescence. In an aspect of this embodiment, a BoNT/B peptide is operably linked to a bacterial luciferase, a dinoflagellate luciferase, a vargula luciferase, a coelenterate luciferase or a beetle luciferase. In another aspect of this embodiment, the presence of anti-BoNT antibody-BoNT/B peptide complexes is quantitatively determined using a luminometer. In another aspect of this embodiment, the absence of anti-BoNT antibody-BoNT/B peptide complexes is quantitatively determined using a luminometer.

In yet another embodiment, a BoNT/B peptide is operably-linked to a peptide necessary for producing a chromogenic product. In an aspect of this embodiment, a BoNT/B peptide is operably linked to an alkaline phosphatase, a horseradish peroxidase, an urease, β-glucourinidase, a glucose oxidase or a β-galactosidase. In another aspect of this embodiment, the presence of anti-BoNT antibody-BoNT/B peptide complexes is quantitatively determined using a spectrophotometer. In another aspect of this embodiment, the absence of anti-BoNT antibody-BoNT/B peptide complexes is quantitatively determined using a spectrophotometer.

Aspects of the present invention provide, in part, comparing the amount of anti-BoNT antibody-BoNT/B peptide complexes formed in the test sample to the amount of anti-BoNT antibody-BoNT/B peptide complexes formed in the control sample. In an embodiment, the amount of anti-BoNT antibody-BoNT/B peptide complexes in the test sample is increased as compared to the amount of anti-BoNT antibody-BoNT/B peptide complexes formed in the control sample. In an aspect of this embodiment, an increase in the amount of anti-BoNT antibody-BoNT/B peptide complexes formed in the test sample as compared to a positive control sample indicates an increase of immunoresistance to a BoNT therapy in the individual. In another aspect of this embodiment, an increase in the amount of anti-BoNT antibody-BoNT/B peptide complexes formed in the test sample as compared to a negative control sample indicates an increase of immunoresistance to a BoNT therapy in the individual. In another embodiment, the amount of anti-BoNT antibody-BoNT/B peptide complexes formed in the test sample is decreased as compared to the amount of anti-BoNT antibody-BoNT/B peptide complexes formed in the control sample. In an aspect of this embodiment, a decrease in the amount of anti-BoNT antibody-BoNT/B peptide complexes formed in the test sample as compared to a positive control sample indicates a decrease of immunoresistance to a BoNT therapy in the individual. In another aspect of this embodiment, a decrease in the amount of anti-BoNT antibody-BoNT/B peptide complexes formed in the test sample as compared to a negative control sample indicates a decrease of immunoresistance to a BoNT therapy in the individual.

In an embodiment, the presence of anti-BoNT antibody-BoNT/B peptide complexes in the test sample indicates the presence of immunoresistance to a BoNT therapy in the individual. In an aspect of this embodiment, the presence of anti-BoNT antibody-BoNT/B peptide complexes in the test sample is compared to the presence of anti-BoNT antibody-BoNT/B peptide complexes in the control sample. In an aspect of this embodiment, the presence of anti-BoNT antibody-BoNT/B peptide complexes in the test sample as compared to a negative control sample indicates the presence of immunoresistance to a BoNT therapy in the individual.

In another embodiment, the absence of anti-BoNT antibody-BoNT/B peptide complexes in the test sample indicates the absence of immunoresistance to a BoNT therapy in the individual. In an aspect of this embodiment, the absence of anti-BoNT antibody-BoNT/B peptide complexes in the test sample is compared to the absence of anti-BoNT antibody-BoNT/B peptide complexes in the control sample. In another aspect of this embodiment, the absence of anti-BoNT antibody-BoNT/B peptide complexes in the test sample as compared to a positive control sample indicates the absence of immunoresistance to a BoNT therapy in the individual.

Aspects of the present invention provide, in part, comparing the amount of free or unbound BoNT/B peptides in the test sample to the amount of free or unbound BoNT/B peptides in the control sample. In an embodiment, the amount of free or unbound BoNT/B peptides in the test sample increases as compared to the amount of free or unbound BoNT/B peptides in the control sample. In an aspect of this embodiment, an increase in the amount of free or unbound BoNT/B peptides in the test sample as compared to a positive control sample indicates a decrease of immunoresistance to a BoNT therapy in the individual. In another aspect of this embodiment, an increase in the amount of free or unbound BoNT/B peptides in the test sample as compared to a negative control sample indicates a decrease of immunoresistance to a BoNT therapy in the individual. In another embodiment, the amount of free or unbound BoNT/B peptides in the test sample decreases as compared to the amount of free or unbound BoNT/B peptides in the control sample. In an aspect of this embodiment, a decrease in the amount of free or unbound BoNT/B peptides in the test sample as compared to a positive control sample indicates an increase of immunoresistance to a BoNT therapy in the individual. In another aspect of this embodiment, a decrease in the amount of free or unbound BoNT/B peptides in the test sample as compared to a negative control sample indicates an increase of immunoresistance to a BoNT therapy in the individual.

Aspects of the present invention provide, in part, comparing the amount of free or unbound anti-BoNT antibodies in the test sample to the amount of free or unbound anti-BoNT antibodies in the control sample. In an embodiment, the amount of free or unbound anti-BoNT antibodies in the test sample increases as compared to the amount of free or unbound anti-BoNT antibodies in the control sample. In an aspect of this embodiment, an increase in the amount of free or unbound anti-BoNT antibodies in the test sample as compared to a positive control sample indicates an increase of immunoresistance to a BoNT therapy in the individual. In another aspect of this embodiment, an increase in the amount of free or unbound anti-BoNT antibodies in the test sample as compared to a negative control sample indicates an increase of immunoresistance to a BoNT therapy in the individual. In another embodiment, the amount of free or unbound anti-BoNT antibodies in the test sample decreases as compared to the amount of free or unbound anti-BoNT antibodies in the control sample. In an aspect of this embodiment, a decrease in the amount of free or unbound anti-BoNT antibodies in the test sample as compared to a positive control sample indicates a decrease of immunoresistance to a BoNT therapy in the individual. In another aspect of this embodiment, a decrease in the amount of free or unbound anti-BoNT antibodies in the test sample as compared to a negative control sample indicates a decrease of immunoresistance to a BoNT therapy in the individual.

Thus, in one embodiment, a method of determining immunoresistance to botulinum toxin therapy in an individual comprising the step of determining the presence or absence in the individual of anti-BoNT antibodies immunoreactive with a BoNT/B peptide, where the presence of the anti-BoNT antibody-BoNT/B peptide complex is indicative of immunoresistance to a BoNT therapy.

In another embodiment, a method of determining immunoresistance to BoNT therapy in an individual, the method comprising the steps of combining a BoNT/B peptide and a test sample under conditions suitable for the selective binding of the BoNT/B peptide to an anti-BoNT antibody and determining the presence of an anti-BoNT antibody-BoNT/B peptide complex, the antibody-peptide complex formed by the selective binding of an anti-BoNT antibody and the BoNT/B peptide, where the presence of the anti-BoNT antibody-BoNT/B peptide complex is indicative of immunoresistance to a BoNT therapy.

In another embodiment, a method of determining immunoresistance to BoNT therapy in an individual, the method comprising the steps of combining a BoNT/B peptide and a test sample under conditions suitable for the selective binding of the BoNT/B peptide to an anti-BoNT antibody and determining the presence of an anti-BoNT antibody-BoNT/B peptide complex, the antibody-peptide complex formed by the selective binding of an anti-BoNT antibody and the BoNT/B peptide and correlating the amount of an antibody-peptide complex formed from the test sample relative to the amount of an antibody-peptide complex formed by the BoNT/B peptide combined to a control sample where the presence of the anti-BoNT antibody-BoNT/B peptide complex is indicative of immunoresistance to a BoNT therapy.

Patients treated with a botulinum toxin therapy can develop immunoresistance to the therapeutic treatment, reducing or eliminating the beneficial effect of botulinum toxin therapy. Methods that prevent or reduce the development of a BoNT-specific immune response in an individual, which in turn can prevent or reduce immunoresistance to a botulinum toxin therapy, are of major importance. These treatments would allow for 1) the suppression of a potential deleterious immune response in a patient undergoing BoNT therapy thereby affording a more prolonged treatment course relative to current therapies; 2) the suppression of a BoNT immunoresponsive state in a patient thereby offering additional treatments that would otherwise have been ineffective. Therefore, these assays present a major benefit in terms of providing better patient care and reducing health care costs. The BoNT/B peptides disclosed in the present specification are useful in methods of determining immunoresistance to botulinum toxin therapy in aindividual. These peptides each contain one or more epitopes recognized by antibodies contained in antisera from animals immunized with BoNT/B, and thus can serve as binding substrates for anti-BoNT/B antibodies. The methods disclosed in the present specification can be useful for preventing or reducing immunoresistance to any of a variety of botulinum toxin therapies including, but not limited to, a BoNT/A therapy, a BoNT/B therapy, a BoNT/C1 therapy, a BoNT/D therapy, a BoNT/E therapy, a BoNT/F therapy and a BoNT/G therapy.

Thus, the present invention provides a method of treating immunoresistance to botulinum toxin therapy in an individual by administering to the individual a tolerogizing composition comprising a tolerogizing agent operably linked to a BoNT/B peptide the administration preventing or reducing immunoresistance to botulinum toxin therapy. Those skilled in the art can readily determine for a particular tolerogizing composition, a suitable pharmacological composition, an appropriate antigen payload; route of administration; volume of dose; and tolerogizing regimen useful in a particular individual, for example, humans.

Aspects of the present invention provide, in part, a method of treating immunoresistance to botulinum toxin therapy, such as, e.g., a BoNT/A immunoresistance condition, a BoNT/B immunoresistance condition, a BoNT/C1 immunoresistance condition, a BoNT/D immunoresistance condition, a BoNT/E immunoresistance condition, a BoNT/F immunoresistance condition or a BoNT/G immunoresistance condition. As used herein, the term "treating," when used in reference to administering to an individual a tolerogizing composition, means reducing a symptom of a condition characterized by resistance to a BoNT therapy, or delaying or preventing onset of a symptom of a condition characterized by a BoNT immunoresistance in the individual. For example, the term "treating" means reducing a symptom of a condition characterized by a BoNT immunoresistance by, e.g., at least 30%, at least 40%, at least 50%, at least 60%, at least 70%, at least 80%, at least 90% or at least 100%. The effectiveness of a tolerogizing composition in treating a condition character-ized by BoNT immunoresistance can be determined by observing one or more clinical symptoms or physiological indicators associated with the condition. An improvement in a condition characterized by BoNT immunoresistance also can be indicated by a reduced need for a concurrent therapy. Those of skill in the art will know the appropriate symptoms or indicators associated with specific conditions and will know how to determine if an individual is a candidate for treatment with a tolerogizing composition disclosed in the present specification. In particular, it is understood that those skilled in the art will be able to determine if a condition is characterized by BoNT immunoresistance, e.g., by comparison of levels of BoNT immunoresistance from an individual suspected to have an immunoresistance to a BoNT therapy with an individual not suspected to have an immunoresistance to a BoNT therapy.

Aspects of the present invention provide, in part, administration of a tolerogizing composition. As used herein, the term "administration" means any delivery mechanism that provides a tolerogizing composition to an individual that potentially results in a clinically, therapeutically, cosmetically or experimentally beneficial result. A tolerogizing composition useful in the methods of the invention can be administered to an individual by any of a variety of routes depending, for example, on the type and location of BoNT immunoresistance to be treated, the tolerogizing composition, or other compound to be included in the composition, and the history, risk factors and symptoms of the subject. Routes of administration suitable for the methods of the invention include both local and systemic administration. Local administration results in significantly more tolerogizing composition being delivered to a specific location as compared to the entire body of the subject, whereas, systemic administration results in delivery of a tolerogizing composition to essentially the entire body of the subject. A tolerogizing composition can also be administered peripherally. As used herein, the term "peripheral administration" or "administered peripherally" means introducing an agent into an individual outside of the central nervous system. Peripheral administration encompasses any route of administration other than direct administration to the spine or brain. As such, it is clear that intrathecal and epidural administration as well as cranial injection or implantation is not within the scope of the term "peripheral administration" or "administered peripherally."

Administration of a tolerogizing composition can be by a variety of routes including, without limitation, orally in any acceptable form, such as, e.g., tablet, liquid, capsule, powder, or the like; topically in any acceptable form, such as, e.g., patch, drops, creams, gels or ointments; by injection, in any acceptable form, such as, e.g., intravenous, intraperitoneal, intramuscular, subcutaneous, parenteral or epidural; and by implant, such as, e.g., subcutaneous pump, intrathecal pump, suppository, bioerodible delivery system, non-bioerodible delivery system or other implanted extended or slow release device or formulation. As a non-limiting example, oral tolerance is well-recognized in the art (see, for example, Weiner, *Hospital Practice*, pp. 53-58 (Sep. 15, 1995). Additionally, an exemplary list of biodegradable polymers and methods of use are described in, e.g., Handbook of Biodegradable Polymers (Abraham J. Domb et al., eds., Overseas Publishers Association, 1997); Controlled Drug Delivery: Designing Technologies for the Future (Kinam Park & Randy J. Mrsny eds., American Chemical Association, 2000); Vernon G. Wong, Method for Reducing or Preventing Transplant Rejection in the Eye and Intraocular Implants for Use Therefor, U.S. Pat. No. 6,699,493 (Mar. 2, 2004); Vernon G. Wong & Mae W. L. Hu, Methods for Treating Inflammation-mediated Conditions of the Eye, U.S. Pat. No. 6,726,918 (Apr. 27, 2004); David A. Weber et al., Methods and Apparatus for Delivery of Ocular Implants, U.S. Patent Publication No. US2004/0054374 (Mar. 18, 2004); Thierry Nivaggioli et al., Biodegradable Ocular Implant, U.S. Patent Publication No. US2004/0137059 (Jul. 15, 2004). In general administration of a tolerogizing composition to an individual can depend on, e.g., the type immunoresistance, the BoNT/B peptide included in the composition, the tolerogizing agent included in the composition, and the history, risk factors and symptoms of the individual.

A tolerogizing composition can be administered to an individual prior to administering botulinum toxin therapy to prevent the development of immunoresistance, during a course of botulinum toxin therapy, or after onset of immunoresistance, such as, e.g., when symptoms of resistance are first apparent. In addition, a tolerogizing composition can be administered to an individual who is at increased risk for immunoresistance to botulinum toxin therapy. Those skilled in the art will be able to determine an appropriate candidate for receiving a tolerogizing composition of the invention based on, e.g., the particular condition to be treated and the presence or likelihood of symptoms of immunoresistance.

Thus, in one embodiment, a method of the present invention is practiced by administering a tolerogizing composition prior to an individual receiving a BoNT therapy, such as, e.g., a BoNT/A therapy, a BoNT/B therapy, a BoNT/C1 therapy, a BoNT/D therapy, a BoNT/E therapy, a BoNT/F therapy or a BoNT/G therapy. Such an individual can be, for, e.g., an individual at increased risk for developing immunoresistance to botulinum toxin therapy. In another embodiment, a method of the present invention is practiced by administering a tolerogizing composition after an individual has received a BoNT therapy, such as, e.g., a BoNT/A therapy, a BoNT/B therapy, a BoNT/C1 therapy, a BoNT/D therapy, a BoNT/E therapy, a BoNT/F therapy or a BoNT/G therapy. In yet another embodiment, a method of the present invention is practiced by administering a tolerogizing composition to an individual who has not been diagnosed with a BoNT immunoresistance condition, such as, e.g., a BoNT/A immunoresistance condition, a BoNT/B immunoresistance condition, a BoNT/C1 immunoresistance condition, a BoNT/D immunoresistance condition, a BoNT/E immunoresistance condition, a BoNT/F immunoresistance condition or a BoNT/G immunoresistance condition. In yet another embodiment, a method of the present invention is practiced by administering a tolerogizing composition to an individual that has been diagnosed with a BoNT/A immunoresistance condition.

In another embodiment, a tolerogizing composition is administered to an individual. In aspects of this embodiment, a tolerogizing composition is administered orally to an individual, a tolerogizing composition is administered topically to an individual, a tolerogizing composition is injected to an individual or a tolerogizing composition is implanted in an individual.

A tolerogizing composition useful in a method of the invention is administered to an individual in an effective amount. As used herein, the term "effective amount" when used in reference to treating BoNT imunniresistance means the minimum dose necessary to achieve the desired therapeutic effect and includes a dose sufficient to reduce a symptom associated with a BoNT immunoresistance response. In aspects of this embodiment, an effect amount of a tolerogizing composition reduces a symptom associated with a BoNT immunoresistance response by, e.g., at least 30%, at least 40%, at least 50%, at least 60%, at least 70%, at least 80%, at least 90% or at least 100%. In other aspects of this embodiment, an effect amount of a tolerogizing composition reduces a symptom associated with a BoNT immunoresistance response by, e.g., at most 30%, at most 40%, at most 50%, at most 60%, at most 70%, at most 80%, at most 90% or at most 100%.

The appropriate effective amount to be administered for a particular application of the methods can be determined by those skilled in the art, using the guidance provided herein. For example, an effective amount can be extrapolated from in vitro assays and in vivo administration studies using animal models prior to administration to humans. Such a effect amount generally is in the range of 0.1-1000 mg/day and can be, e.g., in the range of 0.1-500 mg/day, 0.5-500 mg/day, 0.5-100 mg/day, 0.5-50 mg/day, 0.5-20 mg/day, 0.5-10 mg/day or 0.5-5 mg/day. An effective dose of a tolerogizing composition useful for inducing tolerance in an individual will depend upon the particular BoNT/B peptide used, the tolerogizing agent used, and the route administration. In addition, the actual amount of the effective dose of a tolerogizing composition to be administered to an individual will be determined by a physician taking into account the cause of the BoNT immunoresistance, the severity of the BoNT immunoresistance and the particular characteristics of the individual, such as age, weight, general health and the like. Where repeated administration is used, the frequency of administration depends, in part, on the half-life of the tolerogizing composition. One skilled in the art will recognize that the condition of the individual can be monitored throughout the course of therapy and that the effective amount of a tolerogizing composition that is administered can be adjusted accordingly. It is also understood that the frequency and duration of dosing will be dependent, in part, on the relief desired and the half-life of the tolerogizing composition.

Aspects of the present invention provide, in part, a tolerogizing composition. It is envisioned that any of the tolerogizing composition disclosed in the present specification can be useful in a method of treating immunoresistance to botulinum toxin therapy in an individual, with the proviso that the tolerogizing composition prevents or reduces the immunoresistance to a botulinum toxin therapy. Non-limiting examples include tolerogizing compositions comprising BoNT/B peptide derived from a naturally occurring BoNT/B operably linked to a tolerogizing agent, such as, e.g., BoNT/B peptide derived from the BoNT/B of SEQ ID NO: 1 operably linked to a tolerogizing agent, a BoNT/B peptide derived from a BoNT/B isoform operably linked to a tolerogizing agent or a BoNT/B peptide derived from a BoNT/B subtype operably linked to a tolerogizing agent; and a BoNT/B peptide derived from a non-naturally occurring BoNT/B operably linked to a tolerogizing agent, such as, e.g., a BoNT/B peptide derived from a conservative BoNT/B variant operably linked to a tolerogizing agent, a BoNT/B peptide derived from a non-conservative BoNT/B variant operably linked to a tolerogizing agent and a BoNT/B peptide derived from a chimeric BoNT/B peptide operably linked to a tolerogizing agent. BoNT/B peptides within a tolerogizing composition disclosed in the present specification can be selected on, e.g., immunological factors, such as the selectivity of the BoNT/B peptide for an anti-BoNT antibody, and technical factors, such as chemical synthesis yields. It is also understood that the two or more different BoNT/B peptides can be provided separately or as part of a compound molecule such as a chimeric BoNT/B peptide.

A tolerogizing composition useful in the invention generally is administered in a pharmaceutical acceptable composition. As used herein, the term "pharmaceutically acceptable" means any molecular entity or composition that does not produce an adverse, allergic or other untoward or unwanted reaction when administered to an individual. As used herein, the term "pharmaceutically acceptable composition" means a therapeutically effective concentration of an active ingredient. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

It is also envisioned that a pharmaceutical composition disclosed in the present specification can optionally include a pharmaceutically acceptable carriers that facilitate processing of an active ingredient into pharmaceutically acceptable compositions. As used herein, the term "pharmacologically acceptable carrier" means any carrier that has substantially no long term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, $7^{th}$ ed. 1999); REMINGTON: THE SCIENCE AND PRACTICE OF PHARMACY (Alfonso R. Gennaro ed., Lippincott, Williams & Wilkins, 20 ed. 2000); GOODMAN & GILMAN'S THE PHARMACOLOGICAL BASIS OF THERAPEUTICS (Joel G. Hardman et al., eds., McGraw-Hill Professional, $10^{th}$ ed. 2001); and HANDBOOK OF PHARMACEUTICAL EXCIPIENTS (Raymond C. Rowe et al., APhA Publications, $4^{th}$ edition 2003). These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed.

Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE®. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

In an embodiment, a method of treating immunoresistance to a botulinum toxin therapy in an individual comprises the step of administering to the individual a tolerogizing composition comprising a tolerogizing agent operably linked to a BoNT/B peptide, where the administration prevents or reduces immunoresistance to botulinum toxin therapy.

Patients treated with a BoNT therapy can develop immunoresistance to the treatment, thereby reducing or eliminating the beneficial effect of the BoNT therapy. Therefore, blood purifying methods that reduce or eliminate anti-BoNT antibodies from a patient mounting an immune response against a BoNT therapy are of major importance. Immunoapheretic methods would provide a remedy for BoNT immunoresistance, thereby allowing a patient to continue undergoing a BoNT therapy. Therefore, these methods present a major benefit in terms of providing better patient care and reducing health care costs. The BoNT/B peptides disclosed in the present specification are useful in methods of reducing or eliminating anti-BoNT antibodies from an individual. In general, blood from an individual exhibiting signs of immunoresistance to a BoNT therapy can be treated extracorporeally to remove anti-BoNT antibodies using an immunosorbent composition comprising at least one BoNT/B peptide disclosed in the present specification and the treated blood returned back into the individual. Therapeutic immunopheresis has been successfully applied, see, e.g., A. du Moulin et al., *Antibody-based immunoadsorption as a Therapeutic Means,* 11(3) Blood Purif. 145-149 (1993); W. O. Richter et al., *Efficacy and Safety of Immunoglobulin Apheresis,* 43(1) ASAIO J. 53-59 (1997); Watts A. Foley et al., *Plasma Perfusion by Apheresis Through a Gal Immunoaffinity Column Successfully Depletes anti-Gal Antibody: Experience with* 320 *Aphereses in Baboons,* 7 Xenotransplant. 181-185 (2000); Monika Graninger et al, *Immunoadsorption Therapy (Therasorb) in Patients with Severe Lupus Erythematosus,* 29 Acta. Med. Austriaca 26-29 (2002); Daniel R. Henderson et al., Methods of Enhancing Effectiveness of Therapeutic Viral Immunogenic Agent Administration, U.S. Pat. No. 6,406,861 (Jun. 18, 2002); and Robert Koll et al., Treatment of Cardiomyopathy by Removal of Autoantibodies, U.S. Pat. No. 7,022,322 (Apr. 4, 2006).

Thus, the present invention provides, in part, an anti-BoNT immunoapheresis method of treating immunoresistance to a BoNT therapy in an individual, the method comprising the steps of contacting an anti-BoNT antibody containing component from the individual extracorporeally with a BoNT/B peptide immunosorbent under conditions suitable for the selective binding of the BoNT/B peptide to the anti-BoNT antibody, the BoNT/B peptide having a length of at least 5 amino acids and at most 60 amino acids and returning the anti-BoNT antibody depleted component back into the individual. It is understood that any of the above methods of removing botulinum toxin blocking antibodies from a patient can be practiced by selectively removing IgG anti-botulinum toxin antibodies.

Aspects of the present invention provide, in part, an anti-BoNT immunoapheresis method. As used herein, the term "anti-BoNT immunoapheresis" is synonymous with "anti-BoNT immunoadsorption" and means the separation and removal of anti-BoNT antibodies from an anti-BoNT antibody containing component withdrawn from an individual and the remainder of the treated anti-BoNT antibody containing component returned back into the individual. By definition, anti-BoNT antibody adsorption by anti-BoNT immunoapheresis is an extracorporeal procedure.

Thus, in an embodiment, an anti-BoNT immunoapheresis method of treating immunoresistance to a BoNT therapy in an individual reduces the amount of anti-BoNT antibodies from an anti-BoNT antibody containing component. In aspects of this embodiment, the amount of anti-BoNT antibodies removed from an anti-BoNT antibody containing component is, e.g., at least 10% of the anti-BoNT antibodies from the anti-BoNT antibody containing component, at least 20% of the anti-BoNT antibodies from the anti-BoNT antibody containing component, at least 30% of the anti-BoNT antibodies from the anti-BoNT antibody containing component, at least 40% of the anti-BoNT antibodies from the anti-BoNT antibody containing component, at least 50% of the anti-BoNT antibodies from the anti-BoNT antibody containing component, at least 60% of the anti-BoNT antibodies from the anti-BoNT antibody containing component, at least 70% of the anti-BoNT antibodies from the anti-BoNT antibody containing component, at least 80% of the anti-BoNT antibodies from the anti-BoNT antibody containing component and at least 90% of the anti-BoNT antibodies from the anti-BoNT antibody containing component.

In other aspects of this embodiment, the amount of anti-BoNT antibodies removed from an anti-BoNT antibody containing component is, e.g., at most 10% of the anti-BoNT antibodies from the anti-BoNT antibody containing component, at most 20% of the anti-BoNT antibodies from the anti-BoNT antibody containing component, at most 30% of the anti-BoNT antibodies from the anti-BoNT antibody containing component, at most 40% of the anti-BoNT antibodies from the anti-BoNT antibody containing component, at most 50% of the anti-BoNT antibodies from the anti-BoNT antibody containing component, at most 60% of the anti-BoNT antibodies from the anti-BoNT antibody containing component, at most 70% of the anti-BoNT antibodies from the anti-BoNT antibody containing component, at most 80% of the anti-BoNT antibodies from the anti-BoNT antibody containing component and at most 90% of the anti-BoNT antibodies from the anti-BoNT antibody containing component.

Aspects of the present invention provide, in part, an anti-BoNT antibody containing component from the individual. Non-limiting examples of an anti-BoNT antibody containing component from the individual include, blood, serum, an isolated IgG antibody component and lymph fluid. Typically, blood removal and serum separation are achieved using an automated blood cell separator machine, see, e.g., Alessandro Zuccato and Rigaste S. Zeno, Method for the Specific Immunoadsorption of Selected Pathogenic Factors, PCT Publication WO 96/16666 (Jun. 6, 1996); and Robert Koll et al., Treatment of Cardiomyopathy by Removal of Autoantibodies, U.S. Pat. No. 7,022,322 (Apr. 4, 2006). Non-limiting examples of such a machine include, e.g., an autopheresis-Ctm Therapeutic Plasma System (TPS) is employed (Baxter Healthcare Corp, Deerfield, Ill.) and a COBE-Spectra pheresis unit (Blood Component Technology, Inc., Lakewood, Col.).

Aspects of the present invention provide, in part, a BoNT/B peptide immunosorbent. As used herein, the term "BoNT/B peptide immunosorbent" means a molecule comprising a BoNT/B peptide that selectively binds to an anti-BoNT antibody. It is envisioned that any of the BoNT/B peptides disclosed in the present specification can be useful for anti-BoNT immunoapheresis for extracorporeal removal of anti-BoNT antibodies. Non-limiting examples include a BoNT/B peptide derived from a naturally occurring BoNT/B, such as, e.g., the BoNT/B of SEQ ID NO: 1, SEQ ID NO: 3, SEQ ID NO: 5, SEQ ID NO: 7, SEQ ID NO: 9, SEQ ID NO: 11 or SEQ ID NO: 13, a BoNT/B isoform or a BoNT/B subtype; and a BoNT/B peptide derived from a non-naturally occurring BoNT/B, such as, e.g., a conservative BoNT/B variant, a non-conservative BoNT/B variant and a chimeric BoNT/B peptide. BoNT/B peptides disclosed in the present specification can be selected, e.g., depending on immunological factors, such as potency of the peptide in eliciting an immunogenic response, and technical factors, such as chemical synthesis yields. It is also understood that the two or more different BoNT/B peptides can be provided separately or as part of a compound molecule such as a chimeric BoNT/B peptide.

Thus, in an embodiment, a BoNT/B peptide immunosorbent comprises a BoNT/B peptide having a length of at least 5 amino acids and at most 60 amino acids. In aspects of this embodiment, a BoNT/B peptide immunosorbent comprises a BoNT/B peptide of SEQ ID NO: 1 having a length of at least 5 amino acids and at most 60 amino acids, a BoNT/B peptide of SEQ ID NO: 3 having a length of at least 5 amino acids and at most 60 amino acids, a BoNT/B peptide of SEQ ID NO: 5 having a length of at least 5 amino acids and at most 60 amino acids, a BoNT/B peptide of SEQ ID NO: 7 having a length of at least 5 amino acids and at most 60 amino acids, a BoNT/B peptide of SEQ ID NO: 9 having a length of at least 5 amino acids and at most 60 amino acids, a BoNT/B peptide of SEQ ID NO: 11 having a length of at least 5 amino acids and at most 60 amino acids or a BoNT/B peptide of SEQ ID NO: 11 having a length of at least 5 amino acids and at most 60 amino acids.

In other aspects of this embodiment, a BoNT/B peptide immunosorbent comprises a BoNT/B peptide comprising an amino acid sequence selected from the group consisting of amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, a BoNT/B peptide immunosorbent comprises a BoNT/B peptide comprising an amino acid sequence selected from the group consisting of amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 932-950 of SEQ ID NO: 1, amino acids 932-950 of SEQ ID NO: 5, amino acids 974-992 of SEQ ID NO: 1, amino acids 974-992 of SEQ ID NO: 3, amino acids 974-992 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In still other aspects of this embodiment, a BoNT/B peptide immunosorbent comprises a BoNT/B peptide comprising an amino acid sequence selected from the group consisting of amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In another embodiment, a BoNT/B peptide immunosorbent comprises a BoNT/B peptide having a length of at least 5 amino acids and at most 60 amino acids and is derived from a naturally occurring BoNT/B. In aspects of this embodiment, the naturally occurring BoNT/B is a BoNT/B isoform or a BoNT/B subtype.

In another embodiment, a BoNT/B peptide immunosorbent comprises a BoNT/B peptide having a length of at least 5 amino acids and at most 60 amino acids and is derived from a non-naturally occurring BoNT/B. In aspects of this embodiment, the naturally occurring BoNT/B is a conservative BoNT/B variant or a non-conservative BoNT/B variant.

In aspects of this embodiment, a BoNT/B peptide immunosorbent comprises a BoNT/B peptide comprising, e.g., 1-4 conservative amino acid substitutions to amino acids 610-628 of SEQ ID NO: 1, 1-4 conservative amino acid substitutions to amino acids 736-754 of SEQ ID NO: 1, 1-4 conservative amino acid substitutions to amino acids 736-754 of SEQ ID NO: 5, 1-4 conservative amino acid substitutions to amino acids 778-796 of SEQ ID NO: 1, 1-4 conservative amino acid substitutions to amino acids 778-796 of SEQ ID NO: 5, 1-4 conservative amino acid substitutions to amino acids 820-838 of SEQ ID NO: 1, 1-4 conservative amino acid substitutions to amino acids 820-838 of SEQ ID NO: 3, 1-4 conservative amino acid substitutions to amino acids 820-838 of SEQ ID NO: 5, 1-4 conservative amino acid substitutions to amino acids 820-838 of SEQ ID NO: 7, 1-4 conservative amino acid substitutions to amino acids 862-880 of SEQ ID NO: 1, 1-4 conservative amino acid substitutions to amino acids 862-880 of SEQ ID NO: 7, 1-4 conservative amino acid substitutions to amino acids 890-908 of SEQ ID NO: 1, 1-4 conservative amino acid substitutions to amino acids 890-908 of SEQ ID NO: 3, 1-4 conservative amino acid substitutions to amino acids 890-908 of SEQ ID NO: 5, 1-4 conservative amino acid substitutions to amino acids 890-908 of SEQ ID NO: 7, 1-4 conservative amino acid substitutions to amino acids 918-936 of SEQ ID NO: 1, 1-4 conservative amino acid substitutions to amino acids 918-936 of SEQ ID NO: 3, 1-4 conservative amino acid substitutions to amino acids 932-950 of SEQ ID NO: 1, 1-4 conservative amino acid substitutions to amino acids 932-950 of SEQ ID NO: 5, 1-4 conservative amino acid substitutions to amino acids 960-978 of SEQ ID NO: 1, 1-4 conservative amino acid substitutions to amino acids 960-978 of SEQ ID NO: 3, 1-4 conservative amino acid substitutions to amino acids 960-978 of SEQ ID NO: 7, 1-4 conservative amino acid substitutions to amino acids 974-992 of SEQ ID NO: 1, 1-4 conservative amino acid substitutions to amino acids 974-992 of SEQ ID NO: 3, 1-4 conservative amino acid substitutions to amino acids 974-992 of SEQ ID NO: 7, 1-4 conservative amino acid substitutions to amino acids 1030-1048 of SEQ ID NO: 1, 1-4 conservative amino acid substitutions to amino acids 1030-1048 of SEQ ID NO: 3, 1-4 conservative amino acid substitutions to amino acids 1030-1048 of SEQ ID NO: 5, 1-4 conservative amino acid substitutions to amino acids 1030-1048 of SEQ ID NO: 7, 1-4 conservative amino acid substitutions to amino acids 1058-1076 of SEQ ID NO: 1, 1-4 conservative amino acid substitutions to amino acids 1058-1076 of SEQ ID NO: 3, 1-4 conservative amino acid substitutions to amino acids 1058-1076 of SEQ ID NO: 5, 1-4 conservative amino acid substitutions to amino acids 1058-1076 of SEQ ID NO: 7, 1-4 conservative amino acid substitutions to amino acids 1072-1090 of SEQ ID NO: 1, 1-4 conservative amino acid substitutions to amino acids 1072-1090 of SEQ ID NO: 3, 1-4 conservative amino acid substitutions to amino acids 1072-1090 of SEQ ID NO: 7, 1-4 conservative amino acid substitutions to amino acids 1254-1272 of SEQ ID NO: 1, 1-4 conservative amino acid substitutions to amino acids 1254-1272 of SEQ ID NO: 3, 1-4 conservative amino acid substitutions to amino acids 1268-1291 of SEQ ID NO: 1, 1-4 conservative amino acid substitutions to amino acids 1268-1291 of SEQ ID NO: 3, 1-4 conservative amino acid substitutions to amino acids 1268-1291 of SEQ ID NO: 5 or 1-4 conservative amino acid substitutions to amino acids 1268-1291 of SEQ ID NO: 7.

In other aspects of this embodiment, a BoNT/B peptide immunosorbent comprises a BoNT/B peptide comprising, e.g., 1-4 conservative amino acid substitutions to amino acids 736-754 of SEQ ID NO: 1, 1-4 conservative amino acid substitutions to amino acids 736-754 of SEQ ID NO: 5, 1-4 conservative amino acid substitutions to amino acids 778-796 of SEQ ID NO: 1, 1-4 conservative amino acid substitutions to amino acids 778-796 of SEQ ID NO: 5, 1-4 conservative amino acid substitutions to amino acids 890-908 of SEQ ID NO: 1, 1-4 conservative amino acid substitutions to amino acids 890-908 of SEQ ID NO: 3, 1-4 conservative amino acid substitutions to amino acids 890-908 of SEQ ID NO: 5, 1-4 conservative amino acid substitutions to amino acids 890-908 of SEQ ID NO: 7, 1-4 conservative amino acid substitutions to amino acids 932-950 of SEQ ID NO: 1, 1-4 conservative amino acid substitutions to amino acids 932-950 of SEQ ID NO: 5, 1-4 conservative amino acid substitutions to amino acids 974-992 of SEQ ID NO: 1, 1-4 conservative amino acid substitutions to amino acids 974-992 of SEQ ID NO: 3, 1-4 conservative amino acid substitutions to amino acids 974-992 of SEQ ID NO: 7, 1-4 conservative amino acid substitutions to amino acids 1058-1076 of SEQ ID NO: 1, 1-4 conservative amino acid substitutions to amino acids 1058-1076 of SEQ ID NO: 3, 1-4 conservative amino acid substitutions to amino acids 1058-1076 of SEQ ID NO: 5, 1-4 conservative amino acid substitutions to amino acids 1058-1076 of SEQ ID NO: 7, 1-4 conservative amino acid substitutions to amino acids 1268-1291 of SEQ ID NO: 1, 1-4 conservative amino acid substitutions to amino acids 1268-1291 of SEQ ID NO: 3, 1-4 conservative amino acid substitutions to amino acids 1268-1291 of SEQ ID NO: 5 or 1-4 conservative amino acid substitutions to amino acids 1268-1291 of SEQ ID NO: 7.

In other aspects of this embodiment, a BoNT/B peptide immunosorbent comprises a BoNT/B peptide comprising, e.g., 1-4 conservative amino acid substitutions to amino acids 616-626 of SEQ ID NO: 1, 1-4 conservative amino acid substitutions to amino acids 735-745 of SEQ ID NO: 1, 1-4 conservative amino acid substitutions to amino acids 735-745 of SEQ ID NO: 5, 1-4 conservative amino acid substitutions to amino acids 778-789 of SEQ ID NO: 1, 1-4 conservative amino acid substitutions to amino acids 867-877 of SEQ ID NO: 1, 1-4 conservative amino acid substitutions to amino acids 867-877 of SEQ ID NO: 7, 1-4 conservative amino acid substitutions to amino acids 895-905 of SEQ ID NO: 1, 1-4 conservative amino acid substitutions to amino acids 895-905 of SEQ ID NO: 3, 1-4 conservative amino acid substitutions to amino acids 929-939 of SEQ ID NO: 1, 1-4 conservative amino acid substitutions to amino acids 974-984 of SEQ ID NO: 1, 1-4 conservative amino acid substitutions to amino acids 974-984 of SEQ ID NO: 3, 1-4 conservative amino acid substitutions to amino acids 974-984 of SEQ ID NO: 7, 1-4 conservative amino acid substitutions to amino acids 1039-1049 of SEQ ID NO: 1, 1-4 conservative amino acid substitutions to amino acids 1039-1049 of SEQ ID NO: 5, 1-4 conservative amino acid substitutions to amino acids 1039-1049 of SEQ ID NO: 7, 1-4 conservative amino acid substitutions to amino acids 1065-1075 of SEQ ID NO: 1, 1-4 conservative amino acid substitutions to amino acids 1065-1075 of SEQ ID NO: 3, 1-4 conservative amino acid substitutions to amino acids 1065-1075 of SEQ ID NO: 5, 1-4 conservative amino acid substitutions to amino acids 1065-1075 of SEQ ID NO: 7, 1-4 conservative amino acid substitutions to amino acids 1269-1281 of SEQ ID NO: 1, 1-4 conservative amino acid substitutions to amino acids 1269-1281 of SEQ ID NO: 3, 1-4 conservative amino acid substitutions to amino acids 1269-1281 of SEQ ID NO: 5 or 1-4 conservative amino acid substitutions to amino acids 1269-1281 of SEQ ID NO: 7.

In still other aspects of this embodiment, a BoNT/B peptide immunosorbent comprises a BoNT/B peptide comprising, e.g., 1-4 non-conservative amino acid substitutions to amino acids 610-628 of SEQ ID NO: 1, 1-4 non-conservative amino acid substitutions to amino acids 736-754 of SEQ ID NO: 1, 1-4 non-conservative amino acid substitutions to amino acids 736-754 of SEQ ID NO: 5, 1-4 non-conservative amino acid substitutions to amino acids 778-796 of SEQ ID NO: 1, 1-4 non-conservative amino acid substitutions to amino acids 778-796 of SEQ ID NO: 5, 1-4 non-conservative amino acid substitutions to amino acids 820-838 of SEQ ID NO: 1, 1-4 non-conservative amino acid substitutions to amino acids 820-838 of SEQ ID NO: 3, 1-4 non-conservative amino acid substitutions to amino acids 820-838 of SEQ ID NO: 5, 1-4 non-conservative amino acid substitutions to amino acids 820-838 of SEQ ID NO: 7, 1-4 non-conservative amino acid substitutions to amino acids 862-880 of SEQ ID NO: 1, 1-4 non-conservative amino acid substitutions to amino acids 862-880 of SEQ ID NO: 7, 1-4 non-conservative amino acid substitutions to amino acids 890-908 of SEQ ID NO: 1, 1-4 non-conservative amino acid substitutions to amino acids 890-908 of SEQ ID NO: 3, 1-4 non-conservative amino acid substitutions to amino acids 890-908 of SEQ ID NO: 5, 1-4 non-conservative amino acid substitutions to amino acids 890-908 of SEQ ID NO: 7, 1-4 non-conservative amino acid substitutions to amino acids 918-936 of SEQ ID NO: 1, 1-4 non-conservative amino acid substitutions to amino acids 918-936 of SEQ ID NO: 3, 1-4 non-conservative amino acid substitutions to amino acids 932-950 of SEQ ID NO: 1, 1-4 non-conservative amino acid substitutions to amino acids 932-950 of SEQ ID NO: 5, 1-4 non-conservative amino acid substitutions to amino acids 960-978 of SEQ ID NO: 1, 1-4 non-conservative amino acid substitutions to amino acids 960-978 of SEQ ID NO: 3, 1-4 non-conservative amino acid substitutions to amino acids 960-978 of SEQ ID NO: 7, 1-4 non-conservative amino acid substitutions to amino acids 974-992 of SEQ ID NO: 1, 1-4 non-conservative amino acid substitutions to amino acids 974-992 of SEQ ID NO: 3, 1-4 non-conservative amino acid substitutions to amino acids 974-992 of SEQ ID NO: 7, 1-4 non-conservative amino acid substitutions to amino acids 1030-1048 of SEQ ID NO: 1, 1-4 non-conservative amino acid substitutions to amino acids 1030-1048 of SEQ ID NO: 3, 1-4 non-conservative amino acid substitutions to amino acids 1030-1048 of SEQ ID NO: 5, 1-4 non-conservative amino acid substitutions to amino acids 1030-1048 of SEQ ID NO: 7, 1-4 non-conservative amino acid substitutions to amino acids 1058-1076 of SEQ ID NO: 1, 1-4 non-conservative amino acid substitutions to amino acids 1058-1076 of SEQ ID NO: 3, 1-4 non-conservative amino acid substitutions to amino acids 1058-1076 of SEQ ID NO: 5, 1-4 non-conservative amino acid substitutions to amino acids 1058-1076 of SEQ ID NO: 7, 1-4 non-conservative amino acid substitutions to amino acids 1072-1090 of SEQ ID NO: 1, 1-4 non-conservative amino acid substitutions to amino acids 1072-1090 of SEQ ID NO: 3, 1-4 non-conservative amino acid substitutions to amino acids 1072-1090 of SEQ ID NO: 7, 1-4 non-conservative amino acid substitutions to amino acids 1254-1272 of SEQ ID NO: 1, 1-4 non-conservative amino acid substitutions to amino acids 1254-1272 of SEQ ID NO: 3, 1-4 non-conservative amino acid substitutions to amino acids 1268-1291 of SEQ ID NO: 1, 1-4 non-conservative amino acid substitutions to amino acids 1268-1291 of SEQ ID NO: 3, 1-4 non-conservative amino acid substitutions to amino acids 1268-1291 of SEQ ID NO: 5 or 1-4 non-conservative amino acid substitutions to amino acids 1268-1291 of SEQ ID NO: 7.

In still other aspects of this embodiment, a BoNT/B peptide immunosorbent comprises a BoNT/B peptide comprising, e.g., 1-4 non-conservative amino acid substitutions to amino acids 736-754 of SEQ ID NO: 1, 1-4 non-conservative amino acid substitutions to amino acids 736-754 of SEQ ID NO: 5, 1-4 non-conservative amino acid substitutions to amino acids 778-796 of SEQ ID NO: 1, 1-4 non-conservative amino acid substitutions to amino acids 778-796 of SEQ ID NO: 5, 1-4 non-conservative amino acid substitutions to amino acids 890-908 of SEQ ID NO: 1, 1-4 non-conservative amino acid substitutions to amino acids 890-908 of SEQ ID NO: 3, 1-4 non-conservative amino acid substitutions to amino acids 890-908 of SEQ ID NO: 5, 1-4 non-conservative amino acid substitutions to amino acids 890-908 of SEQ ID NO: 7, 1-4 non-conservative amino acid substitutions to amino acids 932-950 of SEQ ID NO: 1, 1-4 non-conservative amino acid substitutions to amino acids 932-950 of SEQ ID NO: 5, 1-4 non-conservative amino acid substitutions to amino acids 974-992 of SEQ ID NO: 1, 1-4 non-conservative amino acid substitutions to amino acids 974-992 of SEQ ID NO: 3, 1-4 non-conservative amino acid substitutions to amino acids 974-992 of SEQ ID NO: 7, 1-4 non-conservative amino acid substitutions to amino acids 1058-1076 of SEQ ID NO: 1, 1-4 non-conservative amino acid substitutions to amino acids 1058-1076 of SEQ ID NO: 3, 1-4 non-conservative amino acid substitutions to amino acids 1058-1076 of SEQ ID NO: 5, 1-4 non-conservative amino acid substitutions to amino acids 1058-1076 of SEQ ID NO: 7, 1-4 non-conservative amino acid substitutions to amino acids 1268-1291 of SEQ ID NO: 1, 1-4 non-conservative amino acid substitutions to amino acids 1268-1291 of SEQ ID NO: 3, 1-4 non-conservative amino acid substitutions to amino acids 1268-1291 of SEQ ID NO: 5 or 1-4 non-conservative amino acid substitutions to amino acids 1268-1291 of SEQ ID NO: 7.

In still other aspects of this embodiment, a BoNT/B peptide immunosorbent comprises a BoNT/B peptide comprising, e.g., 1-4 non-conservative amino acid substitutions to amino acids 616-626 of SEQ ID NO: 1, 1-4 non-conservative amino acid substitutions to amino acids 735-745 of SEQ ID NO: 1, 1-4 non-conservative amino acid substitutions to amino acids 735-745 of SEQ ID NO: 5, 1-4 non-conservative amino acid substitutions to amino acids 778-789 of SEQ ID NO: 1, 1-4 non-conservative amino acid substitutions to amino acids 867-877 of SEQ ID NO: 1, 1-4 non-conservative amino acid substitutions to amino acids 867-877 of SEQ ID NO: 7, 1-4 non-conservative amino acid substitutions to amino acids 895-905 of SEQ ID NO: 1, 1-4 non-conservative amino acid substitutions to amino acids 895-905 of SEQ ID NO: 3, 1-4 non-conservative amino acid substitutions to amino acids 929-939 of SEQ ID NO: 1, 1-4 non-conservative amino acid substitutions to amino acids 974-984 of SEQ ID NO: 1, 1-4 non-conservative amino acid substitutions to amino acids 974-984 of SEQ ID NO: 3, 1-4 non-conservative amino acid substitutions to amino acids 974-984 of SEQ ID NO: 7, 1-4 non-conservative amino acid substitutions to amino acids 1039-1049 of SEQ ID NO: 1, 1-4 non-conservative amino acid substitutions to amino acids 1039-1049 of SEQ ID NO: 5, 1-4 non-conservative amino acid substitutions to amino acids 1039-1049 of SEQ ID NO: 7, 1-4 non-conservative amino acid substitutions to amino acids 1065-1075 of SEQ ID NO: 1, 1-4 non-conservative amino acid substitutions to amino acids 1065-1075 of SEQ ID NO: 3, 1-4 non-conservative amino acid substitutions to amino acids 1065-1075 of SEQ ID NO: 5, 1-4 non-conservative amino acid substitutions to amino acids 1065-1075 of SEQ ID NO: 7, 1-4 non-conservative amino acid substitutions to amino acids 1269-1281 of SEQ ID NO: 1, 1-4 non-conservative amino acid substitutions to amino acids 1269-1281 of SEQ ID NO: 3, 1-4 non-conservative amino acid substitutions to amino acids 1269-1281 of SEQ ID NO: 5 or 1-4 non-conservative amino acid substitutions to amino acids 1269-1281 of SEQ ID NO: 7.

In another embodiment, a BoNT/B peptide immunosorbent comprises an immunoreactive fragment of a BoNT/B peptide having a length of at least five amino acids and at most 60 amino acids. In aspects of this embodiment, a BoNT/B peptide immunosorbent comprises an immunoreactive fragment of a BoNT/B peptide comprising, e.g., at least 6 consecutive amino acids, at least 7 consecutive amino acids, at least 8 consecutive amino acids, at least 9 consecutive amino acids, at least 10 consecutive amino acids, at least 12 consecutive amino acids, at least 15 consecutive amino acids, at least 18 consecutive amino acids or at least 20 consecutive amino acids. In other aspects of this embodiment, a BoNT/B peptide immunosorbent comprises an immunoreactive fragment of a BoNT/B peptide comprising, e.g., at most 6 consecutive amino acids, at most 7 consecutive amino acids, at most 8 consecutive amino acids, at most 9 consecutive amino acids, at most 10 consecutive amino acids, at most 12 consecutive amino acids, at most 15 consecutive amino acids, at most 18 consecutive amino acids or at most 20 consecutive amino acids.

In still other aspects of this embodiment, a BoNT/B peptide immunosorbent comprises an immunoreactive fragment of a BoNT/B peptide comprising, e.g., at least 6 non-consecutive amino acids, at least 7 non-consecutive amino acids, at least 8 non-consecutive amino acids, at least 9 non-consecutive amino acids, at least 10 non-consecutive amino acids, at least 12 non-consecutive amino acids, at least 15 non-consecutive amino acids, at least 18 non-consecutive amino acids or at least 20 non-consecutive amino acids. In still other aspects of this embodiment, a BoNT/B peptide immunosorbent comprises an immunoreactive fragment of a BoNT/B peptide comprising, e.g., at most 6 non-consecutive amino acids, at most 7 non-consecutive amino acids, at most 8 non-consecutive amino acids, at most 9 non-consecutive amino acids, at most 10 non-consecutive amino acids, at most 12 non-consecutive amino acids, at most 15 non-consecutive amino acids, at most 18 non-consecutive amino acids or at most 20 non-consecutive amino acids.

In still other aspects of this embodiment, a BoNT/B peptide immunosorbent comprises an immunoreactive fragment of a BoNT/B peptide comprising having from five to sixty amino acids, from five to fifty amino acids, from eight to fifty amino acids, from ten to fifty amino acids, from five to twenty amino acids, from eight to twenty amino acids, from ten to twenty amino acids, from twelve to twenty amino acids or from fifteen to twenty amino acids.

In another embodiment, a BoNT/B peptide comprises an immunogenic BoNT/B fragment. In an aspect of this embodiment, an immunogenic BoNT/B fragment comprises at least six consecutive amino acids of a BoNT/B peptide. In other aspects of this embodiment, an immunogenic BoNT/B fragment comprises at least six consecutive amino acids from, e.g., amino acids 610-628 of SEQ ID NO: 1

In another embodiment, a BoNT/B peptide immunosorbent comprises an immunoreactive BoNT/B fragment. In an aspect of this embodiment, a BoNT/B peptide immunosorbent comprises an immunoreactive BoNT/B fragment, the immunoreactive BoNT/B fragment comprising at least six consecutive amino acids of a BoNT/B peptide. In other aspects of this embodiment, a BoNT/B peptide immunosorbent comprises an immunoreactive BoNT/B fragment, the immunoreactive BoNT/B fragment comprising at least six consecutive amino acids from, e.g., amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In other aspects of this embodiment, a BoNT/B peptide immunosorbent comprises an immunoreactive BoNT/B fragment, the immunoreactive BoNT/B fragment comprising at least six consecutive amino acids from, e.g., amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

In another aspect of this embodiment, a BoNT/B peptide immunosorbent comprises an immunoreactive BoNT/B fragment, the immunoreactive BoNT/B fragment comprising at least six non-consecutive amino acids of a BoNT/B peptide. In still other aspects of this embodiment, a BoNT/B peptide immunosorbent comprises an immunoreactive BoNT/B fragment, the immunoreactive BoNT/B fragment comprising at least six non-consecutive amino acids from, e.g., amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

In still other aspects of this embodiment, a BoNT/B peptide immunosorbent comprises an immunoreactive BoNT/B fragment, the immunoreactive BoNT/B fragment comprising at least six non-consecutive amino acids from, e.g., amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

Aspects of an anti-BoNT immunoapheresis method disclosed in the present specification can be practiced using a solid support. As a non-limiting example, a solid phase system can utilize a solid phase matrix which is a solid phrase support comprising one or more a BoNT/B peptide immunosorbents. The blood, plasma or serum containing the anti-BoNT antibodies is passed over the solid support, exiting the solid support and leaving behind the anti-BoNT antibody/BoNT/B peptide complexes. Such solid supports are chemically inert with respect to antibody-containing fluids, have sufficient binding capacity, and generally are in the form of a continuous large surface such as a sheet or column, or in the form of particles or vesicles. Exemplary solid supports useful in the invention, including those useful for affinity chromatography, encompass, without limitation, silica; synthetic silicates, such as, e.g., porous glass, like glass fiber filters; biogenic silicates, such as, e.g., diatomaceous earth; silicate-containing materials, such as, e.g., kaolinite and borosilicate; and synthetic polymers, such as, e.g., polystyrene, polypropylene and polysaccharides, see, e.g., A. Heather Good, et al., Methods and Compositions for Attenuating Antibody-mediated Xenograft Rejection in Human Recipients, U.S. Pat. No. 6,607,723 (Aug. 19, 2003); and Mazid, supra, 1992. An affinity column is a cylindrical container with filters on both ends which contains a solid support to which the one or more BoNT/B peptides are bound. One skilled in the art understands that plasma or serum generally is passed through a column since whole blood contains cells and particulate matter such as platelets which can impede column flow.

Solid supports useful in aspects of the invention further include, yet are not limited to, agarose, which is a neutral linear polysaccharide generally composed of D-galactose and altered 3,6-anhydrogalactose residues, for example, Sepharose; activated gels, cellulose, nitrocellulose, polyvinylchloride, and diazotized paper. The skilled person understands that these and a variety of other well known solid supports can be useful in the methods of the invention.

BoNT/B peptides can be covalently or noncovalently bound to the solid support using well known methods. Supports which can be non-covalently bound by incubation with the immunosorbent include, without limitation, a nitrocellulose support, a borosilicate support, a polyvinylchloride support, a polystyrene support and a diazotized support. Activated solid supports such as activated matrices also are well known in the art and commercially available and useful in the invention. Such activated solid supports encompass, without limitation, an epoxy-activated agarose support, such as, e.g., a CNBr-activated agarose support, a 6-aminohexanoic acid support and a 1,6-diaminohexane-agarose support; a thiopropyl agarose support; a carbonyldiimidazole-activated agarose support; and an aminoethyl support and a hydrazide-activated polyacrylamide support, see, e.g., Daniel R. Henderson et al., Methods of Enhancing Effectiveness of Therapeutic Viral Immunogenic Agent Administration, U.S. Pat. No. 6,406,861 (Jun. 18, 2001; and Joseph P. Balint, Anti-human IGM Immunoadsorbent and Process for Producing Said Immunoadsorbent, U.S. Pat. No. 4,762,787 (Aug. 9, 1988).

In one embodiment, an anti-BoNT immunoapheresis method disclosed in the present specification can be practiced using a solid support comprising one or more a BoNT/B peptide immunosorbents. In an aspect of this embodiment, an anti-BoNT immunoapheresis method disclosed in the present specification can be practiced using an affinity column comprising one or more a BoNT/B peptide immunosorbents.

In other aspects of this embodiment, an anti-BoNT immunoapheresis method disclosed in the present specification can be practiced using a silica support comprising one or more a BoNT/B peptide immunosorbents, a synthetic silicate support comprising one or more a BoNT/B peptide immunosorbents, a biogenic silicate support comprising one or more a BoNT/B peptide immunosorbents and a synthetic polymer support comprising one or more a BoNT/B peptide immunosorbents.

In other aspects of this embodiment, an anti-BoNT immunoapheresis method disclosed in the present specification can be practiced using a Sepharose support comprising one or more a BoNT/B peptide immunosorbents, a polyvinylchloride support comprising one or more a BoNT/B peptide immunosorbents, a cellulose support comprising one or more a BoNT/B peptide immunosorbents, a nitrocellulose support comprising one or more a BoNT/B peptide immunosorbents, a borosilicate support comprising one or more a BoNT/B peptide immunosorbents, a polyvinylchloride support comprising one or more a BoNT/B peptide immunosorbents, a polystyrene support comprising one or more a BoNT/B peptide immunosorbents, a polypropylene support comprising one or more a BoNT/B peptide immunosorbents and a diazotized support comprising one or more a BoNT/B peptide immunosorbents.

In yet other aspects of this embodiment, an anti-BoNT immunoapheresis method disclosed in the present specification can be practiced using an epoxy-activated agarose support comprising one or more a BoNT/B peptide immunosorbents, a thiopropyl agarose support comprising one or more a BoNT/B peptide immunosorbents, a carbonyldiimidazole-activated agarose support comprising one or more a BoNT/B peptide immunosorbents, an aminoethyl support comprising one or more a BoNT/B peptide immunosorbents and a hydrazide-activated polyacrylamide support comprising one or more a BoNT/B peptide immunosorbents. In other aspects of this embodiment, an anti-BoNT immunoapheresis method disclosed in the present specification can be practiced using a CNBr-activated agarose support comprising one or more a BoNT/B peptide immunosorbents, a 6-aminohexanoic acid support comprising one or more a BoNT/B peptide immunosorbents and a 1,6-diaminohexane-agarose support comprising one or more a BoNT/B peptide immunosorbents.

Aspects of an anti-BoNT immunoapheresis method disclosed in the present specification can be practiced using liquid phase separation. Liquid phase separation can be performed, e.g., by conjugating one or more BoNT/B peptide immunosorbents to a hapten such as, without limitation, dinitrophenol or fluorescein. After mixing the hapten/BoNT/B peptide conjugate with an individual's blood, plasma or serum, the BoNT/B peptide conjugate forms complexes with anti-BoNT antibodies. As a non-limiting example, such antibody-peptide complexes can be precipitated using polyethylene glycol (PEG), and the precipitated complexes separated from the blood, plasma or serum using centrifugation, see, e.g., Paul A. Liberti & Paul Pollara, Selective Removal of Immunospecifically Recognizable Substances from Solution, U.S. Pat. No. 4,551,435 (Nov. 5, 1985). One skilled in the art appreciates that these and other solid-phase and liquid-phase systems can be used to separate anti-BoNT antibody-BoNT/B peptide complexes from an individual's blood, plasma or serum.

In an embodiment, an anti-BoNT immunoapheresis method disclosed in the present specification can be practiced using liquid phase separation comprising one or more a BoNT/B peptide immunosorbents. In an aspect of this embodiment, an anti-BoNT immunoapheresis method disclosed in the present specification can be practiced using liquid phase separation comprising one or more a BoNT/B peptide immunosorbents conjugated to hapten. In other aspects of this embodiment, an anti-BoNT immunoapheresis method disclosed in the present specification can be practiced using liquid phase separation comprising one or more a BoNT/B peptide immunosorbents conjugated to dinitrophenol or fluorescein.

In still a further embodiment, one or more BoNT/B peptides are bound to lipid vesicles, and the lipid vesicle-immunosorbent is mixed with a patient's plasma or serum to allow binding to the blocking antibodies. The plasma or serum is subsequently filtered to remove the lipid vesicle-immunosorbent-antibody complex, see, e.g., James F. Marten, Therapeutic Apheresis, U.S. Pat. No. 4,643,718 (Feb. 17, 1987).

It is understood that the blood, serum, plasma or lymph are contacted with the one or more BoNT/B peptides attached to a solid support under conditions that promote binding between the one or more BoNT/B peptides and anti-BoNT antibodies, see, e.g., M. Abdul Mazid, Affinity Supports for Hemoperfusion, U.S. Pat. No. 5,149,425 (Sep. 22, 1992). It is also understood that the blood, serum, plasma or lymph can be contacted with a sequential series of a different BoNT/B peptides, such as, e.g., two or more solid supports each comprising a different BoNT/B peptide. Such conditions can include, without limitation, contact temperatures in the range of 35° C. and 40° C., and contact times of about one to six hours.

Aspects of the present invention provide, in part, returning the anti-BoNT antibody-depleted component back into the individual. It is understood that the unbound portion of the blood, plasma, or serum, which is significantly anti-BoNT antibody-depleted, is reintegrated with cellular components of blood as necessary and reintroduced into the individual on a continuous basis or following collection. It is also understood that the blood can be pre-warmed to body temperature before the blood is returned to the individual. One skilled in the art further understands that, if desired, the antibody-depleted blood, plasma or serum can be assayed prior to reintroduction in the individual, e.g., using one of the BoNT/B peptide binding assays or protection assays disclosed herein.

It is further understood that pre-clearance of antibodies, or a class of antibody such as the IgG class, can be performed prior to selective removal of anti-BoNT antibodies. From the pre-cleared antibody pool, BoNT/B peptide-reactive antibodies can be removed, and the remaining antibodies from the pre-cleared pool reconstituted into the blood and reperfused into the individual, thus reducing the volume to be passed over the blocking antibody selective support and also reducing non-specific binding. As a non-limiting example, non-specific Protein G Sepharose columns such as PROSORBA® (IMRE; Munich, Germany) or Ig-THERASORB® (Plasmaselect; Teterow, Germany) can be used to remove a significant portion of IgG antibody. A variety of additional techniques suitable for general pre-clearance of antibodies are well known in the art and include, yet are not limited to, ammonium sulfate precipitation with ion exchange chromatography; caprylic acid; DEAE-matrices (ion-exchange chromatography); hydroxyapatite chromatography, and gel filtration (Sepharose), see, e.g., Harlow & Lane, supra, 1998a; and Harlow & Lane, supra, 1998b.

The present invention provides, in part, a method of inducing a BoNT/B immune response in an individual, the method comprising the step of administering to the individual an immune response inducing composition comprising an adjuvant and a BoNT/B antigen, where administration of the immune response inducing composition produces an immune response in the individual.

The present invention provides, in part, a method of producing anti-BoNT/B antibodies in an individual, the method comprising the steps of administering to the individual an immune response inducing composition comprising an adjuvant and a BoNT/B antigen, where administration of the immune response inducing composition produces an immune response in the individual; collecting from the individual a sample containing the anti-BoNT/B antibody or anti-BoNT/B antibody-producing cell; and isolating the anti-BoNT/B antibody from the sample. Antibodies to be prepared according to a method of the invention include polyclonal and monoclonal antibodies. Anti-BoNT/B polyclonal antibodies or a monoclonal anti-BoNT/B antibody can be used in a variety of applications, including, without limitation, detection of botulinum toxin in a sample, such as, e.g., a substance suspected to be contaminated with a BoNT/B.

Aspects of the present invention provide, in part, an immune response inducing composition comprising a BoNT/B antigen and an adjuvant capable producing an immune response. It is envisioned that any of the BoNT/B antigens disclosed in the present specification can be useful in an immune response inducing composition, with the proviso that the BoNT/B antigen induces a specific immunological response to a BoNT/B. Non-limiting examples include a BoNT/B antigen derived from a naturally occurring BoNT/B, such as, e.g., the BoNT/B of SEQ ID NO: 1, SEQ ID NO: 3, SEQ ID NO: 5, SEQ ID NO: 7, SEQ ID NO: 9, SEQ ID NO: 11 or SEQ ID NO: 13, a BoNT/B isoform or a BoNT/B subtype; and a BoNT/B antigen derived from a non-naturally occurring BoNT/B, such as, e.g., a conservative BoNT/B variant, a non-conservative BoNT/B variant and a chimeric BoNT/B antigen. BoNT/B peptides disclosed in the present specification can be selected, e.g., depending on immunological factors, such as potency of the peptide in inducing an immune response, and technical factors, such as chemical synthesis yields. It is also understood that the two or more different BoNT/B antigen can be provided separately or as part of a compound molecule such as a chimeric BoNT/B antigen.

It is envisioned that any and all adjuvants can be useful in such an immune response inducing composition. As used herein, the term "adjuvant" when used in reference to an immune response inducing composition means any substance or mixture of substances that increases or diversifies the immune response to an antigenic compound. An adjuvant can, for example, serve to reduce the number of immunizations or the amount of antigen required for protective immunization. The use of adjuvants in an immune response inducing composition is well known. The main objective of these adjuvants is to allow an increase in the immune response. These adjuvants are diverse in nature. Various adjuvants used to increase the immunological response include, but are not limited to, e.g., the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); lipopolysaccharide (LPS), surface active substances, such as, e.g., lysolecithin, pluronic polyols, polyanions, peptides and dinitrophenol; adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate). Such adjuvants are generally used in the form of an emulsion with an aqueous phase, or, more commonly, may consist of water-insoluble inorganic salts. These inorganic salts may consist, for example, of aluminum hydroxide, zinc sulfate, colloidal iron hydroxide, calcium phosphate or calcium chloride. Aluminum hydroxide $(Al(OH)_3)$ is a commonly used adjuvant. Currently, the only FDA-approved adjuvant for use in humans is aluminum salts (Alum) which are used to "depot" antigens by precipitation of the antigens. Adjuvants provided above are merely exemplary. In fact, any adjuvant may be used in the immunogenic composition of the present invention as long as the adjuvant satisfies the requisite characteristics that are necessary for practicing the present invention. As indicated above, the carrier of the compositions of the present invention itself may act as an adjuvant. Specific adjuvants and methods of making and using are described in, e.g., Gupta et al. Vaccine, 11: 993-306, 1993; Arnon, R. (Ed.) Synthetic Vaccines 1:83-92, CRC Press, Inc., Boca Raton, Fla., 1987; and David W. Waggoner, Jr. et al., Immunogenicity-Enhancing Carriers and Compositions Thereof and Methods of Using the Same, U.S. Patent Publication No. 20040057958 (Mar. 25, 2004). Additional adjuvants include any compound described in Chapter 7 (pp 141-227) of "Vaccine Design, The Subunit and Adjuvant Approach" (eds. Powell, M. F. and Newman, M. J.) Pharmaceutical Biotechnology, Volume 6, Plenum Press (New York). Examples from this compendium include Muramyl Dipeptide (MDP) and Montanide 720. Molecules such as Poly Inosine:Cytosine (Poly I:C) or plasmid DNA containing CpG motifs can also be administered as adjuvants in combination with antigens encapsulated in microparticles. In another example, the adjuvant is an agent that facilitates entry of the antigenic compound into the cytoplasm of a cell such as listeriolysin, streptolysin or a mixture thereof.

Aspects of the present invention provide, in part, an anti-BoNT/B antibody. As used herein, the term "antibody" means a molecule made in response to a particular antigen response and includes, without limitation, polyclonal antibodies, monoclonal antibodies and antigenic compound-binding fragments of such antibodies, such as, e.g., Fab, $F(ab')_2$, Fc, Fd, Fv fragments, and single chain derivatives of the same. Polyclonal antibodies refer to a heterogeneous population of antibody molecules that contain at least two species of antibody capable of binding to a particular antigen. By definition, a polyclonal antibody binds to at least two different epitopes.

Monoclonal antibodies refer to a homogeneous population of antibody molecules that contain only one species of antibody capable of binding a particular antigen. By definition, a monoclonal antibody binds to a single epitope. Antibody also includes cell-associated antibodies, such as Ig receptors, for example. In addition, the term "antibody" includes naturally occurring antibodies, as well as non-naturally occurring antibodies, including, for example, chimeric, bi-functional, and humanized antibodies, and related synthetic isoforms.

As used herein, the term "anti-BoNT/B antibody" means an anti-BoNT/B antibody that selectively binds to a BoNT/B. As used herein, the term "selectively" means having a unique effect or influence or reacting in only one way or with only one thing. As used herein, the term "selectively binds" means the discriminatory binding of the antibody to the indicated target epitope such that the antibody does not substantially cross react with unrelated epitopes. Selective binding includes binding properties such as, e.g., binding specificity, binding affinity and binding avidity. Binding specificity is the ability of an antibody to discriminate between a molecule containing its epitope and a molecule that does not contain that epitope. An anti-BoNT/B antibody disclosed in the present specification is characterized by having a binding specificity for its epitope of at least 10-fold greater relative to a BoNT/B not comprising that epitope. In aspects of this embodiment, an anti-BoNT/B antibody binding specificity for its epitope relative to a BoNT/B not comprising that epitope is, e.g., at least 10-fold greater, at least 100-fold greater, at least 1,000-fold greater or at least 10,000-fold greater. Binding affinity is the strength with which an antibody binds its epitope. In an embodiment, an anti-BoNT/B antibody disclosed in the present specification is characterized by having a binding affinity of at least $1\times10^{-5}$ $M^{-1}$. For example, an anti-BoNT/B antibody disclosed in the present specification can bind a target peptide with a binding affinity of at least $1\times10^{-5}$ $M^{-1}$, at least $1\times10^{-6}$ $M^{-1}$, at least $1\times10^{-7}$ $M^{-1}$, at least $1\times10^{-8}$ $M^{-1}$, at least $1\times10^{-9}$ $M^{-1}$, or at least $1\times10^{-10}$ $M^{-1}$.

Binding avidity refers to an antibody that can bind more than one epitope of a target molecule and the binding affinities of these epitopes. It is envisioned that an anti-BoNT/B antibody disclosed in the present specification can selectively bind to any and all epitopes for that antibody. As used herein, an "epitope" is synonymous with "antigenic determinant" and means the site on a target molecule, such as, e.g., a peptide, polysaccharide or lipid-containing molecule, that is bound by a particular antibody or T-cell receptor. The minimal size of a peptide epitope, as defined herein, is about five amino acids, and a peptide epitope typically comprises at least eight amino acids. A peptide epitope may be discontinuous, i.e., it comprises amino acid residues that are not adjacent in the peptide but are brought together into an epitope by way of the secondary, tertiary, or quaternary structure of the peptide. Furthermore, it is also noted that an epitope might comprise a portion of a molecule other than an amino acid sequence, such as, e.g., a carbohydrate moiety, a lipid moiety like lipoproteins or glycolipids, or a chemically-modified amino acid moiety like a phosphorylated amino acid. In aspects of this embodiment, an anti-BoNT/B antibody can selectively bind a BoNT/B epitope comprising at least five amino acids, at least six amino acids, at least seven amino acids, at least eight amino acids, at least nine amino acids, at least ten amino acids or at least 20 amino acids. In other aspects of this embodiment, an anti-BoNT/B antibody can selectively bind a BoNT/B epitope comprising at most five amino acids, at most six amino acids, at most seven amino acids, at most eight amino acids, at most nine amino acids, at most ten amino acids or at most 20 amino acids.

As a non-limiting example, an antibody raised against an antigen will selectively bind a BoNT/B including a portion of, e.g., amino acids 610-628 of SEQ ID NO: 1, amino acids 736-754 of SEQ ID NO: 1, amino acids 736-754 of SEQ ID NO: 5, amino acids 778-796 of SEQ ID NO: 1, amino acids 778-796 of SEQ ID NO: 5, amino acids 820-838 of SEQ ID NO: 1, amino acids 820-838 of SEQ ID NO: 3, amino acids 820-838 of SEQ ID NO: 5, amino acids 820-838 of SEQ ID NO: 7, amino acids 862-880 of SEQ ID NO: 1, amino acids 862-880 of SEQ ID NO: 7, amino acids 890-908 of SEQ ID NO: 1, amino acids 890-908 of SEQ ID NO: 3, amino acids 890-908 of SEQ ID NO: 5, amino acids 890-908 of SEQ ID NO: 7, amino acids 918-936 of SEQ ID NO: 1, amino acids 918-936 of SEQ ID NO: 3, amino acids 932-950 of SEQ ID NO: 1, amino acids 932-950 of SEQ ID NO: 5, amino acids 960-978 of SEQ ID NO: 1, amino acids 960-978 of SEQ ID NO: 3, amino acids 960-978 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, amino acids 1072-1090 of SEQ ID NO: 1, amino acids 1072-1090 of SEQ ID NO: 3, amino acids 1072-1090 of SEQ ID NO: 7, amino acids 1254-1272 of SEQ ID NO: 1, amino acids 1254-1272 of SEQ ID NO: 3, amino acids 1268-1291 of SEQ ID NO: 1, amino acids 1268-1291 of SEQ ID NO: 3, amino acids 1268-1291 of SEQ ID NO: 5 and amino acids 1268-1291 of SEQ ID NO: 7.

As another non-limiting example, an antibody raised against an antigen will selectively bind a BoNT/B including a portion of, e.g., amino acids 616-626 of SEQ ID NO: 1, amino acids 735-745 of SEQ ID NO: 1, amino acids 735-745 of SEQ ID NO: 5, amino acids 778-789 of SEQ ID NO: 1, amino acids 867-877 of SEQ ID NO: 1, amino acids 867-877 of SEQ ID NO: 7, amino acids 895-905 of SEQ ID NO: 1, amino acids 895-905 of SEQ ID NO: 3, amino acids 929-939 of SEQ ID NO: 1, amino acids 974-984 of SEQ ID NO: 1, amino acids 974-984 of SEQ ID NO: 3, amino acids 974-984 of SEQ ID NO: 7, amino acids 1039-1049 of SEQ ID NO: 1, amino acids 1039-1049 of SEQ ID NO: 5, amino acids 1039-1049 of SEQ ID NO: 7, amino acids 1065-1075 of SEQ ID NO: 1, amino acids 1065-1075 of SEQ ID NO: 3, amino acids 1065-1075 of SEQ ID NO: 5, amino acids 1065-1075 of SEQ ID NO: 7, amino acids 1269-1281 of SEQ ID NO: 1, amino acids 1269-1281 of SEQ ID NO: 3, amino acids 1269-1281 of SEQ ID NO: 5 or amino acids 1269-1281 of SEQ ID NO: 7.

An anti-BoNT/B antibody disclosed in the present specification can be produced by a wide variety of methods that are well known in the art. Specific protocols for making and using antibodies as well as detecting, and measuring antibody binding specificity, binding affinity and binding avidity are known in the art, see, e.g., Harlow & Lane, supra, 1998a; Harlow & Lane, supra, 1998b; Molecular Cloning, A Laboratory Manual, supra, 2001; and Current Protocols in Molecular Biology, supra, 2004; David Anderson et al., Therapeutic Polypeptides, Nucleic Acids Encoding Same, and Methods of Use, U.S. Pat. No. 7,034,132 (Apr. 25, 2005); and Beatriz M. Carreno et al., Antibodies Against CTLA4, U.S. Pat. No. 7,034,121 (Apr. 25, 2006).

As a non-limiting example, anti-BoNT/B polyclonal antibodies can be produced by injecting an individual, such as, e.g., a rabbit, a goat, a mouse or another mammal, with one or more injections of an immune inducing composition disclosed in the present specification. The resulting anti-BoNT/B polyclonal antibodies produced can be screened from serum of the immunized individual with a BoNT/B peptide disclosed in the present specification using a radioimmunoassay or enzyme-linked immunosorbent assay.

As another non-limiting example, an anti-BoNT/B monoclonal antibody can be produced using a hybridoma method. In this method, an individual, such as, e.g., a mouse, a hamster, or another appropriate host individual, is typically exposed to one or more injections of an immune inducing composition disclosed in the present specification to elicit lymphocytes that produce or are capable of producing anti-BoNT/B antibodies that will specifically bind to the BoNT/B antigen. Alternatively, the lymphocytes can be immunized in vitro using a suitable cell culture line. Generally, either peripheral blood lymphocytes are used, if cells of human origin are desired, or spleen cells or lymph node cells are used, if non-human mammalian sources are desired. The lymphocytes are then fused with an immortalized cell line using a suitable fusing agent, such as polyethylene glycol, to form a hybridoma cell, see, e.g., Goding, Monoclonal Antibodies: Principles and Practice, Academic Press, (1986) pp. 59-103. Immortalized cell lines are usually transformed mammalian cells, particularly myeloma cells of rodent, bovine and human origin. Usually, rat or mouse myeloma cell lines are employed. The culture medium in which the hybridoma cells are grown can then be assayed for the presence of anti-BoNT/B monoclonal antibodies directed against the BoNT/B antigen disclosed in the present specification, see, e.g., Harlow & Lane, supra, 1998a; and Harlow & Lane, supra, 1998b. For example, hybridoma supernatants can be screened using anti-BoNT/B-positive sera in an immunoprecipitation assay or by an in vitro binding assay, such as, e.g., a radioimmunoassay (RIA) or an enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). After the desired hybridoma cells are identified, the clones can be subcloned by limiting dilution procedures until isolate cell line is produced.

As an alternative to preparing monoclonal antibody-secreting hybridomas, an anti-BoNT/B monoclonal antibody can be identified and isolated by screening a recombinant combinatorial immunoglobulin library, such as, e.g., an antibody phage display library, with a BoNT/B peptide and isolate immunoglobulin library members that bind a BoNT/B peptide. Kits for generating and screening phage display libraries are commercially available, such as, e.g., the Recombinant Phage Antibody System (Pharmacia); and the SurfZAP™ Phage Display Kit (Stratagene). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; McCafferty et al. U.S. Pat. No. 6,172,197; Johnson et al. U.S. Pat. No. 6,140,471; Jespers et al. U.S. Pat. No. 6,017,732; Griffiths et al. U.S. Pat. No. 6,010,884; McCafferty et al. U.S. Pat. No. 5,969,108; Griffiths et al. U.S. Pat. No. 5,962,255; Griffiths et al. U.S. Pat. No. 5,885,793; Borrebaeck et al. U.S. Pat. No. 6,027,930; Borrebaeck et al. U.S. Pat. No. 5,712,089.

Non-naturally occurring anti-BoNT/B antibodies can be constructed using solid phase peptide synthesis, produced recombinantly or obtained, e.g., by screening combinatorial libraries consisting of variable heavy chains and variable light chains as described in, e.g., Huse et al., 246 Science 1275-1281 (1989). These and other methods of making, for example, chimeric, humanized, CDR-grafted, single chain, and bi-functional antibodies are well known to those skilled in the art, see, e.g., Winter and Harris, 14 Immunol. Today 243-246 (1993); Ward et al., 341 Nature 544-546 (1989); Harlow and Lane, supra, 1988a; Hilyard et al., *Protein Engineering: A Practical Approach* (IRL Press 1992); and Borrabeck, *Antibody Engineering*, 2d ed. (Oxford University Press 1995).

Aspects of the present invention provide, in part, collecting a sample containing the anti-BoNT/B antibody or anti-BoNT/B antibody-producing cell. As used herein, the term "sample containing the anti-BoNT/B antibody or anti-BoNT/B antibody-producing cell" means any biological matter that contains or potentially contains at least one anti-BoNT/B antibody. It is envisioned that any and all samples that can contain an anti-BoNT/B antibody can be used in this method, including, without limitation, blood, plasma, serum and lymph fluid. It is also envisioned that any cell capable of producing an anti-BoNT/B antibody can be used in this method, including, without limitation, a CD8 cells, a CTL cell, a helper T-cell and a B-cell. A variety of well known methods can be used for collecting from an individual a sample containing the anti-BoNT/B antibody or anti-BoNT/B antibody-producing cell, see, e.g., Harlow & Lane, supra, 1998a; and Harlow & Lane, supra, 1998b. Similarly, a variety of well known methods can be used for processing a sample to isolate an anti-BoNT/B antibody. A procedure for collecting a sample can be selected based on the type of antibody to be isolated. As a non-limiting example, when isolating anti-BoNT/B polyclonal antibodies, an appropriate sample can be a blood sample containing anti-BoNT/B antibodies, whereas when isolating monoclonal anti-BoNT/B antibodies, an appropriate sample can be an anti-BoNT/B antibody-producing cell such as a spleen cell.

Aspects of the present invention provide, in part, isolating the anti-BoNT/B antibody from the sample. Methods of isolating an anti-BoNT/B antibody, such as, e.g., anti-BoNT/B polyclonal antibodies or a anti-BoNT/B monoclonal antibody are well known to those skilled in the art, see, e.g., Harlow and Lane, supra, 1998a; and Harlow and Lane, supra, 1998b. For example, BoNT/B polyclonal antibodies can be isolated from the sample by well known techniques, such as, e.g., affinity chromatography using protein A or protein G, which provide primarily the IgG fraction of immune serum. Subsequently, or alternatively, the specific BoNT/B polyclonal antibody sought may be immobilized on a column to purify the immune specific antibody by immunoaffinity chromatography. An anti-BoNT/B monoclonal antibody can be isolated from the culture medium or ascites fluid by conventional immunoglobulin purification procedures such as, e.g., protein A-Sepharose, hydroxylapatite chromatography, gel electrophoresis, dialysis, or affinity chromatography.

Thus, in an embodiment, a method of producing an anti-BoNT/B antibody comprises the steps of administering to an animal a BoNT/B antigen, collecting from the animal a sample containing the anti-BoNT/B antibody or anti-BoNT/B antibody-producing cell, and isolating the anti-BoNT/B antibody from the sample. In an aspect of this embodiment, the anti-BoNT/B antibody is a polyclonal anti- BoNT/B antibody. In another aspect of this embodiment, the anti-BoNT/B antibody is a monoclonal anti-BoNT/B antibody.

Aspects of the present invention can also be described as follows:

1. A BoNT/B peptide having a length of at most 60 amino acids, the BoNT/B peptide comprising an amino acid sequence of amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, a conservative variant of each amino acid sequence thereof, or an immunogenic fragment of each amino acid sequence thereof.

2. The BoNT/B peptide according to any one of claim 1, wherein said BoNT/B peptide has a length of at most 45 amino acids.

3. The BoNT/B peptide according to any one of claim 1, wherein said BoNT/B peptide has a length of at most 30 amino acids.

4. The BoNT/B peptide according to claim 1, wherein the BoNT/B peptide consists of amino acid sequence of amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, a conservative variant of each amino acid sequence thereof, or an immunogenic fragment of each amino acid sequence thereof.

5. A tolerogizing composition comprising a tolerogizing agent operably linked to a BoNT/B peptide of SEQ ID NO: 1 having a length of at least five amino acids and at most 60 amino acids, the BoNT/B peptide comprising an amino acid sequence of amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, or amino acids 1058-1076 of SEQ ID NO: 7.

6. The tolerogizing composition according to 5, wherein said BoNT/B peptide has a length of at most 45 amino acids.

7. The tolerogizing composition according to 5, wherein said BoNT/B peptide has a length of at most 30 amino acids.

8. The tolerogizing composition according to 5, wherein the BoNT/B peptide consists of amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, a conservative variant of each amino acid sequence thereof, or an immunogenic fragment of each amino acid sequence thereof.

9. The tolerogizing composition according to 5, wherein a portion of the BoNT/B peptide producing a decrease in an immunological response comprises at least six consecutive amino acids of 736-754 of SEQ ID NO: 1, at least six consecutive amino acids of amino acids 736-754 of SEQ ID NO: 5, at least six consecutive amino acids of amino acids 764-782 of SEQ ID NO: 1, at least six consecutive amino acids of amino acids 764-782 of SEQ ID NO: 3, at least six consecutive amino acids of amino acids 764-782 of SEQ ID NO: 5, at least six consecutive amino acids of amino acids 764-782 of SEQ ID NO: 7, at least six consecutive amino acids of amino acids 848-866 of SEQ ID NO: 1, at least six consecutive amino acids of amino acids 848-866 of SEQ ID NO: 3, at least six consecutive amino acids of amino acids 848-866 of SEQ ID NO: 5, at least six consecutive amino acids of amino acids 848-866 of SEQ ID NO: 7, at least six consecutive amino acids of amino acids 974-992 of SEQ ID NO: 1, at least six consecutive amino acids of amino acids 974-992 of SEQ ID NO: 3, at least six consecutive amino acids of amino acids 974-992 of SEQ ID NO: 7, at least six consecutive amino acids of amino acids 1030-1048 of SEQ ID NO: 1, at least six consecutive amino acids of amino acids 1030-1048 of SEQ ID NO: 3, at least six consecutive amino acids of amino acids 1030-1048 of SEQ ID NO: 5, at least six consecutive amino acids of amino acids 1030-1048 of SEQ ID NO: 7, at least six consecutive amino acids of amino acids 1058-1076 of SEQ ID NO: 1, at least six consecutive amino acids of amino acids 1058-1076 of SEQ ID NO: 3, at least six consecutive amino acids of amino acids 1058-1076 of SEQ ID NO: 5, at least six consecutive amino acids of amino acids 1058-1076 of SEQ ID NO: 7.

10. The tolerogizing composition of 5, wherein the tolerogizing agent is selected from the group consisting of polyethylene glycol (PEG), monomethoxypolyethylene glycol (mPEG) and polyvinyl alcohol (PVA).

11. An immune response inducing composition comprising a BoNT/B antigen, the BoNT/B antigen comprising a BoNT/B peptide of SEQ ID NO: 1 having a length of at least five amino acids and at most 60 amino acids, the BoNT/B peptide comprising an amino acid sequence of amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, a conservative variant of each amino acid sequence thereof, or an immunogenic fragment of each amino acid sequence thereof.

12. The immune response inducing composition according to 11, further comprising a carrier.

13. The immune response inducing composition according to 12, wherein the carrier is selected from the group consisting of a keyhole limpet hemacyanin (KLH), an ovalbumin (OVA), a thyroglobulin (THY), a bovine serum albumin (BSA) and a soybean trypsin inhibitor (STI).

14. The immune response inducing composition according to 11, further comprising an adjuvant.

15. The immune response inducing composition according to 11, wherein said BoNT/B peptide has a length of at most 45 amino acids.

16. The immune response inducing composition according to 11, wherein said BoNT/B peptide has a length of at most 30 amino acids.

17. The immune response inducing composition according to 11, wherein the BoNT/B peptide consists of amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, a conservative variant of each amino acid sequence thereof, or an immunogenic fragment of each amino acid sequence thereof.

18. The immune response inducing composition according to 11, wherein a portion of the BoNT/B peptide immunoreactive with an anti-BoNT antibody comprises at least six consecutive amino acids of 736-754 of SEQ ID NO: 1, at least six consecutive amino acids of amino acids 736-754 of SEQ ID NO: 5, at least six consecutive amino acids of amino acids 764-782 of SEQ ID NO: 1, at least six consecutive amino acids of amino acids 764-782 of SEQ ID NO: 3, at least six consecutive amino acids of amino acids 764-782 of SEQ ID NO: 5, at least six consecutive amino acids of amino acids 764-782 of SEQ ID NO: 7, at least six consecutive amino acids of amino acids 848-866 of SEQ ID NO: 1, at least six consecutive amino acids of amino acids 848-866 of SEQ ID NO: 3, at least six consecutive amino acids of amino acids 848-866 of SEQ ID NO: 5, at least six consecutive amino acids of amino acids 848-866 of SEQ ID NO: 7, at least six consecutive amino acids of amino acids 974-992 of SEQ ID NO: 1, at least six consecutive amino acids of amino acids 974-992 of SEQ ID NO: 3, at least six consecutive amino acids of amino acids 974-992 of SEQ ID NO: 7, at least six consecutive amino acids of amino acids 1030-1048 of SEQ ID NO: 1, at least six consecutive amino acids of amino acids 1030-1048 of SEQ ID NO: 3, at least six consecutive amino acids of amino acids 1030-1048 of SEQ ID NO: 5, at least six consecutive amino acids of amino acids 1030-1048 of SEQ ID NO: 7, at least six consecutive amino acids of amino acids 1058-1076 of SEQ ID NO: 1, at least six consecutive amino acids of amino acids 1058-1076 of SEQ ID NO: 3, at least six consecutive amino acids of amino acids 1058-1076 of SEQ ID NO: 5, at least six consecutive amino acids of amino acids 1058-1076 of SEQ ID NO: 7.

19. A method of determining immunoresistance to botulinum toxin therapy in an individual, the method comprising the steps of:
a) combining a BoNT/B peptide and a test sample under conditions suitable for the selective binding of the BoNT/B peptide to an anti-BoNT antibody, the BoNT/B peptide having a length of at least 5 amino acids and at most 60 amino acids and comprising the amino acid sequence of amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, a conservative variant of each amino acid sequence thereof, or an immunogenic fragment of each amino acid sequence thereof; and
b) detecting the presence of an anti-BoNT antibody-BoNT/B peptide complex, the antibody-peptide complex formed by the selective binding of an anti-BoNT antibody and the BoNT/B peptide;
where the presence of the anti-BoNT antibody-BoNT/B peptide complex is indicative of immunoresistance to a BoNT therapy.

20. The method according to claim 19, wherein the method comprises a further step of correlating the amount of an antibody-peptide complex formed from the test sample relative to the amount of an antibody-peptide complex formed by the BoNT/B peptide combined to a control sample.

21. The method according to claim 19, wherein a portion of the BoNT/B peptide immunoreactive with an anti-BoNT antibody comprises at least six consecutive amino acids of 736-754 of SEQ ID NO: 1, at least six consecutive amino acids of amino acids 736-754 of SEQ ID NO: 5, at least six consecutive amino acids of amino acids 764-782 of SEQ ID NO: 1, at least six consecutive amino acids of amino acids 764-782 of SEQ ID NO: 3, at least six consecutive amino acids of amino acids 764-782 of SEQ ID NO: 5, at least six consecutive amino acids of amino acids 764-782 of SEQ ID NO: 7, at least six consecutive amino acids of amino acids 848-866 of SEQ ID NO: 1, at least six consecutive amino acids of amino acids 848-866 of SEQ ID NO: 3, at least six consecutive amino acids of amino acids 848-866 of SEQ ID NO: 5, at least six consecutive amino acids of amino acids 848-866 of SEQ ID NO: 7, at least six consecutive amino acids of amino acids 974-992 of SEQ ID NO: 1, at least six consecutive amino acids of amino acids 974-992 of SEQ ID NO: 3, at least six consecutive amino acids of amino acids 974-992 of SEQ ID NO: 7, at least six consecutive amino acids of amino acids 1030-1048 of SEQ ID NO: 1, at least six consecutive amino acids of amino acids 1030-1048 of SEQ ID NO: 3, at least six consecutive amino acids of amino acids 1030-1048 of SEQ ID NO: 5, at least six consecutive amino acids of amino acids 1030-1048 of SEQ ID NO: 7, at least six consecutive amino acids of amino acids 1058-1076 of SEQ ID NO: 1, at least six consecutive amino acids of amino acids 1058-1076 of SEQ ID NO: 3, at least six consecutive amino acids of amino acids 1058-1076 of SEQ ID NO: 5, at least six consecutive amino acids of amino acids 1058-1076 of SEQ ID NO: 7.

22. The method according to claim 19, wherein the test sample comprises blood.

23. The method according to claim 19, wherein the test sample comprises serum.

24. The method according to claim 23, wherein the test sample comprises an IgG antibody component separated from the serum.

25. The method according to claim 19, wherein the immunoresistance to botulinum toxin therapy is selected from the group consisting of a BoNT/A immunoresistance, a BoNT/B immunoresistance, a BoNT/C1 immunoresistance, a BoNT/D immunoresistance, a BoNT/E immunoresistance, a BoNT/F immunoresistance and a BoNT/G immunoresistance.

26. The method according to claim 25, wherein the immunoresistance to botulinum toxin therapy is a BoNT/B immunoresistance.

27. The method according to claim 19, wherein the individual is a human.

28. The method according to claim 19, wherein the presence of an anti-BoNT antibody-BoNT/B peptide complex is determined qualitatively.

29. The method according to claim 19, wherein the presence of an anti-BoNT antibody-BoNT/B peptide complex is determined quantitatively.

30. The method according to claim 19, wherein the presence of an anti-BoNT antibody-BoNT/B peptide complex is determined using a competitive assay.

31. The method according to claim 19, wherein the presence of an anti-BoNT antibody-BoNT/B peptide complex is determined using a non-competitive assay.

32. The method according to claim 19, wherein the presence of an anti-BoNT antibody-BoNT/B peptide complex is determined by an assay format selected from the group consisting of a radioimmunoassay, an enzyme-linked immunosorbent assay, an enzyme immunoassay, a fluorescence immunoassay, and a luminescent immunoassay.

33. The method according to claim 19, wherein the presence of at least 10% complex formation of an anti-BoNT antibody to a BoNT/B peptide is indicative of a BoNT immunoresistance.

34. The method according to claim 19, wherein the presence of at least 30% complex formation of an anti-BoNT antibody to a BoNT/B peptide is indicative of a BoNT immunoresistance.

35. The method according to claim 19, wherein the presence of at least 50% complex formation of an anti-BoNT antibody to a BoNT/B peptide is indicative of a BoNT immunoresistance.

36. The method according to claim 19, wherein the presence of at most 10% complex formation of an anti-BoNT antibody to a BoNT/B peptide is indicative of a BoNT immunoresistance.

37. The method according to claim 19, wherein the presence of at most 30% complex formation of an anti-BoNT antibody to a BoNT/B peptide is indicative of a BoNT immunoresistance.

38. The method according to claim 19, wherein the presence of at most 50% complex formation of an anti-BoNT antibody to a BoNT/B peptide is indicative of a BoNT immunoresistance.

39. An anti-BoNT immunoapheresis method of treating immunoresistance to a botulinum toxin therapy in an individual, the method comprising the steps of:
 a) contacting an anti-BoNT antibody containing component from the individual extracorporeally with a BoNT/B peptide immunosorbent under conditions suitable for the selective binding of the BoNT/B peptide to the anti-BoNT antibody, the BoNT/B peptide having a length of at least 5 amino acids and at most 60 amino acids; and
 b) returning the anti-BoNT antibody depleted component back into the individual.

40. The immunoapheresis method according to claim 39, wherein the anti-BoNT antibody containing component comprises blood.

41. The immunoapheresis method according to claim 39, wherein the anti-BoNT antibody containing component comprises serum.

42. The immunoapheresis method according to claim 41, wherein an IgG antibody component from the serum is contacted a BoNT/B peptide immunosorbent.

43. The immunoapheresis method according to claim 39, wherein the immunoresistance to botulinum toxin therapy is selected from the group consisting of a BoNT/A immunoresistance, a BoNT/B immunoresistance, a BoNT/C1 immunoresistance, a BoNT/D immunoresistance, a BoNT/E immunoresistance, a BoNT/F immunoresistance and a BoNT/G immunoresistance.

44. The method according to claim 43, wherein the immunoresistance to botulinum toxin therapy is a BoNT/B immunoresistance.

45. The immunoapheresis method according to claim 39, wherein the individual is a human.

46. The immunoapheresis method according to claim 39, wherein the amount of anti-BoNT antibodies removed from an anti-BoNT antibody containing component is at least 10% of the anti-BoNT antibodies from the anti-BoNT antibody containing component.

47. The immunoapheresis method according to claim 39, wherein the amount of anti-BoNT antibodies removed from an anti-BoNT antibody containing component is at least 30% of the anti-BoNT antibodies from the anti-BoNT antibody containing component.

48. The immunoapheresis method according to claim 39, wherein the amount of anti-BoNT antibodies removed from an anti-BoNT antibody containing component is at least 50% of the anti-BoNT antibodies from the anti-BoNT antibody containing component.

49. The immunoapheresis method according to claim 39, wherein the amount of anti-BoNT antibodies removed from an anti-BoNT antibody containing component is at most 10% of the anti-BoNT antibodies from the anti-BoNT antibody containing component.
50. The immunoapheresis method according to claim 39, wherein the amount of anti-BoNT antibodies removed from an anti-BoNT antibody containing component is at most 30% of the anti-BoNT antibodies from the anti-BoNT antibody containing component.
51. The immunoapheresis method according to claim 39, wherein the amount of anti-BoNT antibodies removed from an anti-BoNT antibody containing component is at most 50% of the anti-BoNT antibodies from the anti-BoNT antibody containing component.
52. A method of treating immunoresistance to a botulinum toxin therapy in an individual, the method comprising the step of administering to the individual a tolerogizing composition, the tolerogizing composition comprising a tolerogizing agent conjugated to a BoNT/B peptide the BoNT/B peptide having a length of at least 5 amino acids and at most 60 amino acids, where the administration of the tolerogizing composition producing a decrease in an immunological response against the botulinum toxin therapy in the individual.
53. The method according to 52, wherein the immunoresistance being treated is selected from the group consisting of a BoNT/A immunoresistance, a BoNT/B immunoresistance, a BoNT/C1 immunoresistance, a BoNT/D immunoresistance, a BoNT/E immunoresistance, a BoNT/F immunoresistance and a BoNT/G immunoresistance.
54. The method according to 53, wherein the immunoresistance being treated is a BoNT/B immunoresistance.
55. The method according to 54, wherein the individual is a human.
56. The method according to 52, wherein the BoNT/B peptide comprising an amino acid sequence of amino acids amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, a conservative variant of each amino acid sequence thereof, or an immunogenic fragment of each amino acid sequence thereof.
57. The method according to 56, wherein the amino acid sequence is selected from the group consisting of amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, a conservative variant of each amino acid sequence thereof, or an immunogenic fragment of each amino acid sequence thereof.
58. The method according to 56, wherein a portion of the BoNT/B peptide producing the decreased immunological response comprises at least six consecutive amino acids of 736-754 of SEQ ID NO: 1, at least six consecutive amino acids of amino acids 736-754 of SEQ ID NO: 5, at least six consecutive amino acids of amino acids 764-782 of SEQ ID NO: 1, at least six consecutive amino acids of amino acids 764-782 of SEQ ID NO: 3, at least six consecutive amino acids of amino acids 764-782 of SEQ ID NO: 5, at least six consecutive amino acids of amino acids 764-782 of SEQ ID NO: 7, at least six consecutive amino acids of amino acids 848-866 of SEQ ID NO: 1, at least six consecutive amino acids of amino acids 848-866 of SEQ ID NO: 3, at least six consecutive amino acids of amino acids 848-866 of SEQ ID NO: 5, at least six consecutive amino acids of amino acids 848-866 of SEQ ID NO: 7, at least six consecutive amino acids of amino acids 974-992 of SEQ ID NO: 1, at least six consecutive amino acids of amino acids 974-992 of SEQ ID NO: 3, at least six consecutive amino acids of amino acids 974-992 of SEQ ID NO: 7, at least six consecutive amino acids of amino acids 1030-1048 of SEQ ID NO: 1, at least six consecutive amino acids of amino acids 1030-1048 of SEQ ID NO: 3, at least six consecutive amino acids of amino acids 1030-1048 of SEQ ID NO: 5, at least six consecutive amino acids of amino acids 1030-1048 of SEQ ID NO: 7, at least six consecutive amino acids of amino acids 1058-1076 of SEQ ID NO: 1, at least six consecutive amino acids of amino acids 1058-1076 of SEQ ID NO: 3, at least six consecutive amino acids of amino acids 1058-1076 of SEQ ID NO: 5, at least six consecutive amino acids of amino acids 1058-1076 of SEQ ID NO: 7.
59. The method according to 52, wherein the tolerogizing composition is administered to the individual systemically.
60. The method according to 52, wherein the tolerogizing composition is administered to the individual peripherally.
61. The method according to 52, wherein the tolerogizing composition is administered to the individual prior to administering a botulinum toxin therapy.
62. The method according to 52, wherein the tolerogizing composition is administered to the individual during a course of botulinum toxin therapy.
63. The method according to 52, wherein the tolerogizing composition is administered to the individual after an onset of a BoNT immunoresistance.
64. The method according to 52, wherein the route of administration is selected from the group consisting of an oral administration, an injection and an implant.
65. A method of inducing a BoNT/B immune response in an individual, the method comprising the step of administering to the individual an immune response inducing composition comprising an adjuvant and a BoNT/B antigen, where administration of the immune response inducing composition produces an immune response in the individual;
wherein the BoNT/B antigen comprises a BoNT/B peptide having a length of at least 5 amino acids and at most 60 amino acids and comprises the amino acid sequence of amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, a conservative variant of each amino acid sequence thereof, or an immunogenic fragment of each amino acid sequence thereof.

66. The method according to 65, wherein the amino acid sequence is selected from the group consisting of amino acids 736-754 of SEQ ID NO: 1, amino acids 736-754 of SEQ ID NO: 5, amino acids 764-782 of SEQ ID NO: 1, amino acids 764-782 of SEQ ID NO: 3, amino acids 764-782 of SEQ ID NO: 5, amino acids 764-782 of SEQ ID NO: 7, amino acids 848-866 of SEQ ID NO: 1, amino acids 848-866 of SEQ ID NO: 3, amino acids 848-866 of SEQ ID NO: 5, amino acids 848-866 of SEQ ID NO: 7, amino acids 974-992 of SEQ ID NO: 1, amino acids 974-992 of SEQ ID NO: 3, amino acids 974-992 of SEQ ID NO: 7, amino acids 1030-1048 of SEQ ID NO: 1, amino acids 1030-1048 of SEQ ID NO: 3, amino acids 1030-1048 of SEQ ID NO: 5, amino acids 1030-1048 of SEQ ID NO: 7, amino acids 1058-1076 of SEQ ID NO: 1, amino acids 1058-1076 of SEQ ID NO: 3, amino acids 1058-1076 of SEQ ID NO: 5, amino acids 1058-1076 of SEQ ID NO: 7, a conservative variant of each amino acid sequence thereof, or an immunogenic fragment of each amino acid sequence thereof.

67. The method according to 65, wherein a portion of the BoNT/B peptide producing the immune response comprises at least six consecutive amino acids of 736-754 of SEQ ID NO: 1, at least six consecutive amino acids of amino acids 736-754 of SEQ ID NO: 5, at least six consecutive amino acids of amino acids 764-782 of SEQ ID NO: 1, at least six consecutive amino acids of amino acids 764-782 of SEQ ID NO: 3, at least six consecutive amino acids of amino acids 764-782 of SEQ ID NO: 5, at least six consecutive amino acids of amino acids 764-782 of SEQ ID NO: 7, at least six consecutive amino acids of amino acids 848-866 of SEQ ID NO: 1, at least six consecutive amino acids of amino acids 848-866 of SEQ ID NO: 3, at least six consecutive amino acids of amino acids 848-866 of SEQ ID NO: 5, at least six consecutive amino acids of amino acids 848-866 of SEQ ID NO: 7, at least six consecutive amino acids of amino acids 974-992 of SEQ ID NO: 1, at least six consecutive amino acids of amino acids 974-992 of SEQ ID NO: 3, at least six consecutive amino acids of amino acids 974-992 of SEQ ID NO: 7, at least six consecutive amino acids of amino acids 1030-1048 of SEQ ID NO: 1, at least six consecutive amino acids of amino acids 1030-1048 of SEQ ID NO: 3, at least six consecutive amino acids of amino acids 1030-1048 of SEQ ID NO: 5, at least six consecutive amino acids of amino acids 1030-1048 of SEQ ID NO: 7, at least six consecutive amino acids of amino acids 1058-1076 of SEQ ID NO: 1, at least six consecutive amino acids of amino acids 1058-1076 of SEQ ID NO: 3, at least six consecutive amino acids of amino acids 1058-1076 of SEQ ID NO: 5, at least six consecutive amino acids of amino acids 1058-1076 of SEQ ID NO: 7.

68. The method according to 65, wherein the method further comprises collecting from the individual a sample containing an anti-BoNT/B antibody or anti-BoNT/B antibody-producing cell; and isolating the anti-BoNT/B antibody from the sample.

69. The method according to 68, wherein anti-BoNT/B antibody isolated is a polyclonal anti-BoNT/B antibody.

70. The method according to 68, wherein anti-BoNT/B antibody isolated is a monoclonal anti-BoNT/B antibody.

71. The method according to 65, wherein the BoNT/B antigen comprises a BoNT/B peptide having a length of at least 5 amino acids and at most 60 amino acids operably linked to a carrier.

72. The method according to 71, wherein the. carrier is selected from the group consisting of a keyhole limpet hemacyanin (KLH), an ovalbumin (OVA), a thyroglobulin (THY), a bovine serum albumin (BSA) and a soybean trypsin inhibitor (STI).

73. The method according to 65, wherein the. adjuvant is selected from the group consisting of a Freund's complete adjuvant (FCA), a Freund's incomplete adjuvant (FIA), a sapogenin glycoside, a carbopol a N-acetylmuramyl-L-alanyl-D-isoglutamine and a lipopolysaccharide.

EXAMPLES

Example 1

Synthesis of BoNT/B Peptides

BoNT/B peptides were prepared by solid-phase peptide synthesis on a benzyloxybenzyl alcohol resin to which 9-fluorenylmethylcar-bonyl (Fmoc)-glycine had been coupled. The $N^\alpha$-Fmoc amino acid derivatives were obtained from Vega or from Peninsula Laboratories. The side-chain protecting groups were as follows: for aspartic acid, β-tert-butyl ester; for glutamic acid, γ-tert-butyl ester; for cysteine, S-tert-butyl; for histidine, im-trityl; for lysine, ε-tert-butoxycarbonyl; for serine, threonine, or tyrosine, O-tert-butyl; for arginine, $N^\omega$-methoxy-2,3,6-trimethylphenyl-sulfonyl. Removal of the $N^\alpha$-Fmoc group before each coupling was done by treatment of the peptide resin with 20% piperidine in dimethylformamide (DMF) for 10 min. This was followed by washing (3 times each, 30 sec) with DMF, methanol, and then DMF. Coupling of consecutive amino acids was done for 2 hr by using 3-molar excess of each of the Fmoc amino acid derivatives, diisopropylcarbodiimide in $DMF/CH_2Cl_2$, 1:1 (vol/vol) and 1-hydroxybenzotriazole. The resin was then washed with DMF and methanol (three times each, 30 sec), followed by two 30-sec washes of $CH_2Cl_2$. The completion of coupling after each residue was monitored by ninhydrin, and recoupling was repeated when necessary. After the last cycle and deprotection of the Fmoc-group, the peptide was cleaved from the resin by treatment (2.5 hr) with 55% trifluoroacetic acid in $CH_2Cl_2$, and the solvent was removed on a rotary evaporator. The peptide was washed three times with cold ether, dissolved in water, and freeze-dried. The products were purified by chromatography on CM-Sephadex C50 or DEAE-Sephadex A50. The peptides thus obtained were homogeneous by high-voltage paper electrophoresis and by analytical HPLC on a C18 column using a gradient of 0.1% trifluoracetic acid in water/0.1% trifluoracetic acid in acetonitrile. The amino acid sequence for each peptide was determined and found to have an amino acid composition consistent with that expected from BoNT/B.

The peptides had a uniform size of 19 residues each (except for peptide C31 which was 24 residues) and overlapped consecutively by 5 residues. Table 2 shows the synthetic consecutive overlapping peptides of the $H_N$ domain of BoNT/B having the indicated residues of SEQ ID NO: 1. Regions of overlap with adjacent peptides are underlined and bolded. Table 3 shows synthetic consecutive overlapping peptides of the $H_C$ domain of BoNT/B having the indicated residues of SEQ ID NO: 1. The regions of overlap with adjacent BoNT/B peptides are underlined and bolded.

TABLE 2

Synthetic Overlapping Peptides from $H_N$ Domain of the BoNT/B Heavy Chain

| Peptide Number | Sequence position | Amino acid sequence |
|---|---|---|
| N1  | 442-460 | A P G I C I D V D N E D L F F I A D K |
| N2  | 456-474 | F I A D K N S F S D D L S K N E R I E |
| N3  | 470-488 | N E R I E Y N T Q S N Y I E N D F P I |
| N4  | 484-502 | N D F P I N E L I L D T D L I S K I E |
| N5  | 498-516 | I S K I E L P S E N T E S L T D F N V |
| N6  | 512-530 | T D F N V D V P V Y E K Q P A I K K I |
| N7  | 526-544 | A I K K I F T D E N T I F Q Y L Y S Q |
| N8  | 540-558 | Y L Y S Q T F P L D I R D I S L T S S |
| N9  | 554-572 | S L T S S F D D A L L F S N K V Y S F |
| N10 | 568-586 | K V Y S F F S M D Y I K T A N K V V E |
| N11 | 582-600 | N K V V E A G L F A G W V K Q I V N D |
| N12 | 596-614 | Q I V N D F V I E A N K S N T M D K I |
| N13 | 610-628 | T M D K I A D I S L I V P Y I G L A L |
| N14 | 624-642 | I G L A L N V G N E T A K G N F E N A |
| N15 | 638-656 | N F E N A F E I A G A S I L L E F I P |
| N16 | 652-670 | L E F I P E L L I P V V G A F L L E S |
| N17 | 666-684 | F L L E S Y I D N K N K I I K T I D N |
| N18 | 680-698 | K T I D N A L T K R N E K W S D M Y G |
| N19 | 694-712 | S D M Y G L I V A Q W L S T V N T Q F |
| N20 | 708-726 | V N T Q F Y T I K E G M Y K A L N Y Q |
| N21 | 722-740 | A L N Y Q A Q A L E E I I K Y R Y N I |
| N22 | 736-754 | Y R Y N I Y S E K E K S N I N I D F N |
| N23 | 750-768 | N I D F N D I N S K L N E G I N Q A I |
| N24 | 764-782 | I N Q A I D N I N N F I N G C S V S Y |
| N25 | 778-796 | C S V S Y L M K K M I P L A V E K L L |
| N26 | 792-810 | V E K L L D F D N T L K K N L L N Y I |
| N27 | 806-824 | L L N Y I D E N K L Y L I G S A E Y E |
| N28 | 820-838 | S A E Y E K S K V N K Y L K T I M P F |
| N29 | 834-852 | T I M P F D L S I Y T N D T I L I E M |

TABLE 3

Synthetic Overlapping Peptides from $H_C$ Domain of the BoNT/B Heavy Chain

| Peptide Number | Peptide Number | Peptide Number |
|---|---|---|
| C1  | 848-866   | I L I E M F N K Y N S E I L N N I I L |
| C2  | 862-880   | N N I I L N L R Y K D N N L I D L S G |
| C3  | 876-894   | I D L S G Y G A K V E V Y D G V E L N |
| C4  | 890-908   | G V E L N D K N Q F K L T S S A N S K |
| C5  | 904-922   | S A N S K I R V T Q N Q N I I F N S V |
| C6  | 918-936   | I F N S V F L D F S V S F W I R I P K |
| C7  | 932-950   | I R I P K Y K N D G I Q N Y I H N E Y |
| C8  | 946-964   | I H N E Y T I I N C M K N N S G W K I |
| C9  | 960-978   | S G W K I S I R G N R I I W T L I D I |
| C10 | 974-992   | T L I D I N G K T K S V F F E Y N I R |
| C11 | 988-1006  | E Y N I R E D I S E Y I N R W F F V T |
| C12 | 1002-1020 | W F F V T I T N N L N N A K I Y I N G |
| C13 | 1016-1034 | I Y I N G K L E S N T D I K D I R E V |
| C14 | 1030-1048 | D I R E V I A N G E I I F K L D G D I |
| C15 | 1044-1062 | L D G D I D R T Q F I W M K Y F S I F |
| C16 | 1058-1076 | Y F S I F N T E L S Q S N I E E R Y K |
| C17 | 1072-1090 | E E R Y K I Q S Y S E Y L K D F W G N |
| C18 | 1086-1104 | D F W G N P L M Y N K E Y Y M F N A G |
| C19 | 1100-1118 | M F N A G N K N S Y I K L K K D S P V |
| C20 | 1114-1132 | K D S P V G E I L T R S K Y N Q N S K |
| C21 | 1128-1146 | N Q N S K Y I N Y R D L Y I G E K F I |
| C22 | 1142-1160 | G E K F I I R R K S N S Q S I N D D I |
| C23 | 1156-1174 | I N D D I V R K E D Y I Y L D F F N L |
| C24 | 1170-1188 | D F F N L N Q E W R V Y T Y K Y F K K |
| C25 | 1184-1202 | K Y F K K E E E K L F L A P I S D S D |
| C26 | 1198-1216 | I S D S D E F Y N T I Q I K E Y D E Q |
| C27 | 1212-1230 | E Y D E Q P T Y S C Q L L F K K D E E |

TABLE 3-continued

Synthetic Overlapping Peptides from H$_C$ Domain of the BoNT/B Heavy Chain

| Peptide Number | Peptide Number | Peptide |
|---|---|---|
| C28 | 1226-1244 | K K D E E S T D E I G L I G I H R F Y |
| C29 | 1240-1258 | I H R F Y E S G I V F E E Y K D Y F C |
| C30 | 1254-1272 | K D Y F C I S K W Y L K E V K R K P Y |
| C31 | 1268-1291 | K R K P Y N L K L G C N W Q F I P K D E G W T E |

Example 2

Mapping of Human Anti-Pentavalent Botulinum Toxoid Antibodies Using Synthetic BoNT/B Peptides This example shows antigenic mapping of BoNT/B with human anti-pentavalent botulinum toxoid antisera using the using 60 synthetic BoNT/B peptides that encompass the H$_N$ and H$_C$ domains of BoNT/B.

Human antisera against BoNT/B were prepared by immunizing human volunteers with a toxoid preparation made from pentavalent toxoid (BoNT/A, /B, /C1, /D and /E), see, e.g., Zouhair M. Atassi et al. *Mapping of the antibody-binding regions on botulinum neurotoxin H-chain domain 855-1296 with anti-toxin antibodies from three host species*, 15(7) J. Prot. Chem. 691-700 (1996). The BoNT/B peptide binding assay described below was performed using IgG fractions of these antisera. For use as a control, an IgG fraction was prepared using pre-immune human serum. BoNT/B was purchased from (Metabiologics, Madison, Wis.).

To conduct a BoNT/B peptide binding assay, BoNT/B peptides (2.5 µg in 50 µl of PBS) or active BoNT/B (1 µg in 50 µl of PBS) were added to the wells of flexible polyvinyl chloride 96-well plates (Becton Dickinson, San Jose, Calif.) and allowed to bind for 18 hours at 4° C. After washing five times with PBS, the plates were blocked for 1 hour at 37° C. with 1% bovine serum albumin (BSA) in PBS. Aliquots (50 µl) of anti-toxin antisera that had been prediluted with 0.1% BSA in PBS (dilutions were human IgG fraction, 1:1000 and 1:2000 (vol/vol)) were pipetted into the appropriate wells and allowed to react for 3 hours at 37° C. The wells were washed five times with PBS before adding 50 µl of affinity-purified rabbit Ig fraction against human IgG and IgM (Dako Corporation; Carpinteria, CA) diluted 1:1000 with 0.1% BSA in PBS to the wells of the plate, and incubating for 2 hours at 37° C.

The wells were then washed five times with PBS, and 50 µl of $^{125}$I-labeled Protein A ($2\times10^5$ cpm in 0.1% BSA in PBS) was distributed to the wells and allowed to incubate for 2 hours at room temperature. Finally, the plates were washed thoroughly to remove unbound radioactivity, the individual wells were cut out and transferred into separate tubes, and bound radioactivity was counted in a gamma-counter (1277 Gamma Master, LKB, Finland). Controls included binding of preimmune sera to BoNT/B and its peptides, as well as binding of immune sera to BSA and BoNT/B-unrelated peptides. Assays were performed in triplicate. Results of the triplicate analyses were expressed as mean of net cpm±SD, after correction for nonspecific binding in control wells that were coated with BSA and unrelated peptides.

Figure 1:
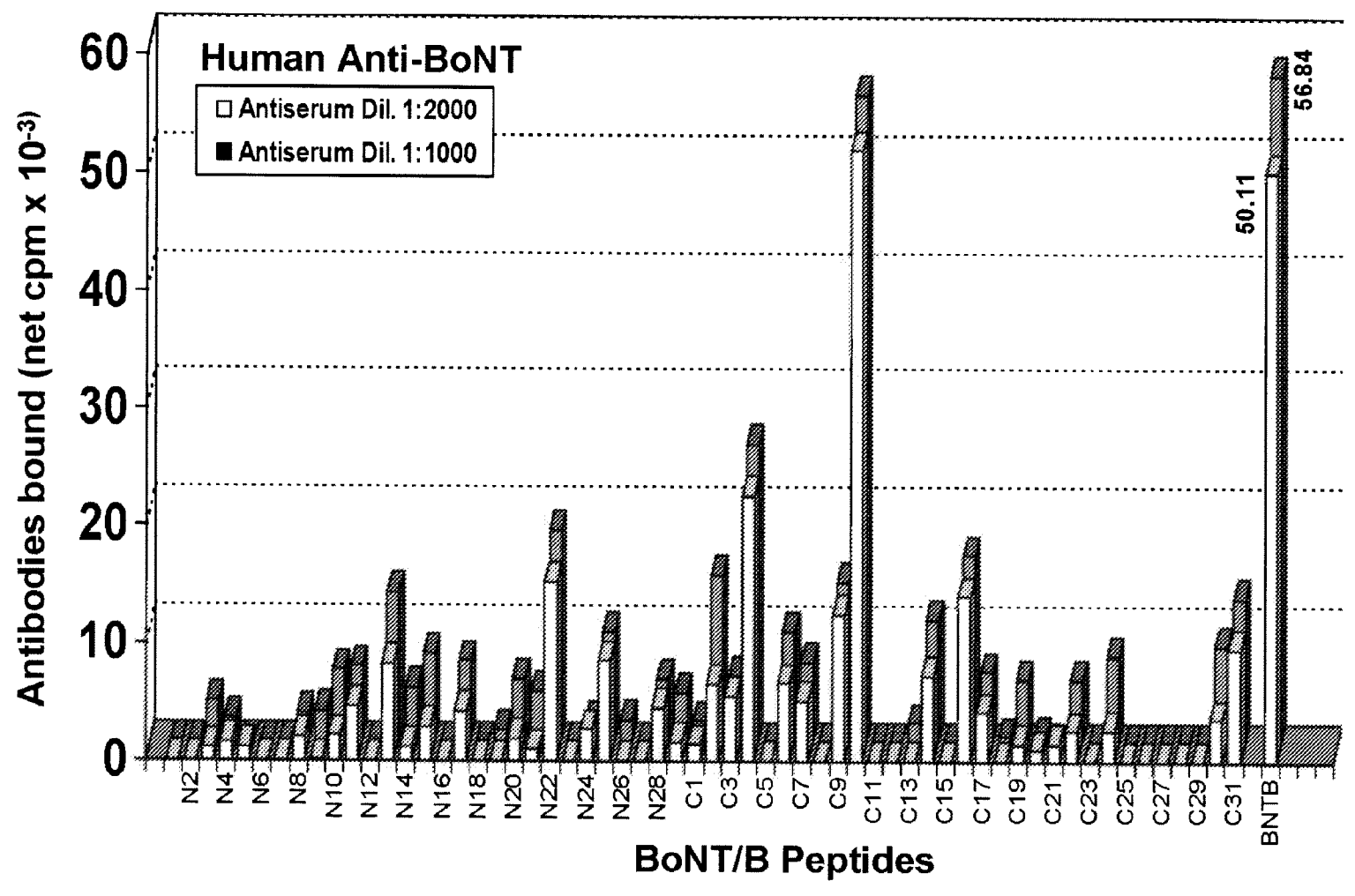

Human anti-BoNT antisera raised against the pentavalent toxoid was observed to bind to several BoNT/B peptides (FIG. 1). Very high levels of antibodies were bound at both dilutions by peptide C10. Antibodies were also bound by the following peptides in decreasing order: C4, N22, C16, C9, C31, N13, C2, C14, N25 and C6/C7 overlap. The remaining BoNT/B peptides bound little or no antibodies. Nonimmune human IgG did not bind to any BoNT/B peptides, and human anti-BoNT antisera showed no antibody binding to unrelated proteins and peptides. The results define antigenic portions of the H$_N$ and H$_C$ domains of BoNT/B.

The three-dimensional structure of BoNT/B reveals the solvent-exposed portions of the primary BoNT/B sequence, see, e.g., S. Swaminathan and S. Eswaramoorthy, *Structural Analysis of the Catalytic and Binding Sites of Clostridium botulinum Neurotoxin B*, 7 Nat. Struct. Biol. 693-699 (2000). Comparison with the results obtained in the present study revealed that the immunodominant antibody-binding regions reside on surface locations on the heavy chain of BoNT/B. In sum, these results demonstrate that BoNT/B peptides N13, N22, N25, C2, C4, C6/C7 overlap, C9, C10, C14, C16 and C31 were recognized by human anti-pentavalent botulinum toxoid antisera.

Example 3

Mapping of Horse Anti-BoNT/B Antibodies Using Synthetic BoNT/B Peptides

This example describes antigenic mapping of BoNT/B with horse anti-BoNT/B antisera using 60 BoNT/B synthetic peptides that encompass the H$_N$ and H$_C$ domains of BoNT/B.

Hyperimmune horse anti-BoNT/B antisera were prepared by subcutaneous immunization, in multiple sites every two weeks for over a year, with a formaldehyde-inactivated BoNT/B in RIBI adjuvant. The antisera tested in the binding studies were obtained after four injections according to procedures described in Atassi et al., supra, 1996. For use as controls, preimmune horse sera were obtained from the animals before immunization.

BoNT/B peptide binding assays were performed as described in Example 2, except that the dilution for horse antisera was 1:500 (vol/vol) and 1:1000 (vol/vol). The secondary antibodies were affinity purified rabbit anti-horse IgG (Accurate Chemical & Scientific Corporation, Weston, N.Y.) and were diluted 1:500 (vol/vol) before use.

The binding profile of horse anti-BoNT/B antibodies to the BoNT/B peptides is shown in FIG. 2. Antibodies were bound, in decreasing amounts to peptides N28, C7/C8 overlap, N25/N26 overlap, C10, N22, C4, C20, C27 and N20. At least 10 other peptides showed very low binding at the antiserum concentration 1:500 (vol/vol), which disappeared at the dilution of 1:1000 vol/vol (FIG. 2). The remaining peptides possessed very low or no binding. Antibodies were also bound by BoNT/B but not to any unrelated (to BoNT/B) proteins or peptides. In sum, these results demonstrate that peptides N20, N22, N25/N26 overlap, N28, C4, C7/C8 overlap, C10, C20 and C27 were recognized by horse anti-BoNT/B antisera.

Example 4

Mapping of Mouse Anti-BoNT/B Antibodies Using Synthetic BoNT/B Peptides

This example describes antigenic mapping of BoNT/B with mouse anti-BoNT/B antisera using 60 BoNT/B synthetic peptides that encompass the $H_N$ and $H_C$ domains of BoNT/B.

Mouse anti-BoNT antisera were prepared in outbred ICR mice by subcutaneous immunization with 10 μg formaldehyde-inactivated BoNT/B in complete Freund's adjuvant and were boosted every four weeks with a similar dose of inactivated toxin in incomplete Freund's adjuvant. Antisera used in these studies were obtained 158 days after the first injection, see, e.g., Atassi et al., supra, 1996. Preimmune mouse sera was employed as a control. Mice were purchased from the National Cancer Institute, and Jackson Laboratory (Bar Harbor, Me.).

BoNT/B peptide binding assays were performed as described in Example 2, except that the dilution for antisera of outbred mice was 1:1000 and 1:2000 (vol/vol). The secondary antibodies (mouse IgG (H+L)+IgM (Mu chain) were obtained from Accurate Chemical & Scientific Corporation (Westbury, N.Y.) and were diluted 1:2000 (vol/vol).

As shown in FIG. 3, mouse anti-BoNT antisera were observed to bind to several BoNT/B peptides. Antibodies were bound in decreasing amounts to the following peptides: C10, C26, C29, N2/N3 overlap, C16/C17 overlap, N22, C31, C14, C7 and C1/C2 overlap. Very low or no binding was exhibited by the remaining BoNT/B peptides. The mouse anti-BoNT antisera exhibited no antibody binding to unrelated proteins and peptides. Preimmune sera from the same mice did not bind to any of the $H_N$ or $H_C$ peptides. In sum, these results demonstrate that peptides N2/N3 overlap, N22, C1/C2 overlap, C7, C10, C14, C16/C17 overlap, C26, C29 and C31 were recognized by mouse anti-BoNT/B antisera.

Example 5

Comparison of BoNT/B Antigenicity between Human Horse and Mouse Antisera

This example defines several common immunogenic regions of BoNT/B by antigen mapping obtained with antisera from three different species.

Figure 4:
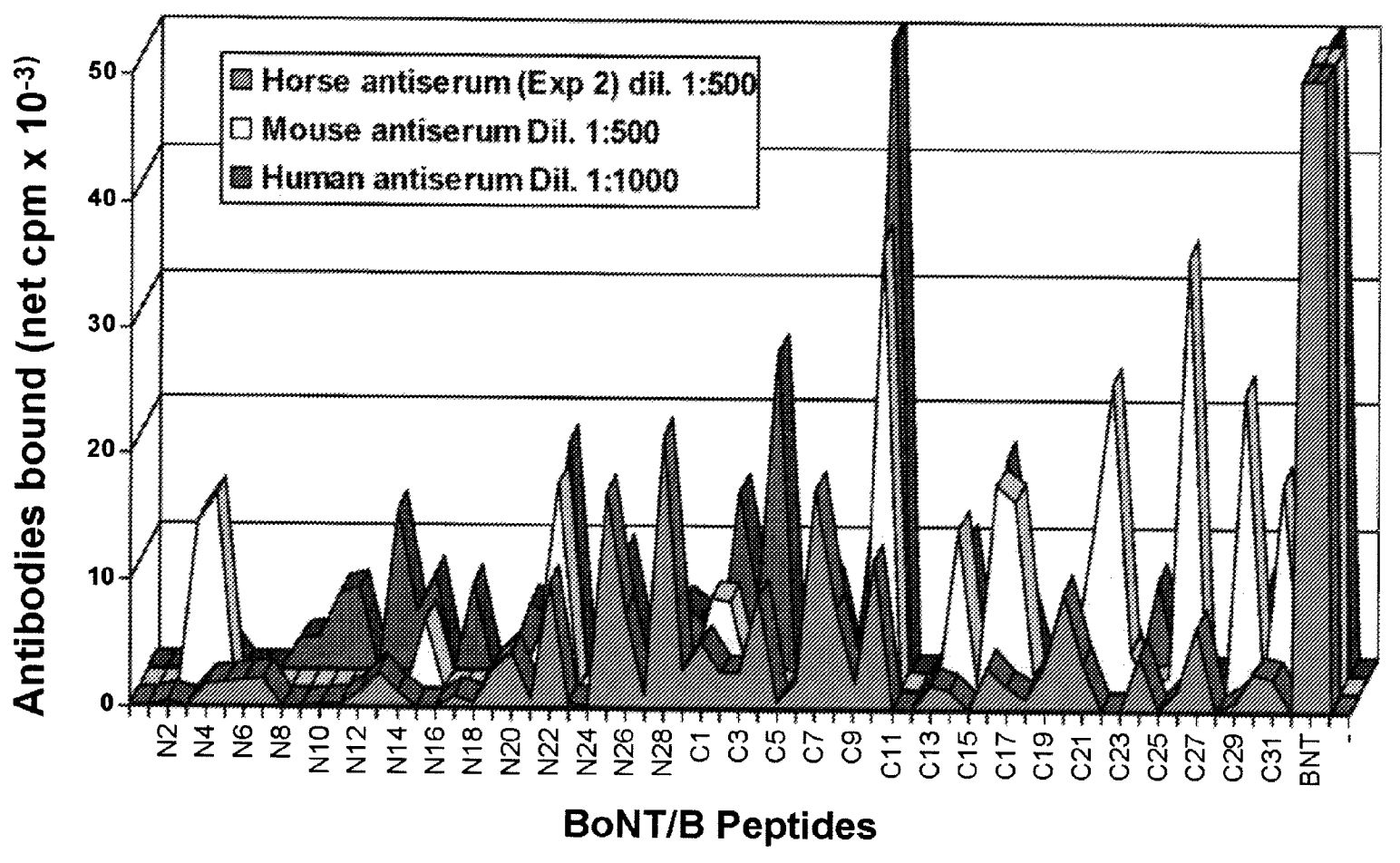

A comparison of the recognition profiles by human, horse and mouse anti-BoNT/B antibodies of the BoNT/B peptides is summarized in Tables 4 and 5 and shown graphically in FIG. 4. The results showed that the antisera of the three host species had for the most part similar recognition profiles with minor shifts to the right or to the left. There were, however, regions that were recognized either by two of the three antisera species or that were unique to one species. The antibodies of all three species recognized peptides N22, N25, C7, C10, C16 and C31. The recognition profiles are even more similar if shifts of binding regions by one peptide up or down are taken into account (Table 2), because such shifts can happen when the boundaries of the sites shift by 1-2 residues to the left or to the right. Shifts to the right or to the left are seen in regions N25/N26, C1/C2, C6/C7, C13/C14 and C30/C31. BoNT/B peptides N10/N11 and N17 bound low amounts of antibodies only with human sera; peptide C8 by horse antibodies, while peptides N2/N3, C22, C26 and C29 bound moderate-to-high amounts of mouse antibodies. In sum, this example shows that anti-BoNT antibodies from human, mouse, horse and chicken recognize several common immunogenic regions from the $H_N$ and $H_C$ domains of the BoNT/B.

TABLE 4

Summary of Antibodies that Recognize BoNT/B $H_N$ Peptides

| Peptide No. | Sequence Position (residues of SEQ ID NO: 1) | anti-BoNT/B Antisera | | |
|---|---|---|---|---|
| | | Human | Horse | Mouse |
| N1 | 442-460 | − | − | − |
| N2 | 456-474 | − | − | − |
| N3 | 470-488 | ± | − | ++ |
| N4 | 484-502 | − | ± | +++ |
| N5 | 498-516 | − | ± | − |
| N6 | 512-530 | − | ± | − |
| N7 | 526-544 | − | ± | − |
| N8 | 540-558 | ± | − | − |
| N9 | 554-572 | − | − | − |
| N10 | 568-586 | + | − | − |
| N11 | 582-600 | + | − | − |
| N12 | 596-614 | − | − | − |
| N13 | 610-628 | ++ | + | − |
| N14 | 624-642 | ± | − | − |
| N15 | 638-656 | + | − | + |
| N16 | 652-670 | − | − | − |
| N17 | 666-684 | + | − | − |
| N18 | 680-698 | − | − | − |
| N19 | 694-712 | − | ± | − |
| N20 | 708-726 | ± | + | − |
| N21 | 722-740 | ± | − | + |
| N22 | 736-754 | +++ | ++ | +++ |
| N23 | 750-768 | − | − | − |
| N24 | 764-782 | − | − | ± |
| N25 | 778-796 | ++ | +++ | + |
| N26 | 792-810 | − | ++ | − |
| N27 | 806-824 | − | − | − |
| N28 | 820-838 | + | +++ | − |
| N29 | 834-852 | ± | ± | − |
| Active BoNT/B | — | +++++ | +++++ | +++++ |

(+) or (−) signs are based on net cpm values and denote the following:
(−), less than 1,500 cpm;
(Å), 1,500-3,000 cpm;
(+), 3,000-7,000 cpm;
(++), 7,000-15,000 cpm;
(+++), 15,000-25,000 cpm;
(++++), 25,000-35,000 cpm;
(+++++), exceeding 35,000 cpm.
Net cpm values were derived from antisera that gave the highest binding.

TABLE 5

Summary of Antibodies that Recognize BoNT/B $H_N$ Peptides

| Peptide No. | Sequence Position (Residues of SEQ ID NO: 1) | anti-BoNT/B Antisera | | |
|---|---|---|---|---|
| | | Human | Horse | Mouse |
| C1 | 848-866 | − | + | ++ |
| C2 | 862-880 | ++ | ± | + |
| C3 | 876-894 | + | ± | − |
| C4 | 890-908 | ++++ | ++ | − |
| C5 | 904-922 | − | − | − |
| C6 | 918-936 | ++ | − | − |
| C7 | 932-950 | + | +++ | ++ |
| C8 | 946-964 | − | ++ | − |
| C9 | 960-978 | ++ | − | − |
| C10 | 974-992 | +++++ | ++ | +++++ |
| C11 | 988-1006 | − | − | − |
| C12 | 1002-1020 | − | − | − |
| C13 | 1016-1034 | − | ± | − |
| C14 | 1030-1048 | ++ | − | ++ |
| C15 | 1044-1062 | − | − | − |
| C16 | 1058-1076 | +++ | + | +++ |
| C17 | 1072-1090 | + | ± | +++ |

TABLE 5-continued

Summary of Antibodies that Recognize BoNT/B H$_N$ Peptides

| | Sequence Position | anti-BoNT/B Antisera | | |
|---|---|---|---|---|
| Peptide No. | (Residues of SEQ ID NO: 1) | Human | Horse | Mouse |
| C18 | 1086-1104 | − | − | − |
| C19 | 1100-1118 | + | + | − |
| C20 | 1114-1132 | − | ++ | − |
| C21 | 1128-1146 | − | + | ++ |
| C22 | 1142-1160 | ± | − | +++ |
| C23 | 1156-1174 | − | − | ± |
| C24 | 1170-1188 | + | + | − |
| C25 | 1184-1202 | − | − | − |
| C26 | 1198-1216 | − | ± | ++++ |
| C27 | 1212-1230 | − | − | − |
| C28 | 1226-1244 | − | − | − |
| C29 | 1240-1258 | − | − | +++ |
| C30 | 1254-1272 | ++ | + | − |
| C31 | 1268-1291 | ++ | ± | +++ |
| Active BoNT/B | — | +++++ | +++++ | +++++ |

(+) or (−) signs are based on net cpm values and denote the following:
(−), less than 1,500 cpm;
(Å), 1,500-3,000 cpm;
(+), 3,000-7,000 cpm;
(++), 7,000-15,000 cpm;
(+++), 15,000-25,000 cpm;
(++++), 25,000-35,000 cpm;
(+++++), exceeding 35,000 cpm.
Net cpm values were derived from antisera that gave the highest binding.

Example 6

Identification of Immunodominant Regions of BoNT/B

This example shows the identification of several immunodominant regions of human anti-BoNT antibodies within the heavy chain of BoNT/B.

The antigenic regions of BoNT were determined using anti-BoNT antisera obtained from human, horse and mouse, as shown in Examples 2 through 4. The location of antigenic regions can be narrowed to shorter domains by the following analysis.

In this analysis, the size of an antigenic site was assigned to be 10-11 residues. The H-chain of BoNT/B was therefore broken down into 10 antigenic sites. The 10 antigenic sites are defined in Table 6, below. The table gives the approximate locations of only the antigenic regions that bind 15,000 cpm of antibody or greater. Although only the immunodominant regions are shown in Table 3, regions binding lower amounts of antibodies can be of equivalent immunological significance. In sum, this example shows that BoNT/B immunodominant regions having 10-11 residues can be determined based on reactivity of anti-BoNT antisera obtained from human, horse and mouse with BoNT/B peptides.

TABLE 6

Major BoNT/B sites that Bind Human anti-BoNT/B Antibodies

| H$_N$ Domain Regions | | H$_C$ Domain Regions | |
|---|---|---|---|
| Antigenic Regions | Amino Acid Residue of SEQ ID NO: 1 | Antigenic Regions | Amino Acid Residue of SEQ ID NO: 1 |
| NR1 | 616-626 | CR1 | 867-877 |
| NR2 | 735-745 | CR2 | 895-905 |
| NR3 | 778-789 | CR3 | 929-939 |
| | | CR4 | 974-984 |
| | | CR5 | 1039-1049 |
| | | CR6 | 1065-1075 |
| | | CR7 | 1269-1281 |

Example 7

BoNT/B Immunophereses in an Individual

This example illustrates an immunophereses method for treating blood in an individual using an anti-BoNT/B immunoaffinity column.

An individual is connected to an extracorporeal circulation circuit where blood is continuously drawn from an antecubital vein via a 15-gauge dialysis needle at a flow rate of approximately 50 to 80 mL/min. The total volume of blood removed from an individual is approximately 300 ml. The processed blood is returned back to the individual. To avoid thrombotic complications, heparin at an input rate of 20 units/min (not to exceed 5000 units per treatment) and anti-coagulant citrate dextrose formula A solution (ACD-A; Baxter Healthcare Corp, Deerfield, Ill.) is administered immediately prior to the procedure to prevent coagulation. The ratio of citrate to whole blood was kept at 1:22.

For primary plasma separation, an autopheresis-Ctm Therapeutic Plasma System (TPS) is employed (Baxter Healthcare Corp, Deerfield, Ill.). Plasma is first separated from the cellular components using the Plasmacell-CR, a rotating cylindrical membrane housed in a plastic casting. The plasma is then directed to a first 150 ml anti-BoNT/B immunoaffinity column where anti-BoNT/B antibodies bind to the immobilized BoNT/B peptides disclosed in the present specification. The perfusion rate of plasma passing through the column is between 15 to 40 ml/min. A continuous flow operation is performed in which the TPS is connected with an adsorption-desorption-automate (ADA; Baxter Healthcare Corp, Deerfield, Ill.) controlling the flow of plasma and regeneration solutions. In general, a predetermined amount of plasma is processed through the first column and then the flow is directed to a second 150 ml anti-BoNT/B immunoaffinity column. While the second column is being loaded, the first column is regenerated using a suitable low pH buffer. Thus, the columns are alternately loaded and regenerated.

After passage though the anti-BoNT/B immunoaffinity column, the treated plasma is reconstituted with the cellular components of the blood and returned back into the individual. The blood can be pre-warmed to body temperature before being returned to the individual. This process is repeated until the desired amount of anti-BoNT/B antibodies is eliminated from the individual's blood.

Example 8

BoNT/B Immunophereses in an Individual

This example demonstrates that an in vitro assay can be used to determine amounts of blocking or protective antibodies against BoNT/B in human serum samples. This example further demonstrates that a combination assay using, for example, two or three synthetic BoNT/A peptides can be used for sensitive detection of the presence of specific anti-toxin antibodies in, for example, BOTOX® treated patients.

A. Methods for Data Analysis

Mouse protection assay (MPA)-positive cervical dystonia (CD) serum samples were obtained from Allergan, Parkinson's Disease Center and Movement Disorders Clinic of Baylor College of Medicine, and the Arizona Dystonia Institute. CD patient sera protected against a lethal dose of BoNT/B in a mouse protection bioassay were screened with 60 synthetic toxin peptides corresponding to the entire H chain of BoNT/B (FIG. 1). Sera from ten individuals who were never treated with BoNT/B was used as a negative control. A 2.5 µg aliquot of each of the 60 synthetic overlapping peptides was dissolved in 50 µl of 0.01 M phosphate buffer, pH 7.2 containing 0.15 M NaCl (1.0 µg/50 µl of PBS), added to three wells of a flexible polyvinyl chloride 96-well plate. Peptides were allowed to bind for two hours at 37° C. followed by overnight incubation at 4° C. Plates were washed five times with PBS to remove unbound peptide and then blocked for one hour at 37° C. with 0.5% bovine serum albumin in PBS (BSA/PBS). An appropriate volume of each of the MPA-positive CD sera was preincubated with an equal volume of TeNT toxoid (1 mg/ml) for three hours at 37° C. after which it was diluted to 1:500 (vol/vol) with 0.1% BSA/PBS, pipetted (50 µl) into peptide-coated wells and allowed to react for three hours at 37° C. followed by further incubation overnight at 4° C. After washing the wells five times with PBS, 50 µl of prediluted (1:500 vol/vol, in 0.1% BSA/PBS) immunoglobulin fraction of rabbit anti-human IgG (DAKO Corporation; Carpinteria, CA A0424)+IgM (Mu chain; DAKO, A0426) was added and allowed to react at 37° C. for two hours. The wells were washed five times with PBS followed by addition of 50 µl of $^{125}$I-Protein A ($2 \times 10^5$ CPM in 0.1% BSA/PBS) to each well and incubation for two hours at room temperature. Finally, plates were washed thoroughly to eliminate unbound radioactivity; individual wells were cut out and transferred into separate tubes; and the incorporated radioactivity was counted in a gamma-counter (1277 Gamma Master; LKB, Finland). The results, which were obtained from triplicate analyses, were expressed as the ratios of mean CPM bound by peptides over CPM bound by control peptides or bovine serum albumin (BSA).

For determining antibody binding to BoNT/B, triplicate wells were coated with the appropriate inactive BoNT/B toxin (0.5 µg/50 µl of PBS). A similar procedure was then used to determine the amount of antibody bound by BoNT/B using human MPA-positive CD sera pre-absorbed with TeNT.

B. Mapping of Epitopes Recognized by Antibodies in of MPA-positive Sera of Cervical Dystonia Patients The results of mapping by the synthetic H-chain peptides of antibodies from 100 CD patients that were MPA positive was determined. Although the peptide recognition profiles varied quantitatively and qualitatively from patient serum to patient serum, there were some peptides that were clearly immunodominant in most patient sera. In order to easily discern the predominant recognition pattern, we made a pool of equal volumes of the 30 CD antisera and analyzed the anti-BoNT/B-antibody binding profile of the serum mixture at a dilution of 1:500 vol/vol. These results showed that high levels of anti-BoNT/B antibodies were bound in decreasing order by peptides C1, C10 and C16, and C14. Medium levels of anti-BoNT/B-antibody were bound by peptides: N15, N21/N22 overlap, N24/N25 overlap and N29. Peptides N3/N4, N27, C2, C4, C6/C7, C17, C24, C29 and C31 exhibited low anti-BoNT/B-antibody binding. The remaining peptides showed very low or no detectable anti-BoNT/B-antibody binding. It should also be noted that the antiserum did not bind to unrelated (to BoNT) proteins and peptides.

To determine the frequency of recognition of a given peptide by the patient sera, results were expressed in percent of antisera which had anti-BoNT/B-antibody that bound to each of the 60 peptides (FIG. 4). Twenty-eight out of 30 patient pools (93.3%) had anti-BoNT/B-antibody that bound to peptides C1, C10 or C14 and C16. The two antisera that had no anti-BoNT/B-antibody-binding to peptide C16 also did not bind to C17. Twenty seven of 30 antisera (90.0%) recognized peptides N22. Two of the antisera that did not recognize peptide N22 also had no anti-BoNT/B-antibody-binding to peptide N21. Of the 30 antisera, 21 (70.0%) showed anti-BoNT/B-antibody-binding to peptides N24; 20 (66.7%) had anti-BoNT/B-antibodies that bound to peptide N15, 16 (53.3%) recognized peptide N25 but the overlap N24/N25 had a higher recognition level (21 of 30 or 70.0%); 11 (36.6.3%) recognized the N3/N4 overlap; and 14 (36.6%) bound to peptide N21. Less than half of the patients had anti-BoNT/B-antibodies against peptides N27, N29, C2, C4, C7, C17, C21, C22, C29, and C31. The remaining peptides either did not bind anti-BoNT/B-antibodies or bound very low levels in 6 or less of the sera. The peptide combinations N24+C1, N22+N24+C1, N24+C1+C10, C10+C14+C16, N22+N24+C1+C10, C1+C10+C14+C16 or N22+N24+C1+C10+C14 were recognized by all 30 (100%) of the antisera containing neutralizing anti-BoNT/B-antibodies (Table 7).

TABLE 7

Detection of Neutralizing anti-BoNT/B Antibodies in Sera of MPA-positive CD patients by BoNT/B Peptide Combinations[a]

| Peptide Combinations | Number of Patients Tested | Percent Detection of Neutralizing anti-BoNT/B Antibodies |
|---|---|---|
| BoNT/B | 30 | 100% (30/30) |
| N24 + C1 | 30 | 100% (30/30) |
| N22 + N24 | 30 | 96.7% (29/30) |
| N22 + C1 | 30 | 96.7% (29/30) |
| C1 + C10 | 30 | 96.7% (29/30) |
| C10 + C14 | 30 | 96.7% (29/30) |
| C14 + C16 | 30 | 96.7% (29/30) |
| N22 + N24 + C1 | 30 | 100% (30/30) |
| N24 + C1 + C10 | 30 | 100% (30/30) |
| C10 + C14 + C16 | 30 | 100% (30/30) |
| C1 + C10 + C14 | 30 | 96.7% (29/30) |
| N22 + N24 + C1 + C10 | 30 | 100% (30/30) |
| C1 + C10 + C14 + C16 | 30 | 100% (30/30) |
| N22 + C1 + C10 + C14 | 30 | 96.7% (29/30) |
| N22 + N24 + C1 + C10 + C14 | 30 | 100% (30/30) |

[a]The table summarizes the levels of detection by analysis of blocking Abs binding to various combinations of the six most active peptides (N22, N24, C1, C10, C14 and C16 (FIG. 7).

What is claimed:

1. An anti-BoNT immunoapheresis method of treating immunoresistance to a botulinum toxin therapy in an individual, the method comprising the steps of:
   a) contacting an anti-BoNT antibody containing component from the individual extracorporeally with a BoNT/B peptide immunosorbent under conditions suitable for the selective binding of the BoNT/B peptide to a neutralizing anti-BoNT antibody, the BoNT/B peptide having a length of at most 60 consecutive amino acid of SEQ ID NO:1 and comprising amino acids 974-992 of SEQ ID NO: 1; and
   b) returning the neutralizing anti-BoNT antibody depleted component back into the individual.

2. The immunoapheresis method according to claim 1, wherein the anti-BoNT antibody containing component comprises blood.

3. The immunoapheresis method according to claim 1, wherein the anti-BoNT antibody containing component comprises serum.

4. The immunoapheresis method according to claim 3, wherein an IgG antibody component from the serum is contacted a BoNT/B peptide immunosorbent.

5. The method according to claim 1, wherein the immunoresistance to botulinum toxin therapy is a BoNT/B immunoresistance.

6. The immunoapheresis method according to claim 1, wherein the individual is a human.

7. The immunoapheresis method according to claim 1, wherein the amount of anti-BoNT antibodies removed from the anti-BoNT antibody containing component is at least 10% of the neutralizing anti-BoNT antibodies from the anti-BoNT antibody containing component.

8. The immunoapheresis method according to claim 1, wherein the amount of anti-BoNT antibodies removed from the anti-BoNT antibody containing component is at most 10% of the neutralizing anti-BoNT antibodies from the anti-BoNT antibody containing component.

9. The immunoapheresis method according to claim 1, wherein the BoNT/B peptide consists of amino acids 974-992 of SEQ ID NO: 1.

10. The immunoapheresis method according to claim 1, wherein the BoNT/B peptide consists of at least six consecutive amino acids 974-792 of SEQ ID NO: 1.

11. An anti-BoNT immunoapheresis method of treating immunoresistance to a botulinum toxin therapy in an individual, the method comprising the steps of:
   a) contacting an anti-BoNT antibody containing component from the individual extracorporeally with a BoNT/B peptide immunosorbent under conditions suitable for the selective binding of the BoNT/B peptide to a neutralizing anti-BoNT antibody, the BoNT/B peptide having a length of at most 60 consecutive amino acid of SEQ ID NO:1 and comprising amino acids 974-984 of SEQ ID NO: 1; and b) returning the anti-BoNT antibody depleted component back into the individual.

12. The immunoapheresis method according to claim 11, wherein the BoNT/B peptide consists of amino acids 974-984 of SEQ ID NO: 1.

13. The immunoapheresis method according to claim 11, wherein the BoNT/B peptide consists of at least six consecutive amino acids 974-784 of SEQ ID NO: 1.

14. The immunoapheresis method according to claim 11, wherein the anti-BoNT antibody containing component comprises blood.

15. The immunoapheresis method according to claim 11, wherein the anti-BoNT antibody containing component comprises serum.

16. The immunoapheresis method according to claim 15, wherein an IgG antibody component of the anti-BoNT antibody containing component is contacted a BoNT/B peptide immunosorbent.

17. The method according to claim 11, wherein the immunoresistance to botulinum toxin therapy is a BoNT/B immunoresistance.

\* \* \* \* \*

UNITED STATES PATENT AND TRADEMARK OFFICE
CERTIFICATE OF CORRECTION

PATENT NO. : 7,670,788 B2 Page 1 of 2
APPLICATION NO. : 12/061952
DATED : March 2, 2010
INVENTOR(S) : M. Zouhair Atassi It is certified that error appears in the above-identified patent and that said Letters Patent is hereby corrected as shown below:

On page 2, under "Other Publications", column 1, line 51, delete "sof" and insert -- of --, therefor.

On page 2, under "Other Publications", column 1, line 52, delete "Immunoresistancey" and insert -- Immunoresistance --, therefor.

On page 2, under "Other Publications", column 1, line 57, delete "eta" and insert -- et --, therefor.

On page 2, under "Other Publications", column 1, line 61, delete "Poreteins" and insert -- Proteins --, therefor.

On page 2, under "Other Publications", column 1, line 62, delete "Plunum" and insert -- Plenum --, therefor.

On page 2, under "Other Publications", column 2, line 37, delete "purifed" and insert -- purified --, therefor.

In column 1, line 10, delete "files" and insert -- filed --, therefor.

In column 13, line 18, delete "Bioinformatics:" and insert -- Bioinformatics,: --, therefor.

In column 17, line 16, delete "hemacyanin" and insert -- hemocyanin --, therefor.

In column 18, line 53, delete "2" and insert -- $2^{nd}$ --, therefor.

In column 35, line 24, delete "inactivatation" and insert -- inactivation --, therefor.

In column 55, line 65-66, delete "hemacyanin" and insert -- hemocyanin --, therefor.

In column 63, line 64, delete "1" and insert -- 1. --, therefor.

In column 75, line 58, delete "chromagenic" and insert -- chromogenic --, therefor.

Signed and Sealed this

Thirteenth Day of July, 2010

David J. Kappos
*Director of the United States Patent and Trademark Office*

In column 76, line 12, delete "$^{35}$Sulfer" and insert -- $^{35}$Sulfur --, therefor.

In column 76, line 12-13, delete "51 Chromium," and insert -- $^{51}$Chromium, --, therefor.

In column 76, line 14, delete "$^{86}$Rubidum" and insert -- $^{86}$Rubidium --, therefor.

In column 76, line 15, delete "$^{13}$Iodine," and insert -- $^{131}$Iodine, --, therefor.

In column 76, line 20, delete "phthaldehyde" and insert -- phthalaldehyde --, therefor.

In column 77, line 14, delete "β-galatosidases" and insert -- β-galactosidases. --, therefor.

In column 77, line 23, delete "glucourinidases" and insert -- glucuronidases --, therefor.

In column 77, line 24, delete "β-galatosidases." and insert -- β-galactosidases. --, therefor.

In column 77, line 33, delete "Pharmaceutocal" and insert -- Pharmaceutical --, therefor.

In column 77, line 61, delete "$^{35}$Sulfer" and insert -- $^{35}$Sulfur --, therefor.

In column 77, line 63, delete "$^{86}$Rubidum" and insert -- $^{86}$Rubidium --, therefor.

In column 78, line 8, delete "phthaldehyde" and insert -- phthalaldehyde --, therefor.

In column 83, line 59, delete "imunniresistance" and insert -- immunoresistance --, therefor.

In column 85, line 45, delete "20" and insert -- 20$^{th}$ --, therefor.

In column 107, line 22, delete "hemacyanin" and insert -- hemocyanin --, therefor.

In column 114, line 11, delete "hemacyanin" and insert -- hemocyanin --, therefor.

In column 114, line 57, delete "trifluoracetic" and insert -- trifluoroacetic --, therefor.

In column 114, line 57, delete "trifluoracetic" and insert -- trifluoroacetic --, therefor.

SEQUENCE LISTING

<160> NUMBER OF SEQ ID NOS: 14

<210> SEQ ID NO 1
<211> LENGTH: 1291
<212> TYPE: PRT
<213> ORGANISM: Clostridium botulinum serotype B1

<400> SEQUENCE: 1

Met Pro Val Thr Ile Asn Asn Phe Asn Tyr Asn Asp Pro Ile Asp Asn
 1               5                  10                  15

Asn Asn Ile Ile Met Met Glu Pro Pro Phe Ala Arg Gly Thr Gly Arg
             20                  25                  30

Tyr Tyr Lys Ala Phe Lys Ile Thr Asp Arg Ile Trp Ile Ile Pro Glu
         35                  40                  45

Arg Tyr Thr Phe Gly Tyr Lys Pro Glu Asp Phe Asn Lys Ser Ser Gly
     50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys

-continued

```
              355                 360                 365
Thr Arg Ala Ser Tyr Phe Ser Asp Ser Leu Pro Pro Val Lys Ile Lys
    370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys Ala Pro Gly Ile Cys Ile Asp
            435                 440                 445
Val Asp Asn Glu Asp Leu Phe Phe Ile Ala Asp Lys Asn Ser Phe Ser
450                 455                 460
Asp Asp Leu Ser Lys Asn Glu Arg Ile Glu Tyr Asn Thr Gln Ser Asn
465                 470                 475                 480
Tyr Ile Glu Asn Asp Phe Pro Ile Asn Glu Leu Ile Leu Asp Thr Asp
                485                 490                 495
Leu Ile Ser Lys Ile Glu Leu Pro Ser Glu Asn Thr Glu Ser Leu Thr
            500                 505                 510
Asp Phe Asn Val Asp Val Pro Val Tyr Glu Lys Gln Pro Ala Ile Lys
            515                 520                 525
Lys Ile Phe Thr Asp Glu Asn Thr Ile Phe Gln Tyr Leu Tyr Ser Gln
            530                 535                 540
Thr Phe Pro Leu Asp Ile Arg Asp Ile Ser Leu Thr Ser Ser Phe Asp
545                 550                 555                 560
Asp Ala Leu Leu Phe Ser Asn Lys Val Tyr Ser Phe Ser Met Asp
                565                 570                 575
Tyr Ile Lys Thr Ala Asn Lys Val Val Glu Ala Gly Leu Phe Ala Gly
            580                 585                 590
Trp Val Lys Gln Ile Val Asn Asp Phe Val Ile Glu Ala Asn Lys Ser
            595                 600                 605
Asn Thr Met Asp Lys Ile Ala Asp Ile Ser Leu Ile Val Pro Tyr Ile
    610                 615                 620
Gly Leu Ala Leu Asn Val Gly Asn Glu Thr Ala Lys Gly Asn Phe Glu
625                 630                 635                 640
Asn Ala Phe Glu Ile Ala Gly Ala Ser Ile Leu Leu Glu Phe Ile Pro
                645                 650                 655
Glu Leu Leu Ile Pro Val Val Gly Ala Phe Leu Leu Glu Ser Tyr Ile
            660                 665                 670
Asp Asn Lys Asn Lys Ile Ile Lys Thr Ile Asp Asn Ala Leu Thr Lys
            675                 680                 685
Arg Asn Glu Lys Trp Ser Asp Met Tyr Gly Leu Ile Val Ala Gln Trp
    690                 695                 700
Leu Ser Thr Val Asn Thr Gln Phe Tyr Thr Ile Lys Glu Gly Met Tyr
705                 710                 715                 720
Lys Ala Leu Asn Tyr Gln Ala Gln Ala Leu Glu Glu Ile Ile Lys Tyr
                725                 730                 735
Arg Tyr Asn Ile Tyr Ser Glu Lys Glu Lys Ser Asn Ile Asn Ile Asp
                740                 745                 750
Phe Asn Asp Ile Asn Ser Lys Leu Asn Glu Gly Ile Asn Gln Ala Ile
            755                 760                 765
Asp Asn Ile Asn Asn Phe Ile Asn Gly Cys Ser Val Ser Tyr Leu Met
    770                 775                 780
```

-continued

```
Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
                835                 840                 845

Leu Ile Glu Met Phe Asn Lys Tyr Asn Ser Glu Ile Leu Asn Asn Ile
850                 855                 860

Ile Leu Asn Leu Arg Tyr Lys Asp Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
                900                 905                 910

Gln Asn Gln Asn Ile Ile Phe Asn Ser Val Phe Leu Asp Phe Ser Val
                915                 920                 925

Ser Phe Trp Ile Arg Ile Pro Lys Tyr Lys Asn Asp Gly Ile Gln Asn
930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
                980                 985                 990

Glu Asp Ile Ser Glu Tyr Ile Asn Arg Trp Phe Phe Val Thr Ile Thr
                995                 1000                1005

Asn Asn Leu Asn Asn Ala Lys Ile Tyr Ile Asn Gly Lys Leu Glu Ser
        1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
                1045                1050                1055

Lys Tyr Phe Ser Ile Phe Asn Thr Glu Leu Ser Gln Ser Asn Ile Glu
                1060                1065                1070

Glu Arg Tyr Lys Ile Gln Ser Tyr Ser Glu Tyr Leu Lys Asp Phe Trp
                1075                1080                1085

Gly Asn Pro Leu Met Tyr Asn Lys Glu Tyr Tyr Met Phe Asn Ala Gly
                1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
                1140                1145                1150

Ser Gln Ser Ile Asn Asp Asp Ile Val Arg Lys Glu Asp Tyr Ile Tyr
                1155                1160                1165

Leu Asp Phe Phe Asn Leu Asn Gln Glu Trp Arg Val Tyr Thr Tyr Lys
                1170                1175                1180

Tyr Phe Lys Lys Glu Glu Glu Lys Leu Phe Leu Ala Pro Ile Ser Asp
1185                1190                1195                1200
```

-continued

```
Ser Asp Glu Phe Tyr Asn Thr Ile Gln Ile Lys Tyr Asp Glu Gln
            1205                1210                1215

Pro Thr Tyr Ser Cys Gln Leu Leu Phe Lys Lys Asp Glu Glu Ser Thr
            1220                1225                1230

Asp Glu Ile Gly Leu Ile Gly Ile His Arg Phe Tyr Glu Ser Gly Ile
        1235                1240                1245

Val Phe Glu Glu Tyr Lys Asp Tyr Phe Cys Ile Ser Lys Trp Tyr Leu
    1250                1255                1260

Lys Glu Val Lys Arg Lys Pro Tyr Asn Leu Lys Leu Gly Cys Asn Trp
1265                1270                1275                1280

Gln Phe Ile Pro Lys Asp Glu Gly Trp Thr Glu
            1285                1290
```

<210> SEQ ID NO 2
<211> LENGTH: 3876
<212> TYPE: DNA
<213> ORGANISM: Clostridium botulinum serotype B1

<400> SEQUENCE: 2

```
atgccagtta caataaataa ttttaattat aatgatccta ttgataataa taatattatt     60
atgatggagc ctccatttgc gagaggtacg gggagatatt ataaagcttt taaaatcaca    120
gatcgtattt ggataatacc ggaaagatat acttttggat ataaacctga ggattttaat    180
aaaagttccg gtatttttaa tagagatgtt tgtgaatatt atgatccaga ttacttaaat    240
actaatgata aaagaatat attttttacaa acaatgatca agttatttaa tagaatcaaa    300
tcaaaaccat gggtgaaaaa gttattagag atgattataa atggtatacc ttatcttgga    360
gatagacgtg ttccactcga gagtttaac acaaacattg ctagtgtaac tgttaataaa    420
ttaatcagta atccaggaga agtggagcga aaaaaaggta ttttcgcaaa tttaataata    480
tttggacctg gccagtttt aaatgaaaat gagactatag atataggtat acaaaatcat    540
tttgcatcaa gggaaggctt cggggggtata atgcaaatga agttttgccc agaatatgta    600
agcgtattta taatgttca agaaaacaaa ggcgcaagta tatttaatag acgtggatat    660
ttttcagatc cagccttgat attaatgcat gaacttatac atgttttaca tggattatat    720
ggcattaaag tagatgattt accaattgta ccaaatgaaa aaaaatttt tatgcaatct    780
acagatgcta tacaggcaga agaactatat acatttggag gacaagatcc cagcatcata    840
actccttcta cggataaaag tatctatgat aaagttttgc aaaatttag agggatagtt    900
gatagactta caaggtttt agtttgcata tcagatccta acattaatat aatatatat    960
aaaaataaat ttaaagataa atataaattc gttgaagatt ctgagggaaa atatagtata   1020
gatgtagaaa gttttgataa attatataaa agcttaatgt ttggttttac agaaactaat   1080
atagcagaaa attataaaat aaaaactaga gcttcttatt ttagtgattc cttaccacca   1140
gtaaaaataa aaattttatt agataatgaa tctatacta tagaggaagg gtttaatata   1200
tctgataaag atatggaaaa agaatataga ggtcagaata aagctataaa taacaagct    1260
tatgaagaaa ttagcaagga gcatttggct gtatataaga tacaaatgtg taaagtgtt    1320
aaagctccag gaatatgtat tgatgttgat aatgaagatt tgttctttat agctgataaa   1380
aatagttttt cagatgattt atctaaaaac gaaagaatag aatataatac acagagtaat   1440
tatatagaaa atgacttccc tataaatgaa ttaatttag atactgattt aataagtaaa   1500
atagaattac aagtgaaaaa tacagaatca cttactgatt taatgtaga tgttccagta   1560
tatgaaaaac aacccgctat aaaaaaaatt tttacagatg aaaaatacat ctttcaatat   1620
```

```
ttatactctc agacatttcc tctagatata agagatataa gtttaacatc ttcatttgat    1680
gatgcattat tattttctaa caaagtttat tcattttttt ctatggatta tattaaaact    1740
gctaataaag tggtagaagc aggattattt gcaggttggg tgaaacagat agtaaatgat    1800
tttgtaatcg aagctaataa aagcaatact atggataaaa ttgcagatat atctctaatt    1860
gttccttata taggattagc tttaaatgta ggaaatgaaa cagctaaagg aaattttgaa    1920
aatgcttttg agattgcagg agccagtatt ctactagaat ttataccaga acttttaata    1980
cctgtagttg gagcctttt attagaatca tatattgaca ataaaaataa aattattaaa    2040
acaatagata atgctttaac taaaagaaat gaaaaatgga gtgatatgta cggattaata    2100
gtagcgcaat ggctctcaac agttaatact caatttata caataaaaga gggaatgtat    2160
aaggctttaa attatcaagc acaagcattg gaagaaataa taaaatacag atataatata    2220
tattctgaaa aagaaaagtc aaatattaac atcgatttta atgatataaa ttctaaactt    2280
aatgagggta ttaaccaagc tatagataat ataaataatt ttataaatgg atgttctgta    2340
tcatatttaa tgaaaaaaat gattccatta gctgtagaaa aattactaga ctttgataat    2400
actctcaaaa aaatttgtt aaattatata gatgaaaata aattatattt gattggaagt    2460
gcagaatatg aaaaatcaaa agtaaataaa tacttgaaaa ccattatgcc gtttgatctt    2520
tcaatatata ccaatgatac aatactaata gaaatgttta ataaatataa tagcgaaatt    2580
ttaaataata ttatcttaaa tttaagatat aaggataata atttaataga tttatcagga    2640
tatgggcaa aggtagaggt atatgatgga gtcgagctta atgataaaaa tcaatttaaa    2700
ttaactagtt cagcaaatag taagattaga gtgactcaaa atcagaatat catatttaat    2760
agtgtgttcc ttgattttag cgttagcttt tggataagaa tacctaaata taagaatgat    2820
ggtatacaaa attatattca taatgaatat acaataatta attgtatgaa aaataattcg    2880
ggctggaaaa tatctattag gggtaatagg ataatatgga ctttaattga tataaatgga    2940
aaaaccaaat cggtattttt tgaatataac ataagagaag atatatcaga gtatataaat    3000
agatggtttt ttgtaactat tactaataat ttgaataacg ctaaaattta tattaatggt    3060
aagctagaat caaatacaga tattaaagat ataagagaag ttattgctaa tggtgaaata    3120
atatttaaat tagatggtga tatagataga acacaattta tttggatgaa atatttcagt    3180
attttttaata cggaattaag tcaatcaaat attgaagaaa gatataaaat tcaatcatat    3240
agcgaatatt taaagatttt tgggggaaat cctttaatgt acaataaaga atattatatg    3300
tttaatgcgg ggaataaaaa ttcatatatt aaactaaaga aagattcacc tgtaggtgaa    3360
attttaacac gtagcaaata taatcaaaat tctaaatata taaattatag agatttatat    3420
attggagaaa aatttattat aagaagaaag tcaaattctc aatctataaa tgatgatata    3480
gttagaaaag aagattatat atatctagat tttttaatt taaatcaaga gtggagagta    3540
tatacctata aatattttaa gaaagaggaa gaaaaattgt ttttagctcc tataagtgat    3600
tctgatgagt tttacaatac tatacaaata aagaatatg atgaacagcc aacatatagt    3660
tgtcagttgc tttttaaaaa agatgaagaa agtactgatg agataggatt gattggtatt    3720
catcgtttct acgaatctgg aattgtattt gaagagtata aagattattt ttgtataagt    3780
aaatggtact aaaagaggt aaaaaggaaa ccatataatt taaaattggg atgtaattgg    3840
cagtttattc ctaaagatga agggtggact gaataa                             3876
```

<210> SEQ ID NO 3

-continued

```
<211> LENGTH: 1291
<212> TYPE: PRT
<213> ORGANISM: Clostridium botulinum serotype B2

<400> SEQUENCE: 3
```

| | | | | | | | | | | | | | | |
|---|---|---|---|---|---|---|---|---|---|---|---|---|---|---|
| Met | Pro | Val | Thr | Ile | Asn | Asn | Phe | Asn | Tyr | Asn | Asp | Pro | Ile | Asp | Asn |
| 1 | | | | 5 | | | | | 10 | | | | | 15 | |
| Asn | Asn | Ile | Ile | Met | Met | Glu | Pro | Pro | Phe | Ala | Arg | Gly | Thr | Gly | Arg |
| | | | 20 | | | | | 25 | | | | | 30 | | |
| Tyr | Tyr | Lys | Ala | Phe | Lys | Ile | Thr | Asp | Arg | Ile | Trp | Ile | Ile | Pro | Glu |
| | | | 35 | | | | | 40 | | | | | 45 | | |
| Arg | Tyr | Thr | Phe | Gly | Tyr | Lys | Pro | Glu | Asp | Phe | Asn | Lys | Ser | Ser | Gly |
| | 50 | | | | | 55 | | | | | 60 | | | | |
| Ile | Phe | Asn | Arg | Asp | Val | Cys | Glu | Tyr | Tyr | Asp | Pro | Asp | Tyr | Leu | Asn |
| 65 | | | | | 70 | | | | | 75 | | | | | 80 |
| Thr | Asn | Asp | Lys | Lys | Asn | Ile | Phe | Leu | Gln | Thr | Met | Ile | Lys | Leu | Phe |
| | | | | 85 | | | | | 90 | | | | | 95 | |
| Asn | Arg | Ile | Lys | Ser | Lys | Pro | Leu | Gly | Glu | Lys | Leu | Leu | Glu | Met | Ile |
| | | | 100 | | | | | 105 | | | | | 110 | | |
| Ile | Asn | Gly | Ile | Pro | Tyr | Leu | Gly | Asp | Arg | Arg | Val | Pro | Leu | Glu | Glu |
| | | | 115 | | | | | 120 | | | | | 125 | | |
| Phe | Asn | Thr | Asn | Ile | Ala | Ser | Val | Thr | Val | Asn | Lys | Leu | Ile | Ser | Asn |
| | 130 | | | | | 135 | | | | | 140 | | | | |
| Pro | Gly | Glu | Val | Glu | Arg | Lys | Lys | Gly | Ile | Phe | Ala | Asn | Leu | Ile | Ile |
| 145 | | | | | 150 | | | | | 155 | | | | | 160 |
| Phe | Gly | Pro | Gly | Pro | Val | Leu | Asn | Glu | Asn | Glu | Thr | Ile | Asp | Ile | Gly |
| | | | | 165 | | | | | 170 | | | | | 175 | |
| Ile | Gln | Asn | His | Phe | Ala | Ser | Arg | Glu | Gly | Phe | Gly | Gly | Ile | Met | Gln |
| | | | 180 | | | | | 185 | | | | | 190 | | |
| Met | Lys | Phe | Cys | Pro | Glu | Tyr | Val | Ser | Val | Phe | Asn | Asn | Val | Gln | Glu |
| | | | 195 | | | | | 200 | | | | | 205 | | |
| Asn | Lys | Gly | Ala | Ser | Ile | Phe | Asn | Arg | Arg | Gly | Tyr | Phe | Ser | Asp | Pro |
| | 210 | | | | | 215 | | | | | 220 | | | | |
| Ala | Leu | Ile | Leu | Met | His | Glu | Leu | Ile | His | Val | Leu | His | Gly | Leu | Tyr |
| 225 | | | | | 230 | | | | | 235 | | | | | 240 |
| Gly | Ile | Lys | Val | Asp | Asp | Leu | Pro | Ile | Val | Pro | Asn | Glu | Lys | Lys | Phe |
| | | | | 245 | | | | | 250 | | | | | 255 | |
| Phe | Met | Gln | Ser | Thr | Asp | Ala | Ile | Gln | Ala | Glu | Glu | Leu | Tyr | Thr | Phe |
| | | | 260 | | | | | 265 | | | | | 270 | | |
| Gly | Gly | Gln | Asp | Pro | Ser | Ile | Ile | Thr | Pro | Ser | Thr | Asp | Lys | Ser | Ile |
| | | | 275 | | | | | 280 | | | | | 285 | | |
| Tyr | Asp | Lys | Val | Leu | Gln | Asn | Phe | Arg | Gly | Ile | Val | Asp | Arg | Leu | Asn |
| | 290 | | | | | 295 | | | | | 300 | | | | |
| Lys | Val | Leu | Val | Cys | Ile | Ser | Asp | Pro | Asn | Ile | Asn | Ile | Asn | Ile | Tyr |
| 305 | | | | | 310 | | | | | 315 | | | | | 320 |
| Lys | Asn | Lys | Phe | Lys | Asp | Lys | Tyr | Lys | Phe | Val | Glu | Asp | Ser | Glu | Gly |
| | | | | 325 | | | | | 330 | | | | | 335 | |
| Lys | Tyr | Ser | Ile | Asp | Val | Glu | Ser | Phe | Asp | Lys | Leu | Tyr | Lys | Ser | Leu |
| | | | 340 | | | | | 345 | | | | | 350 | | |
| Met | Phe | Gly | Phe | Thr | Glu | Thr | Asn | Ile | Ala | Glu | Asn | Tyr | Lys | Ile | Lys |
| | | | 355 | | | | | 360 | | | | | 365 | | |
| Thr | Arg | Ala | Ser | Tyr | Phe | Ser | Asp | Ser | Leu | Pro | Pro | Val | Lys | Ile | Lys |
| | 370 | | | | | 375 | | | | | 380 | | | | |
| Asn | Leu | Leu | Asp | Asn | Glu | Ile | Tyr | Thr | Ile | Glu | Glu | Gly | Phe | Asn | Ile |

-continued

```
           385                 390                 395                 400
Ser Asp Lys Asn Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
                420                 425                 430
Lys Ile Gln Met Cys Lys Ser Val Arg Ala Pro Gly Ile Cys Ile Asp
                435                 440                 445
Val Asp Asn Glu Asp Leu Phe Phe Ile Ala Asp Lys Asn Ser Phe Ser
                450                 455                 460
Asp Asp Leu Ser Lys Asn Glu Arg Ile Glu Tyr Asp Thr Gln Ser Asn
465                 470                 475                 480
Tyr Ile Glu Asn Arg Ser Ser Ile Asp Glu Leu Ile Leu Asp Thr Asn
                485                 490                 495
Leu Ile Ser Lys Ile Glu Leu Pro Ser Glu Asn Thr Glu Ser Leu Thr
                500                 505                 510
Asp Phe Asn Val Asp Val Pro Val Tyr Glu Lys Gln Pro Ala Ile Lys
                515                 520                 525
Lys Ile Phe Thr Asp Glu Asn Thr Ile Phe Gln Tyr Leu Tyr Ser Gln
                530                 535                 540
Thr Phe Pro Leu Asp Ile Arg Asp Ile Ser Leu Thr Ser Ser Phe Asp
545                 550                 555                 560
Asp Ala Leu Leu Phe Ser Asn Lys Val Tyr Ser Phe Phe Ser Met Asp
                565                 570                 575
Tyr Ile Lys Thr Ala Asn Lys Val Val Glu Ala Gly Leu Phe Ala Gly
                580                 585                 590
Trp Val Lys Gln Ile Val Asp Asp Phe Val Ile Glu Ala Asn Lys Ser
                595                 600                 605
Ser Thr Met Asp Lys Ile Ala Asp Ile Ser Leu Ile Val Pro Tyr Ile
                610                 615                 620
Gly Leu Ala Leu Asn Val Gly Asn Glu Thr Ala Lys Gly Asn Phe Glu
625                 630                 635                 640
Asn Ala Phe Glu Ile Ala Gly Ala Ser Ile Leu Leu Glu Phe Ile Pro
                645                 650                 655
Glu Leu Leu Ile Pro Val Val Gly Ala Phe Leu Leu Glu Ser Tyr Ile
                660                 665                 670
Asp Asn Lys Asn Lys Ile Ile Lys Thr Ile Asp Asn Ala Leu Thr Lys
                675                 680                 685
Arg Asp Glu Lys Trp Ile Asp Met Tyr Gly Leu Ile Val Ala Gln Trp
690                 695                 700
Leu Ser Thr Val Asn Thr Gln Phe Tyr Thr Ile Lys Glu Gly Met Tyr
705                 710                 715                 720
Lys Ala Leu Asn Tyr Gln Ala Gln Ala Leu Glu Glu Ile Ile Lys Tyr
                725                 730                 735
Lys Tyr Asn Ile Tyr Ser Glu Lys Glu Lys Ser Asn Ile Asn Ile Asp
                740                 745                 750
Phe Asn Asp Ile Asn Ser Lys Leu Asn Glu Gly Ile Asn Gln Ala Val
                755                 760                 765
Asp Asn Ile Asn Asn Phe Ile Asn Glu Cys Ser Val Ser Tyr Leu Met
                770                 775                 780
Lys Lys Met Ile Pro Leu Ala Val Glu Lys Leu Leu Asp Phe Asp Asn
785                 790                 795                 800
Thr Leu Lys Lys Asn Leu Leu Asn Tyr Ile Asp Glu Asn Lys Leu Tyr
                805                 810                 815
```

-continued

```
Leu Ile Gly Ser Ala Glu Tyr Glu Lys Ser Lys Val Asp Lys His Leu
            820                 825                 830
Lys Thr Ile Ile Pro Phe Asp Leu Ser Met Tyr Thr Asn Asn Thr Ile
            835                 840                 845
Leu Ile Glu Ile Phe Asn Lys Tyr Asn Ser Glu Ile Leu Asn Asn Ile
            850                 855                 860
Ile Leu Asn Leu Arg Tyr Arg Asp Asn Leu Ile Asp Leu Ser Gly
865                 870                 875                 880
Tyr Gly Ala Asn Val Glu Val Tyr Asp Gly Val Glu Leu Asn Asp Lys
                    885                 890                 895
Asn Gln Phe Lys Leu Thr Ser Ser Thr Asn Ser Glu Ile Arg Val Thr
            900                 905                 910
Gln Asn Gln Asn Ile Ile Phe Asn Ser Met Phe Leu Asp Phe Ser Val
            915                 920                 925
Ser Phe Trp Ile Arg Ile Pro Lys Tyr Lys Asn Asp Gly Ile Gln Asn
            930                 935                 940
Tyr Ile His Asn Glu Tyr Thr Ile Ile Asn Cys Ile Lys Asn Asn Ser
945                 950                 955                 960
Gly Trp Lys Ile Ser Ile Arg Gly Asn Arg Ile Ile Trp Thr Leu Thr
                    965                 970                 975
Asp Ile Asn Gly Lys Thr Lys Ser Val Phe Phe Glu Tyr Ser Ile Arg
            980                 985                 990
Glu Asp Ile Ser Asp Tyr Ile Asn Arg Trp Phe Phe Val Thr Ile Thr
            995                 1000                1005
Asn Asn Ser Asp Asn Ala Lys Ile Tyr Ile Asn Gly Lys Leu Glu Ser
        1010                1015                1020
Asn Ile Asp Ile Lys Asp Ile Gly Glu Val Ile Ala Asn Gly Glu Ile
1025                1030                1035                1040
Ile Phe Lys Leu Asp Gly Asp Ile Asp Arg Thr Gln Phe Ile Trp Met
                1045                1050                1055
Lys Tyr Phe Ser Ile Phe Asn Thr Glu Leu Ser Gln Ser Asn Ile Lys
                1060                1065                1070
Glu Ile Tyr Lys Ile Gln Ser Tyr Ser Glu Tyr Leu Lys Asp Phe Trp
                1075                1080                1085
Gly Asn Pro Leu Met Tyr Asn Lys Glu Tyr Tyr Met Phe Asn Ala Gly
            1090                1095                1100
Asn Lys Asn Ser Tyr Ile Lys Leu Lys Lys Asp Ser Ser Val Gly Glu
1105                1110                1115                1120
Ile Leu Thr Arg Ser Lys Tyr Asn Gln Asn Ser Asn Tyr Ile Asn Tyr
                1125                1130                1135
Arg Asn Leu Tyr Ile Gly Glu Lys Phe Ile Ile Arg Arg Lys Ser Asn
            1140                1145                1150
Ser Gln Ser Ile Asn Asp Asp Ile Val Arg Lys Glu Asp Tyr Ile Tyr
            1155                1160                1165
Leu Asp Phe Phe Asn Ser Asn Arg Glu Trp Arg Val Tyr Ala Tyr Lys
            1170                1175                1180
Asp Phe Lys Glu Glu Glu Lys Lys Leu Phe Leu Ala Asn Ile Tyr Asp
1185                1190                1195                1200
Ser Asn Glu Phe Tyr Lys Thr Ile Gln Ile Lys Glu Tyr Asp Glu Gln
                1205                1210                1215
Pro Thr Tyr Ser Cys Gln Leu Leu Phe Lys Lys Asp Glu Glu Ser Thr
            1220                1225                1230
```

```
Asp Glu Ile Gly Leu Ile Gly Ile His Arg Phe Tyr Glu Ser Gly Ile
        1235                1240                1245

Val Leu Lys Asp Tyr Lys Asn Tyr Phe Cys Ile Ser Lys Trp Tyr Leu
        1250                1255                1260

Lys Glu Val Lys Arg Lys Pro Tyr Asn Pro Asn Leu Gly Cys Asn Trp
1265                1270                1275                1280

Gln Phe Ile Pro Lys Asp Glu Gly Trp Ile Glu
            1285                1290

<210> SEQ ID NO 4
<211> LENGTH: 3876
<212> TYPE: DNA
<213> ORGANISM: Clostridium botulinum serotype B2

<400> SEQUENCE: 4
atgccagtta caataaataa ttttaattat aatgatccta ttgataataa taatattatt      60
atgatggaac ccccatttgc gagaggtacg gggagatatt ataaagcttt taaaatcaca     120
gatcgtattt ggataatacc cgaaagatat acttttggat ataaacctga ggattttaat     180
aaaagttccg gtattttaa  tagagatgtt tgtgaatatt atgatccaga ttacttaaat     240
actaatgata aaagaatat  attttttacaa acaatgatca agttatttaa tagaatcaaa     300
tcaaaaccat tgggtgaaaa gttattagag atgattataa atggtatacc ttatcttgga     360
gatagacgtg ttccactcga gagtttaac  acaaacattg ctagtgtaac tgttaataaa     420
ttaatcagta atccaggaga agtggagcga aaaaaaggta ttttcgcaaa tttaataata     480
tttggacctg ggccagtttt aaatgaaaat gagactatag atataggtat acaaaatcat     540
tttgcatcaa gggaaggctt cggggggtata atgcaaatga agttttgccc agaatatgta     600
agcgtattta ataatgttca agaaaacaaa ggcgcaagta tatttaatag acgtggatat     660
ttttcagatc cagccttgat tattaatgcat gaacttatac atgttttaca tggattatat     720
ggcattaaag tagatgattt accaattgta ccaaatgaaa aaaaattttt tatgcaatct     780
acagatgcta tacaggcaga agaactatat acatttggag acaagatcc  cagcatcata     840 actccttcta cggataaaag tatctatgat aaagttttgc aaaattttag aggtatagtt     900
gatagactta acaaggtttt agtttgcata tcagatccta acattaatat taatatatat     960
aaaaataaat ttaaagataa atataaattc gttgaagatt ctgagggaaa atatagtata    1020
gatgtagaaa gttttgataa attatataaa agcttaatgt ttggttttac agaaactaat    1080
atagcagaaa attataaaat aaaaactaga gcttcttatt ttagtgattc cttaccacca    1140
gtaaaaataa aaattttatt agataatgaa atctatacta gaggaaggg  gtttaatata    1200 tctgataaaa atatggaaaa agaatataga ggtcagaata aagctataaa taacaagct     1260 tatgaagaaa ttagcaagga gcatttggct gtatataaga tacaaatgtg taaaagtgtt    1320
agagctccag gaatatgtat tgatgttgat aatgaagatt tgttctttat agctgataaa    1380
aatagttttt cagatgattt atctaaaaac gaaagaatag aatatgatac acagagtaat    1440
tatatagaaa atcgctcttc tatagatgaa ttaattttag atactaattt aataagtaaa    1500
atagaattac caagtgaaaa tacagaatca cttactgatt ttaatgtaga tgttccagta    1560
tatgaaaaac aacccgctat aaaaaaatt  tttacagatg aaaataccat ctttcaatat    1620
ttatactctc agacatttcc tctagatata agagatataa gtttaacatc ttcatttgat    1680
gatgcattat tattttctaa caagtttat tcattttttt ctatggatta tattaaaact    1740
gctaataaag tggtagaagc aggattattt gcaggttggg tgaaacaaat agtagatgat    1800
```

```
tttgtaattg aagctaataa aagcagtact atggataaaa ttgcagatat atctctaatt    1860
gttccttata taggattagc tttaaatgta ggaaatgaaa cagctaaagg aaattttgaa    1920
aatgcttttg agattgcagg agccagtatt ctactagaat ttataccaga acttttaata    1980
cctgtagttg gagccttttt attagaatca tatattgaca ataaaaataa aattattaaa    2040
acaatagata atgctttaac taaaagagat gaaaaatgga ttgatatgta cggattaata    2100
gtagcgcaat ggctctcaac agttaatact caattttata caataaaaga gggaatgtat    2160
aaggctttaa attatcaagc acaagcattg gaagaaataa taaaatacaa atataatata    2220
tattctgaaa agaaaagtc aaatattaat atcgatttta atgatataaa ttctaaactt    2280
aatgagggca ttaaccaagc tgtagataat ataaataatt ttataaatga atgttctgta    2340
tcatatttaa tgaaaaaaat gattccatta gctgtagaaa aattactaga tttttgataat    2400 actctcaaaa aaaatttatt aaattatata gatgaaaata aattatattt gattggaagt    2460
gcagaatatg aaaaatcaaa agtagataaa cacttgaaaa ccattatacc atttgatctt    2520
tcaatgtata ctaataatac aatactaata gaaatattta acaaatataa agcgaaatt    2580 ttaaataata ttatcttaaa tttaagatat agggataata atttaataga tttatcagga    2640
tatggggcaa atgtagaggt tatgatggg gtcgagctta atgataaaaa tcaatttaaa    2700
ttaactagtt caacaaacag tgagattaga gtgactcaaa atcagaatat catatttaat    2760
agtatgtttc ttgattttag tgttagcttt tggataagaa tacctaaata taagaatgat    2820
ggtatacaaa attatattca taatgaatat acaataatta attgcattaa aaataattct    2880
ggctggaaaa tatctattag gggtaatagg ataatatgga ctttaactga tataaatgga    2940
aaaaccaaat cagtattttt tgaatatagc ataagagaag atatatcaga ctatataaat    3000
agatggtttt ttgtaactat tactaataat tcggataacg ctaaaattta tattaatggt    3060
aagctagaat caaatataga tattaaagat ataggagaag ttattgctaa tggtgaaata    3120
atatttaaat tagatggtga tatagataga acacaattta tttggatgaa atatttcagt    3180
atttttaata cagaattaag tcaatcaaat attaaagaaa tatataaaat tcaatcatat    3240
agcgaatatt taaagatttt tggggaaat cctttaatgt acaataaaga atattatatg    3300
tttaatgcgg ggaataaaaa ttcatatatt aaactaaaga aagattcatc tgtaggtgaa    3360
attttaacac gtagcaaata taatcaaaat tccaattata taaattatag aaatttatat    3420
atcggagaaa aatttattat aagaagaaag tcaaattctc aatctataaa tgatgatata    3480
gttagaaaag aagattatat atatctagat tttttttaatt caaatcgaga gtggagagta    3540
tatgcctata aagattttaa ggaagaggaa aaaaaattgt ttttagctaa tatatatgat    3600
tctaatgaat tttacaaaac tatacaaata aagaatatg atgaacagcc aacatatagt    3660
tgtcaattac tttttaaaaa agatgaagaa agtactgatg agataggatt gattggtatt    3720
catcgttttt acgaatctgg aattgtatta aagattatat aaaattattt ttgtataagt    3780
aaatggtact aaaagagggt aaaaaggaaa ccatataacc ccaatttggg gtgtaattgg    3840
caattcattc ctaaagatga aggatggatt gaataa    3876
```

<210> SEQ ID NO 5
<211> LENGTH: 1291
<212> TYPE: PRT
<213> ORGANISM: Clostridium botulinum serotype B Nonproteolytic

<400> SEQUENCE: 5

-continued

```
Met Pro Val Thr Ile Asn Asn Phe Asn Tyr Asn Asp Pro Ile Asp Asn
 1               5                  10                  15

Asp Asn Ile Ile Met Met Glu Pro Pro Phe Ala Arg Gly Thr Gly Arg
             20                  25                  30

Tyr Tyr Lys Ala Phe Lys Ile Thr Asp Arg Ile Trp Ile Ile Pro Glu
             35                  40                  45

Arg Tyr Thr Phe Gly Tyr Lys Pro Glu Asp Phe Asn Lys Ser Ser Gly
 50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Phe Gln Thr Leu Ile Lys Leu Phe
                 85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
                115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
                180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asn Lys Leu Tyr Lys Ser Leu
            340                 345                 350

Met Leu Gly Phe Thr Glu Ile Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Ala Tyr Glu Glu Ile Ser Lys Glu His Leu Ala Val Tyr
```

-continued

```
                420             425             430
Lys Ile Gln Met Cys Lys Ser Val Lys Val Pro Gly Ile Cys Ile Asp
            435             440             445
Val Asp Asn Glu Asn Leu Phe Phe Ile Ala Asp Lys Asn Ser Phe Ser
450             455             460
Asp Asp Leu Ser Lys Asn Glu Arg Val Glu Tyr Asn Thr Gln Asn Asn
465             470             475             480
Tyr Ile Gly Asn Asp Phe Pro Ile Asn Glu Leu Ile Leu Asp Thr Asp
                485             490             495
Leu Ile Ser Lys Ile Glu Leu Pro Ser Glu Asn Thr Glu Ser Leu Thr
            500             505             510
Asp Phe Asn Val Asp Val Pro Val Tyr Glu Lys Gln Pro Ala Ile Lys
            515             520             525
Lys Val Phe Thr Asp Glu Asn Thr Ile Phe Gln Tyr Leu Tyr Ser Gln
            530             535             540
Thr Phe Pro Leu Asn Ile Arg Asp Ile Ser Leu Thr Ser Ser Phe Asp
545             550             555             560
Asp Ala Leu Leu Val Ser Ser Lys Val Tyr Ser Phe Phe Ser Met Asp
                565             570             575
Tyr Ile Lys Thr Ala Asn Lys Val Val Glu Ala Gly Leu Phe Ala Gly
            580             585             590
Trp Val Lys Gln Ile Val Asp Asp Phe Val Ile Glu Ala Asn Lys Ser
            595             600             605
Ser Thr Met Asp Lys Ile Ala Asp Ile Ser Leu Ile Val Pro Tyr Ile
        610             615             620
Gly Leu Ala Leu Asn Val Gly Asp Glu Thr Ala Lys Gly Asn Phe Glu
625             630             635             640
Ser Ala Phe Glu Ile Ala Gly Ser Ser Ile Leu Leu Glu Phe Ile Pro
                645             650             655
Glu Leu Leu Ile Pro Val Val Gly Val Phe Leu Leu Glu Ser Tyr Ile
            660             665             670
Asp Asn Lys Asn Lys Ile Ile Lys Thr Ile Asp Asn Ala Leu Thr Lys
            675             680             685
Arg Val Glu Lys Trp Ile Asp Met Tyr Gly Leu Ile Val Ala Gln Trp
    690             695             700
Leu Ser Thr Val Asn Thr Gln Phe Tyr Thr Ile Lys Glu Gly Met Tyr
705             710             715             720
Lys Ala Leu Asn Tyr Gln Ala Gln Ala Leu Glu Glu Ile Ile Lys Tyr
                725             730             735
Lys Tyr Asn Ile Tyr Ser Glu Glu Lys Ser Asn Ile Asn Ile Asn
            740             745             750
Phe Asn Asp Ile Asn Ser Lys Leu Asn Asp Gly Ile Asn Gln Ala Met
            755             760             765
Asp Asn Ile Asn Asp Phe Ile Asn Glu Cys Ser Val Ser Tyr Leu Met
        770             775             780
Lys Lys Met Ile Pro Leu Ala Val Lys Lys Leu Leu Asp Phe Asp Asn
785             790             795             800
Thr Leu Lys Lys Asn Leu Leu Asn Tyr Ile Asp Glu Asn Lys Leu Tyr
            805             810             815
Leu Ile Gly Ser Val Glu Asp Glu Lys Ser Lys Val Asp Lys Tyr Leu
            820             825             830
Lys Thr Ile Ile Pro Phe Asp Leu Ser Thr Tyr Ser Asn Ile Glu Ile
        835             840             845
```

```
Leu Ile Lys Ile Phe Asn Lys Tyr Asn Ser Glu Ile Leu Asn Asn Ile
    850                 855                 860

Ile Leu Asn Leu Arg Tyr Arg Asp Asn Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asp Ser Lys Ile Arg Val Thr
            900                 905                 910

Gln Asn Gln Asn Ile Ile Phe Asn Ser Met Phe Leu Asp Phe Ser Val
                915                 920                 925

Ser Phe Trp Ile Arg Ile Pro Lys Tyr Arg Asn Asp Asp Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
                995                 1000                1005

Asn Asn Leu Asp Asn Ala Lys Ile Tyr Ile Asn Gly Thr Leu Glu Ser
    1010                1015                1020

Asn Met Asp Ile Lys Asp Ile Gly Glu Val Ile Val Asn Gly Glu Ile
1025                1030                1035                1040

Thr Phe Lys Leu Asp Gly Asp Val Asp Arg Thr Gln Phe Ile Trp Met
                1045                1050                1055

Lys Tyr Phe Ser Ile Phe Asn Thr Gln Leu Asn Gln Ser Asn Ile Lys
            1060                1065                1070

Glu Ile Tyr Lys Ile Gln Ser Tyr Ser Glu Tyr Leu Lys Asp Phe Trp
            1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Val Lys Asp Ser Ser Val Gly Glu
1105                1110                1115                1120

Ile Leu Ile Arg Ser Lys Tyr Asn Gln Asn Ser Asn Tyr Ile Asn Tyr
                1125                1130                1135

Arg Asn Leu Tyr Ile Gly Glu Lys Phe Ile Ile Arg Arg Glu Ser Asn
            1140                1145                1150

Ser Gln Ser Ile Asn Asp Asp Ile Val Arg Lys Glu Asp Tyr Ile His
            1155                1160                1165

Leu Asp Leu Val Leu His His Glu Glu Trp Arg Val Tyr Ala Tyr Lys
    1170                1175                1180

Tyr Phe Lys Glu Gln Glu Glu Lys Leu Phe Leu Ser Ile Ile Ser Asp
1185                1190                1195                1200

Ser Asn Glu Phe Tyr Lys Thr Ile Glu Ile Lys Glu Tyr Asp Glu Gln
                1205                1210                1215

Pro Ser Tyr Ser Cys Gln Leu Leu Phe Lys Lys Asp Glu Glu Ser Thr
            1220                1225                1230

Asp Asp Ile Gly Leu Ile Gly Ile His Arg Phe Tyr Glu Ser Gly Val
            1235                1240                1245

Leu Arg Lys Lys Tyr Lys Asp Tyr Phe Cys Ile Ser Lys Trp Tyr Leu
    1250                1255                1260
```

```
Lys Glu Val Lys Arg Lys Pro Tyr Lys Ser Asn Leu Gly Cys Asn Trp
1265                1270                1275                1280

Gln Phe Ile Pro Lys Asp Glu Gly Trp Thr Glu
                1285                1290

<210> SEQ ID NO 6
<211> LENGTH: 3876
<212> TYPE: DNA
<213> ORGANISM: Clostridium botulinum serotype B Nonproteolytic

<400> SEQUENCE: 6
atgccagtta caataaataa ttttaattat aatgatccta ttgataatga caatattatt      60
atgatggaac ctccatttgc aaggggtacg gggagatatt ataaagcttt taaaatcaca     120
gatcgtattt ggataatacc cgaaagatat acttttggat ataaacctga ggattttaat     180
aaaagttccg gtattttttaa tagagatgtt tgtgaatatt atgatccaga ttacttaaat     240
accaatgata aaagaatat atttttccaa acattgatca agttatttaa tagaatcaaa     300
tcaaaaccat tgggtgaaaa gttattagag atgattataa atggtatacc ttatcttgga     360
gatagacgtg ttccactcga agagtttaac acaaacattg ctagtgtaac tgttaataaa     420
ttaattagta atccaggaga agtggagcga aaaaaaggta ttttcgcaaa tttaataata     480
tttggacctg ggccagtttt aaatgaaaat gagactatag ataggtat acaaaatcat     540 tttgcatcaa gggaaggctt tggggtata atgcaaatga aattttgtcc agaatatgta     600
agcgtattta ataatgttca agaaaacaaa ggcgcaagta tatttaatag acgtggatat     660
ttttcagatc cagccttgat attaatgcat gaacttatac atgttttgca tggattatat     720
ggcattaaag tagatgattt accaattgta ccaaatgaaa aaaaattttt tatgcaatct     780
acagatacta tacaggcaga agaactatat acatttggag acaagatcc cagcatcata     840 tctccttcta cagataaaag tatctatgat aaagttttgc aaaattttag ggggatagtt     900
gatagactta acaaggtttt agtttgcata tcagatccta acattaacat taatatat     960 aaaaataaat ttaaagataa atataaattc gttgaagatt ctgaaggaaa atatagtata    1020
gatgtagaaa gtttcaataa attatataaa agcttaatgt taggttttac agaaattaat    1080
atagcagaaa attataaaat aaaaactaga gcttcttatt ttagtgattc cttaccacca    1140
gtaaaaataa aaaatttatt agataatgaa atctatacta tagaggaagg gtttaatata    1200
tctgataaaa atatgggaaa agaatatagg ggtcagaata aagctataaa taaacaagct    1260
tatgaagaaa tcagcaagga gcatttggct gtatataaga tacaaatgtg taaaagtgtt    1320
aaagttccag gaatatgtat tgatgtcgat aatgaaaatt tgttctttta gctgataaa    1380 aatagttttt cagatgattt atctaaaaat gaaagagtag aatataatac acagaataat    1440
tatataggaa tgactttcc tataaatgaa ttaattttag atactgattt aataagtaaa    1500
atagaattac caagtgaaaa tacagaatca cttactgatt ttaatgtaga tgttccagta    1560
tatgaaaaac aacccgctat aaaaaagtt tttacagatg aaaataccat ctttcaatat    1620
ttatactctc agacatttcc tctaaatata agagatataa gtttaacatc ttcatttgat    1680
gatgcattat tagtttctag caaagtttat tcatttttt ctatggatta tattaaaact    1740
gctaataaag tagtagaagc aggattattt gcaggttggg tgaaacagat agtagatgat    1800
tttgtaatcg aagctaataa aagcagtact atggataaaa ttgcagatat atctctaatt    1860
gttccttata taggattagc tttaaatgta ggagatgaaa cagctaaagg aaattttgaa    1920
agtgcttttg agattgcagg atccagtatt ttactagaat ttataccaga acttttaata    1980
```

-continued

```
cctgtagttg gagtcttttt attagaatca tatattgaca ataaaaataa aattattaaa    2040
acaatagata atgctttaac taaaagagtg gaaaaatgga ttgatatgta cggattaata    2100
gtagcgcaat ggctctcaac agttaatact caatttttata caataaaaga gggaatgtat   2160
aaggctttaa attatcaagc acaagcattg gaagaaataa taaaatacaa atataatata    2220
tattctgaag aggaaaagtc aaatattaac atcaattttta atgatataaa ttctaaactt    2280
aatgatggta ttaaccaagc tatggataat ataaatgatt ttataaatga atgttctgta    2340
tcatatttaa tgaaaaaaat gattccatta gctgtaaaaa aattactaga ctttgataat    2400
actctcaaaa aaatttatt aaattatata gatgaaaata aattatattt aattggaagt     2460
gtagaagatg aaaaatcaaa agtagataaa tacttgaaaa ccattatacc atttgatctt    2520
tcaacgtatt ctaatattga atactaata aaaatattta ataaatataa tagcgaaatt     2580
ttaaataata ttatcttaaa tttaagatat agagataata atttaataga tttatcagga    2640
tatggagcaa aggtagaggt atatgatggg gtcaagctta atgataaaaa tcaatttaaa    2700
ttaactagtt cagcagatag taagattaga gtcactcaaa atcagaatat tatatttaat    2760
agtatgttcc ttgattttag cgttagcttt tggataagga tacctaaata taggaatgat   2820
gatatacaaa attatattca taatgaatat acgataatta attgtatgaa aaataattca    2880
ggctggaaaa tatctattag gggtaatagg ataatatgga ccttaattga tataaatgga    2940
aaaaccaaat cagtattttt tgaatataac ataagagaag atatatcaga gtatataaat    3000
agatggtttt ttgtaactat tactaataat ttggataatg ctaaaattta tattaatggc    3060
acgttagaat caaatatgga tattaaagat ataggagaag ttattgttaa tggtgaaata    3120
acatttaaat tagatggtga tgtagataga acacaattta tttggatgaa atattttagt    3180 attttttaata cgcaattaaa tcaatcaaat attaaagaga tatataaaat tcaatcatat   3240
agcgaatact taaaagattt tgggggaaat cctttaatgt ataataaaga atattatatg    3300
tttaatgcgg ggaataaaaa ttcatatatt aaactagtga agattcatc tgtaggtgaa     3360 atattaatac gtagcaaata taatcagaat tccaattata taaattatag aaatttatat    3420
attggagaaa aatttattat aagaagagag tcaaattctc aatctataaa tgatgatata    3480
gttagaaaag aagattatat acatctagat ttggtacttc accatgaaga gtggagagta    3540
tatgcctata aatattttaa ggaacaggaa gaaaaattgt ttttatctat tataagtgat    3600
tctaatgaat tttataagac tatagaaata aaagaatatg atgaacagcc atcatatagt    3660
tgtcagttgc tttttaaaaa agatgaagaa agtactgatg atataggatt gattggtatt    3720
catcgtttct acgaatctgg agttttacgt aaaaagtata aagattattt ttgtatatagt    3780 aaatggtact taaaagaggt aaaaaggaaa ccatataagt caaatttggg atgtaattgg   3840
cagtttattc ctaaagatga agggtggact gaataa                               3876
```

<210> SEQ ID NO 7
<211> LENGTH: 1291
<212> TYPE: PRT
<213> ORGANISM: Clostridium botulinum serotype B Bivalent 588

<400> SEQUENCE: 7

```
Met Pro Val Thr Ile Asn Asn Phe Asn Tyr Asn Asp Pro Ile Asp Asn
  1               5                  10                  15

Asn Asn Ile Ile Met Met Glu Pro Pro Phe Ala Arg Gly Met Gly Arg
             20                  25                  30
```

-continued

```
Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
        130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
        210                 215                 220

Ala Leu Ile Leu Met His Glu Leu Ile His Val Leu His Gly Leu Tyr
225                 230                 235                 240

Gly Ile Lys Val Asn Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
                260                 265                 270

Gly Gly Gln Asp Pro Ser Ile Ile Ser Pro Ser Thr Asp Lys Ser Ile
            275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
```

```
                450              455              460
Asp Asp Leu Ser Lys Asn Glu Arg Ile Ala Tyr Asn Thr Gln Asn Asn
465                  470                  475                  480

Tyr Ile Glu Asn Asp Phe Ser Ile Asn Glu Leu Ile Leu Asp Thr Asp
                485                  490                  495

Leu Ile Ser Lys Ile Glu Leu Pro Ser Glu Asn Thr Glu Ser Leu Thr
            500                  505                  510

Asp Phe Asn Val Tyr Val Pro Val Tyr Lys Lys Gln Pro Ala Ile Lys
        515                  520                  525

Lys Ile Phe Thr Asp Glu Asn Thr Ile Phe Gln Tyr Leu Tyr Ser Gln
    530                  535                  540

Thr Phe Pro Leu Asp Ile Arg Asp Ile Ser Leu Thr Ser Ser Phe Asp
545                  550                  555                  560

Asp Ala Leu Leu Phe Ser Asn Lys Val Tyr Ser Phe Ser Met Asp
                565                  570                  575

Tyr Ile Lys Thr Ala Asn Lys Val Val Glu Ala Gly Leu Phe Ala Gly
            580                  585                  590

Trp Val Lys Gln Ile Val Asn Asp Phe Val Ile Glu Ala Asn Lys Ser
        595                  600                  605

Ser Thr Met Asp Lys Ile Ala Asp Ile Ser Leu Ile Val Pro Tyr Ile
    610                  615                  620

Gly Leu Ala Leu Asn Val Gly Asn Glu Thr Ala Lys Gly Asn Phe Glu
625                  630                  635                  640

Asn Ala Phe Glu Ile Ala Gly Ala Ser Ile Leu Leu Glu Phe Ile Pro
                645                  650                  655

Glu Leu Leu Ile Pro Val Val Gly Ala Phe Leu Leu Glu Ser Tyr Ile
            660                  665                  670

Asp Asn Lys Asn Lys Ile Ile Glu Thr Ile Asn Ser Ala Leu Thr Lys
        675                  680                  685

Arg Asp Glu Lys Trp Ile Asp Met Tyr Gly Leu Ile Val Ala Gln Trp
    690                  695                  700

Leu Ser Thr Val Asn Thr Gln Phe Tyr Thr Ile Lys Glu Gly Met Tyr
705                  710                  715                  720

Lys Ala Leu Asn Tyr Gln Ala Gln Ala Leu Glu Glu Ile Ile Lys Tyr
                725                  730                  735

Lys Tyr Asn Ile Tyr Ser Glu Lys Glu Arg Ser Asn Ile Asn Ile Asp
            740                  745                  750

Phe Asn Asp Val Asn Ser Lys Leu Asn Glu Gly Ile Asn Gln Ala Ile
        755                  760                  765

Asp Asn Ile Asn Asn Phe Ile Asn Glu Cys Ser Val Ser Tyr Leu Met
    770                  775                  780

Lys Lys Met Ile Pro Leu Ala Val Glu Lys Leu Leu Asp Phe Asp Asn
785                  790                  795                  800

Thr Leu Arg Lys Asn Leu Leu Asn Tyr Ile Asp Glu Asn Lys Leu Tyr
                805                  810                  815

Leu Ile Gly Ser Ala Glu Tyr Glu Lys Ser Lys Val Asp Lys Tyr Leu
            820                  825                  830

Lys Thr Ser Ile Pro Phe Asp Leu Ser Thr Tyr Thr Asn Asn Thr Ile
        835                  840                  845

Leu Ile Glu Ile Phe Asn Lys Tyr Asn Ser Asp Ile Leu Asn Asn Ile
    850                  855                  860

Ile Leu Asn Leu Arg Tyr Arg Asp Asn Lys Leu Ile Asp Leu Ser Gly
865                  870                  875                  880
```

```
Tyr Gly Ala Lys Val Glu Val Tyr Asp Gly Val Lys Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Met Phe Leu Asp Phe Ser Val
            915                 920                 925

Ser Phe Trp Ile Arg Ile Pro Lys Tyr Lys Asn Asp Gly Ile Gln Asn
        930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Met Ile Ile Trp Thr Leu Ile
                965                 970                 975

Asp Ile Asn Gly Lys Ile Lys Ser Val Phe Phe Glu Tyr Ser Ile Lys
                980                 985                 990

Glu Asp Ile Ser Glu Tyr Ile Asn Arg Trp Phe Phe Val Thr Ile Thr
            995                 1000                1005

Asn Asn Ser Asp Asn Ala Lys Ile Tyr Ile Asn Gly Lys Leu Glu Ser
        1010                1015                1020

His Ile Asp Ile Arg Asp Ile Arg Glu Val Ile Ala Asn Asp Glu Ile
1025                1030                1035                1040

Ile Phe Lys Leu Asp Gly Asn Ile Asp Arg Thr Gln Phe Ile Trp Met
                1045                1050                1055

Lys Tyr Phe Ser Ile Phe Asn Thr Glu Leu Ser Gln Ser Asn Ile Glu
                1060                1065                1070

Glu Ile Tyr Lys Ile Gln Ser Tyr Ser Glu Tyr Leu Lys Asp Phe Trp
            1075                1080                1085

Gly Asn Pro Leu Met Tyr Asn Lys Glu Tyr Tyr Met Phe Asn Ala Gly
            1090                1095                1100

Asn Lys Asn Ser Tyr Ile Lys Leu Lys Lys Asp Ser Ser Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
                1140                1145                1150

Ser Gln Ser Ile Asn Asp Asp Ile Val Arg Lys Glu Asp Tyr Ile Tyr
            1155                1160                1165

Leu Asp Phe Phe Asn Leu Asn Gln Glu Trp Arg Val Tyr Met Tyr Lys
        1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
            1205                1210                1215

Pro Thr Tyr Ser Cys Gln Leu Leu Phe Lys Lys Asp Glu Glu Ser Thr
            1220                1225                1230

Asp Glu Ile Gly Leu Ile Gly Ile His Arg Phe Tyr Glu Ser Gly Ile
        1235                1240                1245

Val Phe Lys Glu Tyr Lys Asp Tyr Phe Cys Ile Ser Lys Trp Tyr Leu
        1250                1255                1260

Lys Glu Val Lys Arg Lys Pro Tyr Asn Ser Lys Leu Gly Cys Asn Trp
1265                1270                1275                1280

Gln Phe Ile Pro Lys Asp Glu Gly Trp Thr Glu
                1285                1290
```

<210> SEQ ID NO 8
<211> LENGTH: 3876
<212> TYPE: DNA
<213> ORGANISM: Clostridium botulinum serotype B Bivalent 588

<400> SEQUENCE: 8

| | |
|---|---|
| atgccagtta caataaataa ttttaattat aatgatccta ttgataataa taatattatt | 60 |
| atgatggaac ctccatttgc gagaggtatg gggagatatt ataaagcttt taaaatcaca | 120 |
| gatcgtattt ggataatacc ggaaagatat acttttggat ataaacctga ggattttaat | 180 |
| aaaagttccg gtattttaa tagagatgtt tgtgaatatt atgatccaga ttacttaaat | 240 |
| actaatgata aaagaatat attttacaa acaatgatca agttatttaa tagaatcaaa | 300 |
| tcaaaaccat tgggtgaaaa gttattagag atgattataa atggtatacc ttatcttgga | 360 |
| gatagacgtg ttccactcga gagtttaac acaaacattg ctagtgtaac tgttaataaa | 420 |
| ttaatcagta atccaggaga agtggagcga aaaaaaggta ttttcgcaaa tttgataata | 480 |
| tttggacctg gccagttttt aaatgaaaat gagactatag atataggtat acaaaatcat | 540 |
| tttgcatcaa gggaaggctt cggggggtata atgcaaatga agttttgccc agaatatgta | 600 |
| agcgtattta taatgttca agaaaacaaa ggcgcaagta tatttaatag acgtggatat | 660 |
| ttttcagatc cagccttaat attaatgcat gaacttatac atgttttaca tggattatat | 720 |
| ggcattaaag taaatgattt accaatcgta ccaaatgaaa aaaattttt tatgcaatct | 780 |
| acagatgcta tacaggcaga agaactatat acttttgggg gacaagatcc cagcatcata | 840 |
| agtccttcta cggataaaag tatctatgat aaagttttgc aaaattttag agggatagtt | 900 |
| gatagactta acaaggtttt agtttgcata tcagatccta acattaatat taatatatat | 960 |
| aaaaataaat ttaagataaa atataaattc gttgaagatt ctgagggaaa atatagtata | 1020 |
| gatgtagaaa gtttcgataa attatataaa agcttaatgt ttggttttac agaaactaat | 1080 |
| atagcagaaa attataaaat aaaaactaga gcttcttatt ttagtgattc cttaccacca | 1140 |
| gtaaaaataa aaattttatt agataatgaa atctatacta gaggaaggg gtttaatata | 1200 |
| tctgataaaa atatggaaaa agaatataga ggtcagaata aagctataaa taacaagct | 1260 |
| tatgaagaaa tcagcaagga gcatttggct gtatataaga tacaaatgtg taaaagtgtt | 1320 |
| aaagctccag gaatatgtat tgatgttgat aatgaggatt tgttctttat agctgataaa | 1380 |
| aatagttttt cagatgattt atctaaaaac gaaagaatag catataatac acagaataat | 1440 |
| tatatagaaa atgatttctc tataaatgaa ttaattttag atactgattt aataagtaaa | 1500 |
| atagaattac aagtgaaaaa tacagaatca cttactgatt ttaatgtata tgttccagta | 1560 |
| tataaaaaac aacccgctat aaaaaaaatt tttacagatg aaaataccat ctttcaatat | 1620 |
| ttatactctc agacatttcc tctagatata agagatataa gtttaacatc ttcatttgat | 1680 |
| gatgcattat tattttctaa caagtttat tcattttttt ctatggatta tattaaaact | 1740 |
| gctaataaag tggtagaagc aggattattt gcaggttggg tgaaacagat agtaaatgat | 1800 |
| tttgtaatcg aagctaataa aagcagtact atggataaaa ttgcagatat atctctaatt | 1860 |
| gttccttata taggattagc tttaaatgta ggaaatgaaa cagctaaagg aaattttgaa | 1920 |
| aatgcttttg agattgcagg agccagtatt ctactagaat ttataccaga acttttaata | 1980 |
| cctgtagttg gagcttttt attagaatca tatattgaca ataaaaataa aattattgaa | 2040 |
| acaataaata tgctttaac taaagagatg aaaatggga ttgatatgta cggattaata | 2100 |
| gtagcgcaat ggctctcaac agttaatact caatttttata caataaaaga gggaatgtat | 2160 |

```
aaggctttaa attatcaagc acaagcattg gaagaaataa taaaatacaa atataatata    2220
tattctgaga agaaaggtc aaatattaac atcgatttta atgatgtaaa ttctaaactt    2280
aatgagggta ttaaccaagc tatagataat ataaataatt ttataaatga atgttctgta    2340
tcatatttaa tgaaaaaaat gattccatta gctgtagaaa aattactaga cttcgataat    2400
actctcagaa aaaatttatt aaattatata gatgaaaata aattatattt gattggaagt    2460
gcagaatatg aaaaatcaaa agtagataaa tacttgaaaa ccagtatacc atttgatctt    2520
tcaacgtata ctaataatac aatactaata gaaatatttta ataaatataa tagcgatatt    2580
ttaaataata ttatcttaaa tttaagatat agggataata agttaataga tttatcagga    2640 tatgggcaa aggtagaggt atatgatggg gtcaagctta atgataaaaa tcaatttaaa    2700
ttaactagtt cagcaaatag taagattaga gtgactcaaa atcagaatat catatttaat    2760
agtatgttcc ttgattttag cgttagtttt tggataagaa tacctaaata taagaatgat    2820
ggtatacaaa attatattca taatgaatat acaataatta attgtatgaa aaataattct    2880
ggatggaaaa tatctattag gggtaatatg ataaatatgga ctttaattga tataaatgga    2940
aaaatcaaat cagtattttt tgaatatagc ataaagaag atatatcaga gtatataaat    3000
agatggtttt ttgtaactat tactaataat tcggataacg ctaaaattta tattaatggt    3060
aagctagaat cacatataga tattagagat ataagagaag ttattgctaa tgatgaaata    3120
atatttaaat tagatggtaa tatagataga acacagttca tttggatgaa atatttcagt    3180
atttttaata cggaattaag tcaatcaaat attgaagaaa tatataaaat tcaatcatat    3240
agcgaatatt taaagatttt tggggaaat cctttaatgt acaataaaga atattatatg    3300
tttaatgcgg ggaataaaaa ttcatatatt aaactaaaga aagattcatc tgtaggtgaa    3360
attttaacac gtagcaaata taatcaaaat tccaaatata taaattatag agatttatat    3420
attggagaaa aatttattat aagaagaaag tcaaattctc aatctataaa tgatgatata    3480
gttagaaaag aagattatat atatctagat tttttttaatt taaatcaaga gtggagagta    3540
tatatgtata aatattttaa gaagaggaa gaaaaaattgt ttttagctcc ataagtgat    3600 tctgatgagt tttacaatac tatacaaata aaagaatatg atgaacagcc aacatatagt    3660
tgtcagttgc tttttaaaaa agatgaagaa agtactgatg agataggatt gattggtatt    3720
catcgtttct acgaatctgg aattgtattt aaagagtata agattattt ttgtataagt    3780 aaatggtact aaaagagggt aaaaaggaaa ccatataatt caaaattggg atgtaattgg    3840
cagtttattc ctaaagatga agggtggact gaataa    3876
```

<210> SEQ ID NO 9
<211> LENGTH: 1291
<212> TYPE: PRT
<213> ORGANISM: Clostridium botulinum serotype B Bivalent 593

<400> SEQUENCE: 9

Met Pro Val Thr Ile Asn Asn Phe Asn Tyr Asn Asp Pro Ile Asp Asn
 1               5                  10                  15

Asn Asn Ile Ile Met Met Glu Pro Pro Phe Ala Arg Gly Met Gly Arg
             20                  25                  30

Tyr Tyr Lys Ala Phe Lys Ile Thr Asp Arg Ile Trp Ile Ile Pro Glu
         35                  40                  45

Arg Tyr Thr Phe Gly Tyr Lys Pro Glu Asp Phe Asn Lys Ser Ser Gly
     50                  55                  60

-continued

```
Ile Phe Asn Arg Asp Val Cys Glu Tyr Tyr Asp Pro Asp Tyr Leu Asn
 65                  70                  75                  80

Thr Asn Asp Lys Lys Asn Ile Phe Leu Gln Thr Met Ile Lys Leu Phe
             85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Val Pro Leu Glu Glu
            115                 120                 125

Phe Asn Thr Asn Ile Ala Ser Val Thr Val Asn Lys Leu Ile Ser Asn
        130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asn Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Ala Tyr Asn Thr Gln Asn Asn
465                 470                 475                 480

Tyr Ile Glu Asn Asp Phe Ser Ile Asn Glu Leu Ile Leu Asp Thr Asp
```

-continued

```
                485                 490                 495
Leu Ile Ser Lys Ile Glu Leu Pro Ser Glu Asn Thr Glu Ser Leu Thr
            500                 505                 510
Asp Phe Asn Val Tyr Val Pro Val Tyr Lys Lys Gln Pro Ala Ile Lys
            515                 520                 525
Lys Ile Phe Thr Asp Glu Asn Thr Ile Phe Gln Tyr Leu Tyr Ser Gln
            530                 535                 540
Thr Phe Pro Leu Asp Ile Arg Asp Ile Ser Leu Thr Ser Ser Phe Asp
545                 550                 555                 560
Asp Ala Leu Leu Phe Ser Asn Lys Val Tyr Ser Phe Phe Ser Met Asp
                565                 570                 575
Tyr Ile Lys Thr Ala Asn Lys Val Val Glu Ala Gly Leu Phe Ala Gly
            580                 585                 590
Trp Val Lys Gln Ile Val Asn Asp Phe Val Ile Glu Ala Asn Lys Ser
            595                 600                 605
Ser Thr Met Asp Lys Ile Ala Asp Ile Ser Leu Ile Val Pro Tyr Ile
            610                 615                 620
Gly Leu Ala Leu Asn Val Gly Asn Glu Thr Ala Lys Gly Asn Phe Glu
625                 630                 635                 640
Asn Ala Phe Glu Ile Ala Gly Ala Ser Ile Leu Leu Glu Phe Ile Pro
                645                 650                 655
Glu Leu Leu Ile Pro Val Val Gly Ala Phe Leu Leu Glu Ser Tyr Ile
            660                 665                 670
Asp Asn Lys Asn Lys Ile Ile Glu Thr Ile Asn Ser Ala Leu Thr Lys
            675                 680                 685
Arg Asp Glu Lys Trp Ile Asp Met Tyr Gly Leu Ile Val Ala Gln Trp
690                 695                 700
Leu Ser Thr Val Asn Thr Gln Phe Tyr Thr Ile Lys Glu Gly Met Tyr
705                 710                 715                 720
Lys Ala Leu Asn Tyr Gln Ala Gln Ala Leu Glu Glu Ile Ile Lys Tyr
                725                 730                 735
Lys Tyr Asn Ile Tyr Ser Glu Lys Glu Arg Ser Asn Ile Asn Ile Asp
            740                 745                 750
Phe Asn Asp Val Asn Ser Lys Leu Asn Glu Gly Ile Asn Gln Ala Ile
            755                 760                 765
Asp Asn Ile Asn Asn Phe Ile Asn Glu Cys Ser Val Ser Tyr Leu Met
            770                 775                 780
Lys Lys Met Ile Pro Leu Ala Val Glu Lys Leu Leu Asp Phe Asp Asn
785                 790                 795                 800
Thr Leu Arg Lys Asn Leu Leu Asn Tyr Ile Asp Glu Asn Lys Leu Tyr
                805                 810                 815
Leu Ile Gly Ser Ala Glu Tyr Glu Lys Ser Lys Val Asp Lys Tyr Leu
            820                 825                 830
Lys Thr Ser Ile Pro Phe Asp Leu Ser Thr Tyr Thr Asn Asn Thr Ile
            835                 840                 845
Leu Ile Glu Ile Phe Asn Lys Tyr Asn Ser Asp Ile Leu Asn Asn Ile
            850                 855                 860
Ile Leu Asn Leu Arg Tyr Arg Asp Asn Lys Leu Ile Asp Leu Ser Gly
865                 870                 875                 880
Tyr Gly Ala Lys Val Glu Val Tyr Asp Gly Val Lys Leu Asn Asp Lys
                885                 890                 895
Asn Gln Phe Lys Leu Thr Ser Ser Ala Asn Ser Lys Ile Arg Val Thr
            900                 905                 910
```

```
Gln Asn Gln Asn Ile Ile Phe Asn Ser Met Phe Leu Asp Phe Ser Val
            915                 920                 925

Ser Phe Trp Ile Arg Ile Pro Lys Tyr Lys Asn Asp Gly Ile Gln Asn
        930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Met Ile Ile Trp Thr Leu Ile
                965                 970                 975

Asp Ile Asn Gly Lys Ile Lys Ser Val Phe Phe Glu Tyr Ser Ile Lys
            980                 985                 990

Glu Asp Ile Ser Glu Tyr Ile Asn Arg Trp Phe Phe Val Thr Ile Thr
        995                 1000                1005

Asn Asn Ser Asp Asn Ala Lys Ile Tyr Ile Asn Gly Lys Leu Glu Ser
    1010                1015                1020

His Ile Asp Ile Arg Asp Ile Arg Glu Val Ile Ala Asn Asp Glu Ile
1025                1030                1035                1040

Ile Phe Lys Leu Asp Gly Asn Ile Asp Arg Thr Gln Phe Ile Trp Met
            1045                1050                1055

Lys Tyr Phe Ser Ile Phe Asn Thr Glu Leu Ser Gln Ser Asn Ile Glu
        1060                1065                1070

Glu Ile Tyr Lys Ile Gln Ser Tyr Ser Glu Tyr Leu Lys Asp Phe Trp
    1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Lys Lys Asp Ser Ser Val Gly Glu
1105                1110                1115                1120

Ile Leu Thr Arg Ser Lys Tyr Asn Gln Asn Ser Lys Tyr Ile Asn Tyr
            1125                1130                1135

Arg Asp Leu Tyr Ile Gly Glu Lys Phe Ile Ile Arg Arg Lys Ser Asn
        1140                1145                1150

Ser Gln Ser Ile Asn Asp Asp Ile Val Arg Lys Glu Asp Tyr Ile Tyr
    1155                1160                1165

Leu Asp Phe Phe Asn Leu Asn Gln Glu Trp Arg Val Tyr Met Tyr Lys
    1170                1175                1180

Tyr Phe Lys Lys Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
            1205                1210                1215

Pro Thr Tyr Ser Cys Gln Leu Leu Phe Lys Lys Asp Glu Glu Ser Thr
        1220                1225                1230

Asp Glu Ile Gly Leu Ile Gly Ile His Arg Phe Tyr Glu Ser Gly Ile
    1235                1240                1245

Val Phe Lys Glu Tyr Lys Asp Tyr Phe Cys Ile Ser Lys Trp Tyr Leu
    1250                1255                1260

Lys Glu Val Lys Arg Lys Pro Tyr Asn Ser Lys Leu Gly Cys Asn Trp
1265                1270                1275                1280

Gln Phe Ile Pro Lys Asp Glu Gly Trp Thr Glu
            1285                1290
```

<210> SEQ ID NO 10
<211> LENGTH: 3876
<212> TYPE: DNA
<213> ORGANISM: Clostridium botulinum serotype B Bivalent 593

```
<400> SEQUENCE: 10
atgccagtta caataaataa ttttaattat aatgatccta ttgataataa taatattatt      60
atgatggaac ctccatttgc gagaggtatg gggagatatt ataaagcttt taaaatcaca     120
gatcgtattt ggataatacc ggaaagatat acttttggat ataaacctga ggattttaat     180
aaaagttccg gtattttaa tagagatgtt tgtgaatatt atgatccaga ttacttaaat      240
actaatgata aaagaatat attttacaa acaatgatca agttatttaa tagaatcaaa       300
tcaaaaccat ggggtgaaaa gttattagag atgattataa atggtatacc ttatcttgga     360
gatagacgtg ttccactcga agagtttaac acaaacattg ctagtgtaac tgttaataaa     420
ttaatcagta atccaggaga agtggagcga aaaaaggta ttttcgcaaa tttgataata      480
tttggacctg ggccagtttt aaatgaaaat gagactatag ataggtat acaaaatcat       540
tttgcatcaa gggaaggctt cggggtata atgcaaatga agttttgccc agaatatgta      600
agcgtattta ataatgttca agaaaacaaa ggcgcaagta tatttaatag acgtggatat     660
ttttcagatc cagccttaat attaatgcat gaacttatac atgttttaca tggattatat     720
ggcattaaag taaatgattt accaatcgta ccaaatgaaa aaaattttt tatgcaatct      780
acagatgcta tacaggcaga agaactatat acttttgggg acaagatcc cagcatcata     840
agtccttcta cggataaaag tatctatgat aaagttttgc aaaattttag agggatagtt    900
gatagactta acaaggtttt agtttgcata tcagatccta acattaatat taatatat     960
aaaaataaat ttaagataa atataaattc gttgaagatt ctgagggaaa atatagtata    1020
gatgtagaaa gttcgataa attatataaa agcttaatgt ttggtttac agaaactaat     1080
atagcagaaa attataaaat aaaaactaga gcttcttatt ttagtgattc cttaccacca     1140
gtaaaaataa aaaatttatt agataatgaa atctatacta tagaggaagg gtttaatata    1200
tctgataaaa atatggaaaa agaatataga ggtcagaata aagctataaa taaacaagct    1260
tatgaagaaa tcagcaagga gcatttggct gtatataaga tacaaatgtg taaaagtgtt    1320
aaagctccag gaatatgtat tgatgttgat aatgaggatt tgttcttat agctgataaa    1380
aatagttttt cagatgattt atctaaaaac gaaagaatag catataatac acagaataat    1440
tatatagaaa atgatttctc tataaatgaa ttaattttag atactgattt aataagtaaa    1500
atagaattac caagtgaaaa tacagaatca cttactgatt ttaatgtata tgttccagta    1560
tataaaaaac aacccgctat aaaaaaaatt tttacagatg aaaataccat ctttcaatat    1620
ttatactctc agacatttcc tctagatata agagatataa gtttaacatc ttcatttgat    1680
gatgcattat tattttctaa caaagtttat tcattttttt ctatggatta tattaaaact    1740
gctaataaag tggtagaagc aggattattt gcaggttggg tgaaacagat agtaaatgat    1800
tttgtaatcg aagctaataa aagcagtact atggataaaa ttgcagatat atctctaatt    1860
gttccttata taggattagc tttaaatgta ggaaatgaaa cagctaaagg aaattttgaa    1920
aatgcttttg agattgcagg agccagtatt ctactagaat ttataccaga acttttaata    1980
cctgtagttg gagctttttt attagaatca tatattgaca ataaaaataa aattattgaa    2040
acaataaata gtgctttaac taaaagagat gaaaaatgga ttgatatgta cggattaata    2100
gtagcgcaat ggctctcaac agttaatact caatttttata caataaaaga gggaatgtat    2160
aaggctttaa attatcaagc acaagcattg gaagaaataa taaaatacaa atataatata    2220
tattctgaga agaaaggtc aaatattaac atcgattta atgatgtaaa ttctaaactt    2280
aatgagggta ttaaccaagc tatagataat ataaataatt ttataaatga atgttctgta    2340
```

-continued

```
tcatatttaa tgaaaaaaat gattccatta gctgtagaaa aattactaga cttcgataat    2400
actctcagaa aaatttatt aaattatata gatgaaaata aattatattt gattggaagt    2460
gcagaatatg aaaaatcaaa agtagataaa tacttgaaaa ccagtatacc atttgatctt    2520
tcaacgtata ctaataatac aatactaata gaaatattta ataaatataa tagcgatatt    2580
ttaaataata ttatcttaaa tttaagatat agggataata agttaataga tttatcagga    2640 tatgggcaa aggtagaggt atatgatggg gtcaagctta atgataaaaa tcaatttaaa    2700
ttaactagtt cagcaaatag taagattaga gtgactcaaa atcagaatat catatttaat    2760
agtatgttcc ttgattttag cgttagtttt tggataagaa tacctaaata taagaatgat    2820
ggtatacaaa attatattca taatgaatat acaataatta attgtatgaa aaataattct    2880
ggatggaaaa tatctattag gggtaatatg ataatatgga ctttaattga tataaatgga    2940
aaaatcaaat cagtattttt tgaatatagc ataaaagaag atatatcaga gtatataaat    3000
agatggtttt ttgtaactat tactaataat tcggataacg ctaaaattta tattaatggt    3060
aagctagaat cacatataga tattagagat ataagaaag ttattgctaa tgatgaaata    3120
atatttaaat tagatggtaa tatagataga acacagttca tttggatgaa atatttcagt    3180
atttttaata cggaattaag tcaatcaaat attgaagaaa tatataaaat tcaatcatat    3240
agcgaatatt taaagatttt tgggaaaat cctttaatgt acaataaaga atattatatg    3300
tttaatgcgg ggaataaaaa ttcatatatt aaactaaaga aagattcatc tgtaggtgaa    3360
attttaacac gtagcaaata taatcaaaat tccaaatata taaattatag agatttatat    3420
attggagaaa aatttattat aagaagaaag tcaaattctc aatctataaa tgatgatata    3480
gttagaaaag aagattatat atatctagat tttttttaatt taaatcaaga gtggagagta    3540
tatatgtata aatattttaa gaaagaggaa gaaaaattgt ttttagctcc tataagtgat    3600
tctgatgagt tttacaatac tatacaaata aagaatatg atgaacagcc aacatatagt    3660
tgtcagttgc tttttaaaaa agatgaagaa agtactgatg agataggatt gattggtatt    3720
catcgtttct acgaatctgg aattgtattt aaagagtata agattatttt ttgtataagt    3780
aaatggtact taaaagaggt aaaaaggaaa ccatataatt caaaattggg atgtaattgg    3840
cagtttattc ctaaagatga agggtggact gaataa                              3876
```

<210> SEQ ID NO 11
<211> LENGTH: 1291
<212> TYPE: PRT
<213> ORGANISM: Clostridium botulinum serotype B Bivalent 1436

<400> SEQUENCE: 11

```
Met Ser Val Thr Ile Asn Asn Phe Asn Tyr Asn Asp Pro Ile Asp Asn
 1               5                  10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95
```

```
Asn Arg Ile Lys Ser Lys Pro Leu Gly Glu Lys Leu Leu Glu Met Ile
            100                 105                 110
Ile Asn Gly Ile Pro Tyr Leu Gly Asp Arg Arg Val Pro Leu Glu Glu
            115                 120                 125
Phe Asn Thr Asn Ile Ala Ser Val Thr Val Asn Lys Leu Ile Ser Asn
        130                 135                 140
Pro Gly Glu Val Glu Arg Lys Lys Gly Ile Phe Ala Asn Leu Ile Ile
145                 150                 155                 160
Phe Gly Pro Gly Pro Val Leu Asn Glu Asn Glu Thr Ile Asp Ile Gly
                165                 170                 175
Ile Gln Asn His Phe Ala Ser Arg Glu Gly Phe Gly Ile Met Gln
                180                 185                 190
Met Lys Phe Cys Pro Glu Tyr Val Ser Val Phe Asn Asn Val Gln Glu
            195                 200                 205
Asn Lys Gly Ala Ser Ile Phe Asn Arg Arg Gly Tyr Phe Ser Asp Pro
        210                 215                 220
Ala Leu Ile Leu Met His Glu Leu Ile His Val Leu His Gly Leu Tyr
225                 230                 235                 240
Gly Ile Lys Val Asn Asp Leu Pro Ile Val Pro Asn Glu Lys Lys Phe
                245                 250                 255
Phe Met Gln Ser Thr Asp Ala Ile Gln Ala Glu Glu Leu Tyr Thr Phe
            260                 265                 270
Gly Gly Gln Asp Pro Ser Ile Ile Ser Pro Ser Thr Asp Lys Ser Ile
        275                 280                 285
Tyr Asp Lys Val Leu Gln Asn Phe Arg Gly Ile Val Asp Arg Leu Asn
        290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
        355                 360                 365
Thr Arg Ala Ser Tyr Phe Ser Asp Ser Leu Pro Pro Val Lys Ile Lys
370                 375                 380
Asn Leu Leu Asp Asn Glu Ile Tyr Thr Ile Glu Glu Gly Phe Asn Ile
385                 390                 395                 400
Ser Asp Lys Asn Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys Ala Pro Gly Ile Cys Ile Asp
        435                 440                 445
Val Asp Asn Glu Asp Leu Phe Phe Ile Ala Asp Lys Asn Ser Phe Ser
450                 455                 460
Asp Asp Leu Ser Lys Asn Glu Arg Ile Ala Tyr Asn Thr Gln Asn Asn
465                 470                 475                 480
Tyr Ile Asp Asn Asp Phe Ser Ile Asn Glu Leu Ile Leu Asp Thr Asp
                485                 490                 495
Leu Ile Ser Lys Ile Glu Leu Pro Ser Glu Asn Thr Glu Ser Leu Thr
            500                 505                 510
Asp Phe Asn Val Tyr Val Pro Glu Tyr Lys Lys Gln Pro Ala Ile Lys
```

-continued

```
                515                 520                 525
Lys Ile Phe Thr Asp Glu Asn Thr Ile Phe Gln Tyr Leu Tyr Ser Gln
530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
                580                 585                 590

Trp Val Lys Gln Ile Val Asp Asp Phe Val Ile Glu Ala Asn Lys Ser
                595                 600                 605

Ser Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Glu Thr Ile Asn Ser Ala Leu Thr Lys
                675                 680                 685

Arg Asp Glu Lys Trp Ile Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Arg Ser Asn Ile Asn Ile Asp
                740                 745                 750

Phe Asn Asp Val Asn Ser Lys Leu Asn Glu Gly Ile Asn Gln Ala Ile
                755                 760                 765

Asp Asn Ile Asn Asn Phe Ile Asn Glu Cys Ser Val Ser Tyr Leu Met
770                 775                 780

Lys Lys Met Ile Pro Leu Ala Val Glu Lys Leu Leu Asp Phe Asp Asn
785                 790                 795                 800

Thr Leu Arg Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys Tyr Leu
                820                 825                 830

Lys Thr Ser Ile Pro Phe Asp Leu Ser Thr Tyr Thr Asn Asn Thr Ile
                835                 840                 845

Leu Ile Glu Ile Phe Asn Lys Tyr Asn Ser Asp Ile Leu Asn Asn Ile
850                 855                 860

Ile Leu Asn Leu Arg Tyr Arg Asp Asn Lys Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asn Ser Lys Ile Arg Val Ile
                900                 905                 910

Gln Asn Gln Asn Ile Ile Phe Asn Ser Met Phe Leu Asp Phe Ser Val
                915                 920                 925

Ser Phe Trp Ile Arg Ile Pro Lys Tyr Lys Asn Asp Gly Ile Gln Asn
930                 935                 940
```

| | | | | | | | | | | | |
|---|---|---|---|---|---|---|---|---|---|---|---|
| Tyr | Ile | His | Asn | Glu | Tyr | Thr | Ile | Ile | Asn | Cys | Met | Lys | Asn | Asn | Ser |
| 945 | | | | 950 | | | | | 955 | | | | | 960 | |

Tyr Ile His Asn Glu Tyr Thr Ile Ile Asn Cys Met Lys Asn Asn Ser
945                 950                 955                 960

Gly Trp Lys Ile Ser Ile Arg Gly Asn Met Ile Ile Trp Thr Leu Ile
                965                 970                 975

Asp Ile Asn Gly Lys Ile Lys Ser Val Phe Phe Glu Tyr Ser Ile Lys
                980                 985                 990

Glu Asp Ile Ser Glu Tyr Ile Asn Arg Trp Phe Phe Val Thr Ile Thr
            995                 1000                1005

Asn Asn Ser Asp Asn Ala Lys Ile Tyr Ile Asn Gly Lys Leu Glu Ser
    1010                1015                1020

His Ile Asp Ile Arg Asp Ile Arg Glu Val Ile Ala Asn Asp Glu Ile
1025                1030                1035                1040

Ile Phe Lys Leu Asp Gly Asn Ile Asp Arg Thr Gln Phe Ile Trp Met
                1045                1050                1055

Lys Tyr Phe Ser Ile Phe Asn Thr Glu Leu Ser Gln Ser Asn Ile Glu
                1060                1065                1070

Glu Ile Tyr Lys Ile Gln Ser Tyr Ser Glu Tyr Leu Lys Asp Phe Trp
    1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
                1140                1145                1150

Ser Gln Ser Ile Asn Asp Asp Ile Val Arg Lys Glu Asp Tyr Ile Tyr
                1155                1160                1165

Leu Asp Phe Phe Asn Leu Asn Gln Glu Trp Arg Val Tyr Ile Tyr Lys
    1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
                1220                1225                1230

Asp Glu Ile Gly Leu Ile Gly Ile His Arg Phe Tyr Glu Ser Gly Ile
                1235                1240                1245

Val Phe Lys Glu Tyr Lys Asp Tyr Phe Cys Ile Ser Lys Trp Tyr Leu
    1250                1255                1260

Lys Glu Val Lys Arg Lys Pro Tyr Asn Ser Lys Leu Gly Cys Asn Trp
1265                1270                1275                1280

Gln Phe Ile Pro Lys Asp Glu Gly Trp Thr Glu
                1285                1290

<210> SEQ ID NO 12
<211> LENGTH: 3876
<212> TYPE: DNA
<213> ORGANISM: Clostridium botulinum serotype B Bivalent 1436

<400> SEQUENCE: 12
atgtcagtta caataaataa ttttaattat aatgatccta ttgataatga taatattatt     60
atgatggaac ctccatttgc gagaggtacg gggagatatt ataaagcttt taaaatcaca    120

```
gatcgtattt ggataatacc ggaaagatat acttttggat ataaacctga ggatttttaat    180 aaaagttccg gtattttttaa tagagatgtt tgtgaatatt atgatccaga ttacttaaat    240
actaatgata aaaagaatat attttttacaa acaatgatca agttatttaa tagaatcaaa    300
tcaaaaccat tgggtgaaaa gttattagag atgattataa atggtatacc ttatcttgga    360
gatagacgtg ttccactcga agagtttaac acaaacattg ctagtgtaac tgttaataaa    420
ttaatcagta atccaggaga agtggagcga aaaaaaggta ttttcgcaaa tttaataata    480
tttggacctg ggccagtttt aaatgaaaat gagactatag atataggtat acaaaatcat    540
tttgcatcaa gggaaggctt cggggggtata atgcaaatga agttttgccc agaatatgta    600
agcgtattta ataatgttca agaaaacaaa ggcgcaagta tatttaatag acgtggatat    660
ttttcagatc cagccttgat actaatgcat gaacttatac atgttttaca tggattatat    720
ggcattaaag taaatgattt accaattgtg ccaaatgaaa aaaaattttt tatgcaatct    780
acagatgcta tacaggcaga agaactatat acatttggag ggcaagatcc cagcatcata    840
agtccttcta cggataaaag tatctatgat aaagttttgc aaaattttag agggatagtt    900
gatagactta acaaggtttt agtttgcata tcagatccta acattaatat taatatatat    960
aaaaataaat ttaaagataa atataaattc gttgaagatt ctgaaggaaa atatagtata   1020
gatgtagaaa gtttcgataa attatataaa agcttaatgt ttggttttac agaaactaat   1080
atagcagaaa attataaaat aaaaactaga gcttcttatt ttagtgattc cttaccacca   1140
gtaaaaataa aaaatttatt agataatgaa atctatacta tagaggaagg gtttaatata   1200
tctgataaaa atatggaaaa agaatataga ggtcagaata aagctataaa taaacaagct   1260
tatgaagaaa tcagcaagga gcatttggct gtatataaga tacaaatgtg taaaagtgtt   1320
aaagctccag gaatatgtat tgatgttgat aatgaggatt tgttctttat agctgataaa   1380
aatagttttt cagatgattt atctaaaaac gaaagaatag catataatac acagaataat   1440
tatatagaca atgatttctc tataaatgaa ttaattttag atactgattt aataagtaaa   1500
atagaattac caagtgaaaa tacagaatca cttactgatt ttaatgtata tgttccagaa   1560
tataaaaaac aacccgctat aaaaaaaatt tttacagatg aaaataccat cttcaatat   1620 ttatactctc agacatttcc tctagatata agagatataa gtttaacatc ttcatttgat   1680
gatgcattat tattttctaa caaagtttat tcatttttttt ctatggatta tattaaaact   1740
gctaataaag tggtagaagc aggattattt gcaggttggg tgaaacagat agtgagatgat   1800 tttgtaatcg aagctaataa aagcagtact atggataaaa ttgcagatat atctctaatt   1860
gttccttata taggattagc tttaaatgta ggaaatgaaa cagctaaagg aaattttgaa   1920
aatgcttttg agattgcagg agccagtatt ctactagaat ttataccaga actttttaata   1980 cctgtagttg gagctttttt attagaatca tatattgaca ataaaaataa aattattgaa   2040
acaataaata gtgctttaac taaaagagat gaaaaatgga ttgatatgta cggattaata   2100
gtagcgcaat ggctctcaac agttaatact caattttata caataaaaga gggaatgtat   2160
aaggctttaa attatcaagc acaagcattg gaagaaataa taaaatacaa atataatata   2220
tattctgaga aagaaaggtc aaatattaac atcgatttta tgatgtaaa ttctaaactt   2280 aatgagggta ttaccaagc tatagataat ataaataatt ttataaatga atgttctgta   2340
tcatatttaa tgaaaaaaat gattccatta gctgtagaaa aattactaga cttcgataat   2400
actctcagaa aaaattttatt aaattatata gatgaaaata aattatatttt gattggaagt   2460 gcagaatatg aaaaatcaaa agtagataaa tacttgaaaa ccagtatacc atttgatctt   2520
```

-continued

```
tcaacgtata ctaataatac aatactaata gaaatattta ataaatataa tagcgatatt    2580
ttaaataata ttatcttaaa tttaagatat agggataata agttaataga tttatcagga    2640
tatggggcaa aggtagaggt atatgatggg gtcaagctta atgataaaaa tcaatttaaa    2700
ttaactagtt cagcaaatag taagattaga gtgattcaaa atcagaatat catatttaat    2760
agtatgttcc ttgattttag cgttagtttt tggataagaa tacctaaata taagaatgat    2820
ggtatacaaa attatattca taatgaatat acaataatta attgtatgaa aaataattct    2880
ggatggaaaa tatctattag gggtaatatg ataatatgga ctttaattga tataaatgga    2940
aaaatcaaat cagtattttt tgaatatagc ataaagaag atatatcaga gtatataaat     3000
agatggtttt ttgtaactat tactaataat tcggataacg ctaaaattta tattaatggt    3060
aagctagaat cacatataga tattagagat ataagagaag ttattgctaa tgatgaaata    3120
atatttaaat tagatggtaa tatagataga acacaattca tttggatgaa atatttcagt    3180
atttttaata cggaattaag tcaatcaaat attgaagaaa tatataaaat tcaatcatat    3240
agcgaatatt taaagatttt tgggggaaat cctttaatgt acaataaaga atattatatg    3300
tttaatgccg ggaataaaaa ttcatatatt aaactaaaga aagattcacc tgtaggtgaa    3360
attttaacac gtagcaaata taatcaaaat tccaaatata taaattatag agatttatat    3420
attggagaaa aatttattat aagaagaaag tcaaattctc aatctataaa tgatgatata    3480
gttagaaaag aagattatat atatctagat ttttttaatt taaatcaaga gtggagagta    3540
tatatctata aatattttaa gaaagaggaa gaaaaattgt ttttagctcc tataagtgat    3600
tctgatgagt tttacaatac tatacaaata aaagaatatg atgaacagcc aacatatagt    3660
tgtcagttgc ttttttaaaaa agatgaagaa agtactgatg agataggatt gattggtatt    3720
catcgtttct acgaatctgg aattgtattt aaagagtata aagattattt tgtataagt    3780 aaatggtact taaaagaggt aaaaaggaaa ccatataatt caaaattggg atgtaattgg    3840
cagtttattc ctaaagatga agggtggact gaataa                             3876
```

<210> SEQ ID NO 13
<211> LENGTH: 1291
<212> TYPE: PRT
<213> ORGANISM: Clostridium botulinum serotype B Bivalent 3281

<400> SEQUENCE: 13

```
Met Pro Val Thr Ile Asn Asn Phe Asn Tyr Asn Asp Pro Ile Asp Asn
  1               5                   10                  15

Asn Asn Ile Ile Met Met Glu Pro Pro Phe Ala Arg Gly Met Gly Arg
             20                  25                  30

Tyr Tyr Lys Ala Phe Lys Ile Thr Asp Arg Ile Trp Ile Ile Pro Glu
         35                  40                  45

Arg Tyr Thr Phe Gly Tyr Lys Pro Glu Asp Phe Asn Lys Ser Ser Gly
     50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125
```

-continued

```
Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asn Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ala Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Ala Tyr Asn Thr Gln Asn Asn
465                 470                 475                 480

Tyr Ile Glu Asn Asp Phe Ser Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Tyr Val Pro Val Tyr Lys Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
```

-continued

```
           545                 550                 555                 560
       Asp Ala Leu Leu Phe Ser Asn Lys Val Tyr Ser Phe Ser Met Asp
                   565                 570                 575

Tyr Ile Lys Thr Ala Asn Lys Val Val Glu Ala Gly Leu Phe Ala Gly
                   580                 585                 590

Trp Val Lys Gln Ile Val Asp Phe Val Ile Glu Ala Asn Lys Ser
                   595                 600                 605

Ser Thr Met Asp Lys Ile Ala Asp Ile Ser Leu Ile Val Pro Tyr Ile
                   610                 615                 620

Gly Leu Ala Leu Asn Val Gly Asn Glu Thr Ala Lys Gly Asn Phe Glu
       625                 630                 635                 640

Asn Ala Phe Glu Ile Ala Gly Ala Ser Ile Leu Leu Glu Phe Ile Pro
                   645                 650                 655

Glu Leu Leu Ile Pro Val Val Gly Ala Phe Leu Leu Glu Ser Tyr Ile
                   660                 665                 670

Asp Asn Lys Asn Lys Ile Ile Glu Thr Ile Asn Ser Ala Leu Thr Lys
                   675                 680                 685

Arg Asp Glu Lys Trp Ile Asp Met Tyr Gly Leu Ile Val Ala Gln Trp
       690                 695                 700

Leu Ser Thr Val Asn Thr Gln Phe Tyr Thr Ile Lys Glu Gly Met Tyr
       705                 710                 715                 720

Lys Ala Leu Asn Tyr Gln Ala Gln Ala Leu Glu Glu Ile Ile Lys Tyr
                   725                 730                 735

Lys Tyr Asn Ile Tyr Ser Glu Lys Glu Arg Ser Asn Ile Asn Ile Asp
                   740                 745                 750

Phe Asn Asp Val Asn Ser Lys Leu Asn Glu Gly Ile Asn Gln Ala Ile
                   755                 760                 765

Asp Asn Ile Asn Asn Phe Ile Asn Glu Cys Ser Val Ser Tyr Leu Met
                   770                 775                 780

Lys Lys Met Ile Pro Leu Ala Val Glu Lys Leu Leu Asp Phe Asp Asn
       785                 790                 795                 800

Thr Leu Arg Lys Asn Leu Leu Asn Tyr Ile Asp Glu Asn Lys Leu Tyr
                   805                 810                 815

Leu Ile Gly Ser Ala Glu Tyr Glu Lys Ser Lys Val Asp Lys Tyr Leu
                   820                 825                 830

Lys Thr Ser Ile Pro Phe Asp Leu Ser Thr Tyr Thr Asn Asn Thr Ile
                   835                 840                 845

Leu Ile Glu Ile Phe Asn Lys Tyr Asn Ser Asp Ile Leu Asn Asn Ile
                   850                 855                 860

Ile Leu Asn Leu Arg Tyr Arg Asp Asn Lys Leu Ile Asp Leu Ser Gly
       865                 870                 875                 880

Tyr Gly Ala Lys Val Glu Val Tyr Asp Gly Val Lys Leu Asn Asp Lys
                   885                 890                 895

Asn Gln Phe Lys Leu Thr Ser Ser Ala Asn Ser Lys Ile Arg Val Ile
                   900                 905                 910

Gln Asn Gln Asn Ile Ile Phe Asn Ser Met Phe Leu Asp Phe Ser Val
                   915                 920                 925

Ser Phe Trp Ile Arg Ile Pro Lys Tyr Lys Asn Asp Gly Ile Gln Asn
                   930                 935                 940

Tyr Ile His Asn Glu Tyr Thr Ile Ile Asn Cys Met Lys Asn Asn Ser
       945                 950                 955                 960

Gly Trp Lys Ile Ser Ile Arg Gly Asn Met Ile Ile Trp Thr Leu Ile
                   965                 970                 975
```

-continued

Asp Ile Asn Gly Lys Ile Lys Ser Val Phe Phe Glu Tyr Ser Ile Lys
              980                 985                 990

Glu Asp Ile Ser Glu Tyr Ile Asn Arg Trp Phe Phe Val Thr Ile Thr
        995                1000                1005

Asn Asn Ser Asp Asn Ala Lys Ile Tyr Ile Asn Gly Lys Leu Glu Ser
    1010                1015                1020

His Ile Asp Ile Arg Asp Ile Arg Glu Val Ile Ala Asn Asp Glu Ile
1025                1030                1035                1040

Ile Phe Lys Leu Asp Gly Asn Ile Asp Arg Thr Gln Phe Ile Trp Met
                1045                1050                1055

Lys Tyr Phe Ser Ile Phe Asn Thr Glu Leu Ser Gln Ser Asn Ile Glu
            1060                1065                1070

Glu Ile Tyr Lys Ile Gln Ser Tyr Ser Glu Tyr Leu Lys Asp Phe Trp
        1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Lys Lys Asp Ser Ser Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
            1140                1145                1150

Ser Gln Ser Ile Asn Asp Asp Ile Val Arg Lys Glu Asp Tyr Ile Tyr
        1155                1160                1165

Leu Asp Phe Phe Asn Leu Asn Gln Glu Trp Arg Val Tyr Met Tyr Lys
    1170                1175                1180

Tyr Phe Lys Lys Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
            1220                1225                1230

Asp Glu Ile Gly Leu Ile Gly Ile His Arg Phe Tyr Glu Ser Gly Ile
        1235                1240                1245

Val Phe Lys Glu Tyr Lys Asp Tyr Phe Cys Ile Ser Lys Trp Tyr Leu
    1250                1255                1260

Lys Glu Val Lys Arg Lys Pro Tyr Asn Ser Lys Leu Gly Cys Asn Trp
1265                1270                1275                1280

Gln Phe Ile Pro Lys Asp Glu Gly Trp Thr Glu
                1285                1290

<210> SEQ ID NO 14
<211> LENGTH: 3876
<212> TYPE: DNA
<213> ORGANISM: Clostridium botulinum serotype B Bivalent 3281

<400> SEQUENCE: 14
atgccagtta caataaataa ttttaattat aatgatccta ttgataataa taatattatt      60
atgatggaac ctccatttgc gagaggtatg gggagatatt ataaagcttt taaaatcaca     120
gatcgtattt ggataatacc ggaaagatat acttttggat ataaacctga ggattttaat     180
aaaagttccg gtattttaa tagagatgtt tgtgaatatt atgatccaga ttacttaaat     240
actaatgata aaagaatat attttttacaa acaatgatca agttatttaa tagaatcaaa     300

```
tcaaaaccat tgggtgaaaa gttattagag atgattataa atggtatacc ttatcttgga    360
gatagacgtg ttccactcga agagtttaac acaaacattg ctagtgtaac tgttaataaa    420
ttaatcagta atccaggaga agtggagcga aaaaaaggta ttttcgcaaa tttgataata    480
tttggacctg ggccagtttt aaatgaaaat gagactatag atataggtat acaaaatcat    540
tttgcatcaa gggaaggctt cgggggtata atgcaaatga agttttgccc agaatatgta    600
agcgtattta ataatgttca agaaaacaaa ggcgcaagta tatttaatag acgtggatat    660
ttttcagatc cagccttaat attaatgcat gaacttatac atgttttaca tggattatat    720
ggcattaaag taaatgattt accaatcgta ccaaatgaaa aaaaattttt tatgcaatct    780
acagatgcta tacaggcaga agaactatat actttggggg acaagatccc cagcatcata    840
agtccttcta cggataaaag tatctatgat aaagttttgc aaaattttag agggatagtt    900
gatagactta acaaggtttt agtttgcata tcagatccta acattaatat taatatatat    960
aaaaataaat ttaagataaa atataaattc gttgaagatt ctgagggaaa atatagtata   1020
gatgtagaaa gtttcgataa attatataaa agcttaatgt ttggttttac agaaactaat   1080
atagcagaaa attataaaat aaaaactaga gctgcttatt ttagtgattc cttaccacca   1140
gtaaaaataa aaaatttatt agataatgaa atctatacta tagaggaagg gtttaatata   1200
tctgataaaa atatggaaaa agaatataga ggtcagaata aagctataaa taacaagct    1260 tatgaagaaa tcagcaagga gcatttggct gtatataaga tacaaatgtg taaaagtgtt   1320
aaagctccag gaatatgtat tgatgttgat aatgaggatt tgttctttat agctgataaa   1380
aatagttttt cagatgattt atctaaaaac gaaagaatag catataatac acagaataat   1440
tatatagaaa atgatttctc tataaatgaa ttaattttag atactgattt aataagtaaa   1500
atagaattac caagtgaaaa tacagaatca cttactgatt ttaatgtata tgttccagta   1560
tataaaaaac aacccgctat aaaaaaaatt tttacagatg aaaataccat ctttcaatat   1620
ttatactctc agacatttcc tctagatata agagatataa gtttaacatc ttcatttgat   1680
gatgcattat tattttctaa caaagtttat tcatttttt ctatggatta tattaaaact   1740
gctaataaag tggtagaagc aggattattt gcaggttggg tgaaacagat agtagatgat   1800
tttgtaatcg aagctaataa aagcagtact atggataaaa ttgcagatat atctctaatt   1860
gttccttata taggattagc tttaaatgta ggaaatgaaa cagctaaagg aaattttgaa   1920
aatgcttttg agattgcagg agccagtatt ctactagaat ttataccaga acttttaata   1980
cctgtagttg gagctttttt attagaatca tatattgaca ataaaaataa aattattgaa   2040 acaataaaata gtgctttaac taaaagagat gaaaaatgga ttgatatgta cggattaata   2100
gtagcgcaat ggctctcaac agttaatact caattttata caataaaaga gggaatgtat   2160
aaggctttaa attatcaagc acaagcattg gaagaaataa taaaatacaa atataatata   2220
tattctgaga agaaaggtc aaatattaac atcgattta atgatgtaaa ttctaaactt   2280
aatgagggta ttaaccaagc tatagataat ataaataatt ttataaatga atgttctgta   2340
tcatatttaa tgaaaaaaat gattccatta gctgtagaaa aattactaga cttcgataat   2400
actctcagaa aaatttatt aaattatata gatgaaaata aattatattt gattggaagt   2460
gcagaatatg aaaaatcaaa agtagataaa tacttgaaaa ccagtatacc atttgatctt   2520
tcaacgtata ctaataatac aatactaata gaaatattta ataaatataa tagcgatatt   2580
ttaaataata ttatcttaaa tttaagatat agggataata agttaataga tttatcagga   2640
tatggggcaa aggtagaggt atatgatggg gtcaagctta atgataaaaa tcaatttaaa   2700
```

```
ttaactagtt cagcaaatag taagattaga gtgattcaaa atcagaatat catatttaat    2760
agtatgttcc ttgattttag cgttagtttt tggataagaa tacctaaata taagaatgat    2820
ggtatacaaa attatattca taatgaatat acaataatta attgtatgaa aaataattct    2880
ggatggaaaa tatctattag gggtaatatg ataatatgga ctttaattga tataaatgga    2940
aaaatcaaat cagtattttt tgaatatagc ataaaagaag atatatcaga gtatataaat    3000
agatggtttt ttgtaactat tactaataat tcggataacg ctaaaattta tattaatggt    3060
aagctagaat cacatataga tattagagat ataagagaag ttattgctaa tgatgaaata    3120
atatttaaat tagatggtaa tatagataga acacagttca tttggatgaa atatttcagt    3180
atttttaata cggaattaag tcaatcaaat attgaagaaa tatataaaat tcaatcatat    3240
agcgaatatt taaaagattt ttggggaaat cctttaatgt acaataaaga atattatatg    3300
tttaatgcgg ggaataaaaa ttcatatatt aaactaaaga aagattcatc tgtaggtgaa    3360 atttaacac gtagcaaata taatcaaaat tccaaatata taaattatag agatttatat    3420
attggagaaa aatttattat aagaagaaag tcaaattctc aatctataaa tgatgatata    3480
gttagaaaag aagattatat atatctagat tttttttaatt taaatcaaga gtggagagta    3540
tatatgtata aatattttaa gaaagaggaa gaaaaattgt ttttagctcc tataagtgat    3600
tctgatgagt tttacaatac tatacaaata aagaatatg atgaacagcc aacatatagt    3660
tgtcagttgc ttttaaaaa agatgaagaa agtactgatg agataggatt gattggtatt    3720
catcgtttct acgaatctgg aattgtattt aaagagtata aagattattt ttgtataagt    3780
aaatggtact taaaagaggt aaaaaggaaa ccatataatt caaaattggg atgtaattgg    3840
cagtttattc ctaaagatga agggtggact gaataa                              3876
```